US012459996B2

(12) United States Patent
Kisseleva et al.

(10) Patent No.: US 12,459,996 B2
(45) Date of Patent: Nov. 4, 2025

(54) METHODS FOR TREATING ALCOHOL-INDUCED BRAIN INJURY AND REDUCING ALCOHOL ADDICTION

(71) Applicant: The Regents of the University of California, Oakland, CA (US)

(72) Inventors: Tatiana Kisseleva, La Jolla, CA (US); David Brenner, La Jolla, CA (US); Jun Xu, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 768 days.

(21) Appl. No.: 16/639,514

(22) PCT Filed: Aug. 31, 2018

(86) PCT No.: PCT/US2018/049054
§ 371 (c)(1),
(2) Date: Feb. 14, 2020

(87) PCT Pub. No.: WO2019/046697
PCT Pub. Date: Mar. 7, 2019

(65) Prior Publication Data

US 2021/0017268 A1 Jan. 21, 2021

Related U.S. Application Data

(60) Provisional application No. 62/552,708, filed on Aug. 31, 2017.

(51) Int. Cl.

| | |
|---|---|
| ***A61K 39/395*** | (2006.01) |
| ***A61P 1/16*** | (2006.01) |
| ***A61P 25/32*** | (2006.01) |
| ***C07K 16/24*** | (2006.01) |
| ***C12N 15/113*** | (2010.01) |
| *A61K 39/00* | (2006.01) |

(52) U.S. Cl.
CPC ...... *C07K 16/244* (2013.01); *A61K 39/39541* (2013.01); *A61K 39/3955* (2013.01); *A61P 1/16* (2018.01); *A61P 25/32* (2018.01); *C12N 15/1136* (2013.01); *C12N 15/1138* (2013.01); *A61K 2039/505* (2013.01); *A61K 2039/54* (2013.01); *C12N 2310/11* (2013.01); *C12N 2310/12* (2013.01); *C12N 2310/14* (2013.01)

(58) Field of Classification Search
CPC ....... A61P 1/16; A61P 25/32; A61K 2039/505
See application file for complete search history.

(56) References Cited

U.S. PATENT DOCUMENTS

2011/0177578 A1 7/2011 Nakamura et al.
2015/0004133 A1 1/2015 Kisseleva et al.

FOREIGN PATENT DOCUMENTS

CN 101168049 A 4/2008

OTHER PUBLICATIONS

De la Monte et al. The Liver-Brain Axis of Alcohol-Mediated Neurodegeneration: Role of Toxic Lipids. Int. J. Environ. Res. Public Health 2009, 6, 2055-2075.*

Young, International Search Report and Written Opinion for PCT/US2018/049054, Nov. 21, 2018.

Crews et al., "Neuroimmune Basis of Alcoholic Brain Damage" International Review of Neurobiology, vol. 118, 2014, p. 315-357.

* cited by examiner

*Primary Examiner* — Dong Jiang

(74) *Attorney, Agent, or Firm* — Gregory P. Einhorn; Greer, Burns & Crain, Ltd.

(57) ABSTRACT

In alternative embodiments, provided are compositions, including products of manufacture and kits, and methods, for reducing addiction to alcohol, and for ameliorating, reversing, treating or preventing Alcoholic Liver Disease (ALD), or alcohol-induced brain injury, wherein optionally the alcohol-induced brain injury comprises neuronal death and astrogliosis (reducing alcohol-induced neuronal death and astrogliosis). In alternative embodiments, provided methods for administering to the individual in need thereof a compound or composition capable of inhibiting or decreasing the expression or activity of an IL-17 or IL-17 receptor (IL-17R) or RORγt protein, transcript and/or gene to treat or for use in: reducing addiction to alcohol; or ameliorating, reversing, treating or preventing Alcoholic Liver Disease (ALD) or alcohol-induced brain injury; or, inhibiting ROR γt to effectively block production of IL-17 cytokines and attenuate development of alcohol-induced liver fibrosis and brain damage.

13 Claims, 78 Drawing Sheets

FIG. 6A

| ALD stages: | Acute ASH | Chronic ASH | Alcoholic liver fibrosis |
|---|---|---|---|
| Experimental models: | Lieber-DeCarli + one binge | Lieber-DeCarli + weekly binge | IG alcohol feeding |
| serum alcohol, mg/dL | 370 ± 10 | 437 ± 23 | 471 ± 12 |
| Body weight (g) | 19.9 ± 1.2 | 25.8 ± 2.3 | 27.5 ± 2.7 |
| **Biochemical parameters:** | | | |
| Serum ALT (IU/L) | 110 ± 32 | 121 ± 30 | 215 ± 51 |
| Liver TG (nmol/gl) | 73 ± 5.4 | 94 ± 10.3 | 151 ± 11.2 |
| **Pathological scores:** | | | |
| Steatosis grade | 0 | 1-2 | 3 |
| Steatosis% | 0 | 28 ± 7 | 75 ± 7 |
| Lobular inflammation grade | 1 | 1-2 | 1-3 |
| Portal inflammation grade | 0 | 0 | 0-2 |
| Fibrosis stage | 0 | 0-1 | 2-3 |
| **Histological parameters:** | | | |
| H&E, Lipid area (%) | 4.5 ±1.2 | 6.3 ±2.1 | 21.5 ±7.8 |
| Sirius red area (%) | 1.2 ± 0.4 | 3.8 ± 0.9 | 5.6 ± 0.7 |
| F4/80+ area (%) | 6.9 ± 1.2 | 7.2 ± 0.4 | 13.5 ± 3 |

FIG. 6B

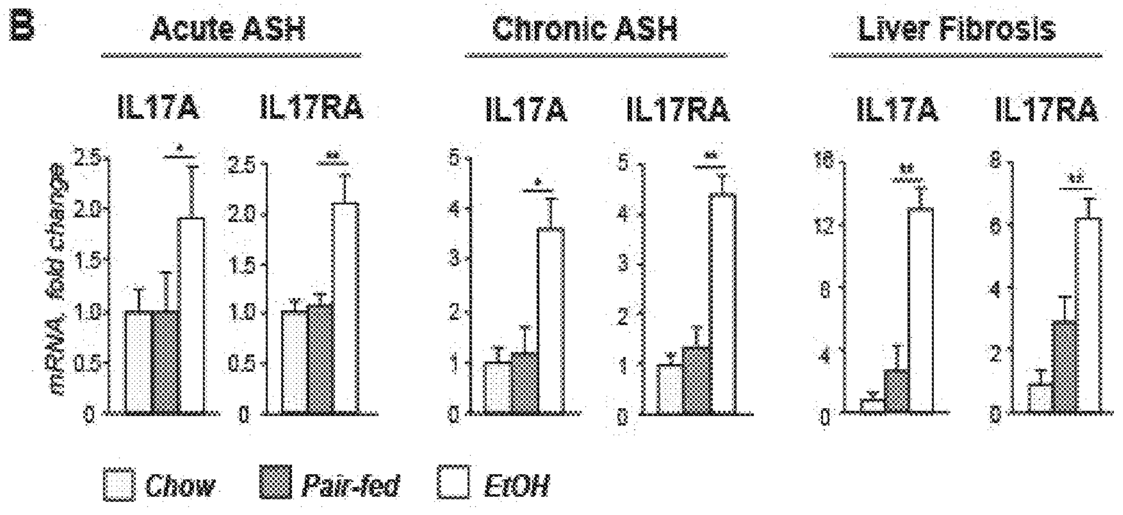

| GO enrichment: (vs healthy controls) | -log (p value) | | |
|---|---|---|---|
| | Early ASH | Severe ASH | ALD progression |
| Role of IL17A in Arthritis | - | 2.27 | 2.75 |
| IL17 signaling | - | - | 2.33 |

Amygdala

FIG. 11F
ELISA, human serum, concentration, pg/ml
0
2
3
4
p=0.07
Patients:
Healthy controls, ALT ≤ 40 U/L
Excessive drinkers, ALT ≤ 40 U/L
Excessive drinkers, ALT ≥ 40 U/L

METHODS FOR TREATING ALCOHOL-INDUCED BRAIN INJURY AND REDUCING ALCOHOL ADDICTION

RELATED APPLICATIONS

This application is a national phase application claiming benefit of priority under 35 U.S.C. § 371 to Patent Convention Treaty (PCT) International Application serial number PCT/US2018/049054, filed Aug. 31, 2018, now pending, which claims the benefit of priority to U.S. Provisional Application Ser. No. 62/552,708, filed Aug. 31, 2017. The aforementioned applications are expressly incorporated herein by reference in their entirety and for all purposes.

STATEMENT AS TO FEDERALLY SPONSORED RESEARCH

This invention was made with government support under AA022614 awarded by the National Institutes of Health. The government has certain rights in the invention.

TECHNICAL FIELD

This invention generally relates to medicine and immunology. In alternative embodiments, provided are compositions, including products of manufacture and kits, and methods, for reducing addiction to alcohol, and for ameliorating, reversing, treating or preventing Alcoholic Liver Disease (ALD), or alcohol-induced brain injury, wherein optionally the alcohol-induced brain injury comprises neuronal death and astrogliosis (reducing alcohol-induced neuronal death and astrogliosis).

BACKGROUND

IL-17A is mainly produced by $CD4^+$ Th17 cells (FIG. 1A), and other immune cells ($CD8^+$ T cells, NKT cells, NK cells, and monocytes)[1-3]. Although the family of IL-17 cytokines is comprised of IL-17A, IL-17F, and others[4], IL-17A homodimers (also known as IL-17) are most abundant in Th17 cells, exhibit higher biological activity, and signal through the receptor IL-17RA[1], which is ubiquitously expressed, but is strongly induced in IL-17-responsive tissues (such as hematopoietic cells, and fibroblasts[6])[5,7].

TGF-β1, IL-6, and IL-23 are upregulated along with IL-17 in response to alcohol-induced injury[8,9]. Differentiation of Th17 cells from naïve Th0 cells[10-12] is driven by TGF-β1, IL-6, IL-21, and IL-23 via activation of retinoid-related orphan receptor γt (RORγt)[2]. Blocking of RORγt suppresses IL-17 production in Th17 cells (and other cells producing IL-17)[2,13-16]. Recently, IL-17 was implicated in liver, lung, and skin fibrosis, and in tumorigenesis[1,4,17-19,20-24].

Chronic alcohol abuse has a detrimental effect on the brain and liver. There is no effective treatment for these patients, mainly because the mechanism underlying alcohol addiction and consequent alcohol-induced damage of the liver/brain axis remains unresolved.

SUMMARY

In alternative embodiments, provided are methods for:

reducing addiction to alcohol, ameliorating, reversing, treating or preventing: Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis), or inhibiting ROR γt to effectively block production of IL-17 cytokines and attenuate development of alcohol-induced liver fibrosis and brain damage, the method comprising:

(a) administering to the individual in need thereof a compound or composition capable of inhibiting or decreasing the expression or activity of an IL-17 or IL-17 receptor (IL-17R) or RORγt protein, transcript and/or gene, or (b) (i) providing a compound or composition capable of inhibiting or decreasing the expression or activity of an IL-17 or IL-17 receptor (IL-17R) or RORγt protein, transcript and/or gene, and (ii) administering the compound or composition to the individual in need thereof, thereby reducing addiction to alcohol, ameliorating, reversing, treating or preventing: Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis), or inhibiting ROR γt to effectively block production of IL-17 cytokines and attenuate development of alcohol-induced liver fibrosis and brain damage.

In alternative embodiments, provided are methods wherein:

(a) the compound or composition capable of inhibiting or decreasing the expression or activity of an IL-17 or IL-17 receptor (IL-17R) or ROR γt protein, transcript and/or gene, is or comprises:

(1) a nucleic acid, and optionally the nucleic acid is an inhibitory nucleic acid comprising: an RNAi inhibitory nucleic acid molecule, a double-stranded RNA (dsRNA) molecule, a microRNA (mRNA), a small interfering RNA (siRNA), an antisense RNA, a short hairpin RNA (shRNA), or a ribozyme capable of capable of inhibiting or decreasing the expression or activity of the IL-17 or IL-17 receptor (IL-17R) or ROR γt protein, transcript and/or gene, (2) a peptide or polypeptide, wherein optionally the polypeptide is or comprises an antibody or fragment thereof or equivalent thereof, capable of specifically binding the IL-17 or IL-17 receptor (IL-17R) or ROR γt protein, transcript and/or gene, and is capable of inhibiting or decreasing the activity of the IL-17 or IL-17 receptor (IL-17R) protein, transcript and/or gene, or (3) a small molecule, lipid, saccharide, nucleic acid or polysaccharide capable of inhibiting or decreasing the activity of the IL-17 or IL-17 receptor (IL-17R) or ROR γt protein, transcript and/or gene, wherein optionally the small molecule RORγt inhibitor comprises or has the structure: VPR-254 (Visionary Pharmaceuticals, San Diego, CA) or PV0347 (Visionary Pharmaceuticals, San Diego, CA), or optionally the small molecule RORγt inhibitor comprises or has a structure as described in WO2015116904 (PCT/US2015/013699); WO2015038350 (PCT/US2014/053227), WO2012027965 (PCT/CN2011/001481), WO2012028100 (PCT/CN2011/079179), WO2012100732 (PCT/CN2012/070676), or WO2012100734 (PCT/CN2012/070678); or, U.S. Pat. Nos. 9,359,315, 9,266,886, 9,624,217, 10,047,085, 10,005,731; or U.S. Pat App Pub nos., US 2016-0213676 A1, US 2016-0213627 A1, US 2018-0112002 A1, US 2018-0162808 A1, or US 2018-0162815 A1, and optionally the small molecule inhibitor comprises or has one of the following structures, or the small molecule inhibitor is a stereoisomer, enantiomer, salt, hydrate and/or solvate thereof of any one of:

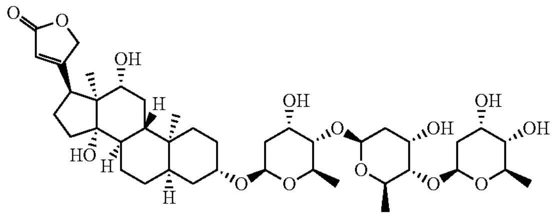

Digoxin

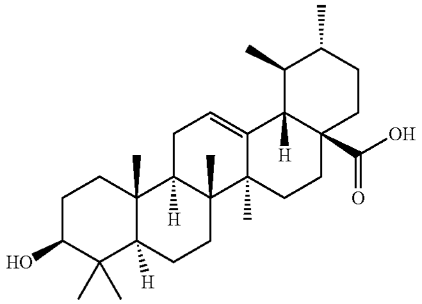

Ursolic acid

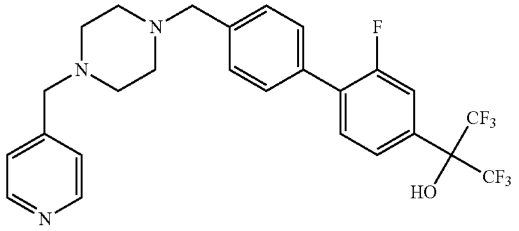

SR2211

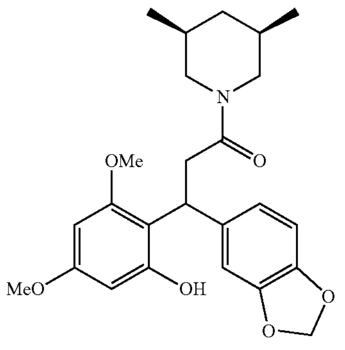

or,

ML 209

-continued

1

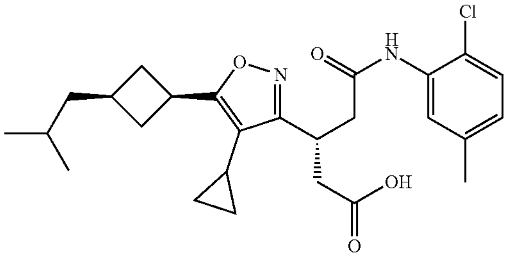

(Japan Tobacco)

2

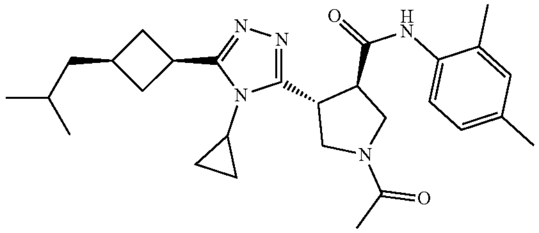

(Japan Tobacco)

3

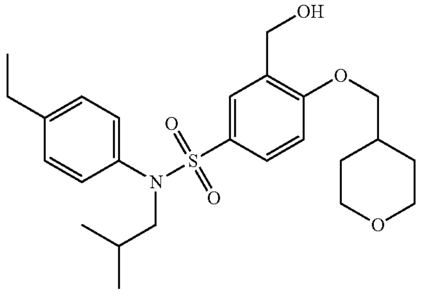

(Glaxo)

4

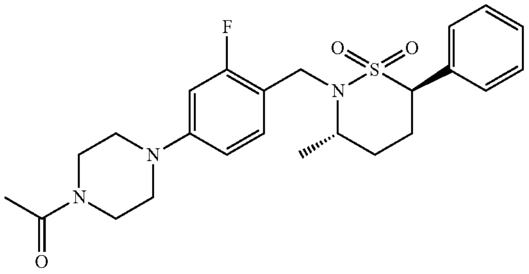

or,

GNE-3500
(Genentech)

2

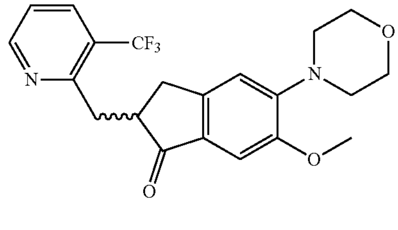

3
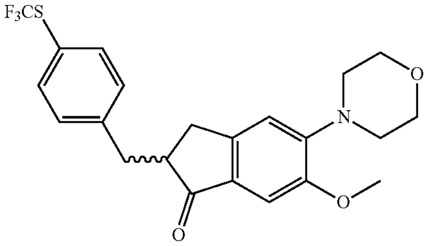
4
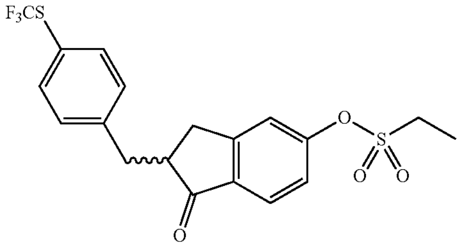
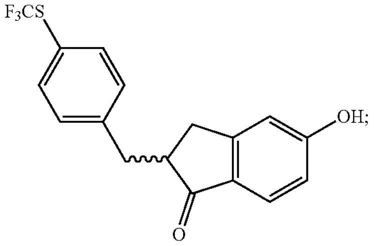
or
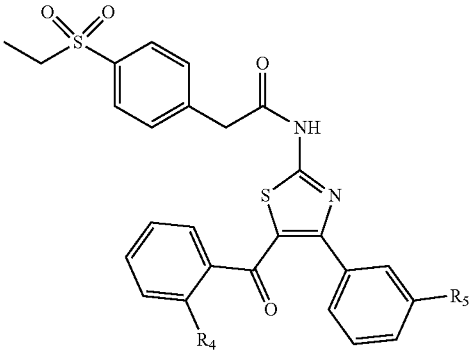
7: $R_4 = R_5 = H$
8: $R_4 = R_5 = Cl$
9
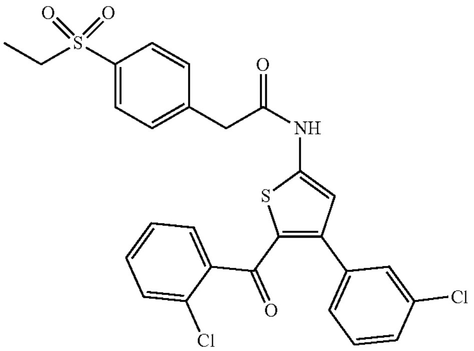
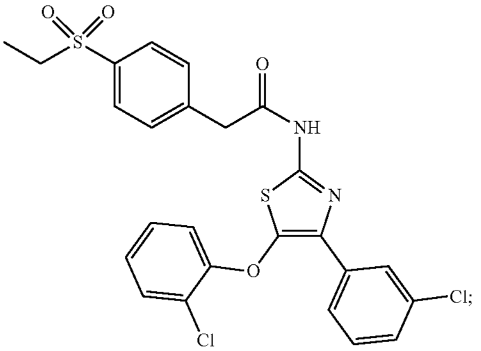
or
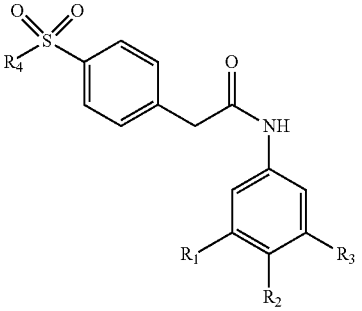
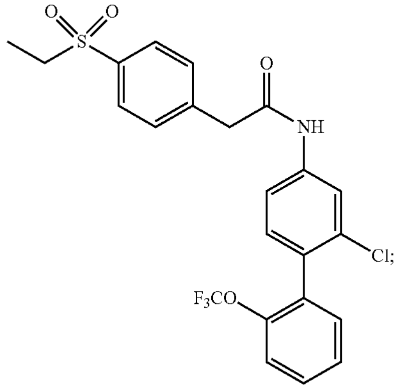
or
14
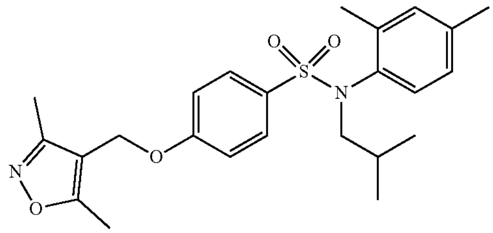
15
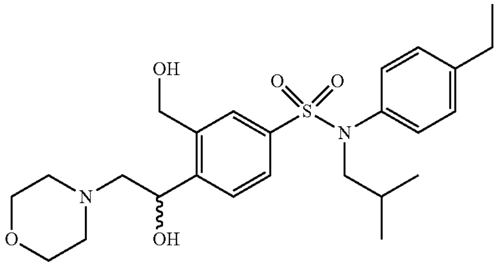

-continued
16
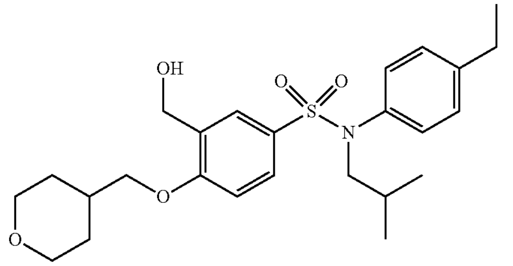
17
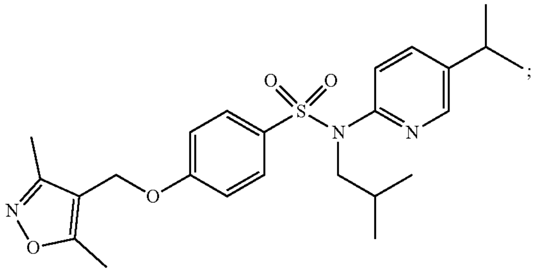
; or
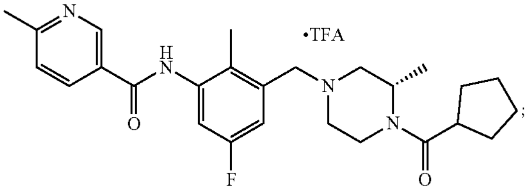
; or
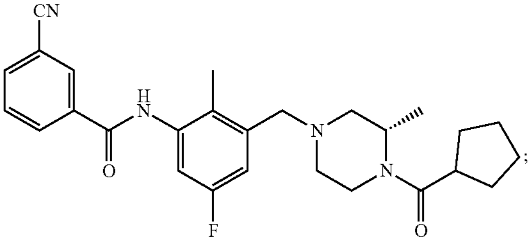
; or
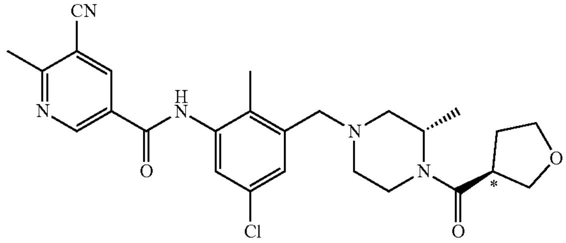
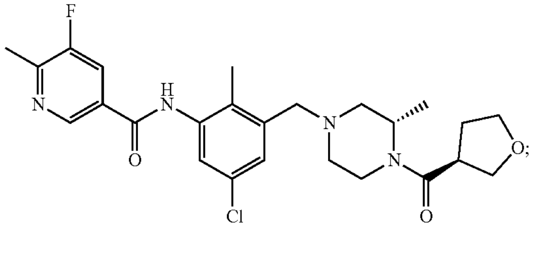
; or
-continued
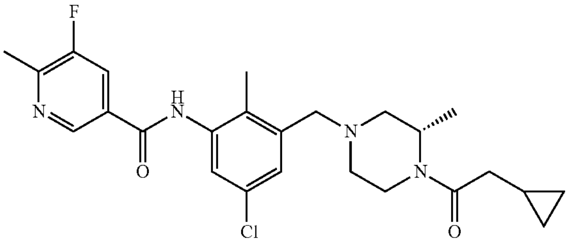
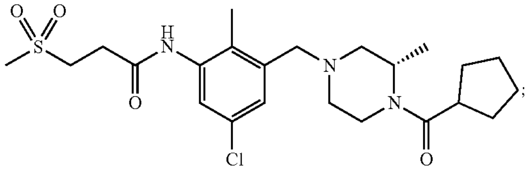
; or
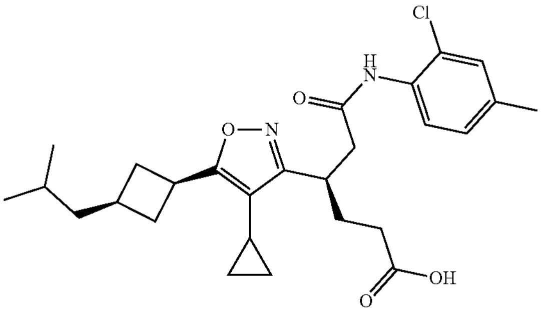
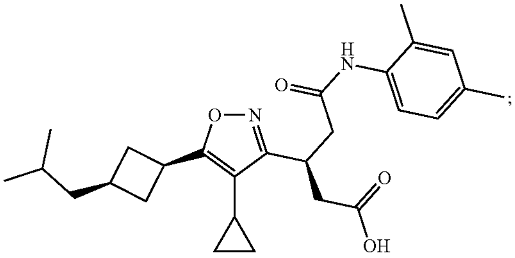
; or
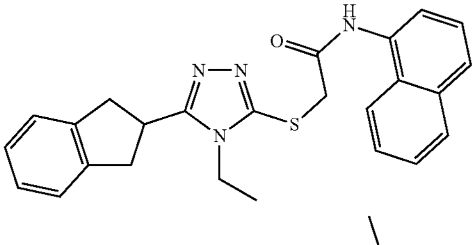
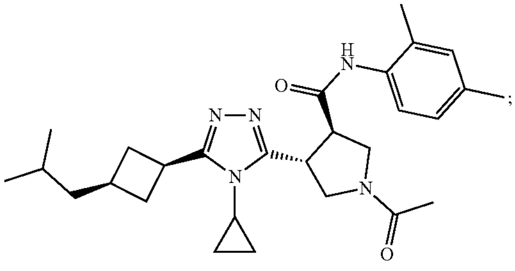
; or
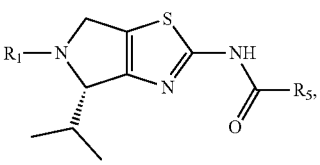

wherein

R5 is any one of:

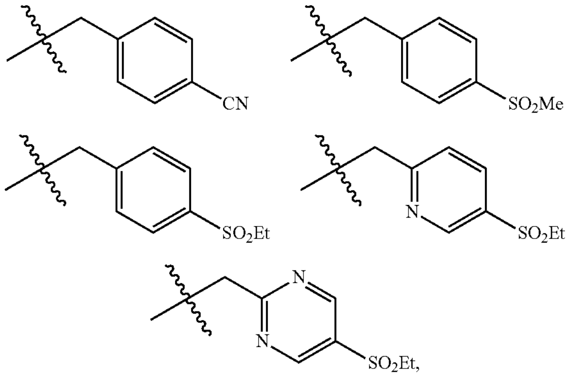

and

R1 is any one of:

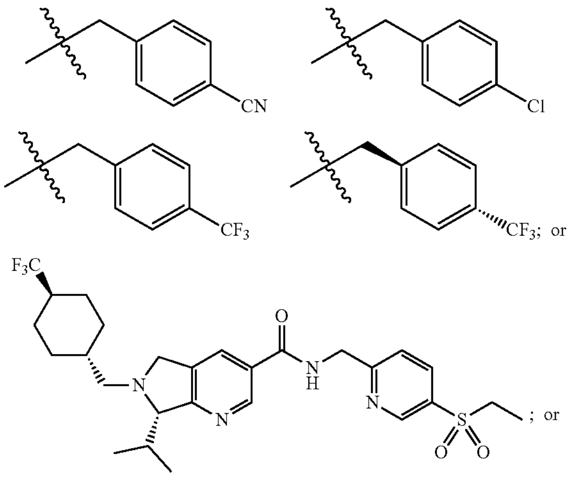

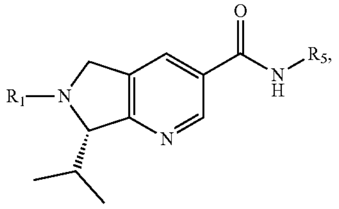

wherein

R5 is any one of:

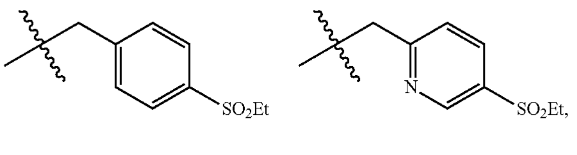

R1 is any one of.

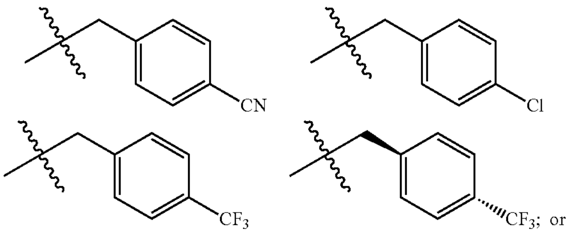

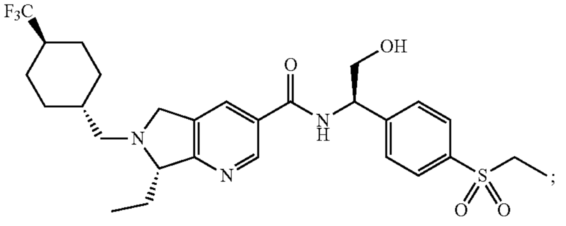

(b) the compound or composition is formulated as a pharmaceutical composition, or is formulated for administration in vivo; or formulated for enteral or parenteral administration, or for oral, intravenous (IV) or intrathecal (IT) administration, wherein optionally the compound or formulation is administered orally, parenterally, by inhalation spray, nasally, topically, intrathecally, intrathecally, intracerebrally, epidurally, intracranially or rectally;

wherein optionally the formulation or pharmaceutical composition is contained in or carried in a nanoparticle, a particle, a micelle or a liposome or lipoplex, a polymersome, a polyplex or a dendrimer; or (c) the compound or composition, or the formulation or pharmaceutical composition, is formulated as, or contained in, a nanoparticle, a liposome, a tablet, a pill, a capsule, a gel, a geltab, a liquid, a powder, an emulsion, a lotion, an aerosol, a spray, a lozenge, an aqueous or a sterile or an injectable solution, or an implant.

In alternative embodiments, provided are methods wherein the nucleic acid capable of inhibiting or decreasing the expression or activity of the IL-17 or IL-17 receptor (IL-17R) or ROR γt protein, transcript and/or gene comprises or is contained in a nucleic acid construct or a chimeric or a recombinant nucleic acid, or an expression cassette, vector, plasmid, phagemid or artificial chromosome, optionally stably integrated into the cell's chromosome, or optionally stably episomally expressed, and optionally the cell is a cancer cell or a cancer cell line, or a carcinoma cell line or an immortalized cell line.

In alternative embodiments, provided are kits comprising a compound or composition or a formulation or a pharmaceutical composition as provided herein, and optionally comprising instructions on practicing a method as provided herein.

In alternative embodiments, provided are Uses of a compound or composition or a formulation as provided herein, in the manufacture of a medicament. In alternative embodiments, provided are Uses of a compound or composition, or a formulation or a pharmaceutical composition as provided herein, or a used in any method as provided herein, in the manufacture of a medicament for:

reducing addiction to alcohol, or ameliorating, reversing, treating or preventing: Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis), or inhibiting ROR γt to effectively block production of IL-17 cytokines and attenuate development of alcohol-induced liver fibrosis and brain damage.

In alternative embodiments, provided are compound or composition or a formulation as provided herein, for use in:

reducing addiction to alcohol, or ameliorating, reversing, treating or preventing: Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis) or inhibiting ROR γt to effectively block production of IL-17 cytokines and attenuate development of alcohol-induced liver fibrosis and brain damage.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIG. 1A schematically illustrates the paradigm of Th17 signaling in response to ALD (explanation in the text); FIG. 1B graphically illustrates RNA analysis of liver biopsy specimens obtained during routine diagnostic; alcoholic liver lesions were assessed, and fibrosis stages were defined as F0 (n=2), F1 (n=5), F2 (n=5), F3 (n=4); and mRNA was isolated from snap frozen tissues; expression of receptor IL-17RA was determined by qRT-PCR with primers for hIL-17RA, and normalized to GAPDH; FIG. 1C graphically illustrates data showing that hepatic expression of IL-17 and IL-17RA mRNA is progressively increased in mice with ASH (HFD+EtOH), versus pair-fed (HFD), qRT-PCR. The data are means±SEM*p<0.03, **p<0.01, as described in detail in Example 1, below.

FIG. 2A left images graphically illustrate levels of alanine transaminase (ALT) and aspartate transaminase (AST) in wild type (WT) and IL-17RA knockout (KO) mice, and (middle images) illustrates images of steatosis (H&E, triglycerides) liver fibrosis (Sirius Red), and right image graphically illustrates liver weight in the WT and KO mice; FIG. 2B illustrates (left) images of the number of activated α-SMA*HSCs and F4/80$^{+}$ Kupffer cells; lipid peroxidation (4-HNE) and CYP2E1 protein were reduced in alcohol-fed IL-17RA$^{-/-}$ mice; FIG. 2C illustrates that hepatic lipid peroxidation was reduced in alcohol-fed IL-17RA$^{-/-}$ mice (as indicated by reduced levels of 4-HNE and TBARS and upregulation of GSH, where images of RNA levels is in left images and protein levels in right graphs; FIG. 2D-G graphically illustrate results of qRT-RCR showing: FIG. 2D, mRNA expression of fibrogenic and myeloid markers; FIG. 2E, cytokines; FIG. 2F, lipogenic genes; and FIG. 2G, ROS production in alcohol-fed IL-17RA$^{-/-}$ and wt mice; *p<0.01, **p<0.05; as described in detail in Example 1, below.

FIG. 3C illustrates images of livers stained with H&E, Sirius Red, α-SMA, Desmin, and F4/80 (left images), with the data graphically illustrated in the accompanying right graphs; FIG. D-G graphically illustrate results of qRT-PCR, which shows mRNA expression of fibrogenic and myeloid markers (FIG. 6D), cytokines (FIG. 6E), lipogenic genes (FIG. 6F), and ROS production (FIG. 6G); *p<0.01, **p<0.05, as described in detail in Example 1, below.

FIG. 4A left image illustrates how mice were subjected to alcohol-induced liver fibrosis±anti-IL-17 Ab (2 w delay; 25 mg/kg/weight, i.p., 1× week) or IgG, and right graphs graphically illustrate detected mRNA levels of IL-17RA; FIG. 4B-C: illustrate data showing analysis of expression of IL-17RA mRNA in samples of isolated cerebellum (Cereb), hippocampus (Hip), Olfactory (Olf), and livers, *p<0.01, p<0.05; brains were stained for: Iba1 (hippocampus) and Caspase 3 (cerebellum) (FIG. 4B), and glial fibrillary acidic protein (GFAP) (FIG. 4**C), nuclei were visualized; GFAP+ area was quantified and shown as percent (images×20 and 40 objectives), as described in detail in Example 1, below.

FIG. 5B-C illustrate data where formalin-fixed brains were analyzed using MRI (FIG. 5B images) left panel: a—cortex, b—corpus collosum, c—hippocampus), or stained for GFAP (images of cortex, ×20, ×40 objectives); and, FIG. 5C graphically illustrates data where MRI: brain volume (mm$^3$) was calculated in dependent and non-dependent mice (n=7/group), *p<0.03; FIG. 5D-E graphically illustrates data from studies where non-dependent and dependent mice were treated with (FIG. 5D) anti-IL-17 Ab (vs IgG), or (FIG. 5E) RORγt inhibitor (vs vehicle); alcohol intake (g/kg weight/2 h) was analyzed in each group, *p<0.01, **p<0.05, as described in detail in Example 1, below.

FIG. 6A-B: FIG. 6A illustrates how alcohol-induced liver injury was assessed by grading hepatic steatosis (steatohepatitis (ASH)), inflammation, and fibrosis; and FIG. 6B graphically illustrates how these models closely recapitulated the stages of ALD in patients, and hepatic expression of IL17A and IL17RA mRNA were progressively increased in mice with acute (↑2 fold) or chronic (↑3 fold) steatohepatitis, and alcoholic liver fibrosis (↑3-6 fold, compared to the corresponding pair-fed controls; as described in detail in Example 2, below.

FIG. 6C illustrates data from archived liver biopsies from patients with an early and severe steatohepatitis (ASH), and alcoholic liver fibrosis were using RNA-Seq; and (FIG. 6C); FIG. 6C-F illustrate gene expression profiling in severe ASH and alcoholic liver fibrosis; as described in detail in Example 2, below.

FIG. 7B illustrates images where livers were stained with H&E, and Sirius Red; and FIG. 7C graphically illustrates the expression of fibrogenic gene mRNA; and FIG. 7D graphically illustrates inflammatory gene mRNA; as described in detail in Example 2, below.

FIG. 7E graphically illustrate expression of adipogenic genes, with increased expression of C/EBPα, SREBP-1c, and suppression of PPARα; FIG. 7F graphically illustrates expression of Nox1, Nox2, Nox4, P22 Phox and P22Phox and P67 Phox (induction of oxidative stress via induction of NOX4, p22 Phox, and p67 Phox); FIG. 7G graphically illustrates expression of Ly6G, MPO, F4/80, IL-8, and neutrophil chemoattractant MIP-1 and MIP-2; FIG. 7H graphically illustrates expression of IL-6, IL-1β, TNF-α, IL17A, IL-10 and IL-22; FIG. 7I graphically illustrates expression of Col1a1, αSMA, TIMP1 and TGF-β1; FIG. 7J illustrates that chronic-multiple binge alcohol fed wt mice developed significant hepatocellular injury and steatosis, as demonstrated by increased ALT, and graphically illustrates ALT and AST levels (wt mice were subjected to chronic-multiple binge alcohol feeding, or chow- or pair-fed), and liver weight, liver/body weight and serum alcohol levels, and images of wt and IL17ra−/−livers; FIG. 7K illustrates upregulation of hepatic triglycerides and levels of products of lipid peroxidation 4-HNE in both images of stained cells, and graphically; FIG. 7L illustrates upregulation of alcohol-metabolizing enzyme cytochrome and P4502E1, and graphically showing that CYP2E1 increases 2 fold vs pair-fed mice; FIG. 7M illustrates GSH levels and TBARS levels in pair-fed and EtOH treated mice; as described in detail in Example 2, below.

FIG. 8A schematically illustrates how IG alcohol-fed wt mice were treated; FIG. 8B: schematically illustrates administration of RORγt inhibitor or anti-IL17A Ab to mice; FIG. 8C: graphically illustrates serum levels of IL17A in RORγt inhibitor and IL17 inhibitory Ab administered mice; FIG. 8D: graphically illustrates ALT and blood EtOH levels in RORγt inhibitor and IL17 inhibitory Ab administered mice; FIG. 8E-F illustrate images of livers stained with H&E and Sirius Red in RORγt inhibitor and IL17 inhibitory Ab administered mice; FIG. 8G-H graphically illustrates levels of expression of inflammatory cytokines (FIG. 8G) and fibrogenic gene mRNA (FIG. 8H) in RORγt inhibitor and IL17 inhibitory Ab administered mice; as described in detail in Example 2, below.

FIG. 8I graphically illustrates AST, liver weight and liver/body weight ratio in wt mice that were surgically operated to insert intragastric catheter, and upon recovery (2 weeks) were subjected to intragastric (IG) alcohol feeding (Tsukamoto-French model) or pair-fed, and shows images of livers from wt and IL17ra−/− mice; FIG. 8J illustrates images liver cells stained for various markers, with levels of the markers graphically shown on the right (shows induction of lipid peroxidation enzyme 4-HNE); FIG. 8K illustrates an image showing the upregulation of P4502E1/CYP2E1 protein, where CYP2E1 has a 5 fold increase vs pair-fed mice; with CYP2E1 levels shown on the right; FIG. 8L shows GSH and TBARS levels in pair-fed vs EtOH administered mice; FIG. 8M-N graphically shows levels of beta-oxidation genes (C/EBPα, PPARα, PPARγ), NOX1, NOX2, Nox4, P22 Phox and p67 Phox, in pair-fed vs EtOH administered mice; FIG. 8O graphically shows levels of various marker in pair-fed vs EtOH administered mice; FIG. 8P graphically shows levels of IL17A and IL-22 mRNA in pair-fed vs EtOH administered mice; as described in detail in Example 2, below.

FIG. 9A-B illustrate images of brains and SCF collected from IG alcohol-fed wt mice, showing coronal sections from IG alcohol-fed mice fed RORγt inhibitor (FIG. 9A) or anti-IL17 Ab (FIG. 9B), both were immunostained for Iba1 or GFAP; FIG. 9C-D graphically illustrates images of Iba1 or GFAP levels in alcohol-fed mice fed RORγt inhibitor or anti-IL17 Ab; FIG. 9E graphically illustrates CSF levels of IL17A and TNF-α as measured by ELISA; as described in detail in Example 2, below.

FIG. 9F schematically illustrates an outline of the experiment where IG alcohol-fed wt mice were therapeutically treated with RORγt inhibitor, or anti-IL17A neutralizing Ab; and graphically shows levels of serum AST; FIG. 9G graphically illustrates serum levels of IL-6, IL-1β, TNF-α, and IL-10 as measured using ELISA; FIG. 9H illustrates an image of hepatic expression of IL17A as analyzed by Western blotting; FIG. 9I graphically illustrates mRNA levels from qRT-PCR of whole livers from IG alcohol-fed wt mice treatment; FIG. 9J illustrates images of livers from IG alcohol-fed wt mice RORγt; FIG. 9K illustrates an image of cells from IG alcohol-fed wt mice±anti-IL17A Ab immunostained for α-SMA, Desmin, Ly6G, F4/80, and graphically shows levels of F5/80, desmin and αSMA on right; FIG. 9L-M graphically illustrates levels of various markers in mice therapeutically treated with RORγt inhibitor, or anti-IL17A neutralizing Ab; as described in detail in Example 2, below.

FIG. 10A schematically shows the experiment where naïve mice were subjected to 2BC sessions to determine baseline voluntary ethanol drinking, and mice were treated either with ±anti-IL17A Ab, or ±RORγt inhibitor; FIG. 10B-C graphically illustrates serum levels of alcohol (FIG. 10B) and IL17A (FIG. 10C); FIG. 10D graphically illustrates voluntary alcohol intake as measured during 2BC sessions; FIG. 10E graphically illustrates Air and CIE mice±RORγt inhibitor; as described in detail in Example 2, below.

FIG. 10F graphically illustrates GO terms of the genes upregulated in hepatocytes from IgG- (vs anti-IL17A Ab-) treated mice; FIG. 10G graphically illustrates GO terms of the genes upregulated in hepatocytes from anti-IL17A Ab- (vs IgG-) treated mice; FIG. 10H graphically illustrates representative genes from selected from GO terms enriched in hepatocytes isolated from IgG or anti-IL17A Ab treated mice; FIG. 10I graphically illustrates GO terms of the genes upregulated in Kupffer cells from IgG (vs anti-IL17A Ab-) treated mice; FIG. 10J graphically illustrates GO terms of the genes upregulated in Kupffer cells from anti-IL17A Ab (vs IgG-) treated mice; as described in detail in Example 2, below.

FIG. 11A illustrates images showing the whole brain MRI; FIG. 11B-D illustrate immunostaining images for GFAP in (FIG. 11B) whole brains coronal sections, (FIG. 11C) hippocampus, and (FIG. 11D) amygdala, sagittal sections; FIG. 11E graphically illustrate levels of GFAP in brain samples; FIG. 11F graphically illustrates serum levels of IL17A protein as measured in excessive drinkers with normal ALT and abnormal ALT and healthy individuals, as described in detail in Example 2, below.

FIG. 11G illustrates images of coronal brain sections immunostained for Iba1 and DAPI to visualize microglial cells; FIG. 11H graphically illustrates the percent of $Iba1^{+}$ staining area and FIG. 11I graphically illustrates the number of $Iba1^{+}DAPI^{+}$ cells in hippocampus, as calculated as percent (%) of all $DAPI^{+}$ cells; FIG. 11J graphically illustrates mRNA expression of IL17ARA, and IL-1β were measured from total brain tissue from chow, Pair-fed and IG alcohol-fed±anti-IL17A Ab mice by qRT-PCR; FIG. 11K illustrates images of coronal brain sections immunostained for active Caspase 3 to visualize apoptotic neurons, with Caspase 3 levels graphically shown on right; FIG. 11L graphically illustrates expression of GFAP mRNA was measured using qRT-PCR in frontal cortex, cerebellum, and hippocampus, as described in detail in Example 2, below.

FIG. 12A illustrates images of the expression of IL17A and IL17ARA mRNA as compared in the brains and livers isolated from the same IG alcohol-fed wt mice, with levels graphically illustrated on the right; FIG. 12B graphically illustrates qRT-PCR for expression of IL17ARA, GFAP, TGF-β1, and TNF-α, IL-1β, CCL7, and IL-6 in cortex, hippocampus, and cerebellum from the brains of IG alcohol-fed wt mice; FIG. 12C graphically illustrates mRNA levels of IL17A. IL17A in IG alcohol-fed mice where coronal brain sections were analyzed by RNA in situ hybridization; FIG. 12D graphically illustrates IL17A and other inflammatory cytokine in cerebrospinal fluid (CSF) isolated from IG-alcohol-fed wt mice using ELISA, as described in detail in Example 2, below.

FIG. 13A graphically illustrates the presence of albumin CSF as tested in the CSF using ELISA; FIG. 13B graphically illustrates levels of various markers in pair-fed vs EtOH fed mice; FIG. 13C graphically illustrates IL-17 and IFN-γ levels in brains from IG alcohol-fed and pair-fed mice RORγt inhibitor; FIG. 13D illustrates images of brain and liver cells stained for IL-17 mRNA in pair-fed vs EtOH fed mice; FIG. 13E graphically illustrates levels of various markers in brain CSF pair-fed vs EtOH fed mice, as described in detail in Example 2, below.

FIG. 14A-B graphically illustrates brain CSF (FIG. 14A) and extravasated albumin (FIG. 14B) levels in pair-fed vs EtOH fed mice RORγt inhibitor; FIG. 14C illustrates images of TGF-β- (vs PBS-) stimulated astrocytes in pair-fed vs EtOH fed mice±RORγt inhibitor, as described in detail in Example 2, below.

FIG. 15A graphically illustrates levels of serum cytokines IL17AA, TNF-α and IL-1β, as measured using ELISA in naïve mice prior to exposure to EtOH vapor (or Air), in alcohol-dependent (after CIE) in non-dependent mice (after Air) mice: FIG. 15B graphically illustrates ethanol intake in mice having developed alcohol dependence (CIE) vs non-dependent controls (Air), and therapeutically treated with ±anti-IL17A Ab (vs IgG); FIG. 15C illustrates images of coronal brain sections from Air and CIE mice±anti-IL17A Ab co-stained for GFAP; FIG. 15D illustrates images of the hippocampus stained for various markers; FIG. 15E graphically illustrates GFAP levels in the cortex or hippocampus area, as described in detail in Example 2, below.

FIG. 16A illustrates images of liver sections isolated from Air and CIE mice and analyzed for steatosis (Oil Red O), development of liver fibrosis (Sirius Red). Livers were stained for Desmin and F4/80 to visualize Hepatic Stellate Cells and Kupffer cells, respectively, levels of the markers are also graphically shown below the images; FIG. 16B shows images of coronal brain sections analyzed by RNA in situ hybridization for expression of IL17A mRNA in CIE mice, levels of the markers are also graphically shown in FIG. 16C; FIG. 16D graphically illustrates expression of fibrogenic and inflammatory genes analyzed in total lung tissues from CIE vs Air mice; FIG. 16E graphically illustrates brain tissue dye levels after being perfused with Evans blue dye and analyzed using spectrophotometry; FIG. 16F graphically illustrates levels of expression of IL17ARA and pro-inflammatory cytokines as measured in the total brain tissues using qRT-PCR; FIG. 16G graphically illustrates levels of markers in cerebrospinal fluid (CSF) isolated from naïve mice, and in alcohol-dependent (after CIE) in non-dependent mice (after Air) mice, and after 2BC sessions, as described in detail in Example 2, below.

Like reference symbols in the various drawings indicate like elements.

DETAILED DESCRIPTION

Figure 1:
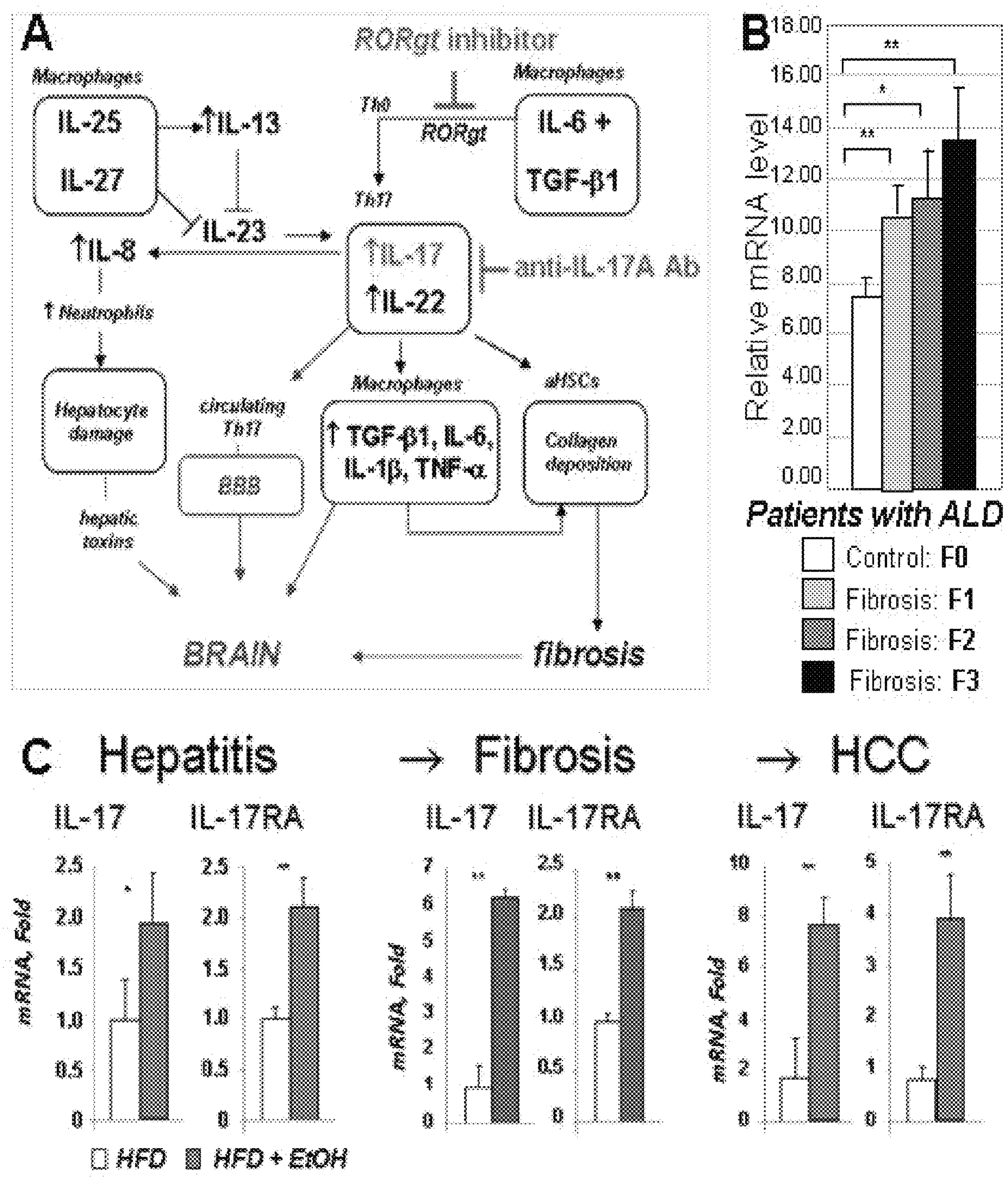
FIG. 1A-C.

In alternative embodiments, provided are compositions, including products of manufacture and kits, and methods, for reducing addiction to alcohol, and for ameliorating, reversing, treating or preventing Alcoholic Liver Disease (ALD), or alcohol-induced brain injury, wherein optionally the alcohol-induced brain injury comprises neuronal death and astrogliosis (reducing alcohol-induced neuronal death and astrogliosis).

We demonstrated that administration of anti-IL-17 blocking antibody (J&J) protects mice from alcohol-induced brain damage (using the art-accepted Tsukamoto-French animal model of intragastric ethanol-feeding) and reduces addiction to alcohol (using the art-accepted addiction animal model: choice of two bottles). Additionally, administration of anti-IL-17 antibody to alcohol-injured mice (using the Tsukamoto-French model) improved brain histology, and in particular, reduced neuronal death and astrogliosis (an abnormal increase in the number of astrocytes due to the destruction of nearby neurons from e.g., CNS trauma, infection, ischemia, stroke, autoimmune responses, and neurodegenerative disease). Two anti-IL-17 blocking reagents (anti-IL-17 Ab (J&J) and RORγt inverse agonists (Visionary Pharmaceuticals)) independently inhibited addiction in mice subjected to "choice of two bottles" experimental model of alcohol addiction.

Alcoholic liver disease (ALD) progresses from steatosis, to steatohepatitis, fibrosis, cirrhosis, and finally hepatocellular carcinoma (HCC)[1-3]. The central nervous system (CNS) is the other major target of alcohol toxicity and degeneration, leading to a range of complications with progressive neurocognitive impairment. Our data shows that genetic deletion or therapeutic inhibition of IL-17 signaling in mice subjected to intragastric alcohol feeding (Tsukamoto-French model) results in inhibition of alcohol-induced liver fibrosis and histological improvement in alcoholic brain injury (reduced astrogliosis). Furthermore, IL-17 inhibition reduces volunteer drinking in alcohol-dependent mice (rodent model of chronic intermittent ethanol vapor inhalation, CIE) when subjected to the sessions of the two-bottle choice (2BC). Accordingly, in alternative embodiments, provided herein are methods for blocking IL-17 signaling for simultaneously reducing alcohol-induced liver and brain injury, and addiction. In alternative embodiments, provided herein are methods comprising the therapeutic inhibition of circulating IL-17, or inhibition of the action of IL-17, to reduce alcohol-induced liver and brain injury, and suppress addiction to alcohol.

Antibodies, Therapeutic and Humanized Antibodies

In alternative embodiments, antibodies used to practice methods as provided herein can be isolated, synthetic or recombinant antibodies that specifically bind to and inhibit an IL-17 or IL-17 receptor, gene or transcript; for example, practicing methods as provided herein can comprise use of a therapeutic monoclonal antibody inhibitory to IL-17 or IL-17 receptor (IL-17R) activity, e.g., where the antibody acts can act as a specific antagonist (is receptor-inhibiting) for IL-17 receptors.

In alternative aspects, an antibody for practicing methods as provided herein can comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. In alternative aspects, an antibody for practicing methods as provided herein includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CHi domains; (ii) a F(ab')2 fragment, a bivalent fragment comprising two Fab fragments linked by a disulfide bridge at the hinge region; (iii) a Fd fragment consisting of the VH and CHi domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N Y (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

In alternative embodiments, methods as provided herein use "humanized" antibodies, including forms of non-human (e.g., murine) antibodies that are chimeric antibodies comprising minimal sequence (e.g., the antigen binding fragment) derived from non-human immunoglobulin. In alternative embodiments, humanized antibodies are human immunoglobulins in which residues from a hypervariable region (HVR) of a recipient (e.g., a human antibody sequence) are replaced by residues from a hypervariable region (HVR) of a non-human species (donor antibody) such as mouse, rat, rabbit or nonhuman primate having the desired specificity, affinity, and capacity. In alternative embodiments, framework region (FR) residues of the human immunoglobulin are replaced by corresponding non-human residues to improve antigen binding affinity.

In alternative embodiments, humanized antibodies may comprise residues that are not found in the recipient antibody or the donor antibody. These modifications may be made to improve antibody affinity or functional activity. In alternative embodiments, the humanized antibody can comprise substantially all of at least one, and typically two, variable domains, in which all or substantially all of the hypervariable regions correspond to those of a non-human immunoglobulin and all or substantially all of Ab framework regions are those of a human immunoglobulin sequence.

In alternative embodiments, a humanized antibody used to practice methods as provided herein can comprise at least a portion of an immunoglobulin constant region (Fc), typically that of or derived from a human immunoglobulin.

However, in alternative embodiments, completely human antibodies also can be used to practice methods as provided herein, including human antibodies comprising amino acid sequence which corresponds to that of an antibody produced by a human. This definition of a human antibody specifically excludes a humanized antibody comprising non-human antigen binding residues.

In alternative embodiments, antibodies used to practice methods as provided herein comprise "affinity matured" antibodies, e.g., antibodies comprising with one or more alterations in one or more hypervariable regions which result in an improvement in the affinity of the antibody for antigen; e.g., IL-17 or IL-17R, compared to a parent antibody which does not possess those alteration(s). In alternative embodiments, antibodies used to practice methods as provided herein are matured antibodies having nanomolar or even picomolar affinities for the target antigen, e.g., IL-17 or IL-17R. Affinity matured antibodies can be produced by procedures known in the art.

Secukinumab, Ixekizumab, Brodalumab

In alternative embodiments, antibodies used to practice methods as provided herein, therapeutic monoclonal antibodies comprising: a fully human monoclonal IgG1κ antibody that targets IL-17A (secukinumab, Cosentyx™ (Novartis Pharma AG)); a humanized IgG4 monoclonal Ab specific for IL-17A (ixekizumab, Eli Lilly & Co.) and a fully human antibody that targets the IL-17 receptor A (brodalumab, Valeant Pharmaceuticals International, Inc.), or a mixture thereof.

In alternative embodiments, for anti-IL-17A ixekizumab, dosaging is about 160 mg; which can be two 80 mg subcutaneous injections at week 0; which can be followed by an 80 mg injection at weeks 2, 4, 6, 8, 10 and 12; which can be followed by 80 mg every 4 weeks thereafter.

In alternative embodiments, for anti-IL-17A receptor brodalumab, dosaging is about 140 mg or 210 mg administered every two weeks, with an extra dose at week one.

In alternative embodiments, for anti-IL-17A secukinumab, patients begin treatment with five booster shots of 300 mg subcutaneous each one taken a week apart, followed by regular injections once a month thereafter for several months or as long as needed.

Antisense Inhibitory Nucleic Acid Molecules

In alternative embodiments, IL-17- or IL-17R-inhibiting, or RORγt-inhibiting, pharmaceutical compositions and formulations methods as provided herein are administered to an individual in need thereof in an amount sufficient to practice methods as provided herein, e.g., for ameliorating, reversing, treating or preventing: Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis).

In alternative embodiments, provided are compositions and methods for, e.g., ameliorating, reversing, treating or preventing: Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis) using an antisense morpholino oligonucleotide (MO), an miRNA, an siRNA and the like.

In alternative embodiments, compositions and methods as provided herein comprise use of an inhibitory nucleic acid molecule or an antisense oligonucleotide inhibitory to expression of an IL-17 or IL-17R, or RORγt gene or transcript. In alternative embodiments, compositions and methods as provided herein comprise use of an inhibitory nucleic acid molecule or antisense oligonucleotide inhibitory to expression of RORγt, or an IL17- and IL-17R, comprising: an RNAi inhibitory nucleic acid molecule, a double-stranded RNA (dsRNA) molecule, a small interfering RNA (siRNA), a microRNA (miRNA) and/or a short hairpin RNA (shRNA), or a ribozyme.

Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol. Appl. Pharmacol. 144:189-197; Antisense Therapeutics, ed. Agrawal (Humana Press, Totowa, N.J., 1996). Antisense oligonucleotides having synthetic DNA backbone analogues can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids.

In alternative embodiments, provided are methods for: (i) inhibiting, negatively affecting or decreasing hereditary microsatellite-stable (MSS) colorectal cancer (CRC) cell survival; (ii) treating, ameliorating, preventing or reversing a hereditary microsatellite-stable (MSS) colorectal cancer (CRC) in an individual in need thereof, comprising administering to the individual in need thereof, or contacting a hereditary microsatellite-stable (MSS) colorectal cancer (CRC) cell with, a compound or composition, e.g., a nucleic acid, capable of inhibiting or decreasing the expression or activity of an IL-17 or IL-17R.

RNA Interference (RNAi)

In alternative embodiments, provided are RNAi inhibitory nucleic acid molecules capable of decreasing or inhibiting expression of one or a set of RORγt, or IL-17 or IL-17R transcripts or proteins, e.g., the transcript (mRNA, message) or isoform or isoforms thereof. In one aspect, the RNAi molecule comprises a double-stranded RNA (dsRNA) molecule. The RNAi molecule can comprise a double-stranded RNA (dsRNA) molecule, e.g., siRNA, miRNA (microRNA) and/or short hairpin RNA (shRNA) molecules.

In alternative aspects, the RNAi is about 11, 12, 13, 14, 15, 16, 17, 18, 19, 20, 21, 22, 23, 24, 25 or more duplex nucleotides in length. While the methods provided herein are not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence.

In one aspect, intracellular introduction of the RNAi (e.g., miRNA or siRNA) is by internalization of a target cell specific ligand bonded to an RNA binding protein comprising an RNAi (e.g., microRNA) is adsorbed. The ligand can be specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, provided are lipid-based formulations for delivering, e.g., introducing nucleic acids used in methods as provided herein, as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Methods for making expression constructs, e.g., vectors or plasmids, from which an inhibitory polynucleotide (e.g., a duplex siRNA) is transcribed are well known and routine. A regulatory region (e.g., promoter, enhancer, silencer, splice donor, acceptor, etc.) can be used to transcribe an RNA strand or RNA strands of an inhibitory polynucleotide from an expression construct. When making a duplex siRNA inhibitory molecule, the sense and antisense strands of the targeted portion of the targeted RES can be transcribed as two separate RNA strands that will anneal together, or as a single RNA strand that will form a hairpin loop and anneal with itself. For example, a construct targeting a portion of a gene, e.g., a RORγt, or an IL-17 or IL-17R coding sequence or transcriptional activation sequence, is inserted between two promoters (e.g., mammalian, viral, human, tissue specific, constitutive or other type of promoter) such that transcription occurs bidirectionally and will result in complementary RNA strands that may subsequently anneal to form an inhibitory siRNA used to practice methods as provided herein.

Alternatively, a targeted portion of a gene, coding sequence, promoter or transcript can be designed as a first and second antisense binding region together on a single expression vector; for example, comprising a first coding region of a targeted gene in sense orientation relative to its controlling promoter, and wherein the second coding region of the gene is in antisense orientation relative to its controlling promoter. If transcription of the sense and antisense coding regions of the targeted portion of the targeted gene occurs from two separate promoters, the result may be two separate RNA strands that may subsequently anneal to form a gene-inhibitory siRNA used to practice methods as provided herein.

In another aspect, transcription of the sense and antisense targeted portion of the targeted gene is controlled by a single promoter, and the resulting transcript will be a single hairpin RNA strand that is self-complementary, i.e., forms a duplex by folding back on itself to create a gene-inhibitory siRNA molecule. In this configuration, a spacer, e.g., of nucleotides, between the sense and antisense coding regions of the targeted portion of the targeted gene can improve the ability of the single strand RNA to form a hairpin loop, wherein the hairpin loop comprises the spacer. In one embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

In alternative embodiment, compositions and methods as provided herein comprise use of ribozymes capable of binding and inhibiting, e.g., decreasing or inhibiting, expression of RORγt, or IL-17 or IL-17R, transcripts or proteins, or an isoform or isoforms thereof.

These ribozymes can inhibit a gene's activity by, e.g., targeting a genomic DNA or an mRNA (a message, a transcript). Strategies for designing ribozymes and selecting a gene-specific antisense sequence for targeting are well described in the scientific and patent literature, and the skilled artisan can design such ribozymes using these reagents. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Small Molecules

In alternative embodiments, small molecules that are RORγt inhibitors are used to practice methods as provided herein; wherein the small molecule inhibitor can be a stereoisomer, enantiomer, salt, hydrate and/or solvate of the RORγt inhibitor.

In alternative embodiments, RORγt inhibitor small molecule compounds used to practice methods as provided herein exist as (comprise) individual respective stereoisomers that are substantially free from another possible stereoisomer. In alternative embodiments, the term "substantially free of other stereoisomers" as used herein means less than about 15%, 20%, 25%, 30%, 35%, 40%, 50% or 55% of other stereoisomers, or less than about 10% of other stereoisomers, or less than about 5% of other stereoisomers, or less than about 2% of other stereoisomers, or less than about 1% or less of other stereoisomers, or less than "X" % of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

In alternative embodiments, compounds used to practice methods as provided herein comprise or are formulated as pharmaceutically acceptable salts. Pharmaceutically acceptable salts of the compounds disclosed herein include suitable acid addition or base salts thereof. In alternative embodiments, compounds used to practice methods as provided herein are formulated as described in Berge et al, *J Pharm Sci*, 66, 1-19 (1977).

In alternative embodiments, compounds used to practice methods as provided herein are formulated as salts that are formed, for example, with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkane-carboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Compounds used to practice methods as provided herein can also encompass salts which are not pharmaceutically acceptable, for example, a salt may still be valuable as an intermediate in a synthetic or analytical process or protocol.

In alternative embodiments, compounds used to practice methods as provided herein comprise any acceptable salt for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Pharmaceutical compositions as disclosed herein can be prepared in accordance with methods well known and routinely practiced in the art. See, e.g., Remington: *The Science and Practice of Pharmacy*, Mack Publishing Co., $20^{th}$ ed., 2000; and *Sustained and Controlled Release Drug Delivery Systems*, J. R. Robinson, ed., Marcel Dekker, Inc., New York, 1978.

In some embodiments, the compounds used to practice methods as provided herein are provided in the form of pharmaceutically acceptable salts comprising an amine that is basic in nature and can react with an inorganic or organic acid to form a pharmaceutically acceptable acid addition salt; e.g., such salts comprise inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids; or optionally such pharmaceutically acceptable salts comprise sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts.

In alternative embodiments, compounds used to practice methods as provided herein, including pharmaceutical compositions and formulations used to practice methods as provided herein, comprise compositions manufactured under "Good manufacturing practice" or GMP, or "current good manufacturing practices" (cGMP), conditions.

In alternative embodiments, formulations and pharmaceutical compositions used to practice methods as provided herein comprise a therapeutically effective dose or efficacious dose of the active ingredient, e.g., one or more compounds used to practice methods as provided herein, e.g., comprising a derivatized form, e.g., a deuterated form, or a stereoisomer, salt, hydrate and/or solvate thereof, which in alternative embodiments is mixed with a pharmaceutically acceptable solvent, carrier or excipient. In alternative embodiments, formulations and pharmaceutical compositions used to practice methods as provided herein comprise a therapeutically effective dose or efficacious dose of an active ingredient, e.g., an inhibitor of RORγt for ameliorating, reversing, treating or preventing: Alcoholic Liver Disease (ALD).

In alternative embodiments, compounds used to practice methods as provided herein can also comprise crystal forms, salts, solvates and hydrates. Thus, these compounds may crystallize with, for example, waters of hydration, or one, a number of, or any fraction thereof of molecules of the mother liquor solvent. The solvates and hydrates of such compounds are included within the scope of this disclosure.

Pharmaceutical Compositions

In alternative embodiments, provided are pharmaceutical compositions and formulations for practicing the methods as provided herein, e.g., methods for ameliorating, reversing, treating or preventing: Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis) in an individual in need thereof.

In alternative embodiments, compositions used to practice the methods as provided herein are formulated with a pharmaceutically acceptable carrier. In alternative embodiments, the pharmaceutical compositions used to practice the methods as provided herein can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents used to practice the methods as provided herein can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions used to practice the methods as provided herein include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations used to practice the methods as provided herein can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, geltabs, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations used to practice the methods as provided herein can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a composition used to practice the methods as provided herein) in admixture with excipients suitable for the manufacture of aqueous suspensions. Such excipients include a suspending agent, such as sodium carboxymethylcellulose, methylcellulose, hydroxypropyl-methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration hydrophobic active agents used to practice the methods as provided herein. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations as provided herein can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing methods provided herein, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing methods provided herein, the pharmaceutical compounds can be delivered by transdermally, by a topical route, formulated as applicator sticks, solutions, suspensions, emulsions, gels, creams, ointments, pastes, jellies, paints, powders, and aerosols.

In practicing methods provided herein, the pharmaceutical compounds can also be delivered as nanoparticles or microspheres for slow release in the body. For example, nanoparticles or microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing methods provided herein, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations used to practice the methods as provided herein can be lyophilized. Provided are a stable lyophilized formulation comprising a composition as provided herein, which can be made by lyophilizing a solution comprising a pharmaceutical as provided herein and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations used to practice the methods as provided herein can be delivered by the use of liposomes or nanoliposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations used to practice the methods as provided herein can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions as provided herein are administered in an amount sufficient to for e.g., treating, ameliorating, preventing or reversing a cancer in an individual in need thereof, facilitating clearance of a senescent cell or cells, or improving longevity in an individual in need thereof. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods as provided herein are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of compositions used to practice the methods as provided herein can be in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods as provided herein can further comprise co-administration with other drugs or pharmaceuticals, e.g., compositions for treating cancer, septic shock, infection, fever, pain and related symptoms or conditions. For example, the methods and/or compositions and formulations as provided herein can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles, Nanolipoparticles and Liposomes

Also provided are nanoparticles, nanolipoparticles, vesicles and liposomal membranes comprising compounds used to practice the methods as provided herein, e.g., to deliver compositions as provided herein (which include RORγt-inhibiting small molecules, or RORγt-inhibiting, or IL17- and IL-17R-inhibiting nucleic acids and polypeptides) to mammalian cells in vivo, in vitro or ex vivo. In alternative embodiments, these compositions are designed to target specific molecules, including biologic molecules, such as polypeptides, including cell surface polypeptides, e.g., for targeting a desired cell type, e.g., a myocyte or heart cell, and endothelial cell, and the like.

Provided are multilayered liposomes comprising compounds used to practice methods as provided herein, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice methods as provided herein.

Liposomes can be made using any method, e.g., as described in Park, et al., U.S. Pat. Pub. No. 20070042031, including method of producing a liposome by encapsulating an active agent (e.g., a RORγt-inhibiting, or an IL17- and IL-17R-inhibiting nucleic acid, small molecule or polypeptide), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice methods as provided herein comprise a substituted ammonium and/or polyanions, e.g., for targeting delivery of a compound (e.g., RORγt-inhibiting, or an IL17- and IL-17R-inhibiting, nucleic acid, small molecule or polypeptide) used to practice methods as provided herein to a desired cell type (e.g., an endothelial cell, a cancer cell, or any tissue in need thereof), as described e.g., in U.S. Pat. Pub. No. 20070110798.

Provided are nanoparticles comprising compounds (e.g., a RORγt-inhibiting, or an IL17- and IL-17R-inhibiting, nucleic acid, small molecule or polypeptide) used to practice methods as provided herein in the form of active agent-containing nanoparticles (e.g., a secondary nanoparticle), as described, e.g., in U.S. Pat. Pub. No. 20070077286. In one embodiment, provided are nanoparticles comprising a fat-soluble active agent used to practice a method as provided herein or a fat-solubilized water-soluble active agent to act with a bivalent or trivalent metal salt.

In one embodiment, solid lipid suspensions can be used to formulate and to deliver compositions used to practice methods as provided herein to mammalian cells in vivo, in vitro or ex vivo, as described, e.g., in U.S. Pat. Pub. No. 20050136121.

Delivery Vehicles

In alternative embodiments, any delivery vehicle can be used to practice the methods as provided herein, e.g., to deliver compositions methods as provided herein (e.g., a RORγt-inhibiting, or an IL17- and IL-17R-inhibiting, nucleic acid, small molecule or polypeptide) to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice a method as provided herein, e.g. as described, e.g., in U.S. Pat. Pub. No. 20040151766.

In one embodiment, a composition used to practice methods as provided herein can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Products of Manufacture and Kits

Provided are products of manufacture and kits for practicing methods as described herein, including for example, the therapeutic RORγt-inhibiting small molecules, or the monoclonal antibodies, as used in methods provided herein or as provided herein.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Exemplary Methods for Treating Alcohol-Induced Disease

This example demonstrates that methods and compositions as provided herein are effective for ameliorating, reversing, treating or preventing Alcoholic Liver Disease (ALD), or alcohol-induced brain injury, wherein optionally the alcohol-induced brain injury comprises neuronal death and astrogliosis or astrocytosis (reducing alcohol-induced neuronal death and astrogliosis).

We have demonstrated that deletion of either IL-17A or receptor IL-17RA in bone marrow (BM)-derived cells decreases liver fibrosis by 50 to 55%, and this effect is mediated via regulation of TGF-β1 production, while deletion of IL-17RA in non-immune liver resident cells decreased liver fibrosis by 25%[25]. IL-17 stimulates Kupffer cells to express cytokines IL-6, IL-1β, TNF-α and TGF-β1 in the alcohol-damaged liver[25]. Increased levels of IL-17 were detected in patients with alcoholic liver fibrosis, and often correlate with a SNP (single nucleotide polymorphism) in Il-17 gene[26]. We also demonstrated that inhibitors of ROR γt effectively block production of IL-17 cytokines and attenuate development of alcohol-induced liver fibrosis and brain damage in mice.

IL-17 and brain injury: In addition to immune cells, microglial and astrocytes express IL-17A[27], while the receptor IL-17RA is widely expressed within the CNS and upregulated under inflammatory conditions[28]. T-helper (Th)-17 cells transmigrate across BBB-ECs, highly express granzyme B, and kill neurons, directly stimulate astrocytes to produce IL-6, and promote BBB permeability via disruption of tight junctions of endothelial cells[28]-30 Alcohol-induced injury of the liver-brain axis. Alcoholic liver disease (ALD) progresses from steatosis, to steatohepatitis, fibrosis, cirrhosis, and finally hepatocellular carcinoma (HCC)[31-33]. The central nervous system (CNS) is the other major target of alcohol toxicity and degeneration, leading to a range of complications with progressive neurocognitive disorders. To-date preclinical studies are designed to study the pathology of a single organ, such as liver or brain, but not both.

IL-17 is a common core mediator of alcohol-induced injury of the liver brain axis. We used complementary mouse models of alcohol-induced liver/brain injury and addiction to assess the role of IL-17 signaling in the liver brain axis.

Mouse models: The intragastric model of chronic alcohol feeding in mice (Tsukamoto-French) recapitulates alcoholic liver fibrosis and mirrors severe alcohol-induced brain damage (similar to that observed in patients with liver cirrhosis and encephalopathy), but does not enable the behavioral study of alcohol addiction in mice. In turn, the rodent model of chronic intermittent ethanol vapor inhalation (CIE) recapitulates physical and motivational signs of dependence, including voluntary drinking escalation (when subjected to the sessions of the two-bottle choice (2BC), compulsive intake and negative affect during withdrawal[34,35] (similar to that observed in alcoholics), but does not cause any damage to the liver. By comparing these two models, which are widely used by hepatologists and behavioral neuroscientists, we can dissect the role of IL-17 signaling in alcohol-induced brain and liver injury and addiction.

Alcoholic Liver Disease (ALD)[36-48] Chronic alcohol consumption directly (via acetaldehyde) or indirectly (via upregulation of cytochrome P4502E1 and intestinal dysbiosis) induces hepatotoxic injury (steatosis, lipid peroxidation, and mitochondrial damage) causing hepatocyte apoptosis and activation of Kupffer cells/macrophage. Activated Kupffer cells release inflammatory (IL-6, IL-1β, TNF-α, IL-17) and fibrogenic (TGF-β1, PDGFO) cytokines and activate hepatic stellate cells (aHSCs) into Collagen Type I producing myofibroblasts[49]. In turn, the loss of detoxifying liver function results in systemic release of hepatotoxins, microbial metabolites, and inflammatory cytokines trafficking across the blood-brain barrier (BBB) that contributes to alcoholic brain injury[50,51].

Alcoholic brain injury. Alcohol is a neurotoxin that directly causes neuronal damage (myelin disruptions, and neural death)[52-61], or via induction of neuroinflammation, activation of microglia (resident brain macrophages), leading to the secretion of IL-1β, TNF-α, IL-6, iNOS, COX-2 that further induce neuronal death and loss of white matter[57,62,63], astrogliosis (compensatory expansion of astrocytes)[64], and the loss of synaptodendritic complexity[65-69]. At the behavioral level, chronic alcohol consumption is associated with alcohol addiction, which is characterized by pathological patterns of alcohol consumption, impulse control and cognitive flexibility resulting from altered activity in the prefrontal cortex (PFC), as well as by negative emotionality regulating from dysregulated activity in the amygdala 70,71.

Functional similarities between cellular populations in liver and brain. HSCs (hepatic stellate cells) in the liver exhibit functional similarities with brain astrocytes, while Kupffer cells and microglia both function as yolk-sac derived resident macrophage of their respective organs[72,73]. Neurons and hepatocytes are the principal cells in their respective organs, but are also the primary targets of alcohol-induced cytotoxicity. The contribution of IL-17 signaling in each cell type to the pathogenesis of alcohol-induced liver/brain injury can be determined by selectively deleting IL-17RA (the main signaling molecule), using conditional Cre-loxP-system in mice[74].

Therapeutic inhibition of IL-17. Autoimmune inflammatory diseases psoriasis and rheumatoid arthritis respond to anti-IL-17 biological therapies[75]. Successful use of other anti-IL-17 antibodies has been reported (ixekizumab, and secukinumab) in clinical trials, while anti-IL-17A Abs SCH-900117 and RG4934 are in early clinical development[75]. In addition to neutralizing Abs, small molecules have been developed to target the IL-17 pathway[76-79]. We have shown that inhibitors of ROR γt effectively block production of IL-17 cytokines and attenuate development of alcohol-induced liver fibrosis and brain damage in mice (see e.g., FIG. 3 and FIG. 4). Existing therapy has been ineffective in treating patients with ALD and alcohol addiction[26,32]. Provided herein is an anti-IL-17 therapy that targets liver-brain axis (see FIG. 1).

Figure 2:
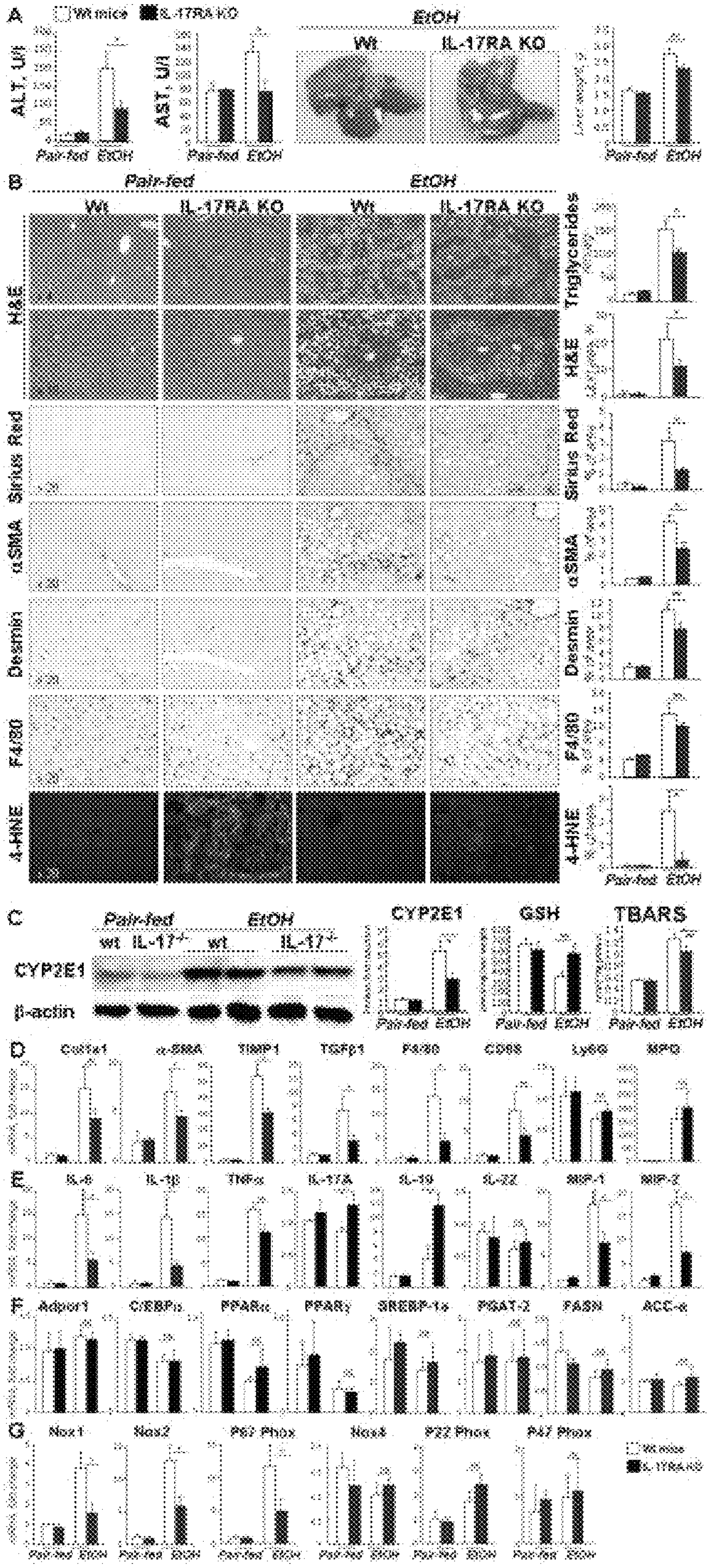
FIG. 2A-G illustrates data showing that alcoholic liver fibrosis is reduced in IL-17RA$^{-/-}$ mice.

We have identified that IL-17 is a critical mediator of alcohol-induced injury in both humans (FIG. 1B) and mice (FIG. 2), and in both liver and brain.

Transgenic technologies: Several transgenic and knockout mice are used to study the crosstalk between alcohol-injured liver and brain. Conditional deletion of IL-17RA in alcohol-fed mice can characterize the tissue-specific role of IL-17 signaling in regulation of the liver-brain axis in alcohol-fed and addicted mice, and determine the mechanism underlying this process. Brain region-specific deletion of IL-17RA can determine the site of action of IL-17 mediating its effects on behavior.

Novel therapeutic approach: Provided herein is a novel approach for the treatment of alcohol-induced liver and brain injury and addiction, where therapeutic inhibition of IL-17 signaling, e.g., by a novel RORγt inhibitor, can attenuate liver fibrosis and astrogliosis in the brain, and reduce the behavioral consequences of chronic alcohol exposure in mice.

Using genetic mouse models, inhibition of IL-17 signaling can be shown to have a therapeutic effect on alcohol-induced liver and brain injury and addiction-related behaviors, and generate preclinical data justifying the role of IL-17 as a therapeutic target.

Therapeutic blocking of Th17 cells. RORγt controls differentiation of Th0 into Th17 cells, and production of all IL-17 cytokines by Th17 and other IL-17-producing cells. Based on our data, therapeutic blocking of IL-17 signaling by a new generation of RORγt inhibitor (VPR-254, Visionary Pharmaceuticals) attenuates development of alcohol-induced liver fibrosis, brain injury and addiction in mice. In alternative embodiments, provided are methods for using RORγt inhibitors in patients with chronic alcoholism for the treatment of chronic alcoholism.

Mechanisms of action: While the invention is not limited by any particular mechanism of action, chronic alcohol consumption in mice activates IL-17 signaling, which has a detrimental effect on the liver-brain axis; and IL-17 signaling regulates the escalated alcohol drinking associated with dependence. Accordingly, provided herein are methods using Th17-blocking antibodies and small molecules to treat patients suffering from alcohol addiction and Alcoholic Liver Disease (ALD).

Alcoholic fibrosis is reduced in IL-17RA$^{-/-}$ mice compared to wt mice: Liver fibrosis was induced in IL-17RA$^{-/-}$ mice and wt C57BL/6 mice (016 w old, n=20/group) using intragastric alcohol-feeding (8 weeks) or pair-fed[47,80,82]. Steatosis was observed in alcohol-fed mice (FIG. 2A). Induction of alcoholic liver fibrosis was strongly attenuate in alcohol-fed IL-17RA$^{-/-}$ mice (vs wt mice) a) Levels of serum ALT and AST (that reflect liver injury) were approximately 50% reduced in alcohol-fed IL-17RA$^{-/-}$ mice (FIG.

2A). b) IL-17RA$^{-/-}$ mice developed less steatosis as shown by H&E, and reduced content of hepatic triglycerides (FIG. 2B). Surprisingly, we did not observe any differences in lipogenic genes Adipor1, C/EBPα, PPARα, PPARγ, CREBP-1, PGAT2, FASN and ACC-α mRNA expression (FIG. 2F), suggesting that IL-17 signaling does not affect de novo lipidogenesis, but rather regulates lipid secretion and/or beta oxidation. c) Hepatic lipid peroxidation was reduced in alcohol-fed IL-17RA$^{-/-}$ mice (as indicated by reduced levels of 4-HNE and TBARS and upregulation of GSH, FIG. 2B-C). In concordance, inhibition of ROS generation (fold reduction ↓1.8 Nox1, ↓1.5 Nox2, ↓2,5 P67Phox) was observed in IL-17RA$^{-/-}$ mice, suggesting that IL-17 might regulate production of phagocytic and non-phagocytic ROS (FIG. 2G). d) Liver fibrosis was reduced in IL-17RA$^{-/-}$ mice, as demonstrated by reduced area of Sirius Red staining (↓3 fold) and downregulation of Col1α1 (↓1.5 fold), α-SMA, TIMP1, and TGFβRI mRNA expression (FIG. 2D). We detected fewer Desmin$^{+}$α-SMA$^{+}$ HSCs (↓2.7 fold) in livers of alcohol-fed IL-17RA$^{-/-}$ mice, compared to wt mice (FIG. 2B). e) Inflammatory response to alcohol was strongly inhibited in IL-17RA$^{-/-}$ mice. Reduced expression of inflammatory cytokines (fold 13 IL-6, ↓2.7 IL-1β, ↓1.5 TNF-α, ↓2 MIP1 and ↓2 MIP2, ↓2.7 F4/80 ↓1.4 CD68 of mRNA) in livers of IL-17RA$^{-/-}$ mice correlated with low numbers of F4/80$^{+}$ and CD68$^{+}$ cells compared to wt mice (FIG. 2B-E). Meanwhile, expression of MPO and Ly6G mRNA was not changed among alcohol-fed wt and IL-17RA−/− mice, suggesting that Kupffer cells/macrophages (but not neutrophils) mediate progression from steatohepatitis to fibrosis at this stage of ALD. Consistently, the mRNA levels of TGF-β1 were reduced (↓2.6 fold) in livers of IL-17RA$^{-/-}$ mice, while IL-10 mRNA was upregulated (↑3 fold, FIG. 2E). Our data suggest that IL-17 regulates ALD by stimulating TGF-β1-producing and inflammatory (M1) Kupffer cells/macrophage, and suppressing IL-10-producing macrophages (M2). Despite the significance of these results, this experiment must be confirmed with a larger number of mice and extended to females.

Therapeutic administration of RORγt inhibitor attenuates development of liver fibrosis in intragastric alcohol-fed mice: Wt mice (♂16 w old, n=10/group, C57BL6 background) were subjected to intragastric alcohol-feeding (8 weeks), and therapeutically treated (with 2 weeks delay) with RORγt inhibitor (VPR-254, 50 mg/kg, i.p, Visionary Pharmaceuticals, San Diego, CA). We observed that liver function was significantly improved (as demonstrated by reduced levels of ALT and AST, FIG. 3A) in RORγt inhibitor-treated mice (vs vehicle-treated mice) and was associated with reduced levels of serum IL-17 and IL-6, and increase of hepatoprotective IL-10 (as shown by ELISA, FIG. 3B). Steatohepatitis, hepatic fibrosis, intrahepatic levels of pro-inflammatory cytokines IL-17, IL-6, IL-1β, TNF-α, and ROS production (Nox1 and Nox2) were strongly suppressed in livers of RORγt inhibitor-treated mice (FIG. 3C-D). Taken together, our data suggest that inhibition of IL-17 signaling by RORγt inhibitor ameliorates alcohol-induced liver injury.

Figure 3:
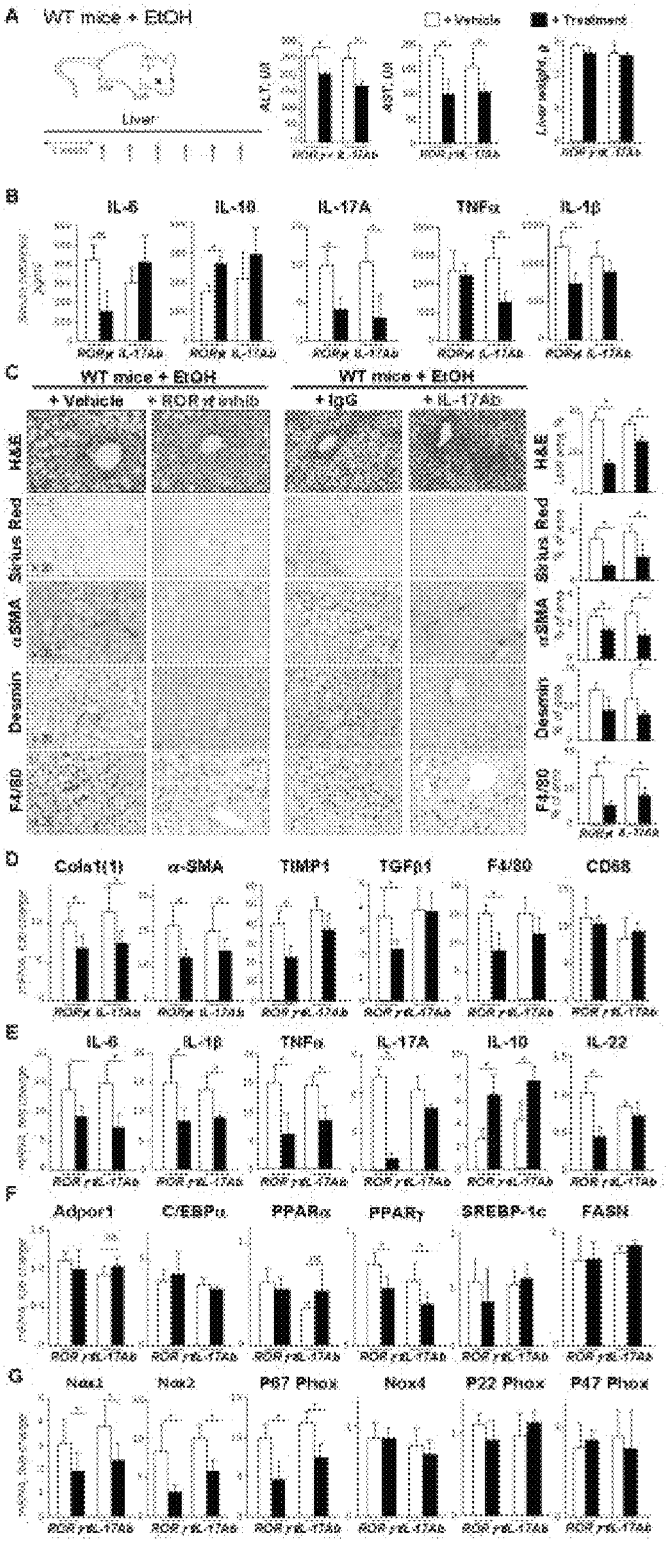
FIG. 3A-G illustrates data showing that the therapeutic blocking of IL-17 using RORγt inhibitor or anti-IL-17 Ab attenuates liver fibrosis in intragastric model of alcohol-feeding in mice, where mice were subjected to alcohol-induced liver fibrosis (8 w) RORγt inhibitor (2 w delay; 50 mg/kg/weight, i.p., 4× week), or vehicle (as schematically illustrated in left image FIG. 3A); or alternatively, alcohol-injured mice were treated±anti-IL-17 Ab (2 w delay; 25 mg/kg/weight, i.p., 1× week) or IgG; all mice were analyzed for: liver function (ALT and AST), as graphically illustrated in the right images of FIG. 3A; serum level of IL-17 and other inflammatory cytokines (ELISA), as graphically illustrated in FIG. 3B.

Therapeutic administration of anti-IL-17 Ab attenuates liver fibrosis in intragastric alcohol-fed mice: Similar results were obtained in a set of independent experiments using anti-IL-17 blocking Ab (J&J), in which wt mice (♂16 w old, n=10) were subjected to intragastric alcohol-feeding (8 weeks), and therapeutically treated (with 2 weeks delay) with anti-IL-17 Ab (25 mg/Kg, i.p., once a week) or isotype-matched IgG (FIG. 3). Similar to RORγt inhibitor treated mice, hepatic steatohepatitis and fibrosis were significantly inhibited in mice treated with anti-IL-17 Ab (vs IgG-treated mice, FIG. 3A-D). Interestingly, attenuation of hepatic steatosis was not associated with de novo lipidogenesis (since expression of lipidogenic genes was not changed, FIG. 3F), and most likely is regulated via lipid secretion or peroxidation. Furthermore, administration of anti-IL-17 Ab successfully depleted serum and hepatic IL-17, and correlated with reduced levels of hepatic IL-1β, TNF-α, and IL-6 and ROS production (FIG. 3A, D, G). We also detected significant upregulation of IL-10 (FIG. 3B, E), indicating that IL-17-producing Th17 cells might suppress production of IL-10 via regulation of M1 vs M2 macrophages. In contrast to RORγt inhibitor, hepatic expression of TGF-1 mRNA was not reduced in IL-17 Ab-treated mice (FIG. 3D), suggesting that depletion of Th17 cells (but not IL-17 cytokine) might regulate TGF-1 production in Kupffer cells.

Therapeutic administration of anti-IL-17 Ab attenuates brain injury in intragastric alcohol-fed mice: Brains were collected from the same alcohol-fed wt mice anti-IL-17 Ab and analyzed. Expression of IL-17RA mRNA was detected in liver, cerebellum, hippocampus, and olfactory regions (microdissected from brains) of alcohol-fed mice, and was not changed between anti-IL-17 Ab- or IgG-treated groups. Histological analysis revealed that activation of Iba1$^{+}$ microglial cells was suppressed in the hippocampus of anti-IL-17 Ab-treated mice (vs IgG-mice), as demonstrated by reduced size and the number of cellular processes (FIG. 4B). Activated caspase 3 was detected along the axons of Purkinje cells in cerebellum of alcohol-fed IgG-treated mice (consistent with development of tremors and ataxia in these mice), but was markedly reduced by anti-IL-17 Ab treatment. Furthermore, increased astrogliosis was detected in the frontal cortex of alcohol-fed IgG-treated mice, as shown by increased GFAP$^{+}$ immunoreactivity (5.3±1.0% positive area compared to 1.0±0.3% in uninjured mice), but was downregulated in anti-IL-17 Ab-treated mice (2.7±1.2%), suggesting that blocking of circulating IL-17 cytokine attenuates neuronal apoptosis and reactive astrogliosis.

Chronic intermittent ethanol (CIE) inhalation causes volumetric loss and astrogliosis in the brain: To test the potential implication of IL-17 signaling in the motivation to drink alcohol, we tested the effect of the anti-IL-17 Ab or RORγt inhibitor in C57BL6 mice subjected to the CIE-2BC model of ethanol dependence, in which chronic intermittent ethanol inhalation (CIE) produces an escalation of voluntary ethanol drinking in limited-access two-bottle choice (2BC) sessions. Mice were subjected to the CIE-2BC paradigm and were intracardially perfused with PBS followed by 4% PFA 3 days following their last 2BC drinking session, which was 10 days after their last passive ethanol vapor exposure. Volumetric analysis by ex vivo MRI indicated the cortex volume was approximately 1.6 fold reduced in dependent (vs non-dependent) mice, but at this time point was not altered by administration of anti-IL-17 Ab (vs IgG) (FIG. 5A-C). In addition, immuno-histochemical analysis of these brains revealed a significant induction of GFAP expression in the cortex of CIE-exposed mice (FIG. 5C). We also observed decrease in the volume of corpus collosum (1.2 fold, which was lessened by treatment with anti-IL-17 Ab (FIG. 5D). MRI volumetric analysis and GFAP staining is used to measure the impact of alcohol dependence on the brain.

Therapeutic administration of anti-IL-17 Ab reduces alcohol drinking in dependent mice: Administration of the anti-IL-17 Ab (25 mg/Kg, i.p., once a week, Monday) significantly decreased alcohol intake in ethanol-dependent (CIE-exposed) mice (compared to IgG-treated CIE mice)

(C57BL6, ♂16 w old, n=7-10/group), as demonstrated by reduced daily alcohol intake in control (FIG. 5C), but had no effect in non-dependent (air-exposed) mice. The maximal inhibition of volunteer alcohol-intake in anti-IL-17 Ab-treated CIE group mice was observed Monday through Wed (in two independent experiments). The lack of therapeutic effect Thu-Fri may be explained by reduced levels of circulating anti-IL-17 Ab.

Therapeutic administration of RORγt inhibitor reduces alcohol drinking in dependent mice: Administration of RORγt (50 mg/kg, i.p., 10 h and 2 h prior to 2BC) significantly decreased alcohol intake by ethanol-dependent (CIE) mice (C57BL6, ♂16 w old, n=7-10/group), as demonstrated by reduced daily alcohol intake in control (FIG. 5E left panel). A preliminary test in females revealed a similar pattern (FIG. 5E right panel). Our data demonstrate that blocking of IL-17 suppresses volunteer alcohol drinking in dependent mice.

Progression of ALD is associated with elevated levels of IL-17[83,84]. Using complementary genetic and pharmacological inhibition of IL-17, the role of IL-17 signaling in the pathogenesis of liver and brain injury are investigated in mice subjected to the intragastric model of alcohol feeding. Activated by chronic alcohol consumption, IL-17 signaling plays a critical role in the pathogenesis of alcoholic liver and brain injury in mice. Inhibition of IL-17 signaling ameliorates alcohol-induced liver and brain injury.

All mice are subjected to chronic intragastric feeding[38]. Mice (♂ and ♀ in C57BL6 background, 16 weeks old, n≥20/sex per experimental group) are first fed ad libitum "Western diet", a solid diet high in cholesterol and saturated fat (HCFD:1% w/w cholesterol, 21% calories from lard, 17% calories from corn oil) for 2 weeks. The mice are then operated for implantation of gastric catheters for intragastric feeding of liquid high fat diet (36% calories from corn oil) plus ethanol or isocaloric dextrose at 60% of daily caloric intake for 8 weeks for males[80,81]. Ethanol dose is increased from 19 to 32 g/kg/day. During 8 w intragastric feeding period, mice continue to consume ad libitum HCFD to match caloric intake.

Genetic deletion of IL-17RA in mice. IL-17RA$^{-/-}$ and wt littermates (♂ and ♀ on C57BL6 background, 16 w old, n≥20/sex/per experimental group) are subjected to intragastric alcohol feeding (8 w) or pair-fed[85] (see "Vertebrate Animals" for details). All mice are sacrificed at the end of the 8$^{th}$ week of intragastric alcohol feeding; serum, livers and brains are collected and analyzed as described in 1.5.4. This experiment is designed to determine if global deletion of IL-17 signaling pathway ameliorates development of alcoholic liver fibrosis and simultaneously attenuates alcohol-induced brain injury in IL-17RA$^{-/-}$ mice (vs wt mice).

Pharmacological inhibition of IL-17-producing cells using RORγt inhibitor. Wt littermates (♂ and ♀, C57BL6, 16 w old, n≥20/sex/group) are subjected to intragastric alcohol feeding, and 2 weeks later are therapeutically treated with RORγt inhibitor (50 mg/kg, i.p., once a week, PV0347 Visionary Pharmaceuticals, San Diego, CA) or vehicle. RORγt inhibitor has been chosen in this study (over anti-IL-17 Abs) due to the following advantages: a) rather than binding one particular IL-17 isoform (as IL-17 antibodies do), RORγt inhibitor will effectively reduce secretion of all IL-17 isoforms (IL-17A, F, B, C, and E)[79]; b) low molecular weight (approximately 350 Da), which leads to fewer toxic side effects[78]. All mice are sacrificed at the end of the 8$^{th}$ week of intragastric alcohol feeding; serum, livers and brains are collected and analyzed as described herein.

Tissue collection: 4 days prior to sacrifice: mice are injected with fresh BrdU (100 mg/Kg, 4 times every 2 h) to visualize proliferating cells[86]. 2 hours prior to sacrifice: blood samples (200 μl/mouse) are collected via tail vein for cytokine and metabolite profiling; mice are transcardiac perfused with Evans Blue (Sigma) to assess the severity of BBB breaching[63]. Some mice are perfused with 4% paraformaldehyde, and fixed livers and brains are analyzed by immunocytochemistry. Some mice are processed for protein and RNA extraction. Specific brain regions (cortex, hippocampus, corpus callosum, and cerebellum) are isolated by microdissection and used for qRT-PCR, Western blotting.

Tissue analysis: Serum is analyzed: a) blood alcohol are measured using Ethanol Colorimetric Assay (BioVision). b) Liver function are assessed by measuring serum ALT, AST (in alcohol vs pair-fed mice). c) serum levels of inflammatory (IL-17A, IL-17F, IL-6, TNFα, IL-1β, IL-10), and fibrogenic (TGFβ1, PDGFβ, CTGF) cytokines, and cytokines promoting Th17 differentiation (IL-6, TGFβ1, IL-23, IL-21, IL-25, IL-27) are measured by ELISA[25]. The correlation between the levels of circulating cytokines and the alcohol-induced liver/brain injury are established. d) serum levels of metabolites are compared, such as hepatotoxins (ammonia, bilirubin, bile acids, ceramides), fatty acid metabolites (acylcarnitines, lysophosphatidyl-cholines, 5-lipoxygenase, 8-lipoxygenase, 15-lipoxygenase products, and branched-chain amino acids), and microbial products (IPA, TMA) (analyzed by Dr. Jain, UCSD metabolomic core facility[87,88]). The correlation between the "metabolite signature" and the alcohol-induced liver/brain injury are established.

Livers: a) Liver fibrosis are evaluated by Hydroxyproline content[89], H&E, Sirius-red staining, immunohistochemistry for myofibroblast markers α-SMA, Desmin[90], and expression of fibrogenic genes (Col1a1, α-SMA, TIMP-1, TGF-βRI and TGF-β1)[25,38] by qRT-PCR. b) Hepatic expression of inflammation related cytokines (IL-6, TNFα, IL-1β, IL-17, IL-22, IFNγ, IL-10, MCP-1, and MIP-1β)[25], and fibrogenic cytokines (TGFβ1, FGF, CTGF) are measured by qRT-PCR[17]. c) Hepatic levels of ROS generating enzymes (Nox1, Nox2, Nox4) are measured[91]. d) Cytochrome P4502E1 (CYP2E1) expression is evaluated using Western blotting. e) Hepatic lipid content (triglycerides) and expression of adipogenic genes (PPARγ, PPARα, Adipor, Adpf1) are measured using qRT-PCR. f) The cellular sources of IL-17 cytokine(s) in alcohol-damaged liver are evaluated by co-staining for IL-17A (IL-17F) and CD45, CD4, CD8, F4/80 (since hepatic cells do not express IL-17)[25].

Brains: a) neuronal apoptosis (specifically, in the prefrontal cortex (PFC), hippocampus and amygdala) are analyzed using co-staining for NeuN/Caspase-3a (or TUNEL). b) Astrogliosis: astrocyte proliferation/activation/reactivity are assessed by co-staining for GFAP$^+$Sox9$^+$ and Ki67 (or BrdU)[61], and estimated by intensity of GFAP staining, size and morphology of GFAP$^+$Sox9$^+$ cells[61]. c) Microglia activation are assessed using immunostaining for markers of Iba1, CD11b, CD68[61] Arginase, and iNOS. In addition, specific brain structures (cortex, hippocampus, cerebellum) are analyzed by qRT-PCR and Western blotting to assess expression levels of TGF-β1, IL-6, IL-1β, IL-17A, IL-17F, IL-10, TNFα. d) BBB permeability are estimated via quantification of extravasated proteins (Evans blue, or biotinylated dextrans, or albumin) which are not present in the normal brain[92]. Brains are also co-stained for CD4 (or CD45) to visualize infiltration with circulating T cells. e) The cellular source(s) of IL-17 cytokine(s) in alcohol-damaged brain are evaluated by co-staining for IL-17A (IL-17F) and GFAP+ astrocytes[93] and Iba1+ microglia[27], for IL-17 and CD4 (CD8) infiltrating T cells[94].

Intragastric alcohol feeding induces liver/brain injury that resembles histological changes associated with severe chronic alcoholic fibrosis and hepatic encephalopathy in patients[95]. We predict that IL-$17RA^{-/-}$ mice (vs wt littermates) are protected from alcohol-induced liver fibrosis. We predict that brain injury is reduced in alcohol-fed IL-$17RA^{-/-}$ mice. By comparing serum metabolites in alcohol- and pair-fed wt mice (♂ and ♀) the "metabolic signature" induced by chronic exposure to alcohol in wt and IL-$17RA^{-/-}$ mice are identified, which may identify novel biomarkers.

Whole body IL-$17RA^{-/-}$ mice are widely used as the gold standard for determination of the IL-17 signaling pathways associated with different pathologies, but deletion of IL-17RA may produce compensatory cytokine dysregulation. Complimentary comparative analysis of the RORγt inhibitor-treated mice and IL-$17RA^{-/-}$ mice (and appropriate control wt mice) is critical for identification of the true IL-17 regulated targets/pathways.

In alternative embodiments, therapeutic administration of RORγt inhibitor to alcohol-fed wt mice (vs vehicle-treated wt mice) results in attenuation of liver and brain injury, and overall improvement of the level of circulating pro-inflammatory cytokines and "metabolite signature".

IL-17 is mainly produced by the bone marrow (BM)-derived CD4 T cells in response to cholestatic liver injury[25]. To determine the source of IL-17 in alcohol-injured mice, the reporter IL-17A-GFP mice (in which all IL-17A-expressing cells are labeled by expression of GFP)[96,97] are subjected to intragastric alcohol feeding, livers and brains are co-stained for CD4, CD8, F4/80, GFAP, Iba1, Thy-1. In alternative embodiments, $CD4^+$ T cells in the liver, and astrocytes, microglia and infiltrating lymphocytes (that penetrate BBB) are the main source of IL-17 cytokines in alcohol-injured liver and brain.

Experimental Methods

Detection of the alcohol blood content is performed using Ethanol Colorimetric Assay kit from BioVision (K620-100), and calculated as absorbance (at 570 nm).

Cell proliferation: 4 days prior to sacrifice, mice are injected with BrdU (5 mg/ml, i.p., 10 ul/g of body weight)[86]; fixed tissue are co-stained with Ki67 and cellular markers (GFAP, Iba1 and NeuN)[86].

Immunostaining is performed on formalin-fixed livers using Abs anti-α-SMA (Abcam), Desmin (Dako), Iba1 (Wako), GFAP (Abcam), Albumin (Biorad), CD31 (BD Bioscience) Caspase-3 (Abcam) and IL-17A (Abcam)[25]. Images are taken with a digital camera mounted on a Zeiss epifluorescence microscope (Zeiss Axio Observer M1) using 10×, 20× or 100× objective lenses, and analyzed by Image J.

Statistical analysis. All data are expressed as means standard deviation (SD). Differences between experimental and control groups are assessed by two-tailed unpaired Student's t-tests using Graph Pad Prism 5.0 (GraphPad Software, San Diego, CA). p-values less than 0.05 are statistically significant.

Determine the cellular targets by which IL-17 regulates alcohol injury in liver and brain. The overall detrimental effect of IL-17 signaling on the alcohol-induced injury in mice are determined in AIM1. In AIM2, the mechanism by which IL-17 signaling regulates alcohol-induced injury in different tissues of the liver (or brain) are investigated. For this purpose, tissue-specific conditional IL-17RA knockout mice[98] are generated and subjected to intragastric alcohol feeding. The tissue specific role of IL-17 signaling in the mediation of crosstalk between alcohol-injured liver and brain are established.

IL-17 signaling in the liver facilitates brain injury, and vice versa. Therefore, conditional deletion of IL-17RA in Kupffer cells (hepatocytes, or HSCs) of alcohol-fed mice will ameliorate development of alcoholic liver fibrosis, and also reduce brain injury. In turn, conditional deletion of IL-17RA in microglial cells (neurons, or astrocytes) will reduce alcohol-induced brain injury, and also attenuate liver fibrosis.

Cellular targets of IL-17 signaling in alcohol-fed mice can be determined using liver and brain tissue-specific conditional IL-17RA-deficient mice (ΔIL-17RA mice). The role of IL-17 signaling can be characterized in tissue-specific responses to alcohol. Specific cells in which IL-17 signaling is most detrimental can be identified for development of alcohol-induced liver and/or brain injury.

Design: a) IL-17RA-floxed mice, in which il-17ra gene is flanked by floxP-Stop-floxP cassette (generated by Dr. Karin)[98], are crossed with tissue-specific Cre-expressing mice to generate conditional deletion of il-17ra gene in specific tissues, ΔIL-17RA mice. Cre-expressing mice are crossed with $Rosa26^{floxP\text{-}Stop\text{-}floxP}$ mice to generate control wt mice in which successful Cre-LoxP recombination are estimated by upregulation of YFP in the targeted tissues. The efficiency of Cre-LoxP recombination are calculated for each strain as a percent of $YFP^+$ cells (vs total cells). b) All tissue-specific ΔIL-17RA and wt mice (♂ and ♀ in C57BL6 background, 16 weeks old, n≥20/sex per experimental group) are subjected to intragastric alcohol feeding (8 w) or pair-fed. Mice are sacrificed at the end of the $8^{th}$ week; serum, livers and brains are collected and analyzed (as described in 1.5.4). The details describing each strain of conditional ΔIL-17RA mice and specificity of tissue analysis are listed below.

The Role of IL-17 Signaling in the Liver:

Deletion of IL-17RA in Kupffer cells. a) Mice:LysozymeM$^{Cre}$ (LyzM$^{Cre}$) mice were shown to efficiently target Kupffer cells in the liver, but also approximately 40% of microglial cells in the brain[99]. To avoid the unwanted Cre-LoxP recombination in microglia, LyzM$^{Cre}$ mice are crossed with IL-17RA-floxed mice, and used as donors for bone marrow transplantation into clodronate-treated lethally irradiated wt mice[100] to generate ΔIL-17RA$^{KC}$-into-wt BM chimeric mice. Control mice are generated by transplantation of the BM from LyzM$^{Cre}$×Rosa26$^{flox\text{-}Stop\text{-}flox\text{-}YFP}$ mice to generate wt$^{KC}$-into-wt mice. ΔIL-17RA$^{KC}$-into-wt and wt$^{KC}$-into-wt mice will recuperate and at age 16 weeks are subjected to intragastric alcohol feeding. b) Tissue analysis: In addition to analysis described in 1.5.4, the following tissue specific analysis are performed: To estimate the severity of inflammation, liver sections are stained for CD45, F4/$80^+$, $CD11b^+$ macrophages and monocytes, $CD11c^+$ dendritic cells (DCs), NK1.$1^+$ cells, and $Lyc6G^+$ and myeloperoxidase$^+$ ($MPO^+$) neutrophils.

Complementary flow cytometry is performed to quantify the numbers of wt and IL-17RA-deficient Kupffer cells, and determine the composition of inflammatory cells in non-parenchymal liver fractions isolated from ΔIL-17RA$^{KC}$ and wt$^{KC}$ mice[25,101]. Wt and IL-17RA-deficient Kupffer cells are sort purified, and subjected to RNA-Seq. By comparing wt and IL-17RA-deficient Kupffer cells, we will identify the major signaling pathways regulated by IL-17. Based on our data, in alternative embodiments, IL-17RA-deficient Kupffer cells produce less IL-6, TGF-β1 and IL-1β1 cytokines compared to wt Kupffer cells. In alternative embodiments, IL-17 signaling suppresses production of hepatoprotective IL-10 in Kupffer cells and prevents their polarization into M2 type phenotype (Arg1, Mgl1, Mrc2, IL-10)[25,102].

Deletion of IL-17RA in Hepatocytes. a) Mice: Albumin$^{Cre}$ mice express Cre specifically in hepatocytes, but not in brain cells[103] Albumin$^{Cre}$ mice are crossed with IL-17RA-floxed mice to generate hepatocyte-specific IL-17RA knockout mice, ΔIL-17RA$^{Hep}$ mice. Development of alcohol-induce liver and brain injury are compared in ΔIL-17RA$^{Hep}$ and wt$^{Hep}$ mice. b) Tissue analysis: Hepatocyte apoptosis, proliferation, and cytokine secretion are investigated in ΔIL-17RA$^{Hep}$ and wt$^{Hep}$ mice. Based on our data, in alternative embodiments, IL-17 signaling regulates hepatic steatosis (FIG. 2B). While deletion of IL-17 signaling in hepatocytes does not change de novo adipogenesis, it may affect 1) fatty β-oxidation[104], or 2) lipid secretion in VLDL[105]. Alcohol-induced oxidative stress are analyzed by measuring thiobarbituric acid-reactive components (TBARS), glutathione (GSH) levels, formation of 3-nitrotyrosine (3-NT), DHE (dihydroethidine), and 4-HNE (4-hydroxynonenal) protein adducts. Expression of liver proteins affected by alcohol, including PPARγ, PPARα, acyl CoA oxidase (AOX), stearoyl CoA desaturase-1 (SCD-1), Bcl XL, pJNK, INK and antioxidant enzymes (catalase, thioredoxin (Trx), SOD-1 and SOD-2), are determined by qRT-PCR and Western blot. The activity of the alcohol metabolizing enzyme CYP2E1 are measured in alcohol-fed ΔIL-17RA$^{Hep}$ and wt$^{Hep}$ mice (vs pair-fed mice) by the rate of oxidation of p-nitrophenol to p-nitrocatechol in isolated hepatic microsomes, and by Western blot for mouse and human CYP2E1 as described[106,107]. We will determine if IL-17 directly regulates CYP2E1 activity and lipogenesis in alcohol-injured hepatocytes. Serum are analyzed for the presence of toxic metabolites. In alternative embodiments, alcohol-induced damage of hepatocytes is reduced in ΔIL-17RA$^{Hep}$ compared wt$^{Hep}$ hepatocytes, and as a result, brain damage (neuronal apoptosis, astrogliosis, and neuroinflammation) is also reduced.

Deletion of IL-17RA in HSCs. a) Mice: Expression of Cre in Lrat$^{Cre}$ mice (gift of Dr. Schwabe)[108] is driven by HSC-specific Lrat promoter[109-111], and is not expressed in the brain. HSC-specific IL-17RA knockout ΔIL-17RA$^{HSCs}$ mice are generated by crossing Lrat$^{Cre}$ mice with IL-17RA-floxed mice. ΔIL-17RA$^{HSCs}$ and wt$^{HSCs}$ mice are subjected to alcohol-induced liver injury (or pair-fed). a) Tissue analysis: In alternative embodiments, IL-17-deficient aHSCs exhibit a defect in activation and Collagen Type I production, and therefore, ΔIL-17RA$^{HSCs}$ mice are protected from alcoholic liver fibrosis. The role of IL-17 signaling in the brain:

Deletion of IL-17RA in microglia. a) Mice: Similar to Kupffer cells, microglia also express CD11b, the F4/80 antigen, the CSF1 receptor (CSF1R, M-CSF receptor), Cx3cr1, and Lysozyme M (LysM)[112]. Cx3cr1$^{Cre}$ mice[113,114] have been shown to selectively target Cx3cr1$^+$ cells resulting in targeting of >99% microglia. To avoid unwanted Cre-loxP recombination in Kupffer cells, Cx3cr1$^{Cre}$ mice are crossed with IL-17-floxed mice and used as donors for BMT into lethally irradiated wt mice to generate ΔIL-17RA$^{Microgla}$ mice. Control mice are generated by transplantation of BM from Cx3cr1$^{Cre}$×Rosa26$^{floxP\text{-}Stop\text{-}floxP}$ mice into clodronate-treated lethally irradiated wt mice[25,100] to generate wt$^{Microgla}$ mice. ΔIL-17RA$^{Microglia}$ and wt$^{Microglia}$ a mice recuperate, and at age 16 weeks are subjected to intragastric model of alcohol feeding. b) Tissue analysis: Here we test if IL-17 signaling in microglia regulates alcohol-mediated neuroinflammation. Expression of Toll-like receptors (TLRs, TLR4 and 2) and nucleotide-binding oligomerization domain (NOD)-like receptors (NLRs)[53-60], shown to be upregulated by microglia in response to increased levels of circulating LPS, and hepatotoxins, increased BBB permeability[52], are compared in alcohol-fed ΔIL-17RA$^{Microglia}$ and wt$^{Microglia}$ mice (vs pair-fed mice). Microglial activation are evaluated by expression of CD68/ED-1 (phagocytic microglia), production of IL-1β, TNF-α, IL-6, iNOS, COX-2, which in turn, can cause neuronal death[71]. In addition, activation of microglia is evaluated by co-staining for Iba-1 (and Glucose transporter-5, GluT5) and MHCII, and components of the inflammasome (IL-1β1, IL-6, Caspase I, and NLRP3). Increased permeabilization of the BBB are assessed by the presence of circulating CD4$^+$ T cells, CD45$^+$CD11b$^+$ monocytes (vs CD45$^-$CD11b$^+$ microglia), and disruption of the tight junction between brain endothelial cells (co-staining for CD31 (PECAMI) and ZO-1, or Occludin, Claudin-5). Finally, microglia produce IL-17 upon injury or stress[27]. Brains from alcohol-fed ΔIL-17RA$^{Microglia}$ and wt$^{Microglia}$ mice are stained for expression of IL-17A, or IL-17F cytokines in Iba-1+ cells. In alternative embodiments, IL-17 signaling in microglia plays a critical role in mediation of neuroinflammation and neurodegenerations[57,64].

Deletion of IL-17RA in neurons. a) Mice: Thy-1$^{Cre}$ mice are chosen in this study to induce deletion of IL-17RA in neurons, since expression of Cre is limited to neurons (and is not induced in Thy-1$^+$ T cells (Jackson Labs, 006143, Expression Data). Thy-1$^{Cre}$ mice are crossed with IL-17RA-floxed mice (or Rosa26$^{floxP\text{-}Stop\text{-}floxP}$ mice) to generate neuron-specific ΔIL-17RA$^{Neuron}$ mice or control wt$^{Neuron}$ mice respectively. Mice are subjected to intragastric alcohol feeding (or pair fed). 4 days prior to sacrifice all mice are injected with BrdU to label proliferating cells. b) Tissue analysis: Brains from the alcohol-fed wt$^{Neuron}$ and ΔIL-17RA$^{Neuron}$ mice (or pair-fed mice) are co-stained with Thy-1, GFAP, Iba-1, (neurons/astrocyte/microglia markers) for the neuronal and microglial density/distribution, and phenotyping of BrdU$^+$ proliferating cells. Neuronal apoptosis are assessed by expression of Caspase 3 (or Tunel staining), increased astrogliosis (co-staining for GFAP$^+$Ki67$^+$SOX9 markers), and loss of axonal proteins (neurofilament light and heavy) in different brain structures are evaluated by immunohistochemistry. Alterations in adult neurogenesis (including cell survival/integration) are assessed by expression of BrdU in NeuN$^+$ cells (marker of mature neurons, 1 month old) and doublecortin and β-Tubulin III (immature Doublecortin-expressing neurons), a microtubule-associated protein found exclusively in developing and immature neurons, specifically in the sub-granular zone (SGZ) of the dentate gyrus of the hippocampus (the primary sites for neurogenesis in the mammalian adult brain)[115]. We will test if alcohol-induced neuronal degeneration caused either by axonal de-myelination[61,116] or damage to the neuronal cell bodies[117] is reduced in ΔIL-17R$^{Neuron}$ mice (vs wt$^{Neuron}$ mice). Alcohol-induced axonal myelination are assessed using staining with Luxol fast blue followed by nuclear counter-staining, and compared in various parts of the brain (prefrontal cortex (PFC), cerebellum, hippocampus). In a different set of experiments, unfixed brain structures from alcohol-fed ΔIL-17RA$^{Neuron}$wt$^{Neuron}$ mice are analyzed by qRT-PCR or Western Blotting for myelin components including 2',3,-cyclic nucleotide 3-phosphodiesterase (CNPase), myelin basic protein (MBP), myelin-associated glycoprotein, calpain and calpastatin (endogenous inhibitor of de-myelination). In alternative embodiments, the number of total neurons and their myelination is preserved in alcohol-fed ΔIL-$17RA^{Neuron}$ mice (vs $wt^{Neuron}$ mice). In parallel, livers from alcohol-fed $wt^{Neuron}$ and ΔIL-$17RA^{Neuron}$ mice are isolated and examined for development of alcohol-induced liver fibrosis.

Deletion of IL-17RA in astrocytes. a) Mice: $GFAP^{Cre}$ mice have been extensively characterized and express Cre in astrocytes but not in HSCs in the liver[108,118] Astrocyte-specific IL-17RA knockout ΔIL-$17RA^{Astro}$ mice mice are generated by crossing $GFAP^{Cre}$ mice with IL-17RA-floxed mice, and compared to $wt^{Astro}$ mice ($GFAP^{Cre}$× $Rosa26^{floxP-Stop-floxP}$ mice). b) Tissue analysis: Development of alcohol-induced astrogliosis are compared in fixed brains isolated from alcohol-fed ΔIL-$17RA^{Astro}$ and $wt^{Astor}$ mice (vs pair-fed mice). Expansion of $GFAP^{+}Sox9^{+}$ astrocytes are analyzed in four major regions of PFC (the prelimbic and infralimbic, medial cortex, anterior cingulate, and the orbitofrontal cortex), implicated in ethanol-related behaviors[119,120], and hippocampus from alcohol-fed $wt^{Astro}$ and ΔIL-$17RA^{Astro}$ mice. Astrocyte density, volume, size, and intensity of GFAP immunostaining (astrocyte activation) in specific regions is compared and quantified. Proliferation of astrocytes is assessed by expression of or BrdU (or Ki-67) in $GFAP^{+}$ astrocytes[86]. Furthermore, astrocytes play a dual role in regulation of alcohol-mediated responses, they serve as a significant source of inflammatory cytokines and bidirectional regulation of neuronal communication[121]. Different brain structures (cortex, cerebellum, hypocampus) are dissected from unfixed brains of alcohol-fed ΔIL-$17RA^{Astro}$ and $wt^{Astro}$ mice, and analyzed for expression of inflammatory cytokines (IL-6, TNF-α, IL-1β) and inflammasome proteins (NALP1 and NALP3) using qRT-PCR and Western blotting, or RNA-Seq. By comparing the gene expression profile in different brain regions of alcohol-fed ΔIL-$17RA^{Astro}$ and $wt^{Astor}$ mice, the major alcohol-induced IL-17 signaling pathways in astrocytes are identified. Next, we will test if IL-17 signaling in astrocytes is involved in modulation of neurotransmission neuronal plasticity via shaping both excitatory and inhibitory synaptic integration, synchrony, and synaptogenesis[122]. Astrocytes detect synaptic activity through the activation of metabotropic glutamate receptors (mGluRs) or ionotropic glutamate receptors (iGuRs: AMPA (GuR5-7), kainate and NMDA receptors), which results in $Ca2^{+}$ influx and release of gliotransmitters (glumatamate, and D-D-serin) by astrocytes, and formation of "tripartite synapses" within the extracellular space surrounding astrocytes. Therefore, expression of mGluR, kainate receptors (KA1/2), NMDA receptors (NR1, NRL) synapsin, and synaptophysis is evaluated in wt and IL-17RA-deficient $GFAP^{+}Sox9^{+}$ astrocytes by immunohistochemistry and qRT-PCR.

In alternative embodiments, deletion of IL-17 signaling in Kupffer (or microglial cells) has a major effect on attenuation of alcohol-induced liver/brain injury due to reduced production of hepatic and circulating inflammatory cytokines, reduced neuroinflammation and BBB permeability[123]. In alternative embodiments, IL-17 is a master regulator of alcohol-induced inflammation.

In alternative embodiments, selective deletion of IL-17 signaling in astrocytes (in ΔIL-$17RA^{Astro}$ mice) will ameliorate alcohol-induced brain injury. In alternative embodiments, deletion of IL-17 signaling in HSCs will attenuate alcohol-induced liver fibrosis in ΔIL-$17RA^{HSCs}$ mice due to reduced fibrogenic activation HSCs.

Global changes in the liver-brain axis are caused by chronic exposure to intragastric alcohol, and tissue-specific deletion of IL-17 signaling can prevent alcohol-induced injury of the liver and brain via suppression of chronic inflammation, and prevention of neuronal and hepatic apoptosis.

If deletion of IL-17 signaling in Kupffer cells (and microglial cells) strongly attenuates alcohol-induced liver/brain injury, the synergistic effect of IL-17 signaling on activation of Kupffer cells+microglia are examined in alcohol-fed ΔIL-$17RA^{KC+Microglia}$ mice, generated by crossing $Cx3cr1^{Cre}$×IL-17-floxed mice (no BMT).

Methods:

Cytochrome P4502E. Expression of CYP2E1 is measured in hepatic microsomes[124] by Western blotting[125]. CYP2E1 activity is measured by the rate of oxidation of p-nitrophenol to p-nitrocatechol[126].

IL-17 signaling contribution to development of alcohol addiction-related behaviors in mice can be determined: AIMs 1-2 will determine the role of IL-17 signaling in histopathology of alcohol-induced liver/brain injury. The role of IL-17 signaling in the development of alcohol addiction is unknown. Based on our preliminary data, pharmacological inhibition of IL-17 (by anti-IL-17 Abs, or RORγt inhibitor) suppresses preferential drinking of alcohol (vs water) in dependent (CIE) mice subjected to sessions of the two-bottle choice (2BC)[127]. Since this model of voluntary drinking does not cause liver injury in mice, this effect can be solely attributed to IL-17 signaling in the brain.

In alternative embodiments, blocking of IL-17 signaling can reduce preferential alcohol drinking in addicted mice. In alternative embodiments, therapeutic administration of RORγt inhibitor can suppress alcohol addiction-related behaviors in mice. In alternative embodiments, IL-17 signaling in specific brain structures (prefrontal cortex (PFC), amygdala, or both) regulates development of alcohol addiction in mice.

Design:

All mice (♂ and ♀ on C57B/6 background, 16 weeks old, n=10/sex per experimental group) are subjected to the CIE-2BC paradigm, in which weeks of 2BC drinking are alternated with weeks of CIE exposure in inhalation chambers[127-129]. Mice are first trained to self-administer ethanol (15% v:v) in 2-h two-bottle choice (2BC) sessions started at the beginning of the dark phase and conducted every week day. Once ethanol intake stabilizes, mice are split into two groups of equivalent baseline drinking that are exposed to either chronic intermittent ethanol (CIE, dependent mice, excessive drinkers) or air (non-dependent mice, moderate drinkers) inhalation. Weeks of CIE consist of 4 cycles of 16-h intoxication/8-h withdrawal (Mon-Fri) followed by 72-h withdrawal (Fri-Mon). Each 16-h period of ethanol vapor exposure is primed with an i.p. injection of ethanol (1.5 g/kg) to initiate intoxication (target blood alcohol level=175-225 mg/dl) and pyrazole (an alcohol dehydrogenase inhibitor, 1 mmol/kg) to normalize ethanol clearance rate between individual mice. Air-exposed mice receive injections of pyrazole only. 2BC is resumed the following Monday and from that point onward, weeks of 2BC are alternated with weeks of CIE. Repeated rounds of CIE increases voluntary consumption of ethanol during 2BC sessions, which is reflected by a higher intake in CIE mice compared to Air mice.

Pharmacological inhibition of IL-17-producing cells using RORγt inhibitor. It can be confirmed that systemic inhibition of Th-17/IL-17 following treatment with RORγt inhibitor attenuates alcohol drinking (and its associated negative effects, such as withdrawal) in CIE-exposed wt mice. Air- and CIE-exposed mice are pre-treated with RORγt inhibitor (50 mg/kg body weight, i.p.) or vehicle 10 and 2 h prior to 2BC sessions (daily, Monday through Friday). In addition, the effect of the RORγt inhibitor on negative affect during withdrawal are assessed in the novelty-suppressed feeding test and bottle-brush test, which provide measures of anxiety-like behavior and irritability in CIE-exposed mice[127].

Tissue analysis: In alternative embodiments, CIE exposure causes morphological changes that are similar but less extensive compared to that observed in intragastric alcohol-fed mice (AIM1). All mice are sacrificed at the end of each experiment, serum, and brains are analyzed as described in 1.5.4. Development of astrogliosis, neuronal apoptosis, activation of microglial cells, increased BBB permeability, and upregulation/suppression of the receptors involved in neurotransmission are evaluated in CIE mice RORγt inhibitor (vs air RORγt inhibitor). Brain regions (cortex, hippocampus and amygdala) are microdissected, and analyzed by qRT-PCR expression of genes associated with alcohol reinforcement (GABA, glutamate, and dopamine, corticotropin-releasing factors CRF and neuropeptide Y), and genes involved in neural function, either generally such as the serotonin receptor 3A (Htr3a) and the rho2 subunit of the GABA C receptor (Gabrr2), or specifically such as the calcium calmodulin kinase 2b (Camk2b), which removes unwanted synapses together with Arc[130], and four-jointed ortholog (Fjx1)[131]. Since the suppressive effect of RORγt inhibitor on alcohol-intake in addicted mice occurs rather rapidly (within 2 h), we hypothesize that inhibition of IL-17 signaling disrupts the circuits responsible for alcohol addiction[132-134]. In particular repeated administration of RORγt inhibitor may prevent the upregulation of Crh and Crhr1 expression in the central amygdala that can be observed 2 weeks into withdrawal from CIE[135].

Genetic deletion of IL-17RA in specific brain regions. Addiction to alcohol is associated with structural and functional changes within specific brain regions including amygdala and prefrontal cortex[136-138]. The role of IL-17 signaling in specific brain regions for reinforcing alcohol drinking in non-dependent and dependent mice are examined in this study using the CIE-2BC paradigm. Targeted deletion of IL-17RA in specific brain regions are achieved using the Cre-loxP system through intracranial bilateral stereotaxic injections of an adeno-associated virus expressing Cre-recombinase (AAV 2-2-Cre-IRES-GFP)[139] (or control virus AAV8-GFP) into the prefrontal cortex (PFC) or amygdala of adult homozygous IL-17RA-floxed mice. Viral vector injections are performed at the end of 2BC baselining and mice will recover 3 weeks to enable viral vector transduction and Cre recombination prior to starting air/CIE exposure. Successful expression of Cre in specific brain regions are visualized by GFP expression, quantified, and normalized per mouse/phenotype/experimental group. The assessment of alcohol intake (ethanol intake (g/kg) during each test period is analyzed using ANOVA, with group (EtOH or control) as a between-subjects factor and day (1-5) as a repeated measure[128]), Deletion of IL-17 signaling in amygdala: IL-17RA-floxed mice (♂ and ♀ mice, C57BL6, 16 weeks old, n≥20/sex per experimental group) are subjected to intracranial injections to amygdala with AAV 2-2 with constructed Cre-IRES-GFP or GFP only vector[139]. The resulting ΔIL-17RA$^{Amigdala}$ and wt$^{Amigdala}$ mice are analyzed. In alternative embodiments, development of dependence to alcohol in wt$^{Amigdala}$ mice is associated with increased expression/activity of corticotrophin releasing factor (CRF) and decreased NPY, which is suppressed in ΔIL-17RA$^{Amigdala}$ mice. The type 1 CRF receptor (CRF-1) is found mainly in the pituitary, amygdala, bed nucleus of the stria terminalis (BNST) and is generally associated with increases in anxiety-like behavior[140]. Therefore, the negative affect during withdrawal are assessed in dependent (vs non-dependent) ΔIL-17RA$^{Amigdala}$ and wt$^{Amigdala}$ mice using the novelty-suppressed feeding test and bottle-brush test, which provides measures of anxiety-like behavior and irritability in CIE-exposed C57BL6 mice[128].

Deletion of IL-17 in prefrontal cortex (PFC): IL-17RA-floxed mice (♂ and ♀ in C57BL6 background, 16 w old, n≥20/sex per experimental group) are subjected to intracranial injections to prefrontal cortex with AAV 2-2 with constructed Cre-IRES-GFP or GFP only vectors[139]. The resulting ΔIL-17RA$^{PFC}$ and wt$^{PFC}$ mice are analyzed, as described above.

In alternative embodiments, circulating levels of IL-17 cytokine(s) are upregulated in response to chronic exposure to alcohol vapor in dependent (CIE) mice. In alternative embodiments, therapeutic administration of RORγt inhibitor (vs vehicle) will reduce alcohol consumption in dependent wt mice (vs). In alternative embodiments, inhibition of IL-17 signaling reduces astrogliosis, neuronal apoptosis, and release of GABA, glutamate, and dopamine, CRF.

In alternative embodiments, deletion of IL-17 signaling in dependent ΔIL-17RA$^{Amigdala}$ will suppress volunteer alcohol drinking (vs non-dependent wt$^{Amigdala}$ mice), similar to that observed in RORγt inhibitor-treated dependent CIE-wt mice. In alternative embodiments, alcohol consumption is reduced in dependent CIE-ΔIL-17RA$^{PFC}$ and wt$^{PFC}$ mice.

IL-17 signaling might be involved in development of alcohol dependence in CIE mice. Therefore, ΔIL-17RA$^{H/EA}$ and ΔIL-17RA$^{PFC}$ mice might be less susceptible to chronic exposure to alcohol vapor (compared to wt$^{H/EA}$ and wt$^{PFC}$ mice). NPY specific inhibitor or agonist can be used to prove this concept.

To determine the role of IL-17 signaling in both amigdala and prefrontal cortex (PFC), IL-17-floxed mice are crossed with Emx1-Cre mice (Jackson Labs, 005628), which express Cre in both PFC and amygdala. Resulting ΔIL-17RA$^{PFC/Amigdala}$ and WP$^{FC/Amigdala}$ mice are subjected to 2BC, volunteer alcohol drinking in CIE (vs air) mice are compared. Upon successful completion of AIM3, the evaluation of the tissue-specific effects of IL-17 signaling in the pathogenesis of alcohol addiction in mice can be pursued. For this purpose, ΔIL-7RA$^{Glia}$, ΔIL-17RA$^{Neuron}$, and ΔIL-17RA$^{Astro}$ mice (and wt littermates) generated in AIM2 are instrumental in determining the role of microglial cells, neurons, and astrocytes in the pathogenesis of CIE-induced dependence in mice.

Methods:

Intracranial injections: IL-17RA-floxed mice are injected with AAV2-2-Cre and control viruses (titer of $0.5\times10^{12}$ TU/ml) using Hamilton syringe attached to a fine glass pipette mounted on a stereotaxic device for injection. For the prefrontal cortex model, both left and right sensorimotor cortex are injected with 200 nl of virus (+0.1, +0.6, and +1.1 mm posterior to the bregma; +/−1.0 and +/−1.4 mm lateral (left and right), −0.7 mm deep)[141]. For amygdala injections, bi-lateral injections of 50 nl are performed at the following coordinates (−1.4 mm anterior to bregma +/−3.5 mm lateral, −5 mm deep[141].

Example 2: Blockade of IL-17A Reverses Alcohol-Induced Liver Damage, Brain Damage, and Excessive Alcohol Drinking in Mice This example demonstrates that methods and compositions as provided herein are effective for ameliorating, reversing, treating or preventing Alcoholic Liver Disease (ALD), or alcohol-induced brain injury.

Here we used models of ALD, and excessive drinking in alcohol-dependent mice to investigate the role of IL17 signaling. Chronic high doses of alcohol raised the levels of IL17A in mice, reproducing the findings in patients. Of greater importance, genetic and pharmacological inhibition of IL17 demonstrated that IL17 signaling critically facilitates progression of ALD, alcohol-induced brain injury, and escalation of alcohol drinking in mice.

Here we compared experimental models of alcoholic liver disease (ALD) and alcohol dependence in mice, and demonstrated that genetic ablation of IL17 Receptor ($IL17RA^{-/-}$), or pharmacological blockade of IL17 signaling effectively suppressed the increased voluntary alcohol drinking in alcohol-dependent mice, and significantly reversed alcohol-induced hepatocellular and neurological damage. Our data demonstrated that IL17A is a critical common mediator of excessive alcohol consumption and alcohol-induced liver/brain injury, and targeting IL17A provides a novel strategy for treatment of alcohol-induced pathology.

Results:

ALD Progression in Mice is Associated with Activation of IL17 Signaling

Wt mice subjected to three experimental models of alcohol-induced liver injury: a) acute alcoholic steatohepatitis (ASH) (10 days, ethanol Lieber-DeCarlie diet+single alcohol binge)[19]; b) chronic ASH (8 weeks, ethanol Lieber-DeCarlie diet+weekly binges)[20]; and c) liver fibrosis in intragastric (IG) alcohol-fed mice (8 weeks, ad libitum high cholesterol/saturated fat diet+alcohol infusion+binges)[21] (see Suppl. Methods, below). Alcohol-induced liver injury was assessed by grading hepatic steatosis, inflammation, and fibrosis (see FIG. 6A). These models closely recapitulated the stages of ALD in patients, and were used in this study to investigate the role of IL17 signaling in ALD progression. We determined that hepatic expression of IL17A and IL17RA mRNA were progressively increased in mice with acute (↑2 fold) or chronic (↑3 fold) steatohepatitis, and alcoholic liver fibrosis (↑3-6 fold, compared to the corresponding pair-fed controls (FIG. 6B), suggesting that activation of IL17 signaling correlates with the severity of alcohol-induced liver injury in mice.

IL17 Signaling was Progressively Induced in Patients with ALD

Figures 6C, 6D:
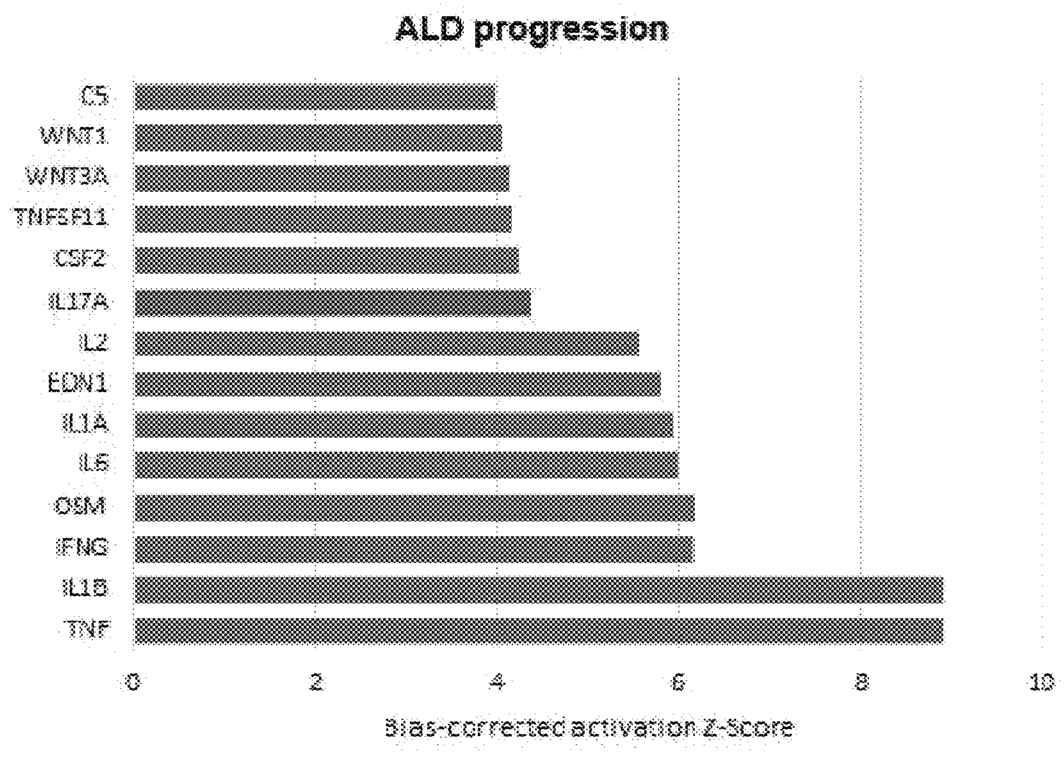
FIG. 6C-F illustrate that IL17 signaling was progressively induced in patients with ALD.

Archived liver biopsies from patients with an early and severe steatohepatitis (ASH), and alcoholic liver fibrosis were using RNA-Seq (FIG. 6C). Gene expression profiling revealed that progression of severe ASH to alcoholic liver fibrosis was associated with increasing activation of hepatic L17A cytokine, suppression of IL-10, and correlated with upregulation of hepatic IL-6, TNF-α, IL-1β mRNA (compared to healthy controls, (FIG. 6C-F). These cytokines are used throughout this study to evaluate alcohol-induced injury and inflammation.

Development of Acute Alcoholic Steatohepatitis is not Attenuated in $IL17ra^{-/-}$ Mice Next, the contribution of IL17 signaling to experimental models of ALD progression was further investigated using wt and $IL17ra^{-/-}$ mice. Hence, both wt and $IL17ra^{-/-}$ mice displayed similar symptoms of acute alcoholic steatohepatitis and liver injury (ALT 110±40 IU/L vs 104±36 IU/L, see FIG. 6G-H, suggesting that IL17 minimally contributes to the onset of ALD in mice.

Development of chronic alcoholic steatohepatitis is partially attenuated in $IL17ra^{-/-}$ mice. When wt and $IL17ra^{-/-}$ mice were compared, hepatocellular injury, lipid peroxidation, and expression of CYP2E1 and NOX4 were markedly reduced in $IL17ra^{-/-}$ mice, see FIGS. 7A-D, and correlated with reduced (↓2 fold) expression of hepatic IL-8, MIP-1, and IL-6, and upregulation of IL-10 mRNA (↑3 fold, see FIGS. 7E-H), suggesting that IL17 signaling facilitates hepatocellular damage, and negatively regulates IL-10 production.

$IL17ra^{-/-}$ Mice are Largely Protected from Alcohol-Induced Liver Fibrosis

Figure 7A:
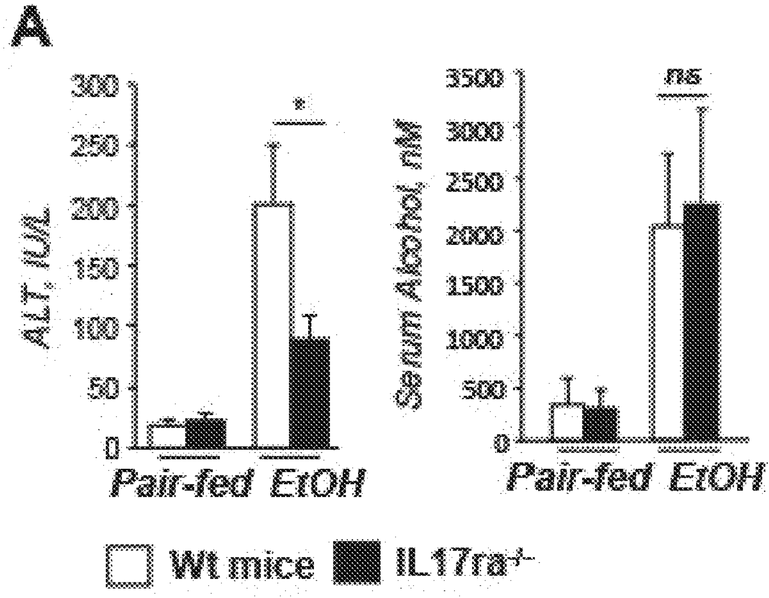
FIG. 7A-D illustrate that IL17RA$^{-/-}$ mice are protected from alcoholic liver fibrosis: where Wt and IL17ra$^{-/-}$ littermates were IG alcohol fed, and FIG. 7A graphically illustrates serum levels of ALT (IU/L) and EtOH (nM)
Figure 8A:
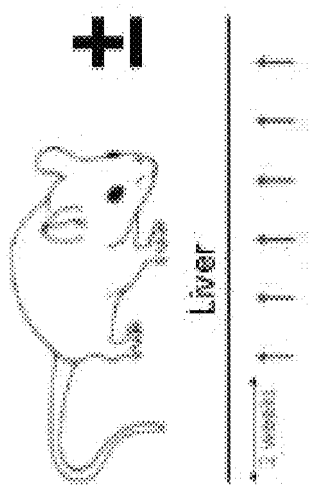
FIG. 8A-H illustrates that therapeutic blockade of IL17A reduces alcoholic liver fibrosis by approximately 50%.
Figure 8B:
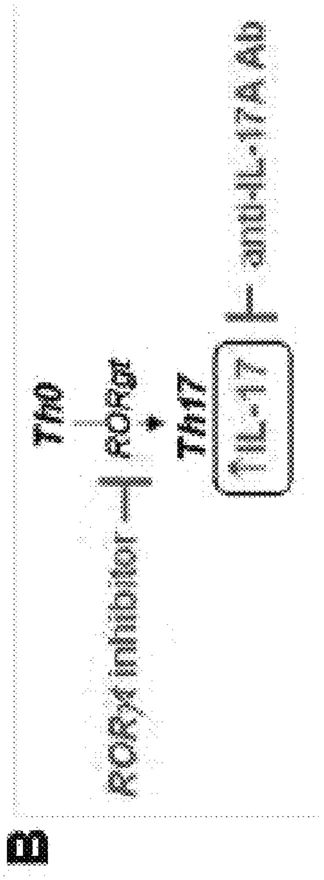
Figure 8C:
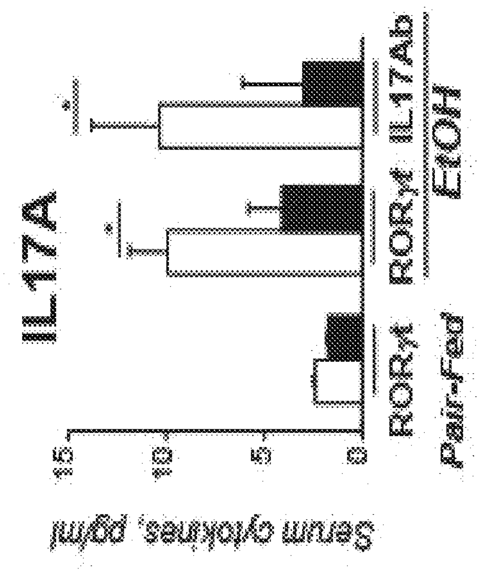
Figure 8D:
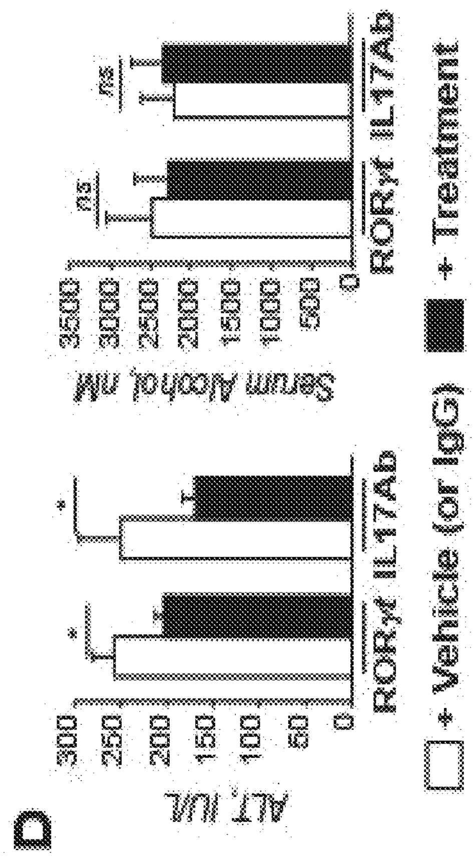
Figures 8E, 8F:
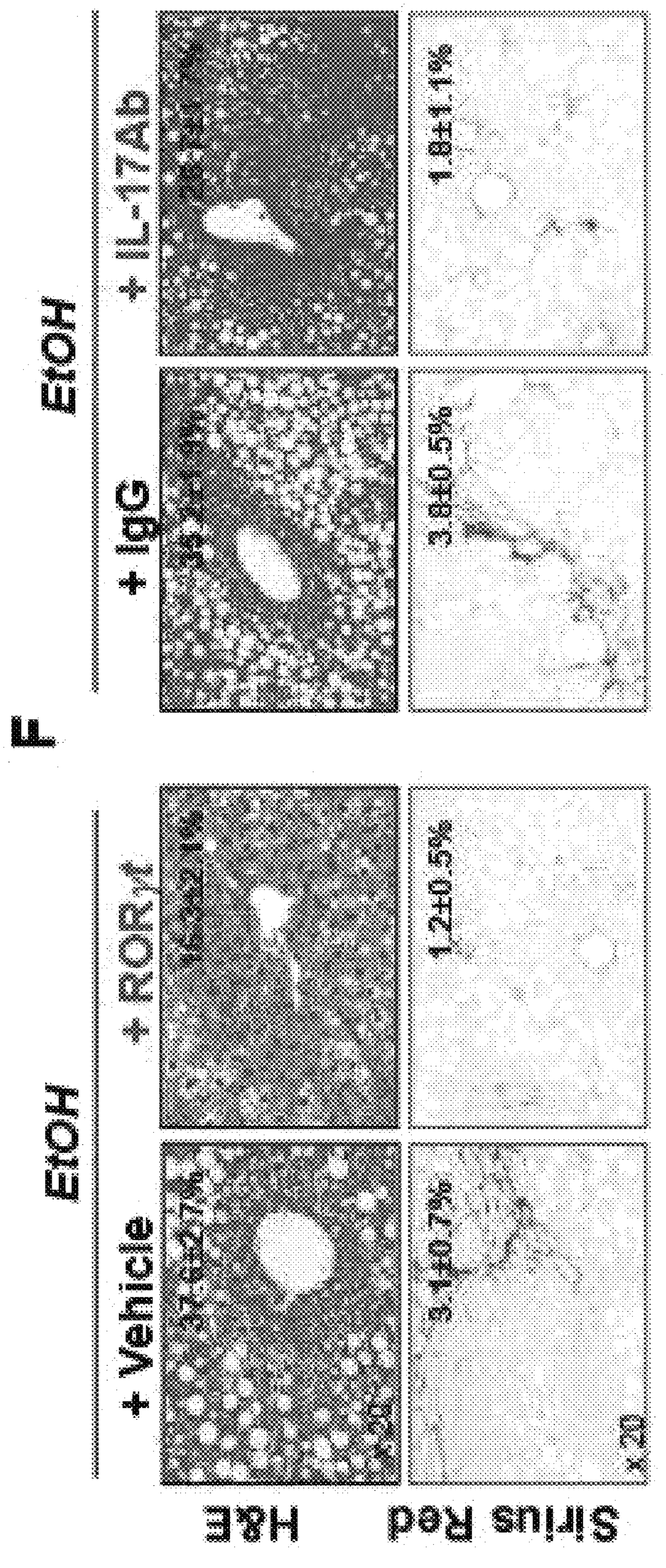
Figure 8G:
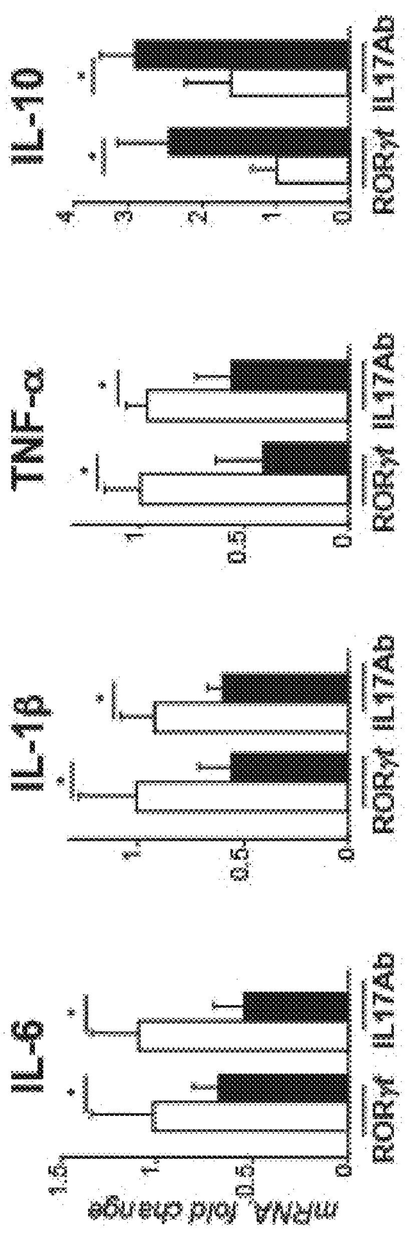
Figure 8H:
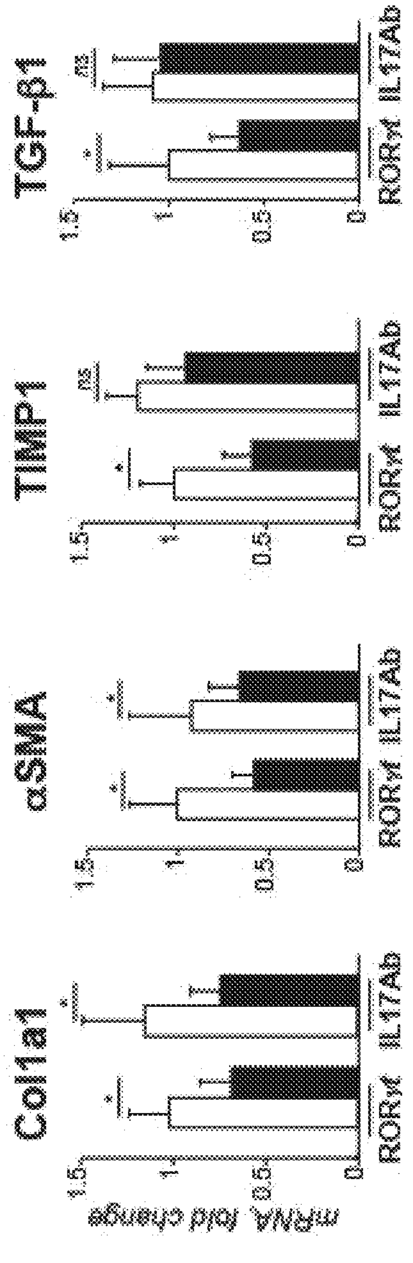
Figure 8I:
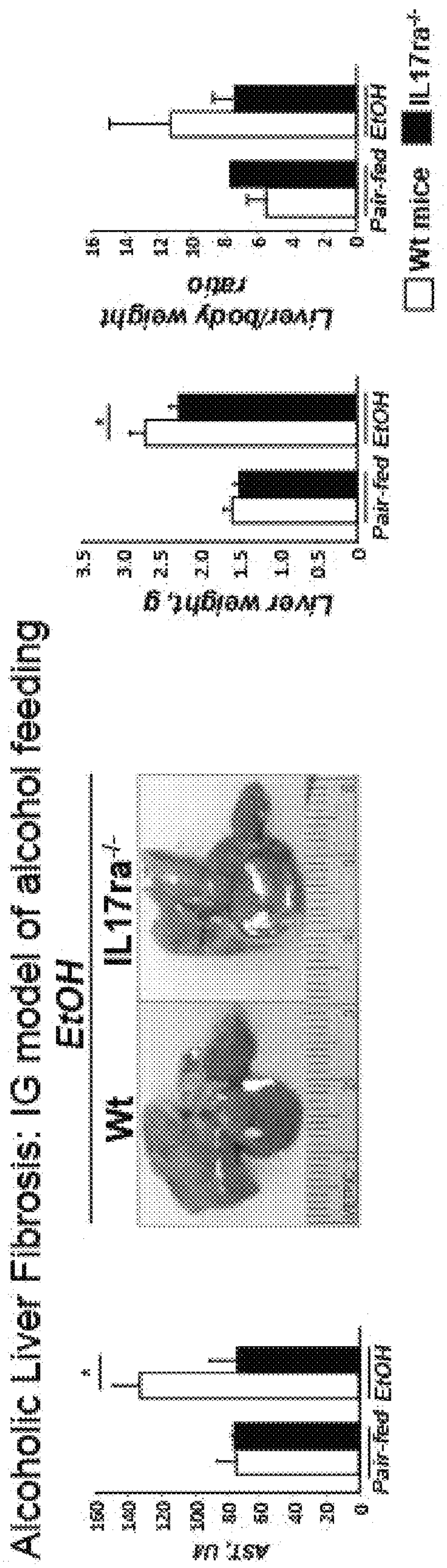
FIG. 8I-P illustrate an experimental model of alcoholic liver fibrosis in wt mice.

Liver injury, hepatic steatosis, triglyceride synthesis, lipid peroxidation (↓6 fold), and oxidative stress (↓2 NOX½ fold) were also strongly suppressed in $IL17ra^{-/-}$ mice (FIG. 7A, FIG. 8I). Furthermore, $IL17ra^{-/-}$ mice were protected from alcohol-induced liver fibrosis, as shown by reduction of fibrous scar (↓3 fold Sirius Red stained area), and downregulation of fibrogenic (Colla1, α-SMA, Timp1, FIGS. 8B-F), and inflammatory gene expression (IL-6, IL-1β, TNF-α, FIG. 7D, Suppl. FIGS. 8G-H). Overall, IL17 signaling appears to regulate progression of alcoholic steatohepatitis to fibrosis, and inhibition of IL17A might be beneficial for patients with advanced stages of ALD.

Therapeutic Blockade of IL17 Signaling Reverses Alcohol-Induced Liver Fibrosis:

The effect of IL17A blockade on development of alcohol-induced liver fibrosis was tested in IG alcohol-fed wt mice therapeutically (after 10 days delay) treated, either with anti-IL17A Ab (that blocks IL17A protein vs IgG)[22] or RORγt inhibitor (that prevents differentiation of Th17 cells, vs vehicle, FIG. 8A-B)[23].

Figures 9A, 9B:
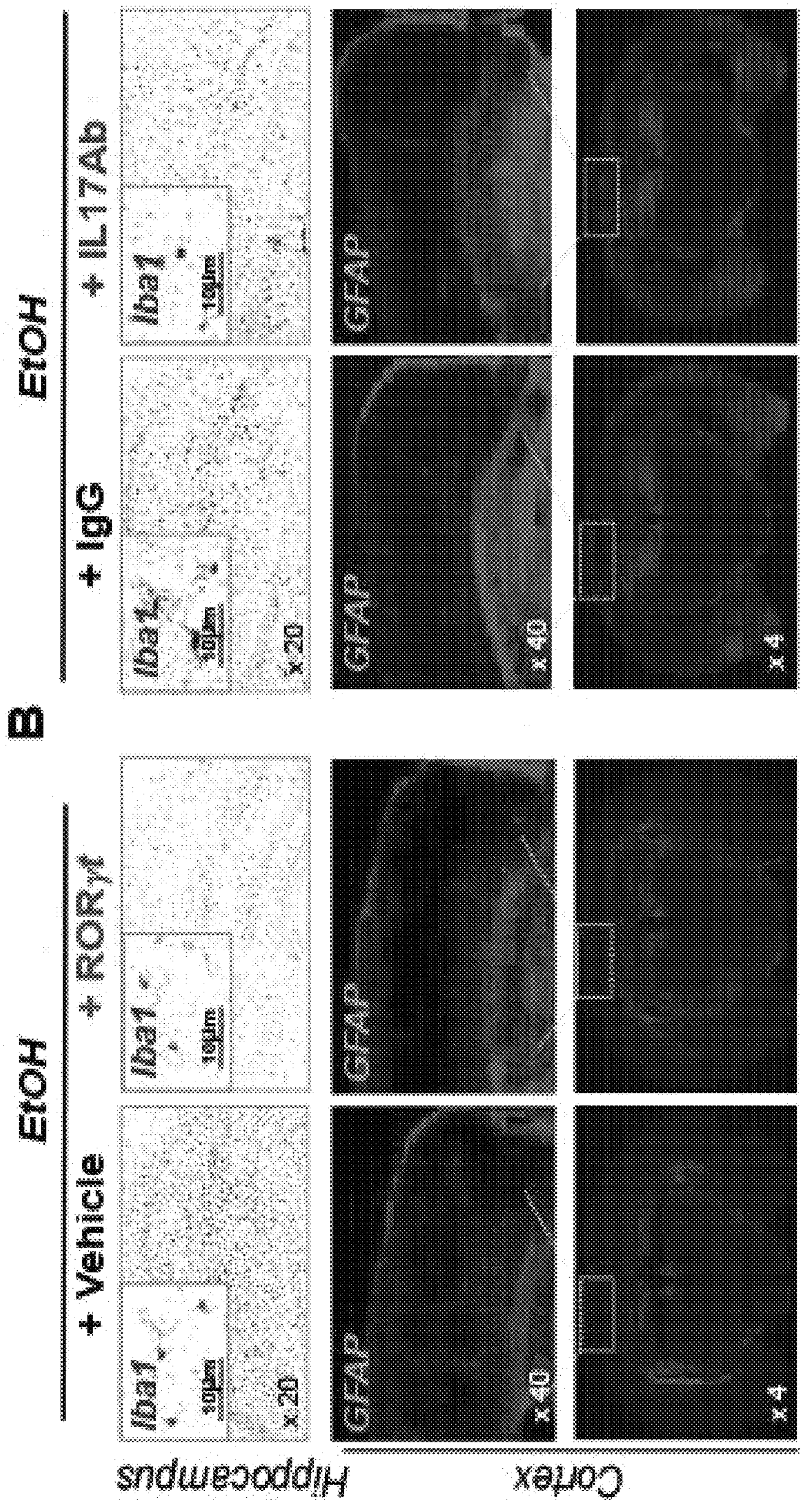
FIG. 9A-E illustrate data showing that systemic and therapeutic IL17A blockade ameliorates astrogliosis in the brains of IG alcohol-fed mice and alcohol-induced brain injury and neuroinflammation.
Figure 9D:
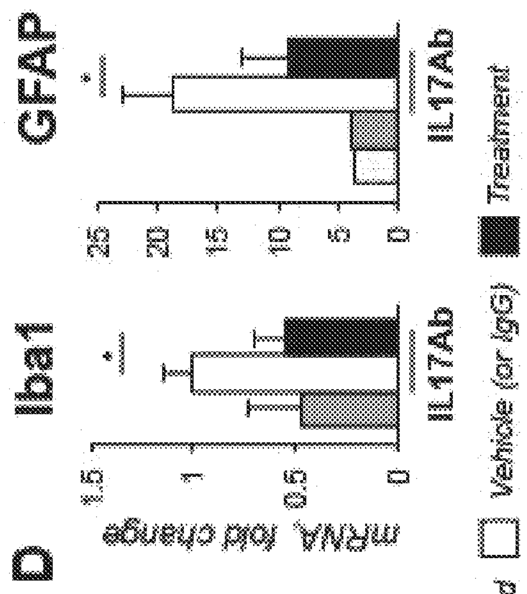
Figure 9C:
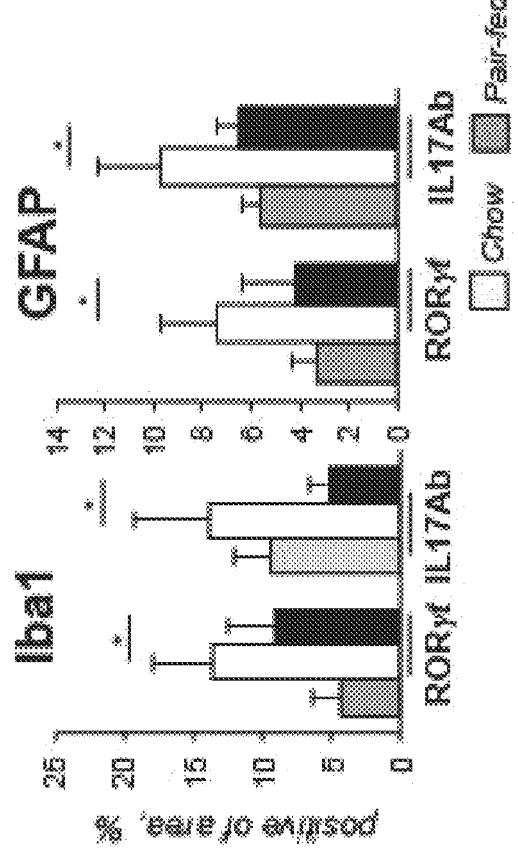
Figure 9E:
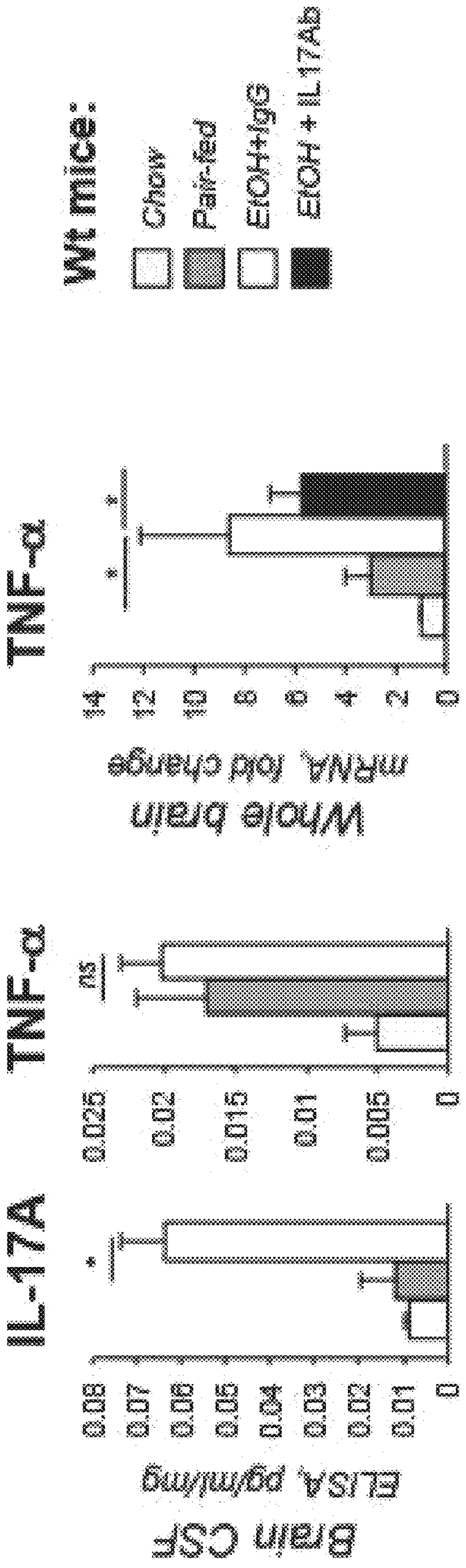
Figure 9F:
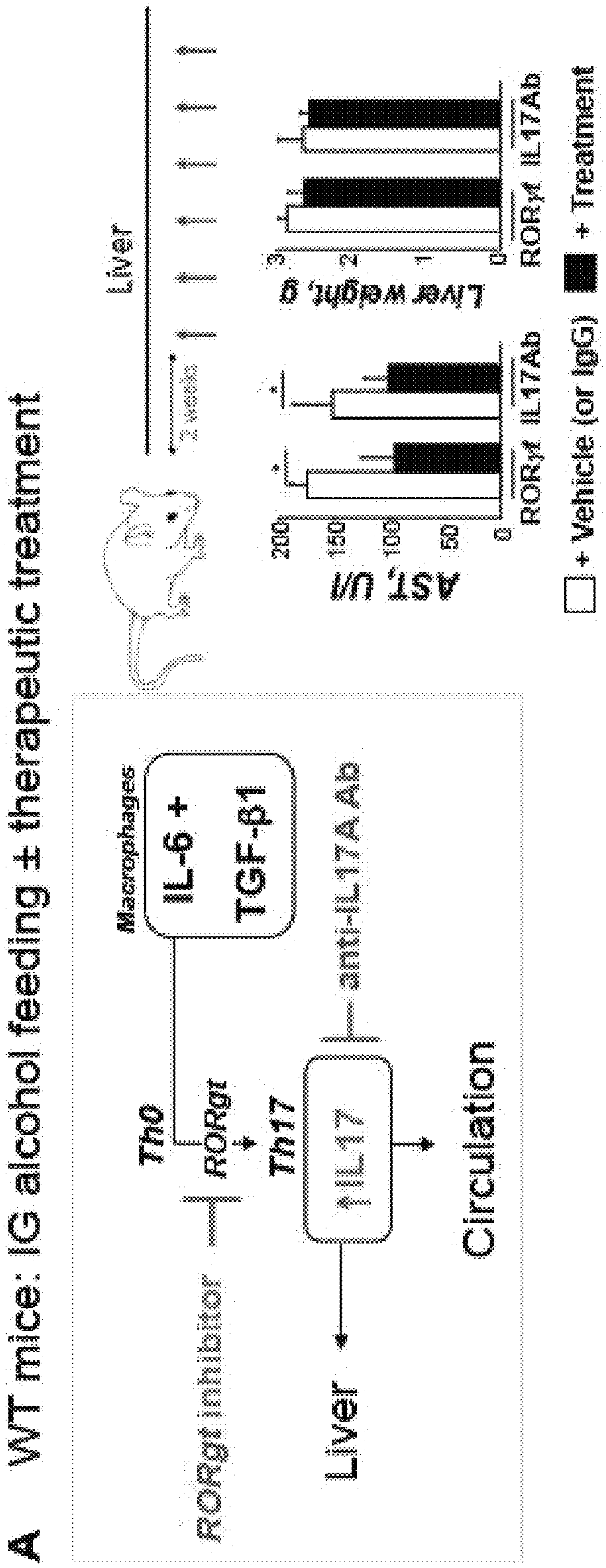
FIG. 9F-M illustrates that the therapeutic blocking of IL17A reduces alcoholic liver fibrosis.
Figure 9G:
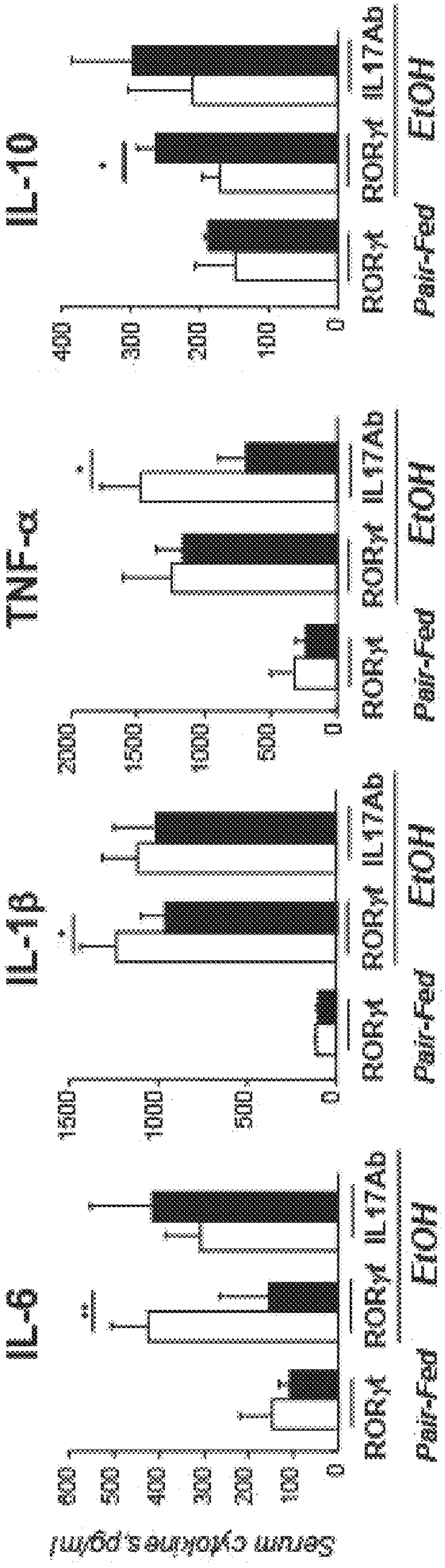
Figure 9H:
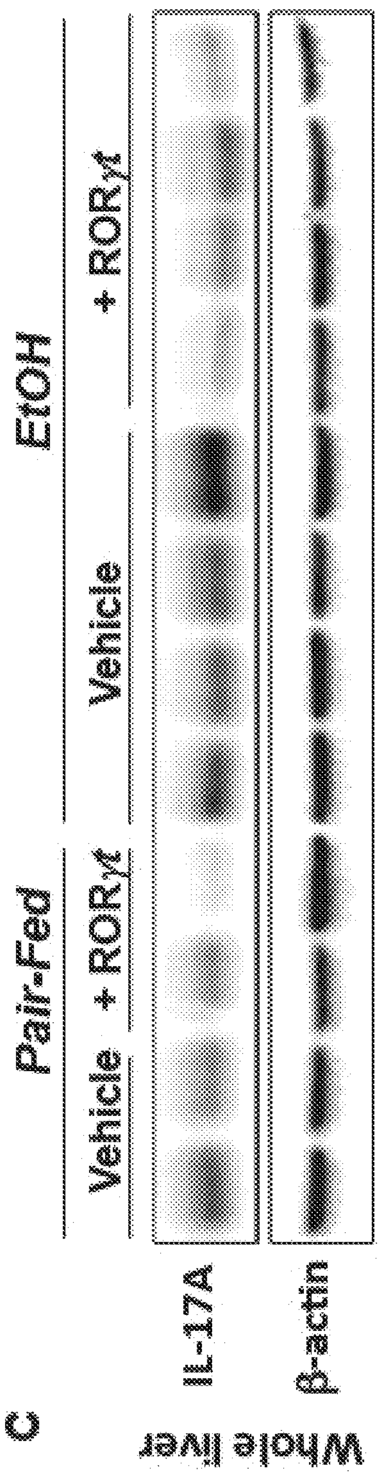
Figure 9I:
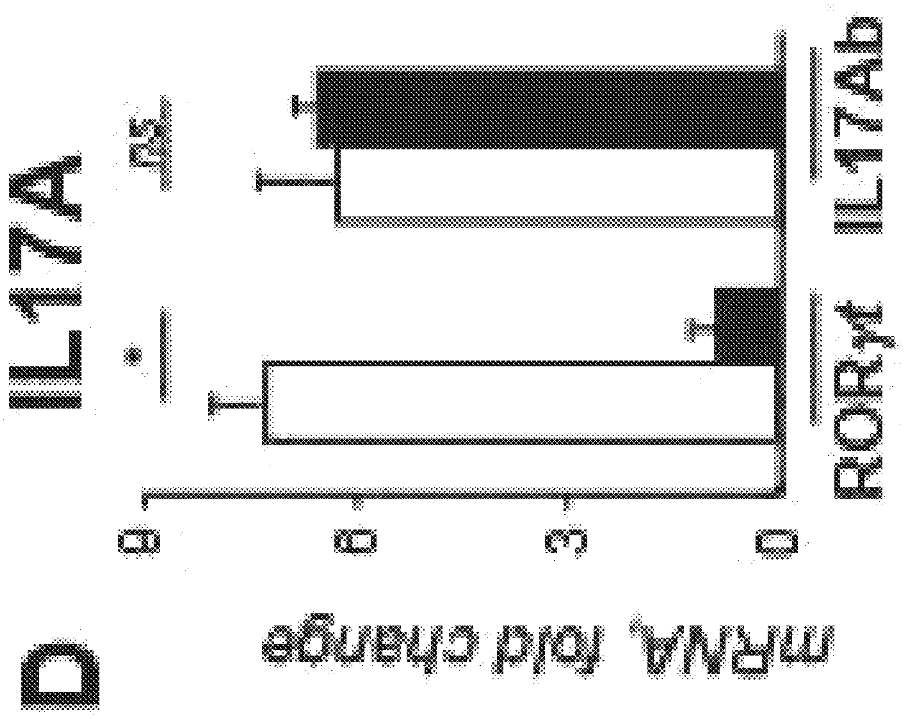
Figures 9J, 9K:
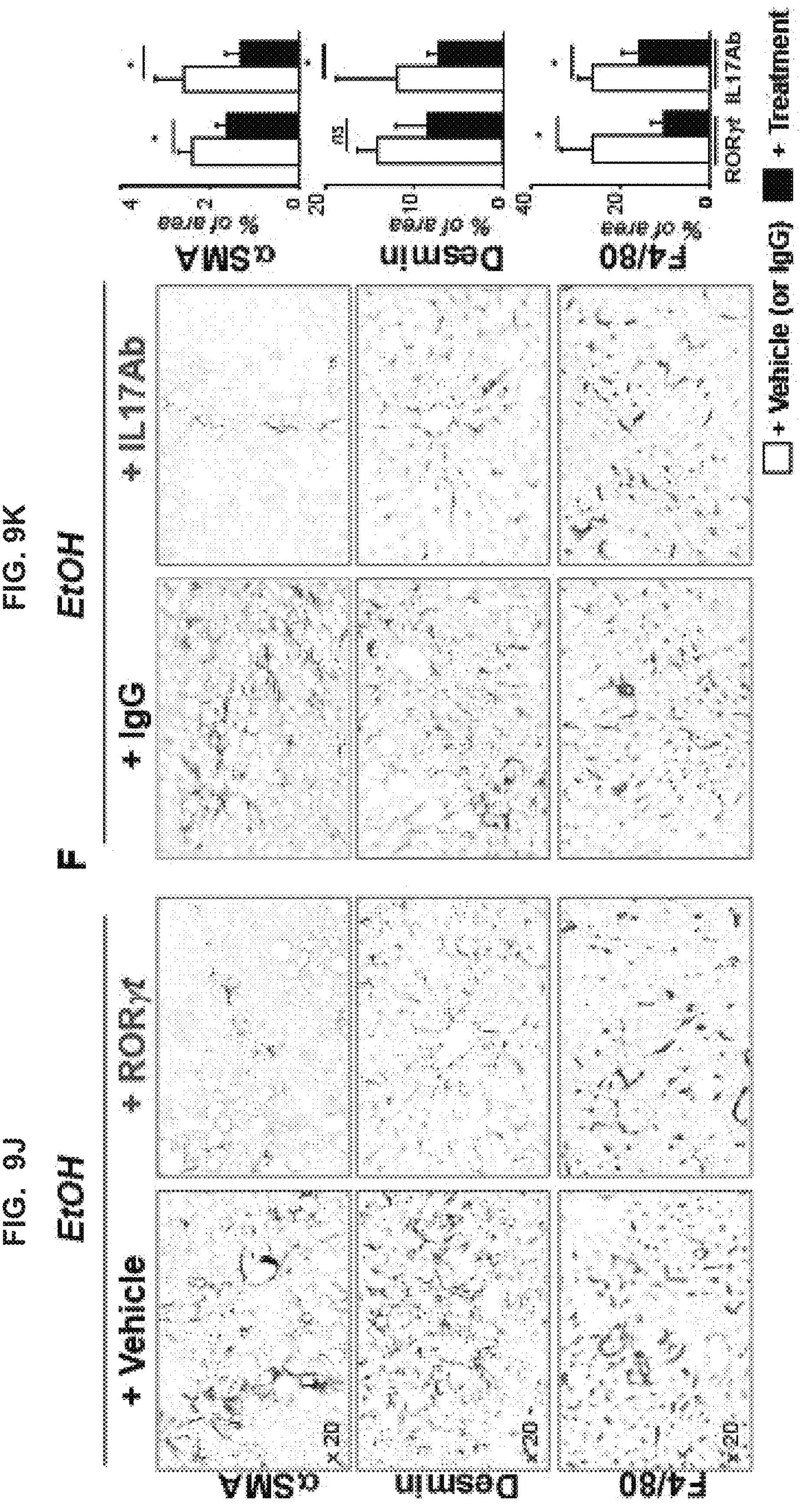

Therapeutic administration of RORγt inhibitor to IG alcohol-fed mice reduced serum and hepatic levels of IL17A (↓2.3 and ↓7 fold, respectively) and other inflammatory cytokines (FIGS. 8C & G, FIG. 9F-I), improved liver function (FIG. 8D) and hepatic steatosis (↓2 fold), and reversed development of alcoholic liver fibrosis by approximately 50%, as shown by reduced Sirius Red stained area (↓2.7 fold, FIG. 8E), downregulation of inflammatory and fibrogenic genes (vs vehicle-treated mice, FIG. 8G-H, FIG. 9J). Similarly, effect was observed in IG alcohol-fed wt mice therapeutically treated with neutralizing anti-IL17A Ab. Depletion of circulating IL17A (↓3.4 fold vs IgG-treated mice, FIG. 8C) prevented hepatotoxicity and lipidogenesis in alcohol-damaged hepatocytes (FIGS. 10F-H), and suppressed activation of Kupffer cells (FIGS. 10I-J), and ameliorated alcohol-induced liver fibrosis by approximately 50% (FIGS. 8F-H, FIG. 9K).

Taken together, using two classes of IL17A inhibitors, we demonstrated that blockade of IL17A can reverse alcohol-induced liver fibrosis to a level similar to that observed in $IL17ra^{-/-}$ mice.

Figure 11A:
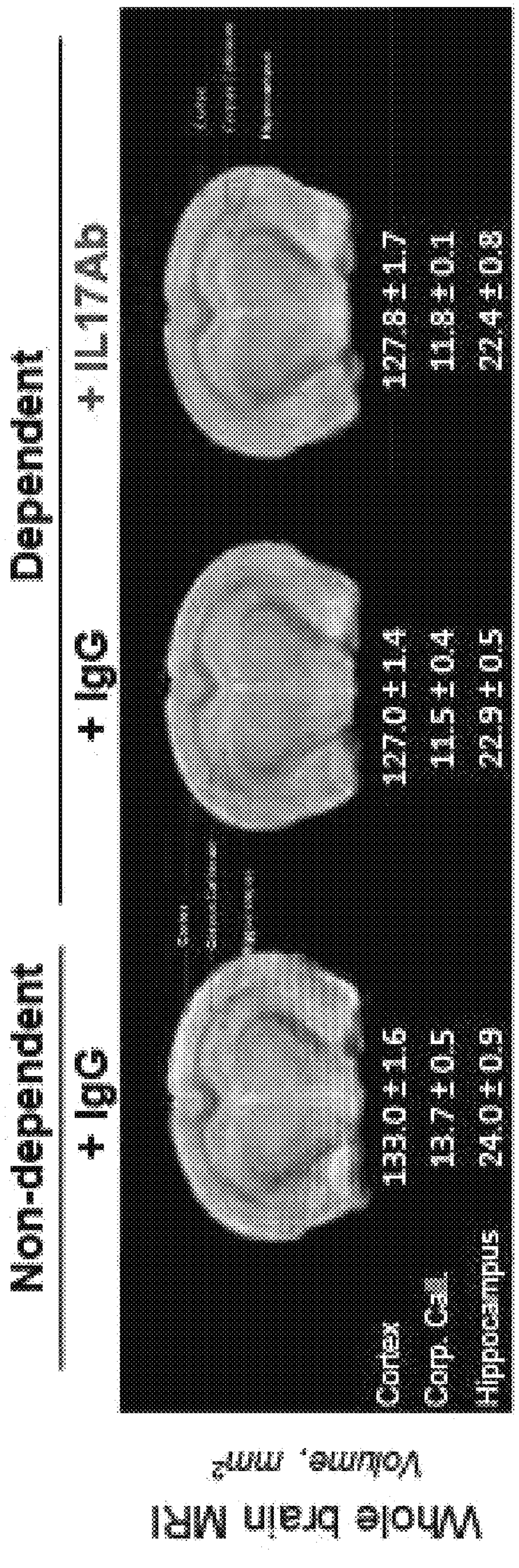
FIG. 11A-F illustrate data showing that therapeutic inhibition of IL17 suppresses voluntary alcohol drinking in alcohol-dependent mice: brains from Air and CIE mice±anti-IL17 Ab were analyzed.
Figure 11B:
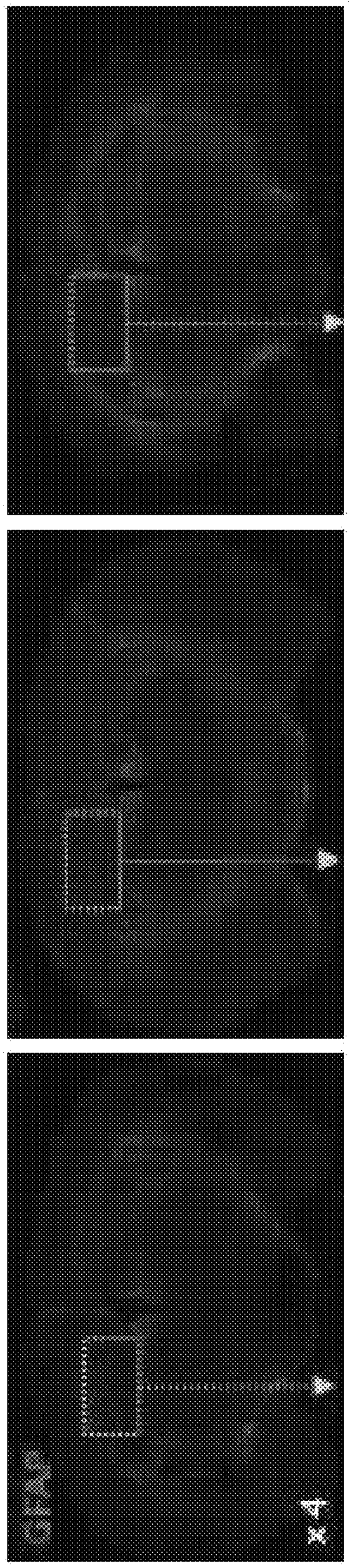
Figure 11C:
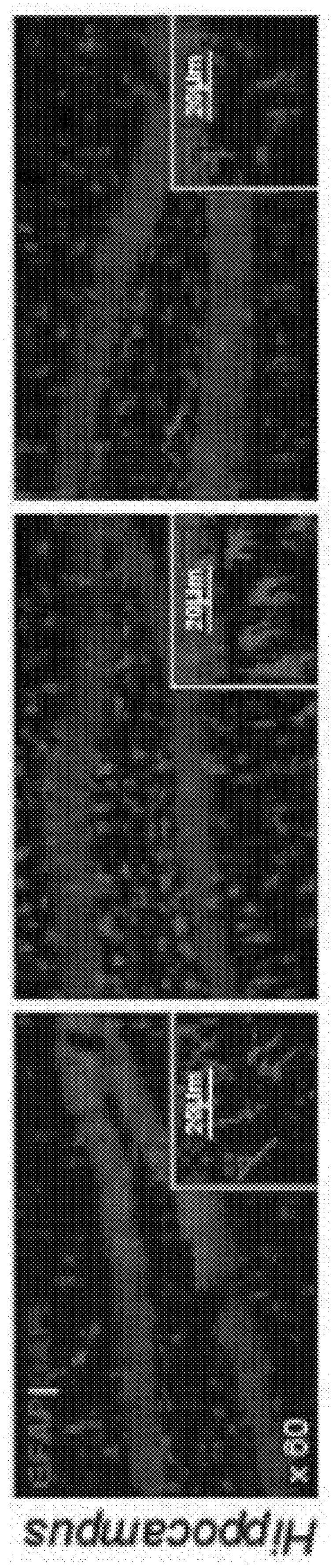
Figure 11D:
Figure 11E:
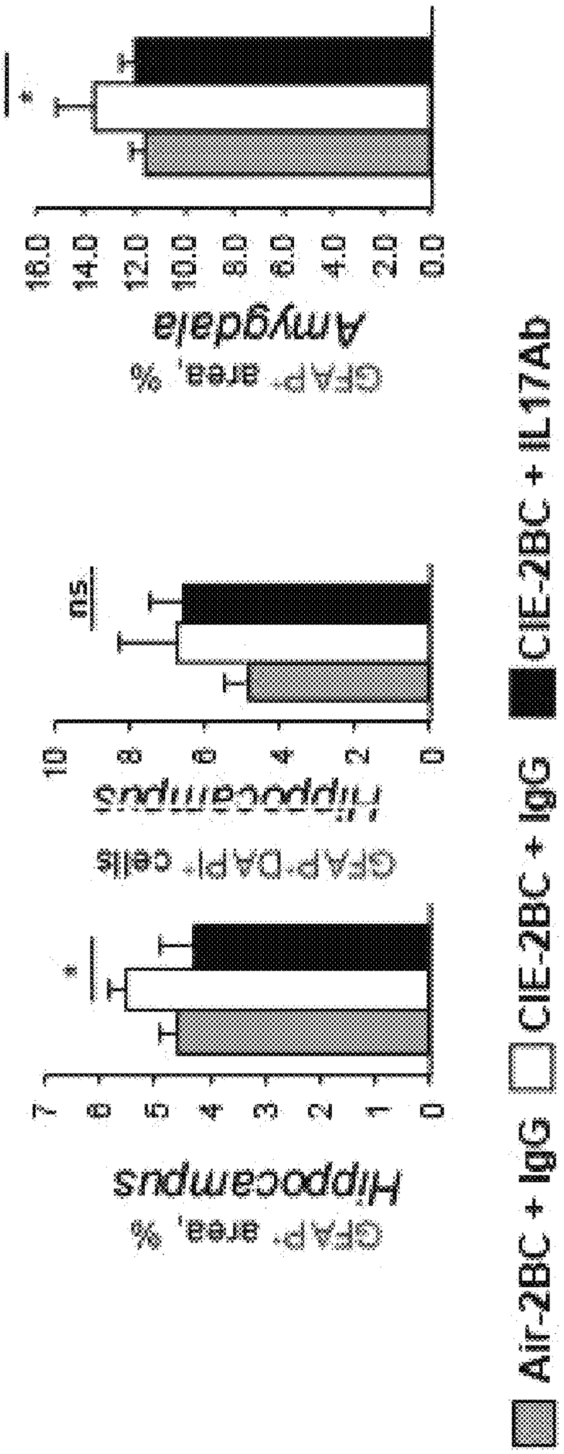
Figure 11F:
Figure 11G:
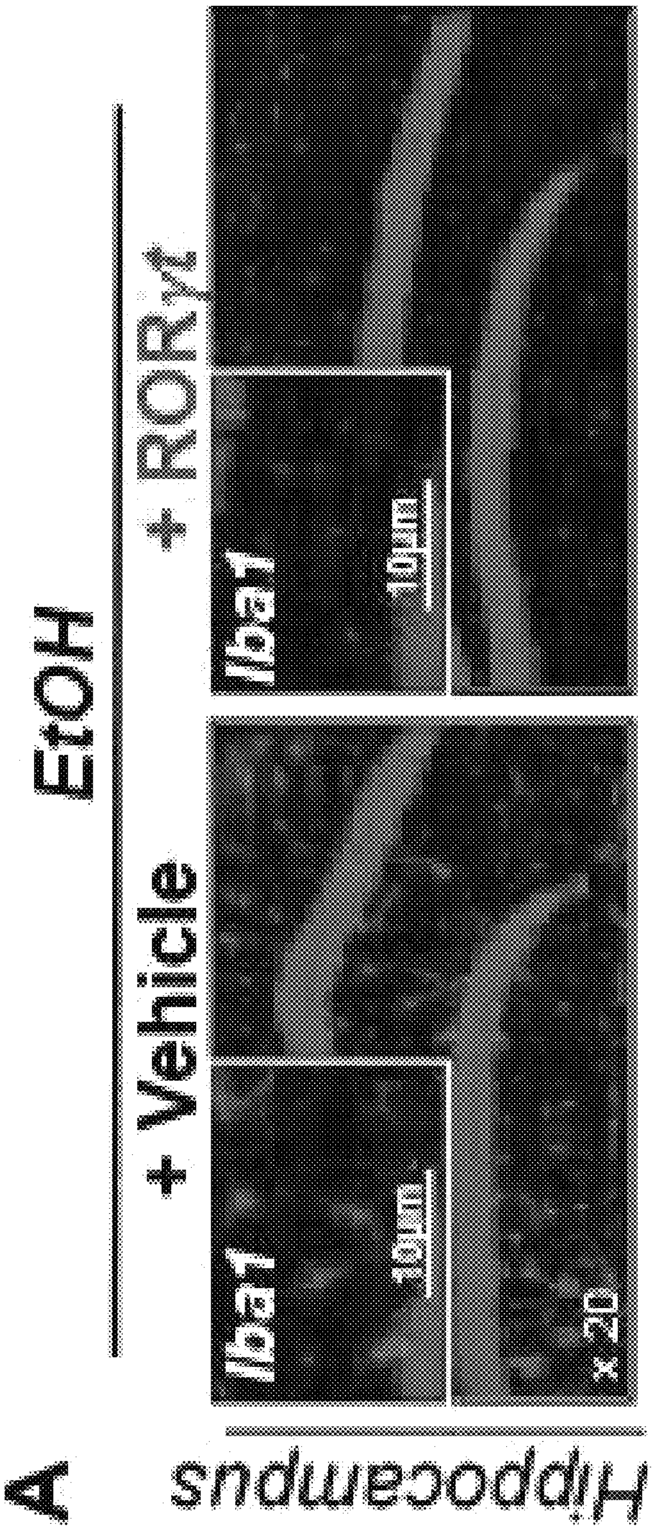
FIG. 11G-L illustrate data showing that therapeutic blocking of IL17A reduces alcohol-induced brain injury and neuroinflammation: brains were collected from IG alcohol-fed mice RORγt inhibitor (or anti-IL17A Ab) and analyzed.
Figures 11H, 11I:
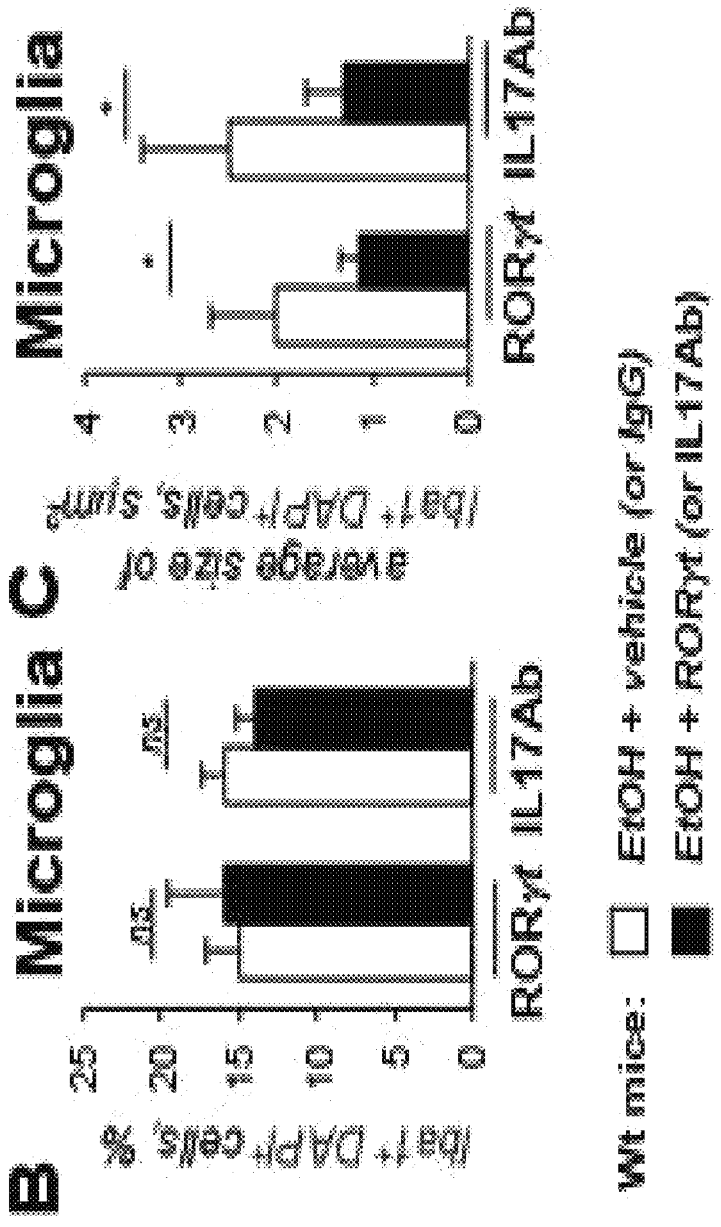
Figure 11J:
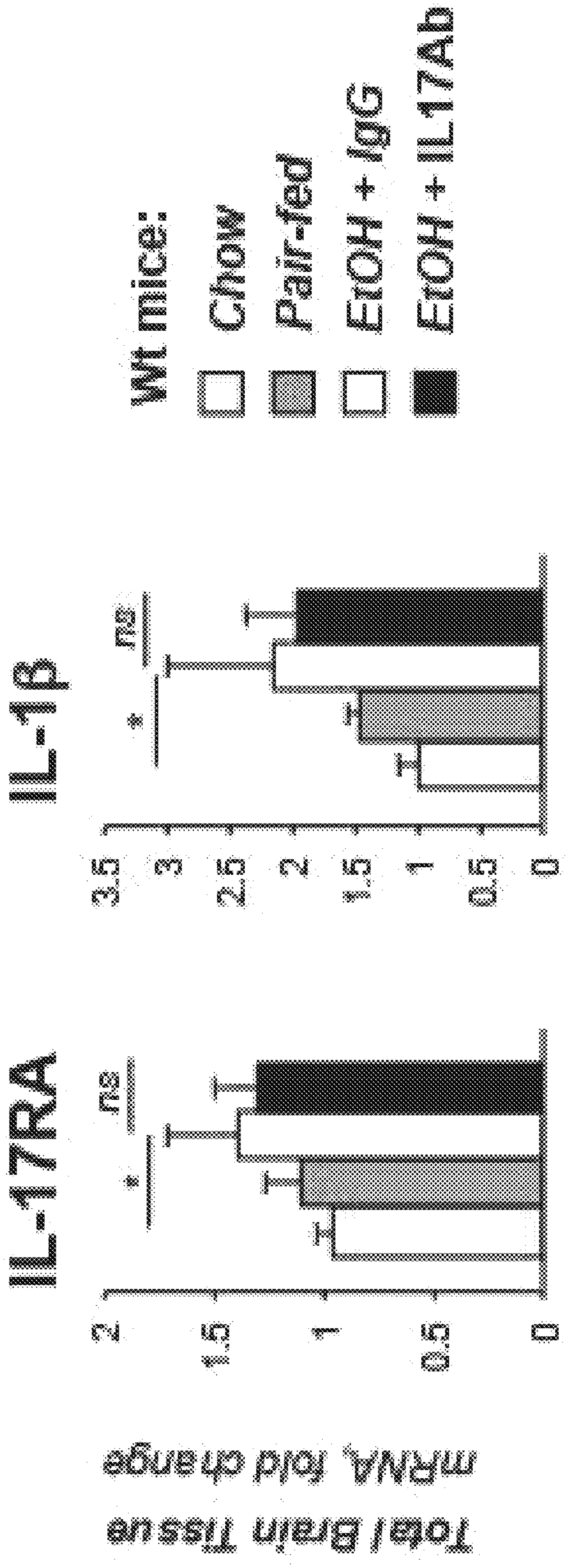
Figure 11K:
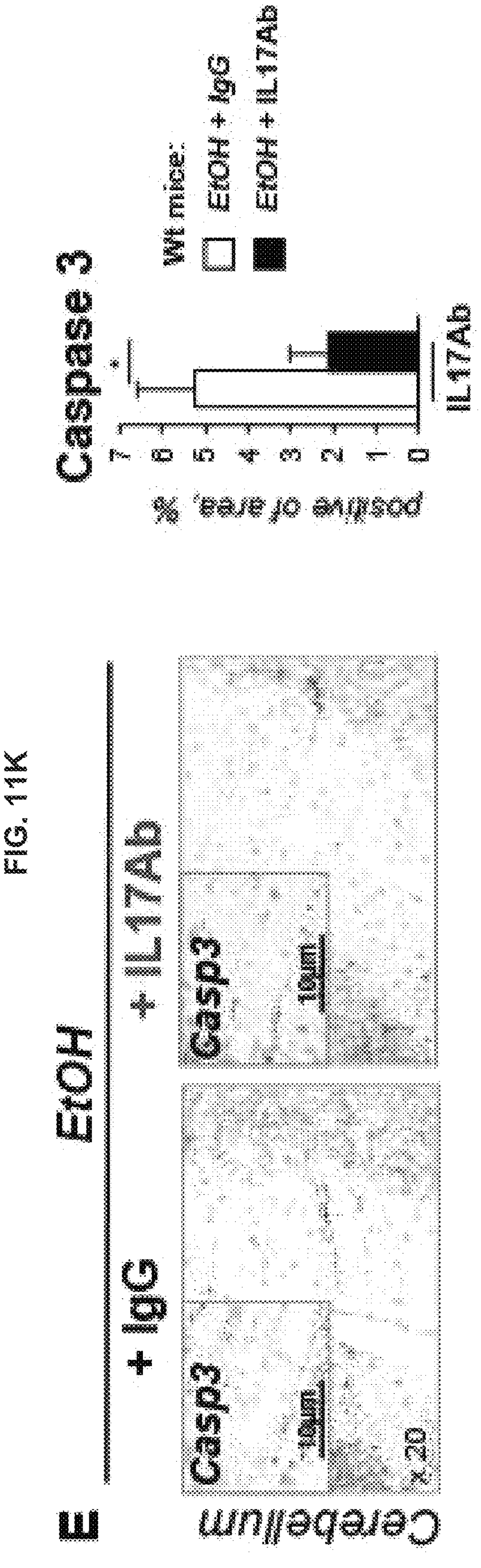

Systemic IL17A Blockade Ameliorates Astrogliosis in the Brains of IG Alcohol-Fed Mice The alcohol-induced liver and brain injury are interconnected[24,25]. The effect of systemic IL17A blockade on alcohol-induced brain injury was evaluated in IG alcohol-fed mice. Indeed, administration of anti-IL17A Ab (or RORγt inhibitor) significantly suppressed activation of $Iba1^+$ microglial cells (FIG. 9A-C) especially in hippocampus, as demonstrated by reduced cellular size (1.1±0.4 s$\mu m^2$ per cell vs 2.4±0.3 control mice, FIG. 11G-I), downregulation of Iba1 mRNA (1.35 fold), and expression of TNF-α and IL-1β mRNA in the whole brains of IG alcohol-fed wt mice (FIG. 9C-E, FIG. 11G-J). Neuronal apoptosis was assessed by immunostaining for active Caspase 3. Expression of Caspase 3 was observed only in the cerebellum of IG alcohol-fed mice, and was significantly reduced (↓2.5 fold)

in anti-IL17A Ab-treated mice (2.0±0.8% positive area vs 5.1±1.0% vs IgG-treated mice, see FIG. 11K). Furthermore, therapeutic blockade of IL17A prevented astrocyte proliferation and activation (astrogliosis[26], FIG. 8A-D), as demonstrated by shrinkage of astrocyte size (1.1±0.4 s$\mu$m$^2$ per cell vs 2.4±0.3 s$\mu$m$^2$ in IgG-treated mice), reduced expression of GFAP mRNA in the whole brain (↓2 fold) and specific brain structures (fold ↓1.5 frontal cortex; ↓1.7 cerebellum; and ↓3 hippocampus, FIG. 11L). Taken together, inhibition of IL17A overall ameliorated alcohol-induced brain injury, most effectively suppressed alcohol-induced astrogliosis in IG alcohol-fed mice.

IL17A Facilitates Activation of Primary Astrocytes and Microglia.

Figure 12A:
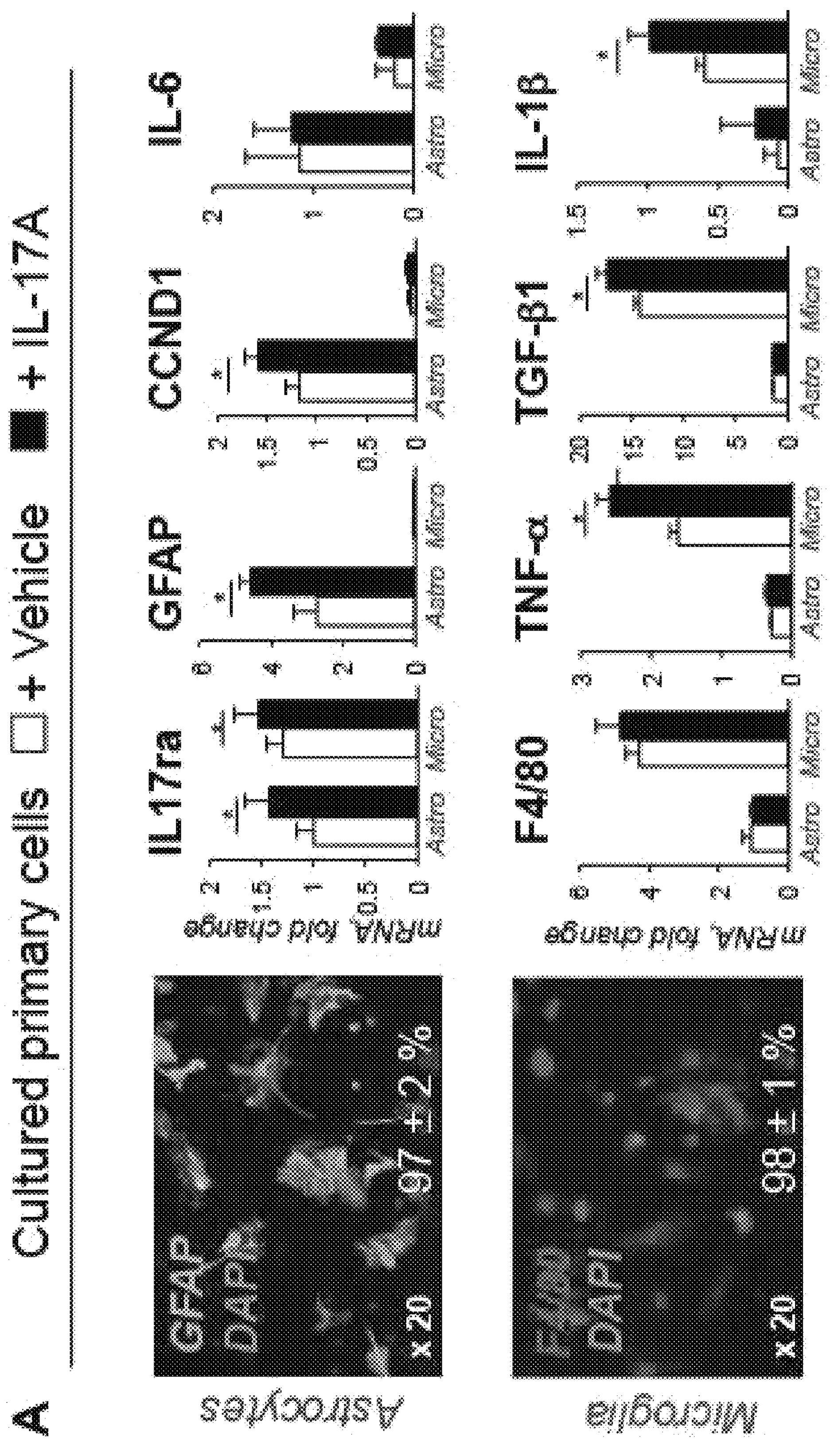
FIG. 12A-D illustrate data showing that IG alcohol-induced brain injury is associated with development of neuroinflammation.
Figure 12B:
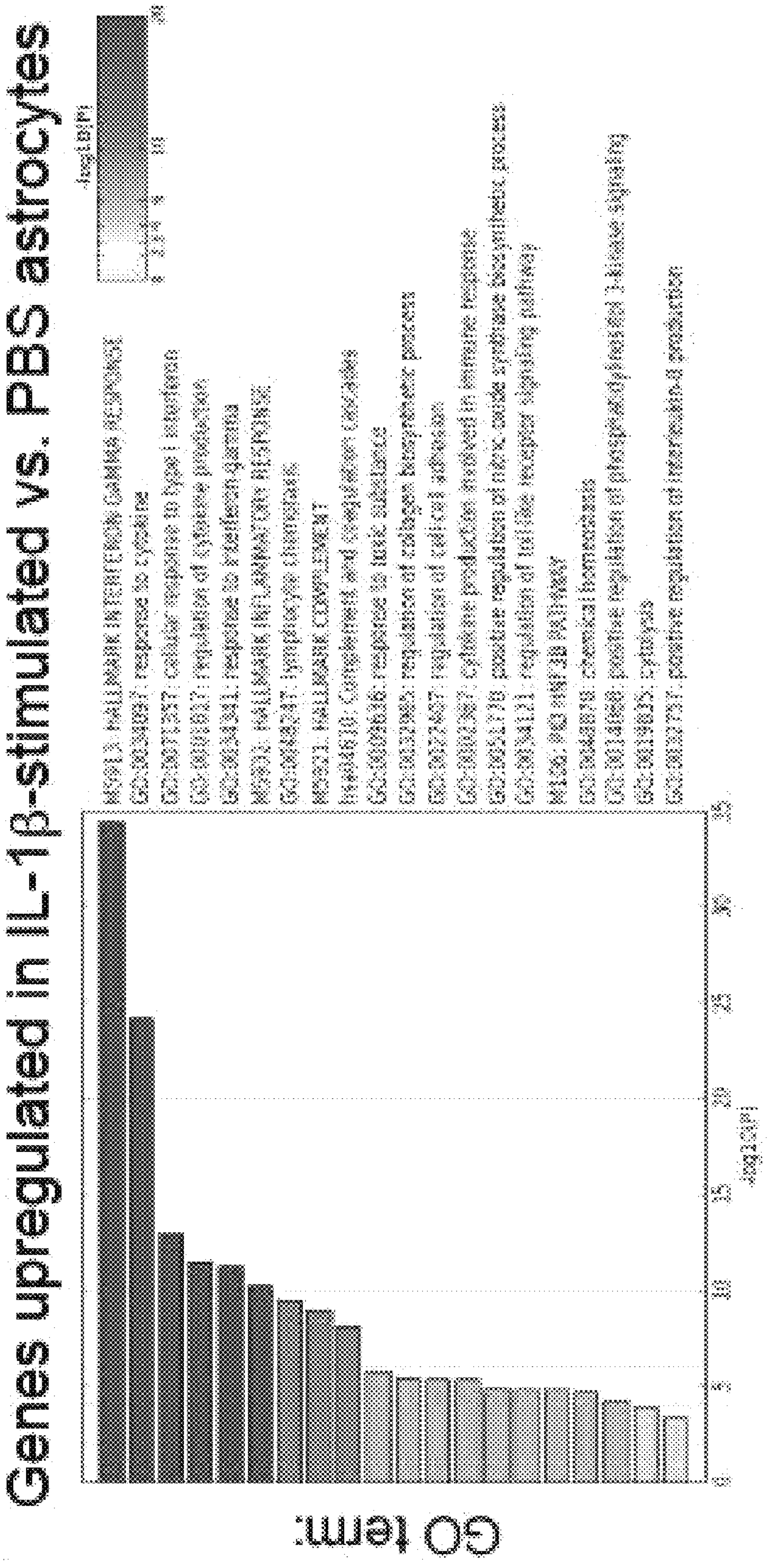
Figure 12C:
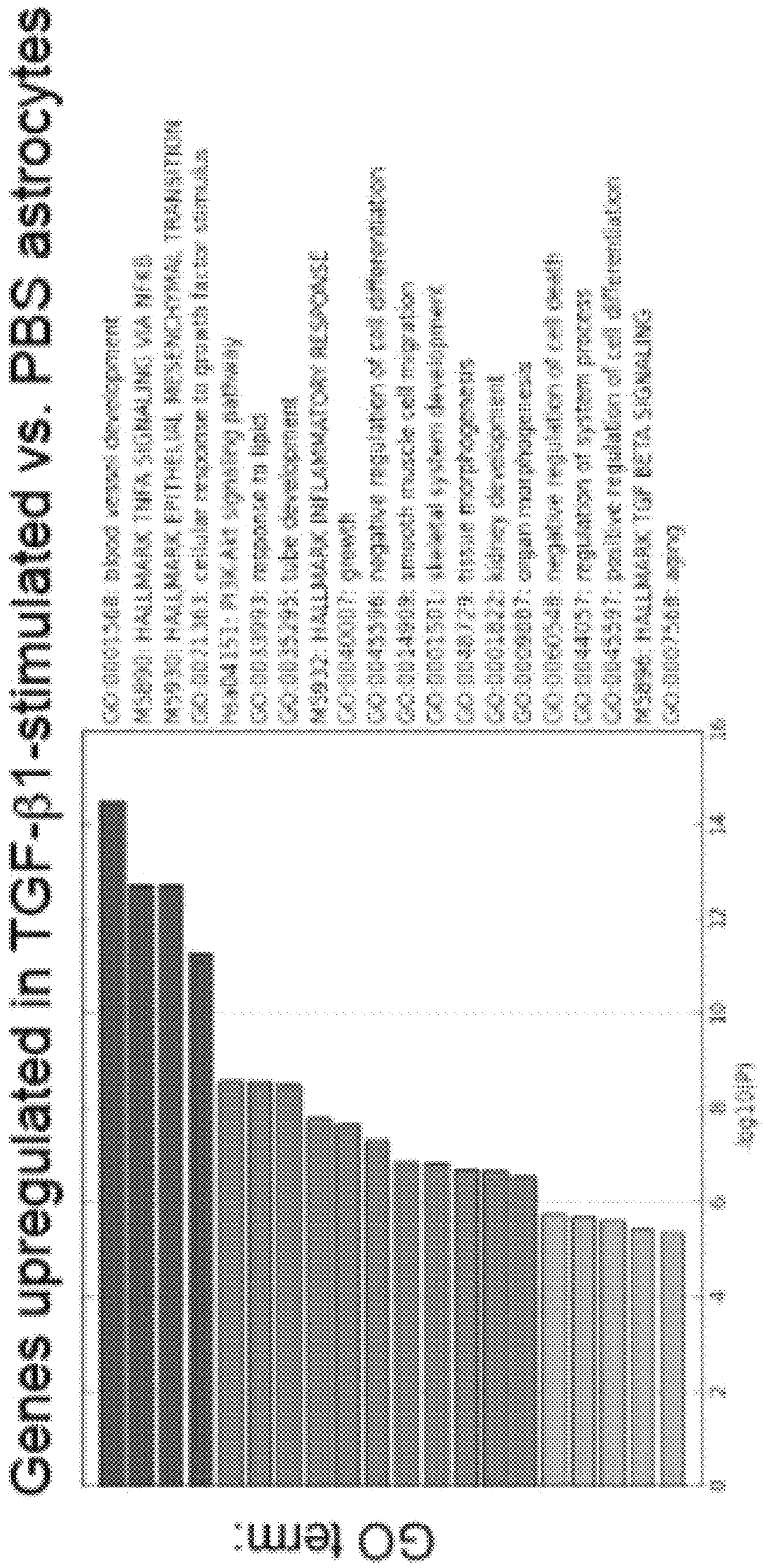
Figure 12D:
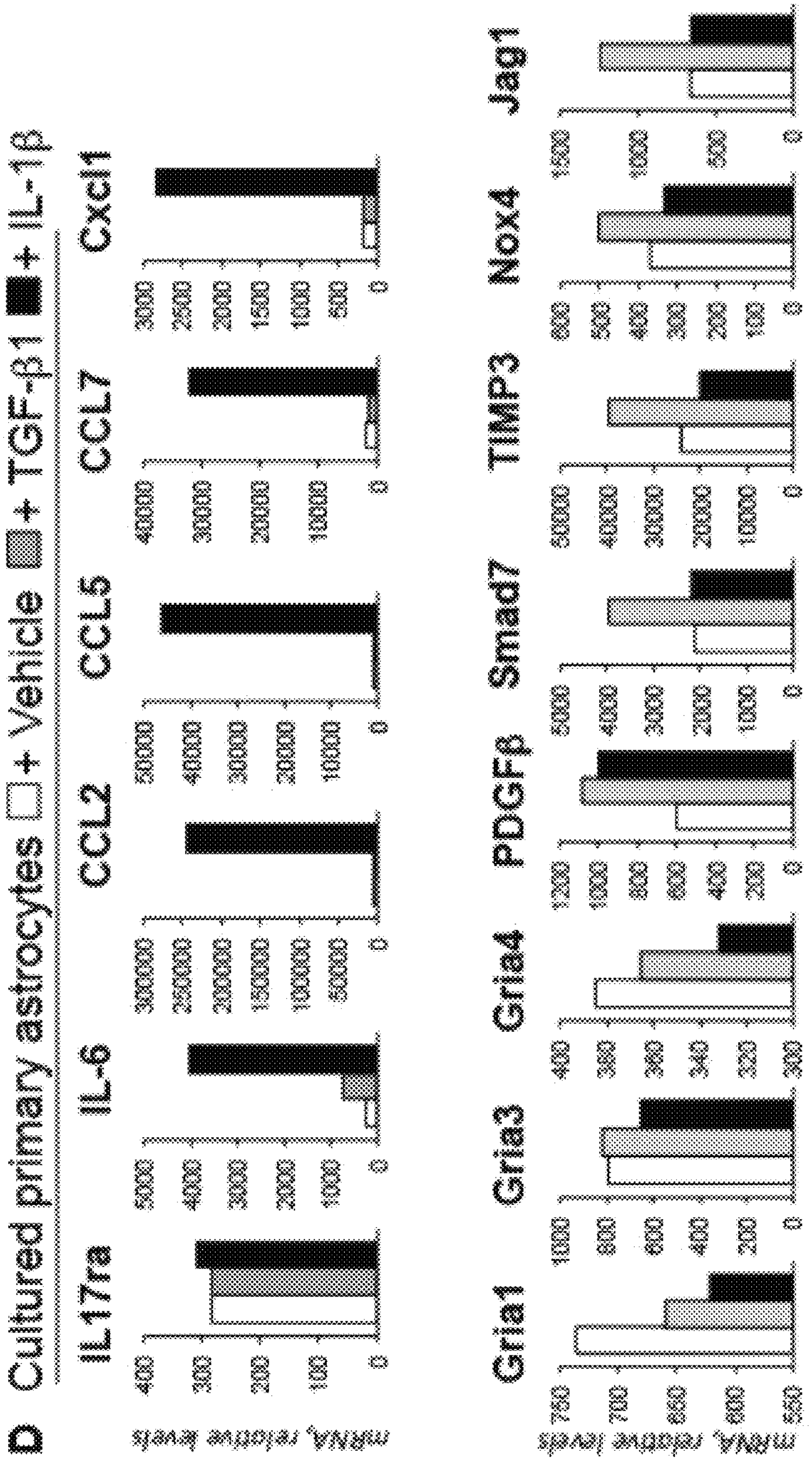

The effect of IL17A on immunoregulatory properties of astrocytes and microglia was tested in vitro[27]. In response to IL17A stimulation, GFAP$^+$ astrocytes and GFAP-F4/80$^+$ microglia upregulated expression of IL17RA, indicating that both cell types respond to IL17 signaling (FIG. 12A). IL17A prompted astrocytes for activation and proliferation (fold upregulation ↑1.8 GFAP, and ↑1.5 CCND1); and stimulated microglia cells to produce TGF-β1 (↑1.3 fold), TNF-α (↑1.7 fold), and IL-1β (↑1.6 fold). In turn, TGF-β1 and IL-1β exerted strong inflammatory responses in cultured astrocytes (FIG. 12B-D). We concluded that IL17A critically regulates alcohol-induced astrogliosis, either directly (facilitating astrocyte proliferation), or indirectly (via activation of microglial cells).

Development of Astrogliosis is Associated with Neuroinflammation in IG Alcohol-Fed Mice As many cell types respond to IL17A stimulation by upregulation of IL17RA[6], IL17RA mRNA was significantly induced in the cortex (↑1.3 fold), hippocampus (↑1.7 fold), and cerebellum (↑1.4 fold vs chow mice, Suppl. FIG. 8A-B) of IG alcohol-fed mice, indicating that chronic exposure to alcohol activates IL17 signaling in the CNS. Although brain cells did not express IL17A mRNA (FIG. 13A-D), IL17A protein was detected in the cerebrospinal fluid (CSF) of IG-alcohol-fed mice (↑6 fold vs pair-fed mice), suggesting that IL17A might enter CSF from circulation. The CSF levels of IL-1β, TGF-β1, and TNF-α were also increased, and correlated with increased mRNA expression of these cytokines in the whole brains of IG alcohol-fed mice (FIG. 13B-D), indicating that with an exception of IL17A, brain cells serve as a significant source of cytokines and contribute to neuroinflammation. Therapeutic administration of anti-IL17A Ab suppressed expression of TNF-α and lowered expression of IL-1β mRNA in the brains of IG alcohol-fed mice (FIG. 9E, FIG. 11J), and reversed alcohol-induced neuropathology.

Serum IL17A Passes Across the Damaged Blood-Brain Barrier (BBB) into the Brains of IG Alcohol-Fed Wt Mice To determine the mechanism by which IL17A enters the CSF, the blood-brain barrier (BBB) permeability was examined in IG alcohol-fed mice. Increase of albumin content (↑3 fold) was observed in the CSF of IG alcohol-fed wt mice (vs pair-fed mice, FIG. 14A). Immunostaining for tight junction protein Zo-1 (to visualize blood vessels) and albumin, revealed the presence of extravasated albumin in the brain parenchyma of IG alcohol-fed mice (but not in pair-fed mice, FIG. 14B-C). We concluded that serum IL17A enters the brain across damaged BBB. Our data is in concordance with previous reports demonstrating that the integrity of the BBB is compromised by chronic alcohol consumption in patients, and contributes to neuroinflammation[28]. In contrast to a previous report[29], IL-17A blockade did not ameliorate BBB disruption in IG alcohol-fed mice (FIG. 14A-C), indicating that IL17 signaling is not directly responsible for the loss of BBB integrity in these mice.

Circulating IL17A is Upregulated in Alcohol-Dependent Mice

Figure 10A:
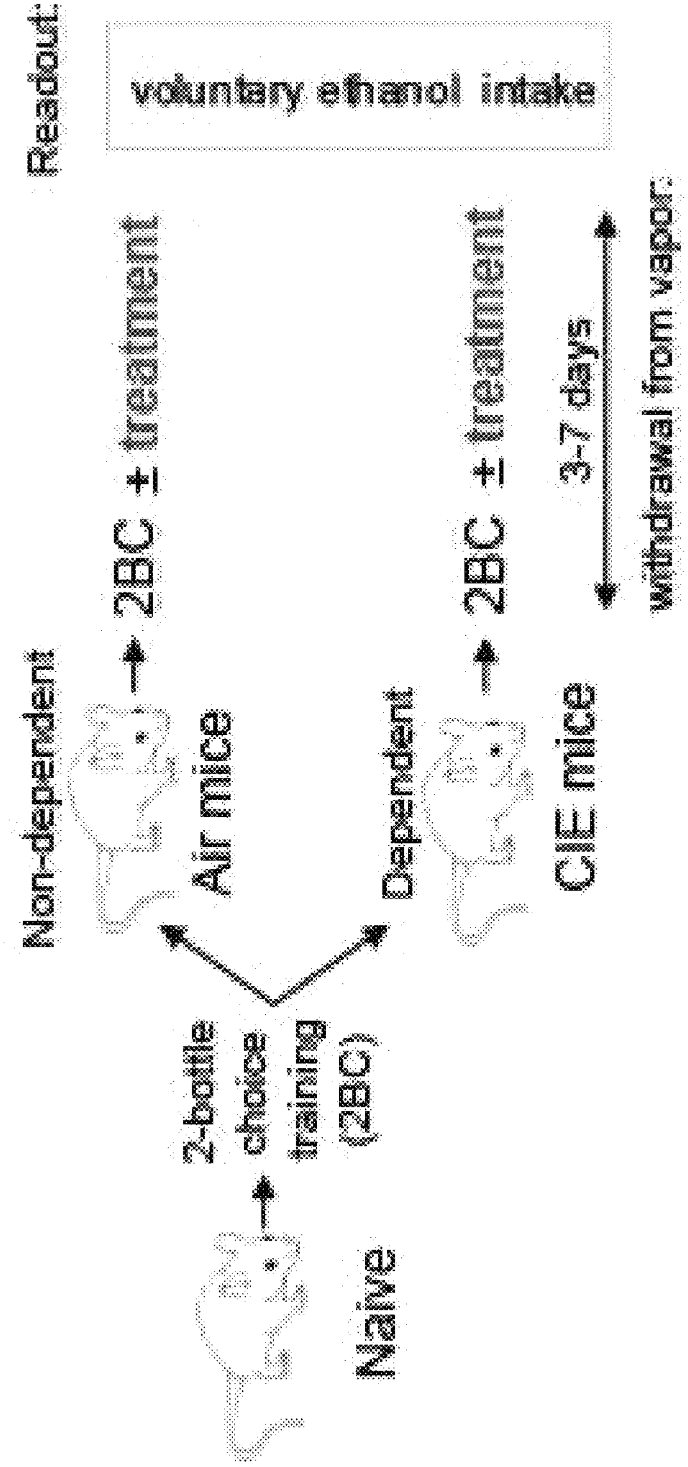
FIG. 10A-E illustrate data showing that therapeutic inhibition of IL17 suppresses voluntary alcohol drinking in alcohol-dependent mice.
Figure 10C:
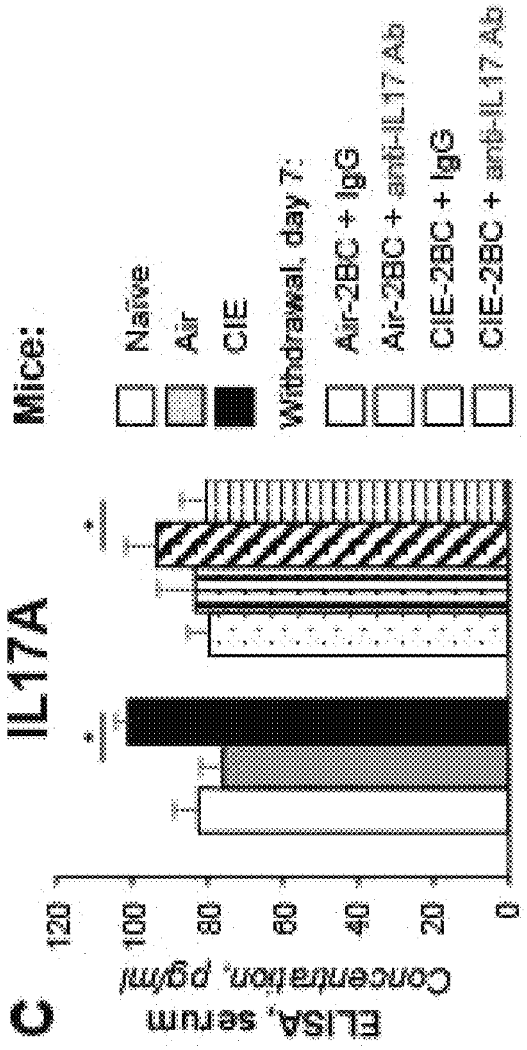
Figure 10B:
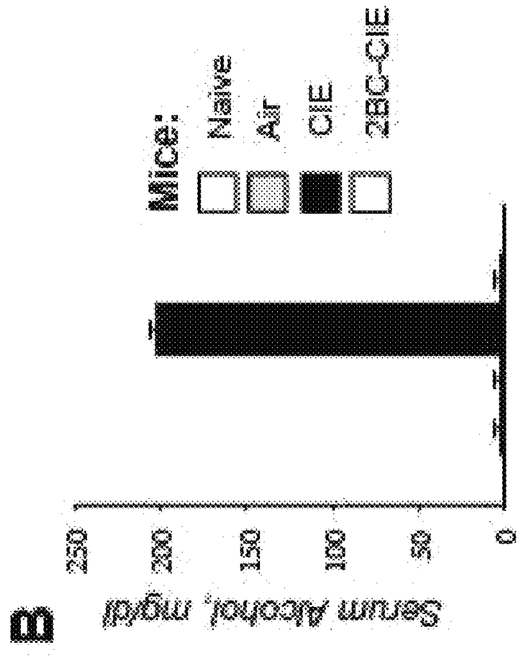
Figure 10D:
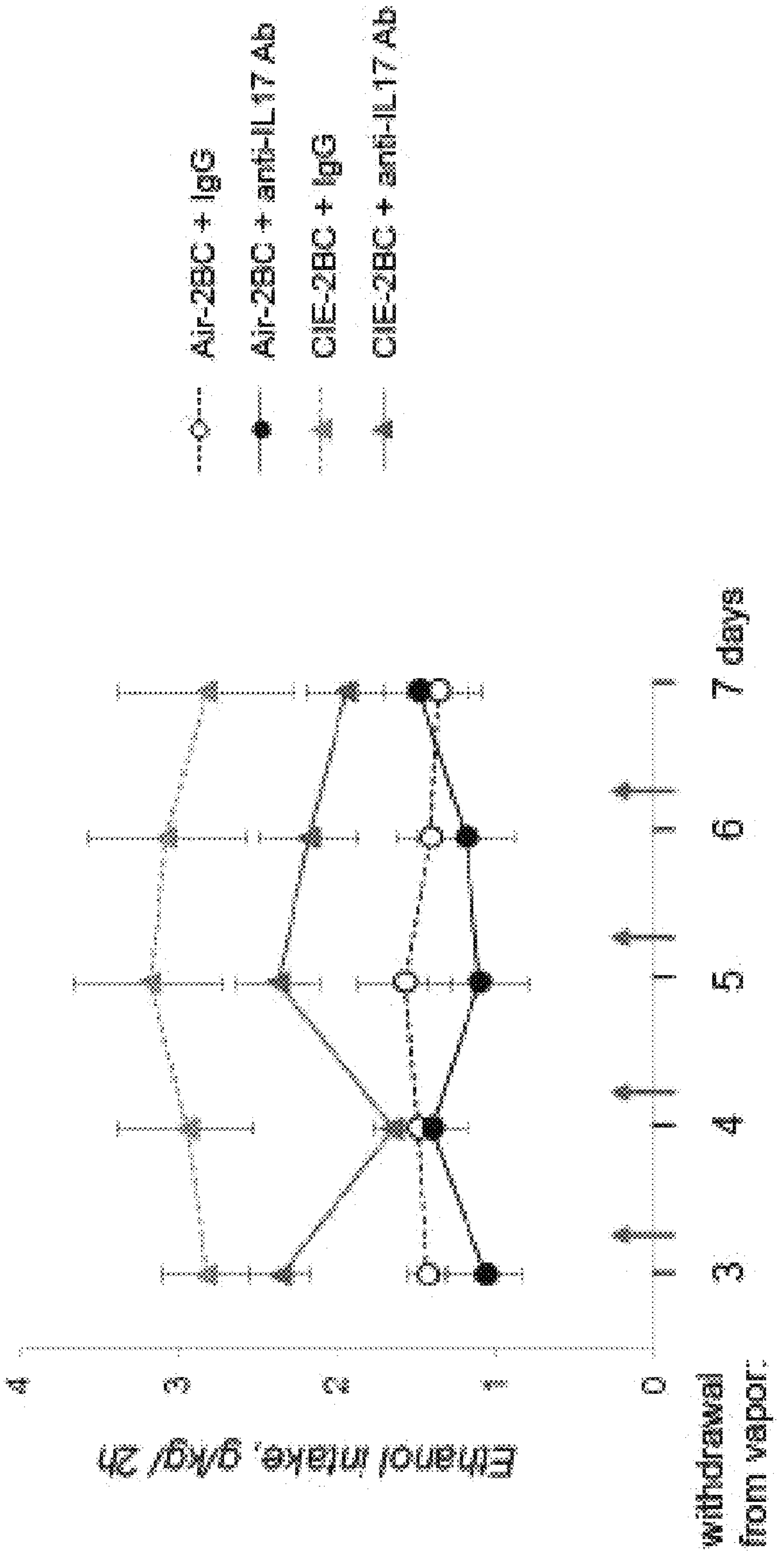
Figure 10E:
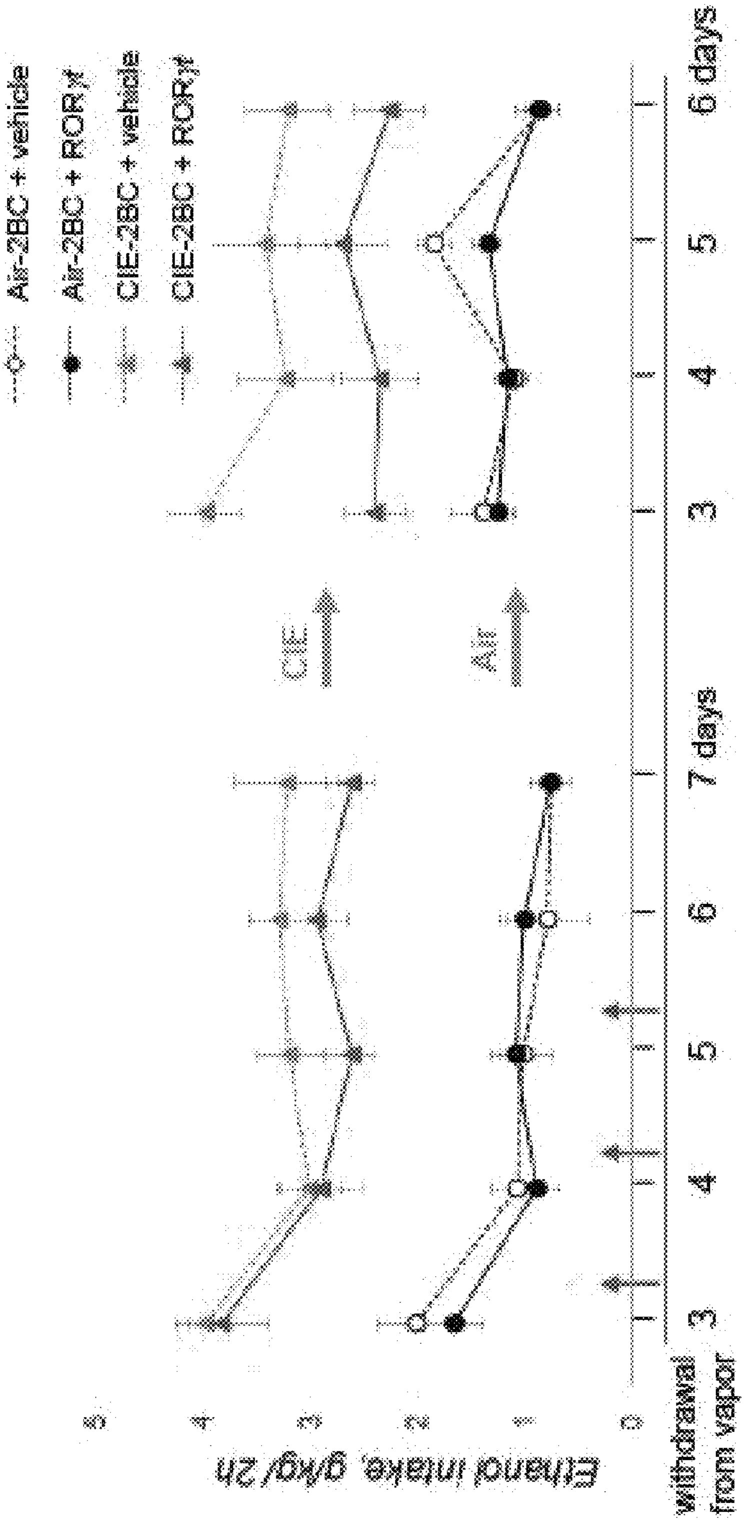
Figure 15A:
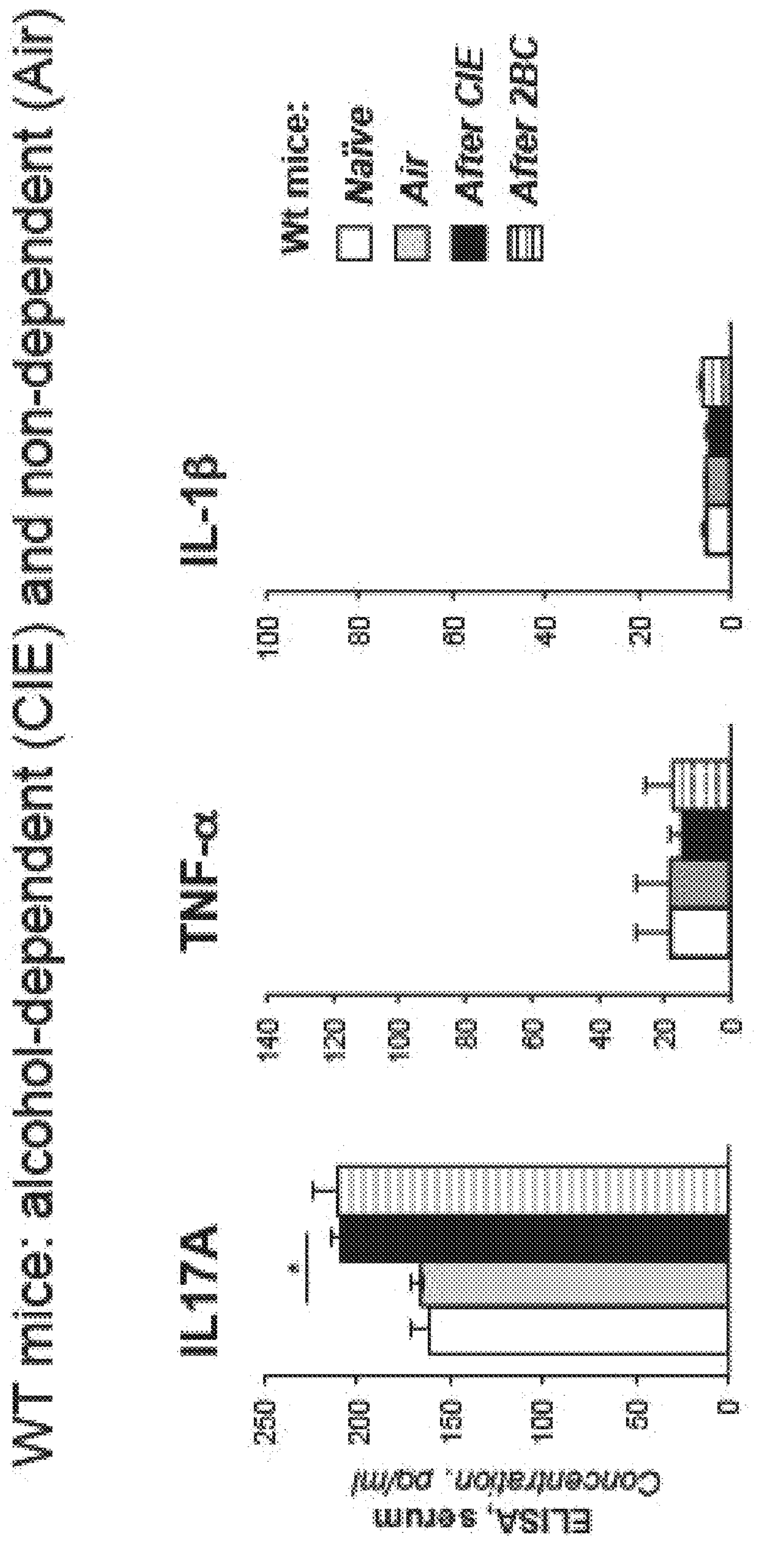
FIG. 15A-E illustrate data showing that IL17A signaling facilitates astrocyte activation in alcohol-dependent mice.

The potential role of IL17 signaling in the motivational aspects of chronic alcohol abuse was studied using a mouse model of ethanol dependence that combines chronic intermittent inhalation of ethanol vapor (CIE, repeated rounds of intoxication (4 cycles, 16 h, target blood alcohol level=200 mg/dL, followed by 8 h withdrawal) with voluntary ethanol drinking during limited-access two-bottle choice sessions (2BC, water vs ethanol 15% v:v, 2 h/day, 3-7 days withdrawal from vapor, FIG. 10A-B). In this model, CIE-exposed mice became alcohol dependent, and developed gradual escalation of voluntary ethanol drinking compared to non-dependent (Air) mice[30]. On average, CIE mice consumed 3 times more alcohol than Air mice, similar to that observed during 2BC session at day 3 into withdrawal from ethanol vapor (FIG. 10D-E). Development of alcohol dependence in CIE mice was also associated with significant increase of serum IL17A cytokine (↑1.3 fold, vs Air mice) that persisted for more than 4 days into withdrawal from ethanol vapor (FIG. 10C, FIG. 15A). Serum levels of other inflammatory cytokines (IL-1β and TNF-α) were not changed between CIE and Air mice, and were comparable to those observed in naïve mice (FIG. 15A). Among all tested cytokines, IL17A was the only cytokine systemically upregulated in the blood of CIE mice.

Figure 15B:
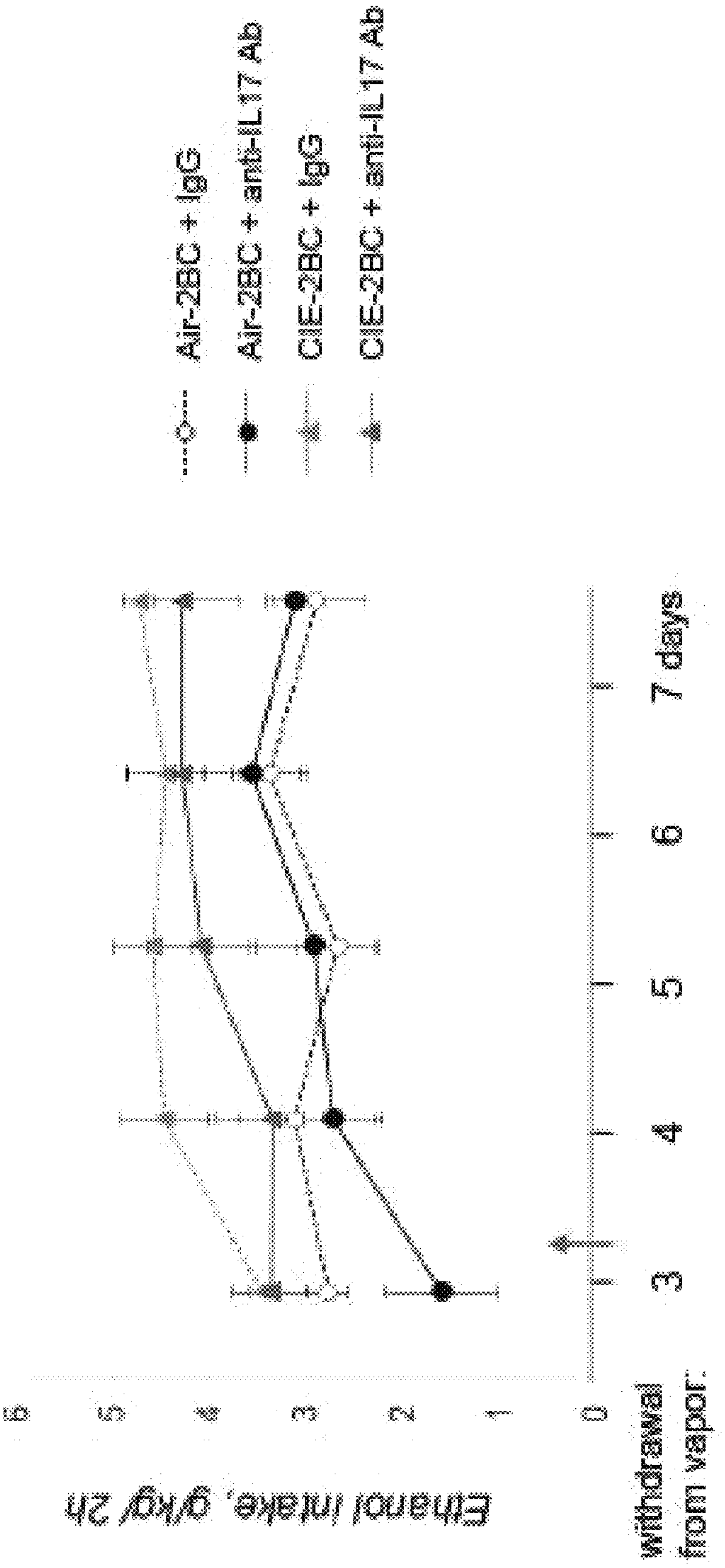

Therapeutic Blockade of IL17A Suppressed Voluntary Ethanol Drinking in Dependent Mice Dependent (CIE) and non-dependent (Air) mice were further divided into two groups (n=6/group) and treated with a single dose of anti-IL17A Ab (25 mg/kg, i.p., or IgG). 18 h later the intake of alcohol (vs water) was measured in these mice during 2BC sessions (at days 4-7 into withdrawal from ethanol vapor). Voluntary ethanol consumption was selectively reduced in anti-IL17A Ab-treated dependent mice (vs IgG-treated dependent mice), but had no effect on non-dependent mice (FIG. 15B). The effect of anti-IL17A Ab was most robust on the first day, and gradually dissipated. When anti-IL17 Ab was administered daily, voluntary alcohol intake was reduced in dependent mice throughout the whole week (FIG. 10D).

Similar effect was observed in alcohol-dependent CIE mice treated with RORγt inhibitor (3×50 mg/kg, oral gavage, 18 h prior to 2BC sessions, FIG. 10E). Administration of RORγt inhibitor significantly reduced alcohol intake in dependent mice following exposure to an additional week of CIE, and this effect persisted for 1 week (vs vehicle-treated dependent mice). Our data suggest that blockade of IL17 signaling suppresses voluntary alcohol drinking in alcohol-dependent mice.

Therapeutic Blockade of IL17A Signaling Suppresses Astrocyte Activation in Alcohol Dependent CIE Mice To identify objective and measurable changes associated with development of alcohol dependence in mice, the brains of the alcohol-dependent and non-dependent mice were collected 3 days after the last 2BC session and analyzed. The volume of the cortex, hippocampus and corpus callosum were significantly reduced in alcohol-dependent mice, (FIG. 11A), while the size of GFAP$^+$ astrocytes in hippocampus and amygdale was increased (FIGS. 11B-D), and was associated with elevated levels of circulating IL17A (FIG. 10C). Administration of anti-IL17A Ab reduced serum levels of IL17A to baseline (FIG. 10C), but had no effect on the overall brain volume in these mice (FIG. 11A). In turn, the size of hippocampal astrocytes was significantly reduced in anti-IL17A Ab-treated CIE mice (1.1±0.4 s$\mu m^2$ vs 2.4±0.3 s$\mu m^2$ in IgG-treated CIE mice, FIG. 11E), and correlated with decreased GFAP expression in amygdala (FIG. 11E). Our data indicate that depletion of circulating IL17A reduced activation of brain astrocytes, and suppressed voluntary alcohol drinking in alcohol-dependent mice.

Serum Levels of IL17A are Elevated in Patients with Severe Alcohol Use Disorder

Serum levels of IL17A were measured in healthy individuals and excessive drinkers with no history al ALD (FIG. 11F). The correlation between excessive alcohol consumption and serum levels of IL17A was established in patients with normal liver function (ALT≤40 U/L) or abnormal ALT (≥40 U/L) (Suppl. Table 1). Strikingly, high levels of serum IL17A were detected only in excessive drinkers, but not in healthy individuals. The level of circulating IL17A positively correlated with the alcohol use (137-194 drinks/month), and to lesser extend with patient's liver function (ALT ranking 25-67 U/L). We concluded that systemic upregulation of IL17A is the hallmark of excessive alcohol consumption, and IL17A might play a role in the pathogenesis of alcohol addiction in patients with severe alcohol use disorder.

Discussion

We compared multiple mouse models to demonstrate that IL17A is elevated in response to chronic exposure to high blood alcohol. More importantly, blockade of IL17A either genetically or pharmacologically suppresses excessive alcohol drinking in mice, reverses astrocytic reactivity, and inhibits development of alcohol induced liver fibrosis. Thus, IL17A may be the common mediator required for many of the effects of alcohol abuse.

Development of neuroinflammation and neurodegenerative disorders, neuronal death, and astrogliosis has been reported in patients with severe alcohol use, and was often linked to development of liver fibrosis[28]. Elevated levels of circulating and hepatic IL17A in patients with alcohol-induced liver fibrosis were well documented, but only recently IL17A was linked to alcohol dependence in patients and experimental animals[16,18,31]. Our study provides an evidence that excessive drinking is associated with a strong increase of serum IL17A levels in patients, even their liver function is still normal (FIG. 11F), suggesting that release of IL17A precedes alcohol-induced liver injury. Production of IL17A was further increased in patients with ALD, and exacerbated inflammation and alcohol-induced liver injury (FIG. 6C-D).

IL17A Signaling Facilitates Alcohol-Induced Liver Injury

Similar to that observed in patients[7,17], IL17A was increasingly induced in mice with alcohol-induced acute and chronic steatohepatitis and liver fibrosis. Collectively, these experimental models can be used to study ALD progression in mice. Here we demonstrate that IL17A plays a critical role in ALD progression in patients and mice, and suggest that IL17A is a major activator of fibrosis in multiple organs and tissues[7]. IL17A regulates a variety of responses to alcohol in the damaged liver, including alcohol metabolism (CYP2E1), steatosis, inflammation (IL-6, IL-1β, TNF-α, ROS production), and fibrosis (TGF-β1, activation of HSCs/myofibroblasts). Similar to ALD, IL17 signaling was implicated in the pathogenesis of experimental non-alcoholic steatohepatitis (NASH)[32], although responses to IL17A (steatohepatitis, fibrosis, and inflammation) were strongly amplified in alcohol-fed mice (FIG. 7). Our results provide the mechanism for previous studies that have demonstrated that elevated levels of serum and hepatic IL17A correlate with severity of alcoholic steatohepatitis and fibrosis in patients with severe alcohol use[7].

IL17 Signaling Contributes to Alcohol-Induced Brain Injury

Alcohol affects multiple organs and systems, including brain and liver[4]. Experimental models of alcohol-dependence (CIE) and IG alcohol-feeding in mice closely recapitulate pathological changes observed in patients with mild to severe alcohol use disorder[33]. In both models, the effect IL-17 signaling was associated with increased astrocyte reactivity. And systemic blockade of IL17A reversed alcohol-induced reactive astrogliosis (characterized by proliferation, hypertrophy of astrocytes, and upregulation of astrocyte-specific markers GFAP and vimentin)[34], improved neuroinflammation, and reversed morphological changes associated with alcohol-induced brain injury. We propose that targeting IL17A can be beneficial for treatment of alcohol addiction in patients.

Genetic deletion of IL17ra gene causes increased IL17A production in mice[35]. To avoid potentially adverse effects of the dysregulated cytokine network (such as upregulation of IL17F, or IL-10)[7,36] on the alcohol drinking pattern in dependent mice, neither IL17ra$^{-/-}$ nor IL17a$^{-/-}$ mice were used for the behavioral studies. Our data are primarily based on pharmacological inhibition of IL17 signaling. Using two classes of IL17A inhibitors, neutralizing anti-IL17A Ab[22] and RORγt inhibitor (that prevents Th17 cell expansion but does not affect facultatively expressing IL17A cells, e.g. mast cells, and eosinophils)[23], we demonstrate that blockade of IL17A suppresses escalation of voluntary drinking in dependent mice. Anti-IL-17A Ab produced an immediate but short-lasting (24 h) effect on alcohol-dependent mice. The effect of RORγt inhibitor was more deferred (most likely due to persistence of circulating IL17A), but lasted for more than 2 weeks. Suppression of voluntary ethanol drinking in dependent mice was attributed to IL17A cytokine (and in part IL17F, but not other members of Th17 cytokine family)[6,37], since anti-IL17A Abs specifically neutralize IL17A homodimers and IL17A/F heterodimers. Our study provides the first preclinical evidence for targeting IL-17A in patients with alcohol addiction and compulsive alcohol drinking.

Astrocyte Functions in Alcohol-Dependent Mice

Astrocytes functionally interact with the endothelial cells and synaptic terminals of active neurons, enabling nutrient exchange between blood vessels and brain tissue, and intercellular trafficking of neurotransmitters and cytokines. Astrocytes maintain extracellular homeostasis, provide support to BBB, regulate vascular tone and cerebral blood flow, and control synaptic neurotransmission via uptake and clearance of the major excitatory amino acid transmitters. Astrocytes were also implicated in modulation of the motivational properties of alcohol, which is regulated on several levels[38]. Activation of the acute reinforcing effects of alcohol (context dependent reinstatement) is mediated by the dopamine, glutamate, and GABA systems in amygdala and hippocampus. In turn, reinforcement of negative emotional state that drives motivation to seek alcohol is linked to activation of corticotropin-releasing factor (CRF) systems in amygdala and bed nucleus of the stria terminalis (BNST)[39]. CRF induced sensitization to alcohol withdrawal is further enhanced by adaptive responses of astrocytes to cytokines[38,40]. We speculate that IL17A-mediated reactive astrogliosis drives CRY production in the amygdala and BNST. IL17A affects motivational aspects of alcohol drinking behaviors in alcohol-dependent mice, and similar mechanism might be activated in response to other reinforcing stimuli.

Overall, circulating levels of IL17A are elevated in patients with excessive alcohol abuse and in alcohol-dependent mice. IL17A-induced reactive astrogliosis is a common neuropathology in mice chronically exposed to alcohol. Alcohol-induced liver injury further facilitates systemic release of IL-17A and inflammation. We provide preclinical data demonstrating that blockade of serum IL-17A ameliorates alcohol-induced liver fibrosis and astrogliosis, and suppresses excessive alcohol drinking in alcohol-dependent mice.

Materials and Methods:

Mice and reagents: IL17ra$^{-/-}$ mice and wt littermates (Amgen)[41], wt mice (♂ C57BL/6 mice, Charles River) were treated with anti-IL17 Ab or IgG (CNTO 8096 and 6601, 25 mg/kg, i.p., Janssen)[22], or RORγt inhibitor (VPR-254, 50 mg/kg, oral gavage, Visionary Pharmaceuticals Inc., San Diego, CA) or vehicle (40% PEG400, 18% solutal in $H_2O$). Mouse protocols are approved by IACUC of UC San Diego, University of Southern California, and The Scripps Research Institute.

Experimental model of alcohol-induced liver fibrosis: (intragastric (IG) alcohol feeding HCFD hybrid alcohol infusion+weekly binges)[21]. Mice (♂ C57BL/6, 12 w old, n=10/group) were fed ad libitum diet+a solid diet high in cholesterol and saturated fat (HCFD:1% w/w cholesterol, 21% calories from lard, 17% calories from corn oil) for 2 weeks. The mice were then operated for implantation of gastric catheters, and 2 weeks later were subjected to intragastric (IG) feeding of liquid high fat diet (36% calories from corn oil) plus ethanol or isocaloric dextrose at 60% of daily caloric intake for 8 weeks for males. Ethanol dose was increased from 19 to 32 g/kg/day. During 8 w intragastric feeding period, mice continued to consume ad libitum HCFD to match caloric intake+weekly binges.

RNA-Seq of archived human liver biopsies: Archived liver biopsies from patients without liver disease (controls, n=10), early ASH (n=12), severe AH (n=18) and, ALD progression (terminal AH, n=10) were obtained from patients who had AH-related liver failure were obtained from the Liver Unit of the Hospital Clinic (Barcelona, Spain), Hôpital Huriez, (Lille, France), and Cliniques Universitaires Saint-Luc (Brussels, Belgium) and analyzed by RNA-Seq.

Detection of serum IL17A in patients with severe alcohol use disorder: Archived serum from healthy controls (n=18, Roudebush Veterans Administration Medical Center, Indianapolis) and excessive drinkers[42] (n=57, Fairbanks Drug and Alcohol Treatment Center, Indianapolis) were analyzed by ELISA (#433914, Biolegend). The study was approved by the Indiana University Purdue University Institutional Review Board, the Research and Development Committee at Roudebush Va., and Fairbanks Drug and Alcohol Treatment Center, see Suppl. Methods.

Experimental CIE-2BC model of alcohol dependence in mice: Single-housed male mice (♂ C57BL/6J, 10 w old) were trained to self-administer ethanol (15% v:v) in 2 h two-bottle choice (2BC) sessions conducted daily[43]. Upon stabilization of ethanol intake, mice were split, and exposed to either chronic intermittent ethanol (CIE, dependent mice) or Air (non-dependent mice) inhalation. Weeks of CIE consist in 4 cycles of 16 h intoxication/8 h withdrawal, followed by withdrawal from vapor days 3-7. Prior to each 16 h intoxication, CIE mice were primed with ethanol (1.5 g/kg, imp., target blood alcohol level=200 mg/dl) and pyrazole (1 mmol/kg, i.p., to stabilize ethanol clearance rate) to inhibit alcohol dehydrogenase and prevent alcohol metabolism in the liver. Air mice were treated with pyrazol alone. 2BC resumed after withdrawal day 3-7; weeks of 2BC were alternated with weeks of CIE. Repeated rounds of CIE increased voluntary consumption of ethanol during 2BC sessions, as measured by a higher intake of CIE mice compared to Air mice during withdrawal days 3-7.

Statistics: Comparisons of 2 groups were analyzed using an unpaired, 2-tailed Student's t test, and presented as the mean+SD. ANOVA with a Bonferroni's test was used for multiple pair-wise comparison between different groups. Comparing voluntary alcohol intake in 2BC-CIE mice are the mean±SEM. A p value <0.05 was considered statistically significant.

Experimental model of acute alcoholic steatohepatitis: (the NIAAA model: chronic ethanol Lieber-DeCarlie diet+single alcohol binge)[1]. Mice (♂ C57BL/6, 12 w old, n=7/group) were fed with a liquid diet containing 5% ethanol for 10 days, and at day 11 gavaged with a single dose of ethanol (5 g/kg, 20% ethanol), and sacrificed 9 h post binge. Control littermates were pair-fed with 9 g maltose dextrin/kg of body weight.

Experimental model of chronic alcoholic steatohepatitis: (chronic ethanol Lieber-DeCarlie diet+weekly binges[2]): Mice (♂ C57BL/6, 12 w old, n=8/group) were fed ad libitum for 2 weeks with a liquid "Western diet" (high in cholesterol (1%) and saturated fat (27% Cal), following by 8 weeks of an ethanol-containing Western diet. Ethanol intake was gradually increased from 1% (w/v) on day 1 to 4.5% (w/v) on day 12 until the end of 8th week of feeding. From the second week of ethanol feeding, a weekly binge dose of ethanol (gradually increased from 3.5 g/kg to 4.5 g/kg) was given via a stomach tube and repeated 7 times. Mice were sacrificed 24 h after the alcohol-binge treatment.

Detection of serum IL17A in patients with severe alcohol use disorder: Healthy controls (n=18, non-smokers without underlying medical illnesses) were recruited at the Roudebush Veterans Administration Medical Center (Indianapolis, IN). Excessive drinkers (n=57, defined by NIH/NIAAA guideline: ≥21 years of age; >4 standard drinks/day (or >14 drinks/week) in men; and >3 drinks/day (or >7 drinks/week) in women[3] were recruited from Fairbanks Drug and Alcohol Treatment Center (Indianapolis, IN). Exclusion criteria: active and chronic medical diseases; history of chronic HCV/HBV, or systemic infection within 4 weeks prior to the study. The Time Line Follow-Back questionnaire was used to determine the quantity of alcohol consumption over the 30-day period before the enrollment[4,5]. Blood samples were obtained for complete blood count and hepatic panel, serum was analyzed using IL-17A ELISA kit (R&D Systems, #D1700). Excessive drinkers were further dichotomized into those with normal (ALT<40 U/L) and elevated ALT (ALT≥40 U/L). The study was approved by the Indiana University Purdue University Institutional Review Board, the Research and Development Committee at Roudebush Va., and Fairbanks Drug and Alcohol Treatment Center. All participants provided written informed consent.

Serum ALT and AST measurement: The serum concentrations of alanine aminotransferase (ALT) and aspartate amino-transaminase (AST) were evaluated according to the kit protocol (Fisher Infinity., #ALT NC9511745).

Histology and immunohistochemistry: Immunohistochemistry was performed on formalin-fixed tissues using anti-α-SMA Ab (Abcam, #ab5694 1:200), anti-desmin (Fisher Neuromarkers, #RB-9014-P0 1:100), anti-F4/80 Ab (eBioscience, #14-4801-82 1:100), anti-4-HNE Ab (Alpha Diagnostic international Inc., #HNE11-S 1:100), GFAP (BD Bioscience, 556330 1:1000), Iba1 (Abcam, ab5076 1:200), Albumin (Biorad, AHP1478 1:100), Caspase 3 (Abcam, ab13847 1:100), Zo-1 (BD Bioscience, 610966 1:100), and DAPI (Invitrogen, D21490). HRP or fluorescein conjugated secondary antibodies were obtained from Invitrogen or Vector ImmPress (anti-rabbit MP-7401 and anti-rat MP-7444), and visualized by 3,3'-diaminobenzidine tetrahydrochloride staining (Vector Laboratories). Slides were counterstained with Hematoxylin. Images of seven non-overlapping fields were randomly selected were taken using Olympus microscope, and quantified using Image J™ (https://imagej.net/docs/examples/stained-sections/index-.html), and (https://imagej.nih.gov/ij/developer/macro/macros.html).

Quantitative RT-PCR was performed using ABI 7700 Sequence Detector™ (Applied Biosystems). Frontal cortex, hippocampus, and cerebellum were micro-dissected using dissection microscope from fresh isolated brain tissues. Total RNA was isolated from livers or brains using RNeasy columns (Qiagen). Expression level of selected genes were calculated vs housekeeping gene HPRT using the ΔΔ CT™ method (Invitrogen). The data are relative mRNA level compared to control, mean+SD, $*p<0.05$, $**p<0.01$.

The whole brain MRI: Dependent and non-dependent mice were treated with the anti-IL-17A Ab or IgG, brains were perfused with a fixative 7 days after the final administration of anti-IL17A ab (3 days after the last 2BC session). Macrostructural changes of the brain were evaluated by volumetric analysis of T2-weighted MRI scans of the whole brains.

Western Blotting analysis: The primary antibodies and dilutions were as follows: anti-CYP2E1 Ab (Fisher ab1252 1:3000), anti-IL17A Ab (eBiosciences 14-7175-81 1:1000) and anti-β-actin Ab (Sigma, a5441, 1:5000).

In situ RNA hybridization: IL17A mRNA was detected in samples using RNAscope in situ RNA hybridization. Livers and brains were formalin fixed and paraffin embedded. 4 μm tissue sections were collected in an RNase-fee manner, dried overnight, backed (for 32 min at 60° C.), de-paraffinized, and subjected to antigen retrieval (two sequential treatments with protease at 65° C. and 75° C. for 12 min each, Advanced Cell Diagnostics). In situ hybridization (ISH) was performed on a Ventana Discovery Ultra automated stainer; IL17A-specific RNA target z-DNA probe sets[6] were provided by the manufacturer (Ventana Medical Systems, Tucson, USA). Following amplification, horseradish peroxidase-labeled mRNA was visualized using 3,3' diaminobenzidine (DAB), sections counterstained with hematoxylin.

Isolation of hepatocytes and Kupffer cells: Livers were perfused using pronase/collagenase method. Single-cell suspensions were centrifuged at 50 g for 1 min to pellet the hepatocyte fraction. The remaining non-parenchymal cell fraction was collected. Kupffer cells were isolated by gradient centrifugation (15% NYCODENZ™) following by magnetic sorting with anti-CD11b magnetic beads (Miltenyi Biotec)[7].

Isolation of astrocytes and microglial cells: Primary astrocytes were isolated from the postnatal pups (P1) using DNase (300 g/ml, Roche) and trypsin (0.25%, Sigma-Aldrich) digestion method, cultured and sort purified[8]. Primary microglial cells were isolated using anti-CD11b Ab-conjugated magnetic beads (Miltenyi Biotech). Cells ($5\times10^5$) were cultured (DMEM with 10% FBS), and treated with IL17A cytokine (5 ng/ml) or PBS for 6 h, harvested and analyzed by qRT-PCR.

RNA-Seq of archived human liver biopsies: Patients were admitted to the Liver Unit of the Hospital Clinic (Barcelona, Spain), Hôpital Huriez, (Lille, France) and Cliniques Universitaires Saint-Luc (Brussels, Belgium) between January 2007 and December 2009. All patients included gave written informed consent. Liver biopsies were obtained using a trans-jugular approach except for explanation samples which were collected at the time of surgery. Blood samples were obtained at the time of biopsy for complete blood count and hepatic panel or before surgery to determine laboratory. A total of 51 patients with ALD were included: a) Patients with Early ASH, who were non-obese high alcohol intake patients who presented mild elevation of transaminases and histologic criteria of steatohepatitis (n=12); b) patients with severe AH, with MDF>32 (n=18); c) ALD progression ("terminal" AH), which were obtained from patients who had AH-related liver failure and who undergone liver transplantation (n=10). These groups were compared with samples from control subjects with non-diseased liver (N=10) for whom liver biopsy was performed for reasons unrelated to liver disease. Exclusion criteria: malignancies, liver disease of non-ASH origin. High throughput transcriptome profiling by RNA sequencing (RNA-Seq) was performed with liver samples. High quality total-RNA was sequenced using Illumina HiSeq2000 platform. Libraries were built using Illumina TruSeq Stranded Toral RNA Ribo-Zero GOLD™. Sequencing was paired end (2×100 bp) and multiplexed. Ninety-eight paired-end sequenced samples obtained an average of 36.9 million total reads with 32.5 million (88%) mapped to GRCh37/hg19 human reference. Short read alignment was performed using STAR alignment algorithm with default parameters[9]. Normalization of gene expression level across samples was computed as transcripts per million mapping read. To quantify expression from transcriptome mappings we employ RSEM[10]. Principal component analysis (PCA) were done using made4 library[11]. Analyses of differential expression were performed with the Limma™ package by the Limma Voom™ method. Cyclic loess normalization was applied, followed by log transformation of the counts per million and mean-variance adjustment using the voom function. Limma™ workflow was used to assess the differential expressed genes. Ingenuity Pathway analysis was used to determine the enrichment of IL17 related pathways (canonical pathways analysis) and the footprint of IL17 in the transcriptome (upstream regulator analysis).

Whole mouse genome gene expression via RNA-Seq: Strand specific mRNA-sequencing libraries (polyA+) were generated using Illumina's TruSeq™ stranded mRNA library prep kits, and sequenced on an Illumina HiSeq2500™ to a depth of approximately 25 million reads. Sequencing reads were aligned to the mouse genome (NCBI MGSCv37, mm9) using STAR[9]. Gene expression levels, gene ontology, and clustering were performed using HOMER and Cluster3.0/Java Tree View™ [12]. Differentially expressed genes were identified using edgeR[13].

Whole mouse genome gene expression via Microarray: Primary astrocytes ($5\times10^5$) were stimulated with IL-1β (5 ng/ml), TGF-β1(5 ng/ml) or vehicle for 24 h, harvested, and mRNA was purified using RNAeasy™ columns (Qiagen); and 160 ng of purified RNA per sample was labeled using the LRILAK PLUS™, 2-color, low RNA input Linear Amplification kit and hybridized to a Whole Mouse Genome Microarray 4×44 K™ 60mer slide according to the manufacturer's instructions (Agilent, Santa Clara, CA). Slides were scanned using the Agilent GZ505B Scanner™ and analyzed using the Gene Spring Software™ (Agilent). Differentially regulated genes were defined as those with significant absolute expression (>9-$\log_2$ intensity value) and exhibiting 2-fold compared with the maximal value in all other samples.

Enzyme linked immunosorbant assay (ELISA): Serum and cerebrospinal fluid (CSF)[14] were collected, the levels of L17A (Biolegend, #432501), TNF-α (Biolegend, #430901), IL-1β (Biolegend, #432601), TGF-β1 (eBioscience, #88-8350-22), IL-6 (Biolegend, #431301) were measured[15]. The concentration of CSF cytokines was calculated as ng/ml and normalized by total protein concentration.

Vascular permeability assay: Air, and CIE mice were injected with Evans blue solution (30 mg/kg, i.v., Sigma)[16] immediately after the last vapor session, and sacrificed 1 h later. Tissues were perfused with 20 ml PBS. Evans blue dye was extracted in 0.5 ml formamide (55° C., 24 h). Yield of dye was measured spectrophotometrically (λ=610 nm), the data are ng/mg of brain tissue.

Figure Legends

FIG. 6

Progression of ALD is Associated with Activation of IL17 Signaling

Wt mice (♂ C57BL/6, 8 w old, n=7-10/group, 2-3 independent experiments) were subjected to acute and chronic ASH; alcoholic liver fibrosis. Livers were stained with H&E, Sirius Red, and anti-F4/80$^+$ Ab, positive area was calculated as percent (FIG. 6A), or analyzed by qRT-PCR, data are fold induction vs chow-fed mice, student's test, *p<0.01 (FIG. 6B). FIGS. 6C-D: Archived liver biopsies from patients with early and severe ASH, and alcoholic liver fibrosis were subjected to RNA-Seq, FIG. 6C: the data are GO terms (vs healthy controls). FIG. 6D: Signaling pathways activated in livers of patients with alcoholic liver fibrosis; see also FIGS. 6E-H and FIGS. 7E-M).

FIG. 7

IL17RA$^{-/-}$ mice are protected from alcoholic liver fibrosis

Figure 7B:
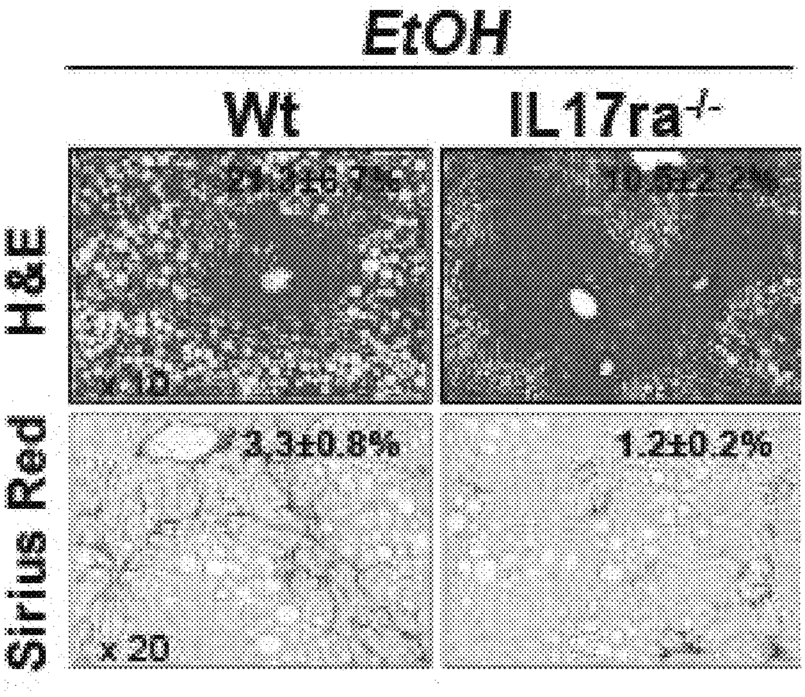
Figure 7C:
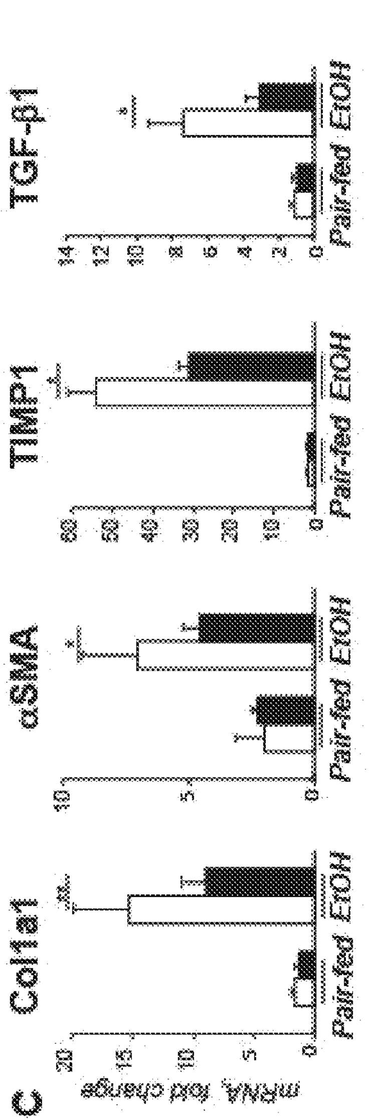
Figure 7D:
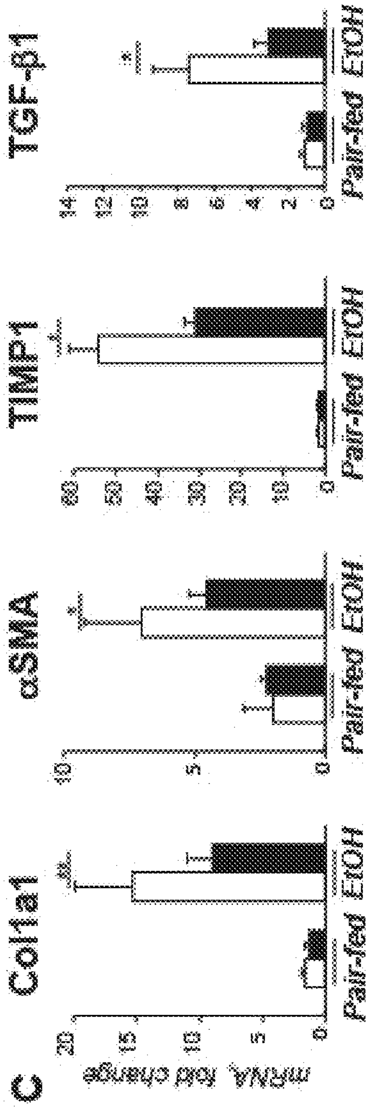

Wt and IL17ra$^{-/-}$ littermates (♂ C57BL/6, 12 w old, n=5-9/group, 2 independent experiments) were IG alcohol fed. FIG. A: Serum levels of ALT (IU/L) and EtOH (nM) were measured. FIG. 7B: Livers were stained with H&E, and Sirius Red, positive area was calculated as percent, micrographs are shown using ×20 objective. FIG. 7C: Expression of fibrogenic and FIG. 7D: inflammatory gene mRNA, data are fold change (vs IG alcohol-fed wt mice), student's test, *p<0.05, p<0.01, see also FIG. 8**I-P.

FIG. 8

Therapeutic Blockade of IL17A Reduces Alcoholic Liver Fibrosis by Approximately 50%

Figure 4:
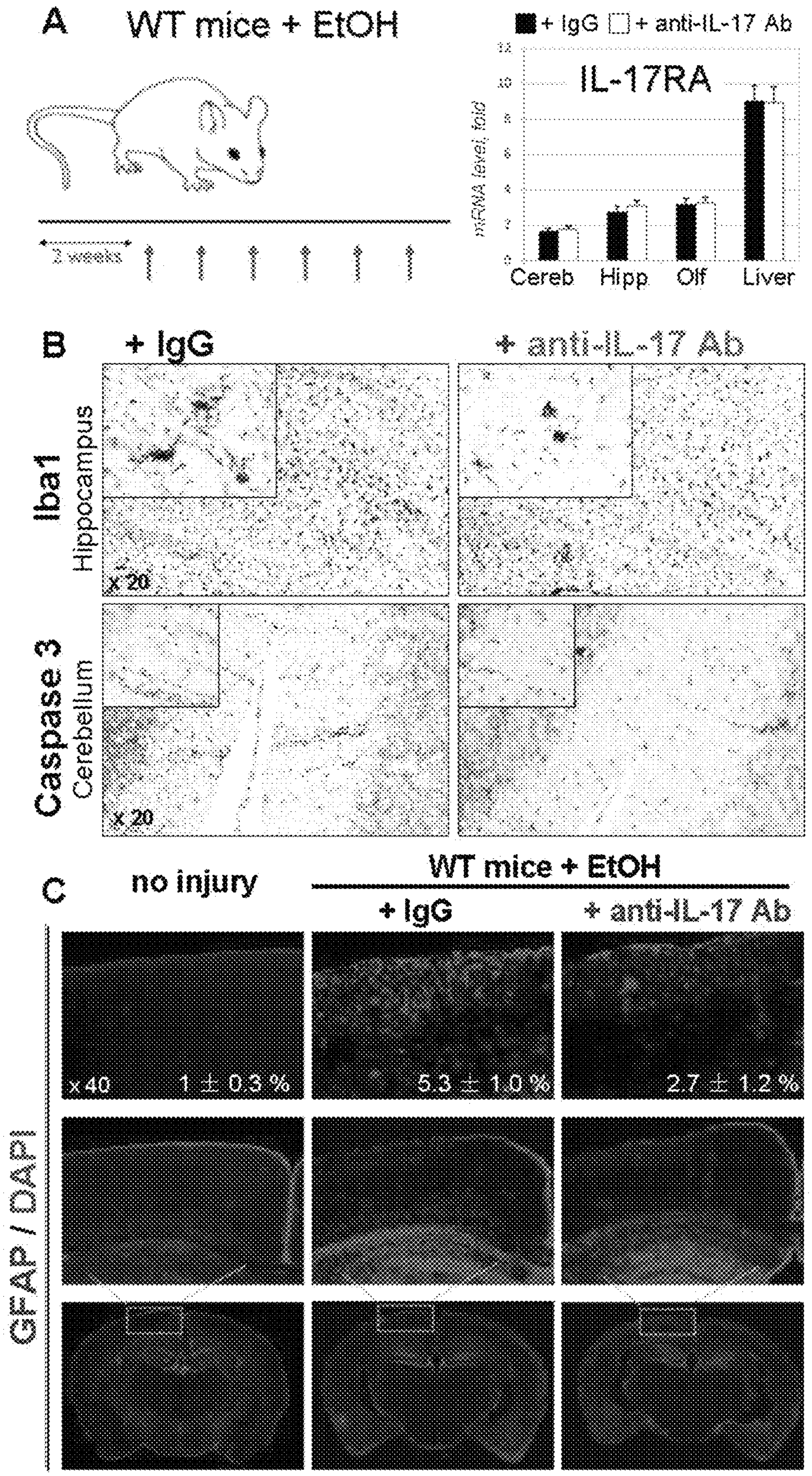
FIG. 4A-C illustrates data showing that alcohol induced brain injury is reduced in mice therapeutically treated with anti-IL-17 Ab.
Figure 5:
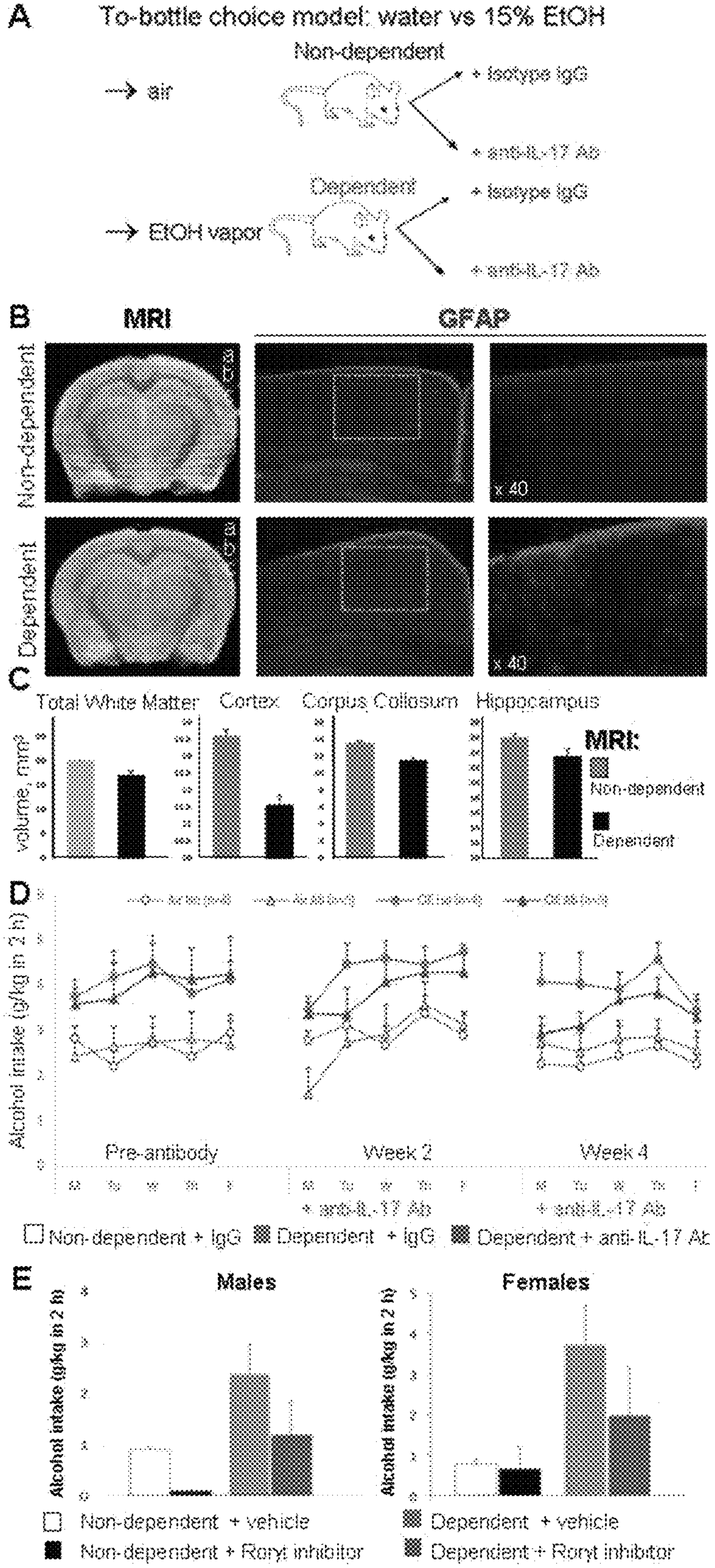
FIG. 5A-E illustrates data showing that treatment with anti-IL-17 Ab or RORγt inhibitor prevents volunteer alcohol drinking in dependent mice: FIG. A schematically illustrates how mice (♂, 16 w old, n=5/group) were subjected to the CIE or air model of alcohol dependence.

FIG. 8A: IG alcohol-fed wt mice (♂ C57BL/6, 12 w old, n=12/group, 3 independent experiment) were treated; FIG. 8B: RORγt inhibitor (50 mg/kg/weight vs vehicle, oral gavage 4× week, or vehicle), or anti-IL17A Ab (25 mg/kg/weight vs IgG, i.p. once×week). FIG. 8C: Serum levels of IL17A (pg/ml), FIG. 8D: ALT (IU/L), and blood EtOH (nM) were measured. FIG. 8E-F: Livers were stained with H&E, and Sirius Red, positive area was calculated as percent, micrographs are shown using ×20 objective. FIG. 8G: Expression of inflammatory and FIG. 8H: fibrogenic gene mRNA, data are fold change (vs vehicle- or IgG-treated mice), student's test, *p<0.05, p<0.01 (see Suppl. FIGS. 4 and 5**)

FIG. 9

Therapeutic Blockade of IL17 Ameliorates Alcohol-Induced Brain Injury and Neuroinflammation Brains and SCF were collected from IG alcohol-fed wt mice (♂ C57BL/6, 12 w old, n=12/group, 3 independent experiment). Coronal sections from IG alcohol-fed mice; FIG. 9A: RORγt inhibitor or FIG. 9B: anti-IL17 Ab were immunostained for Iba1 (hippocampus, ×20 and ×100 objectives) or GFAP (cortex, ×4 and 40 objectives), FIG. 9C: positive area was calculated as percent. FIG. 9D: Expression of Iba1 and GFAP mRNA, data are fold change. FIG. 9E: CSF levels of L17A and TNF-α were measured by ELISA, (pg/ml), mRNA expression of TNF-α was measured by qRT-PCR, student's test, *p<0.05, p<0.01 (see FIG. 11, FIG. 12, FIG. 13, FIG. 14**).

FIG. 10

Therapeutic Inhibition of TL17 Suppresses Voluntary Alcohol Drinking in Alcohol-Dependent Mice FIG. 10A: Naïve mice (♂ C57BL/6J, n=4-6/experimental condition, 4 independent experiments) were subjected to 2BC sessions to determine baseline voluntary ethanol drinking. Mice were then exposed to either Air (non-dependent mice) or CIE (dependent mice). CIE produced an escalation of voluntary ethanol drinking during 2BC sessions conducted 3-7 days into withdrawal from vapor (vs non-dependent mice). Dependent and non-dependent mice (n=4-6/group) were treated either with ±anti-IL17A Ab, or RORγt inhibitor. Serum level of alcohol FIG. 10B, and IL17A; FIG. 10C: serum were measured. FIG. 10D: Voluntary alcohol intake (g ethanol/kg body weight) was measured during 2BC sessions (2 h) in Air and CIE mice±anti-IL17 Ab. The most significant effect was detected on the first day of treatment (withdrawal day 4: effect of Ab, $F(1,19)=6.6$, $p<0.05$; effect of CIE, $F(1,19)=9.7$, $p<0.01$; Ab by CIE interaction, $F(1, 19)=5.1$, $p<0.05$), and persisted throughout the week (withdrawal days 4-7: effect of Ab: $F(1,19)=3.5$, $p<0.08$). FIG. 10E: Air and CIE mice RORγt inhibitor. There was no immediate effect of RORγt inhibitor on voluntary ethanol drinking. The mice were then exposed to an additional week of CIE (or Air) and resumed 2BC sessions. The most significant effect was observed on withdrawal day 3 (effect of inhibitor, $F(1,20)=10.1$, $p<0.01$; effect of CIE, $F(1,20)=47.3$, $p<0.001$; inhibitor by CIE interaction, $F(1, 20)=7.2$, $p<0.05$) but persisted throughout the week (withdrawal days 3-6: effect of inhibitor, $F(1,20)=5.5$, $p<0.05$). The regimen of IL17A inhibition is specified (red arrows), student's test *p<0.05; and two way ANOVA (see FIG. 15).

FIG. 11

Therapeutic Inhibition of IL17 Suppresses Voluntary Alcohol Drinking in Alcohol-Dependent Mice Brains from Air and CIE mice anti-IL17 Ab were analyzed by FIG. 11A: the whole brain MRI (n=5-7/group), brain volume was calculated as $mm^3$, *p<0.05, or FIG. 11B-D) immunostaining for GFAP; FIG. 11B: whole brains (coronal sections), FIG. 11C: hippocampus and FIG. 11D: amygdala (sagittal sections) are shown, images are ×4, ×60 objectives, FIG. 11E: positive area was calculated as percent. FIG. 11F: Serum levels of IL17A protein were measured in excessive drinkers with normal ALT (<40 U/L, n=XX) and abnormal ALT (≥40 U/L, n=X), and healthy individuals (n=18). Data are IL17A concentration, pg/ml, presented as mean±S.D; p values were obtained from student's test, (see FIG. 16)

FIG. 6E

Analysis of liver pathology in mice subjected to experimental models of ALD (supports FIG. 6A) was performed by a pathologist in a double blinded manner. Mice with acute alcoholic steatohepatitis developed no steatosis or fibrosis. Mice with chronic alcoholic steatohepatitis developed grade 1-2 steatosis (median grade 1). Steatosis was primarily observed in hepatocytes in zone 2 (versus the typical centrizonal/zone 3 observed in patients). These mice also developed lobular inflammation (grade 1-2), minimal fibrosis (stage 0-1), no hepatocyte ballooning or Mallory-Denk bodies. Mice with alcoholic liver fibrosis developed steatosis (grade 3) with highest fat concentration in zone 2 followed by zones 1 and 3, a significant lobular inflammation (grade 2), hepatic fibrosis (stage 1-2), and spotty necrosis of hepatocytes, but no hepatocyte ballooning or Mallory-Denk bodies.

FIG. 6G

Experimental Model of Acute Alcoholic Steatohepatitis in Wt Mice:

Acute alcoholic steatohepatitis caused significant damage to hepatocytes (ALT 110±32 IU/L), mild hepatic inflammation, recruitment of neutrophils, upregulation of IL17A (↑2 fold), IL17RA (↑2 fold), and IL-23 (↑1.8 fold)[1]. Expression of fibrogenic genes (Colla1, α-SMA, TGFβRI) was not induced in these mice, suggesting that chronic-binge model of alcohol feeding mimics initial stages of alcoholic steatohepatitis in patients, and can be used to study the onset of ALD.

FIG. 7E-M

Experimental Model of Chronic Alcoholic Steatohepatitis in Wt Mice

Wt mice (♂ C57BL/6, 8 w old, n=12) were subjected to chronic-multiple binge alcohol feeding, or chow- or pair-fed. Chronic-multiple binge alcohol fed wt mice developed significant hepatocellular injury and steatosis, as demonstrated by increased ALT (121±30 U/I vs 60 U/I in the pair-fed mice, FIG. 7J), upregulation of alcohol-metabolizing enzyme cytochrome and P4502E1 (CYP2E1, increase ↑2 fold vs pair-fed mice, FIG. 7L), induction of oxidative stress (via induction of NOX4, p22 Phox, and p67 Phox, FIG. 7H), upregulation of hepatic triglycerides (↑2 fold), products of lipid peroxidation 4-HNE (↑3 fold) (FIG. 7K), and expression of adipogenic genes (increased expression of SREBP-1c, and suppression of PPARα, FIG. 7E). Increased flux of inflammatory cells (increase ↑2 fold vs pair-fed mice), including $Ly6G^+$ neutrophils (↑6 fold) and $F4/80^+$ Kupffer cells (↑2 fold) (FIG. 7K) was observed in livers of alcohol fed mice, and was associated with upregulation of pro-inflammatory cytokines IL-6 (↑2 fold), IL-1β (↑3.5 fold) (FIG. 7H), and neutrophil chemoattractant MIP-1 (↑10 fold) and MIP-2 (↑2.5 fold) (FIG. 7G), and TGF-β1 (↑1.5 fold, FIG. 7I), while expression of IL-8 and TNF-α was not significantly changed between alcohol- and pair-fed mice. Although hepatic expression of α-SMA (↑1.3 fold), Colla1 (↑2.2 fold), and TIMP1 (↑5 fold) (FIG. 7I) were upregulated above the basal level, the number of $Desmin^+$ HSCs in livers of alcohol-fed mice was moderately increased (↑1.5 fold vs pair-fed mice, FIG. 7K), indicating that these mice exhibited activation of HSCs associated with the very onset of liver fibrosis, suggesting that this model of alcohol feeding recapitulates advanced alcoholic steatohepatitis similar to that observed in patients.

FIG. 8I-P

Figure 7J:
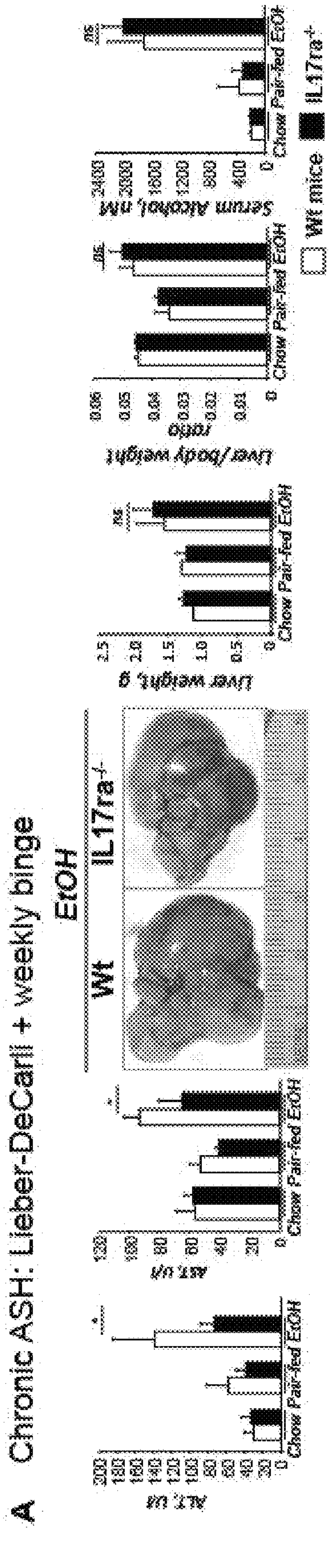
Figure 7K:
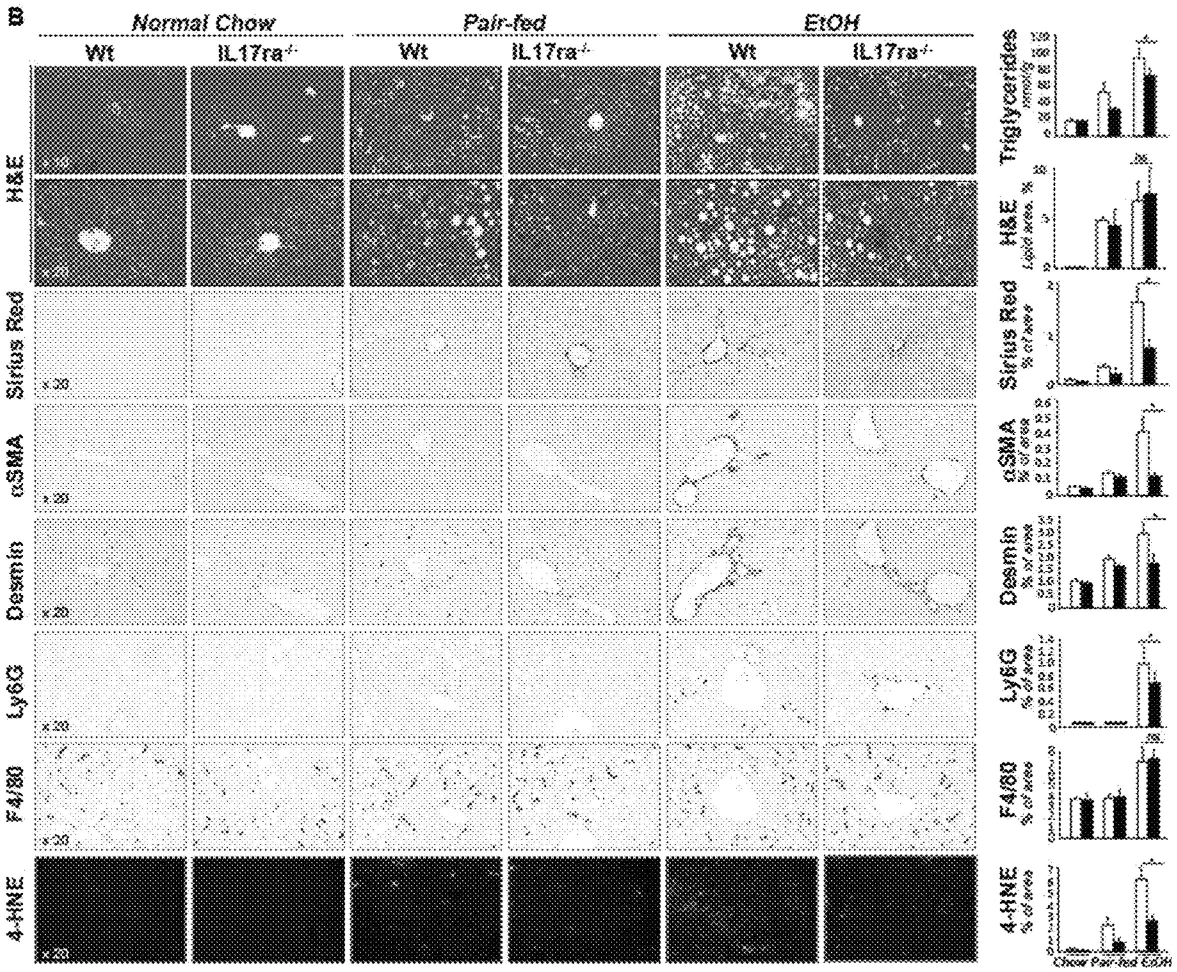
Figure 8J:
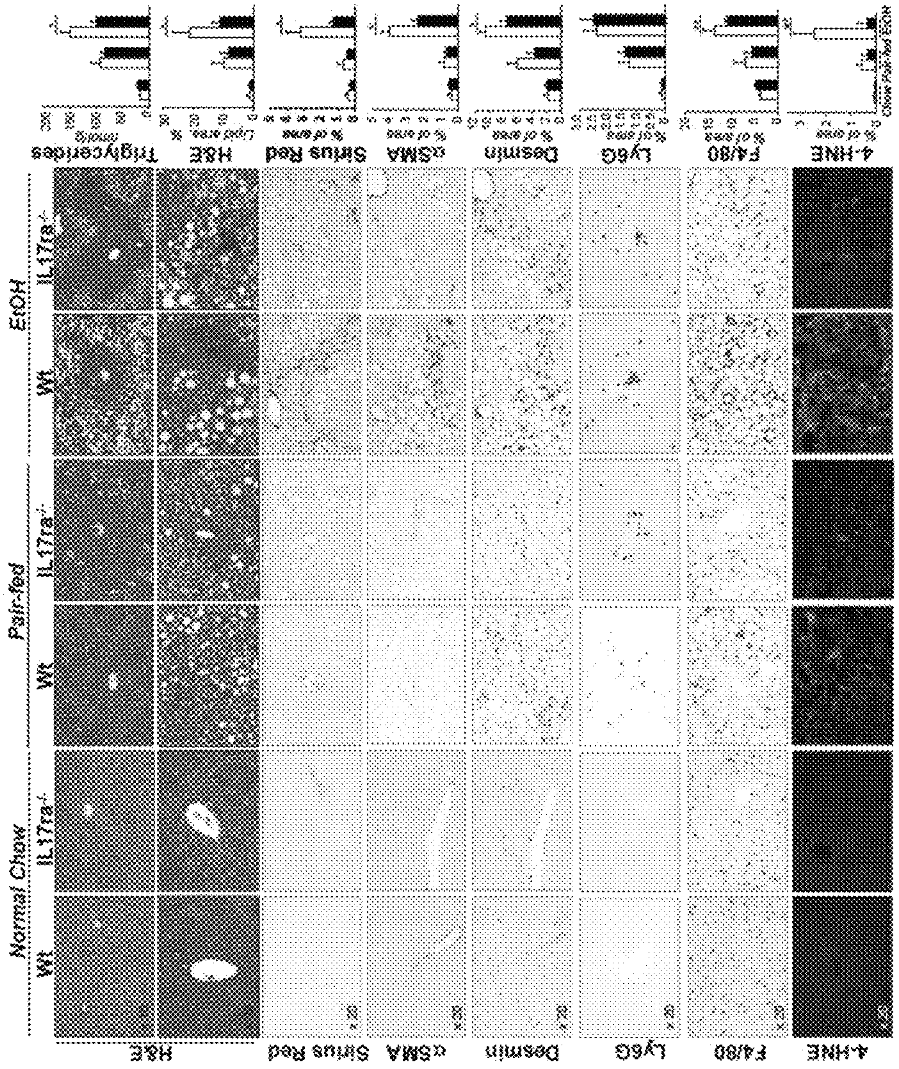
Figure 8K:
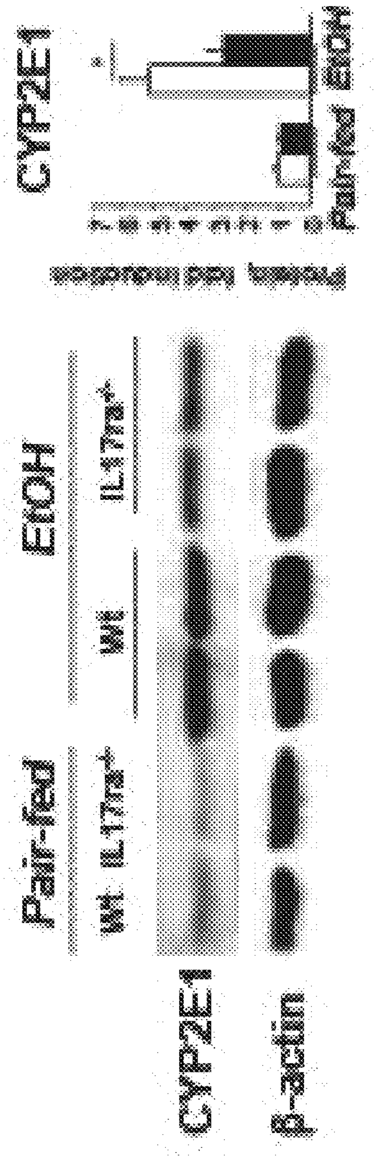
Figure 8L:
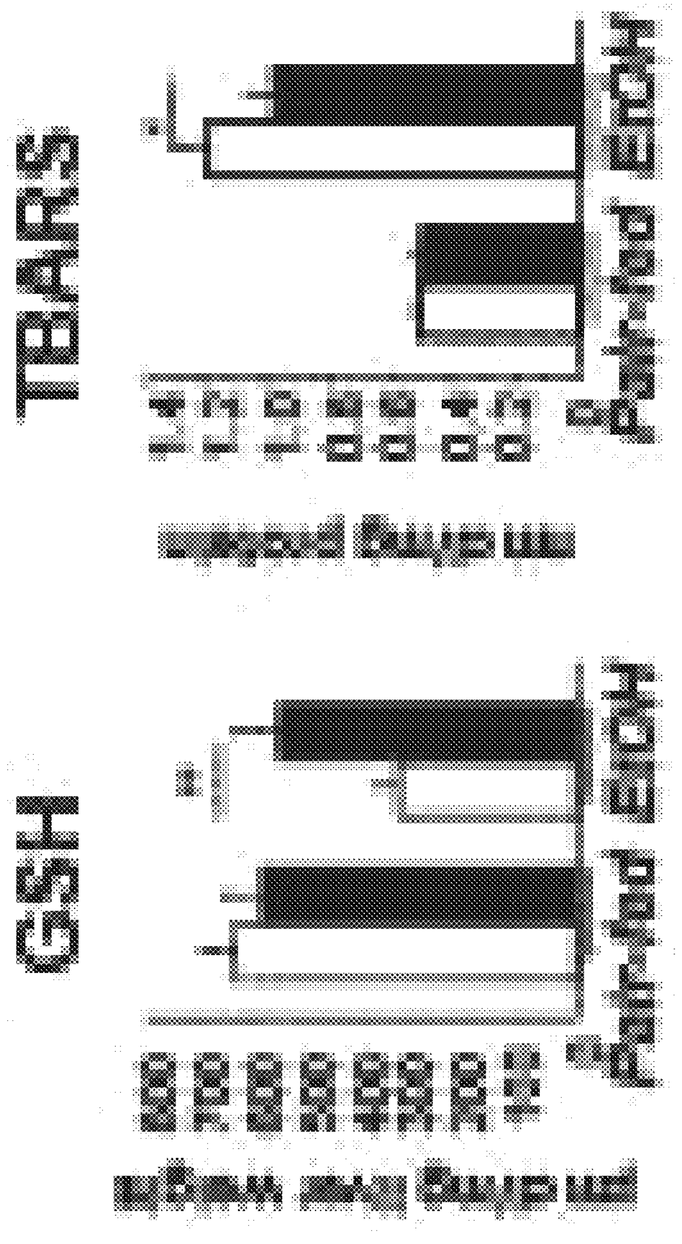
Figure 8M:
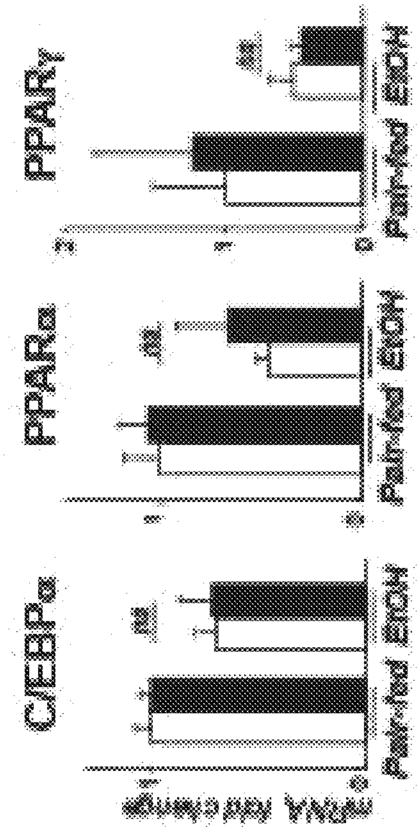
Figure 8N:
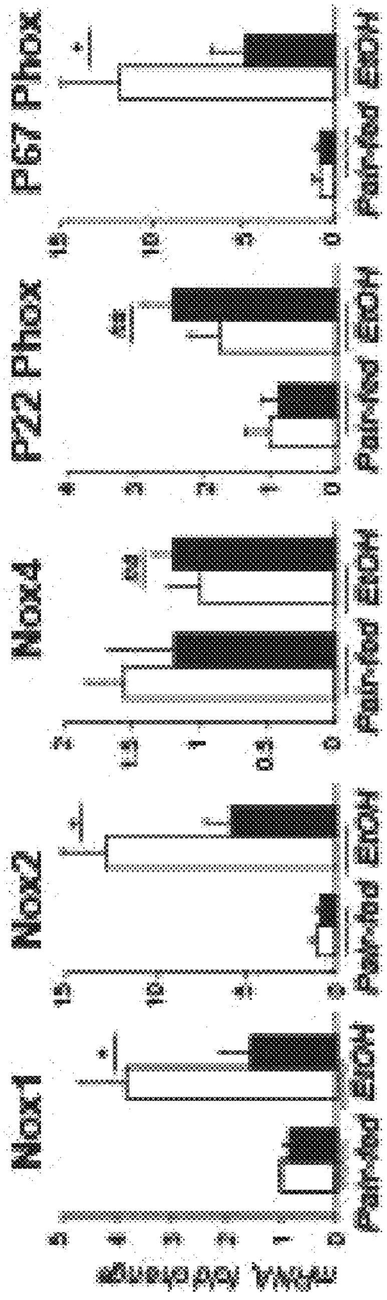
Figure 8O:
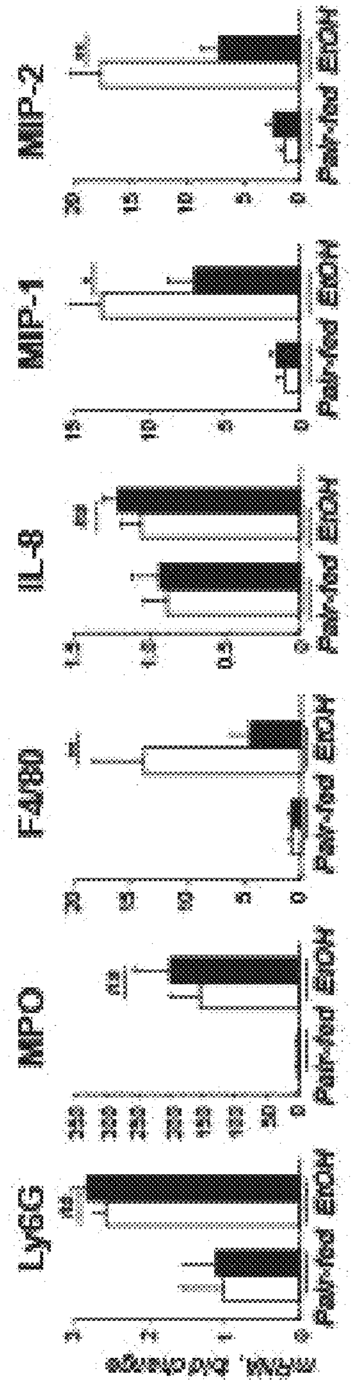
Figure 8P:
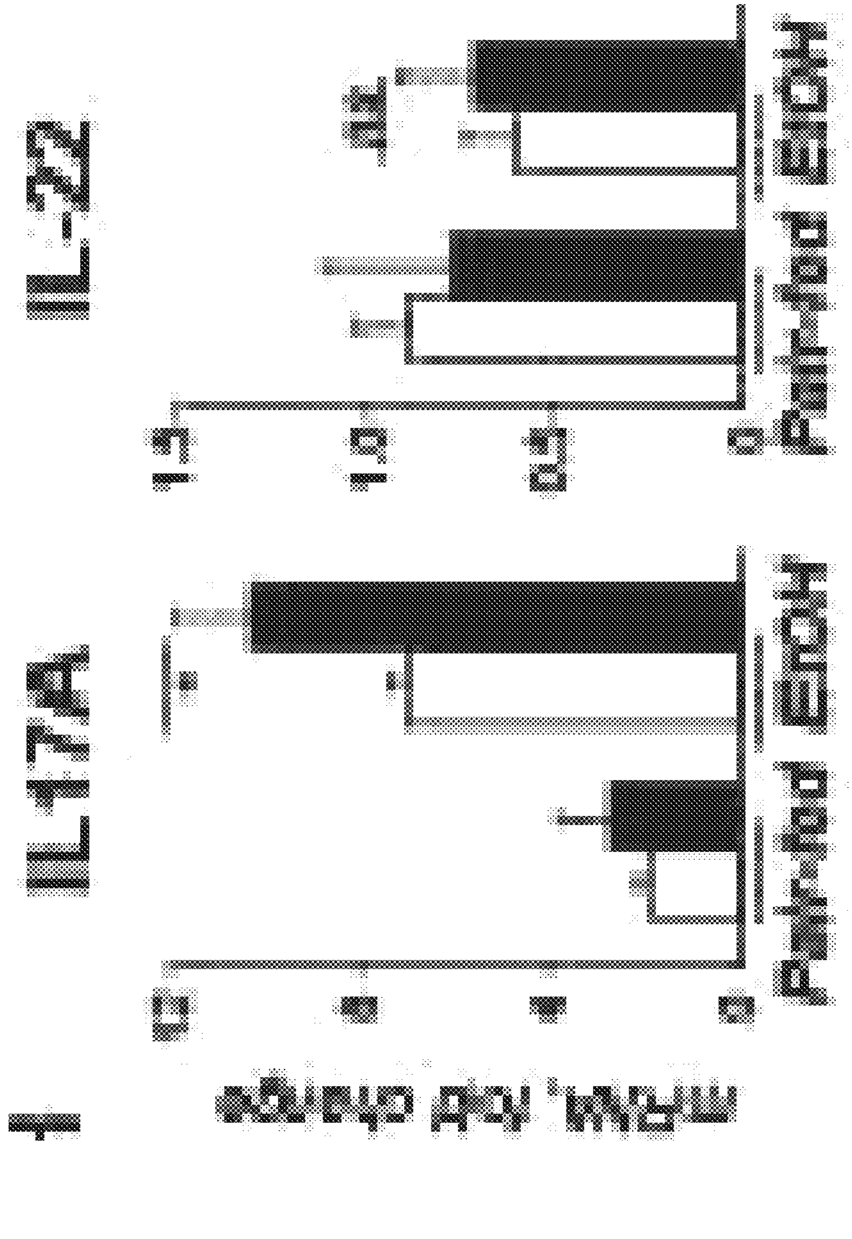

Experimental model of alcoholic liver fibrosis in wt mice (supports Suppl. FIG. 3) Wt mice (♂ C57BL/6, 8 w old, n=8) were surgically operated to insert intragastric catheter, and upon recovery (2 weeks) were subjected to intragastric (IG) alcohol feeding (Tsukamoto-French model)[17-20] or pair-fed. In comparison, chronic alcohol fed mice+multiple binge, IG alcohol-fed mice developed severe hepatocellular injury, as shown by increased ALT (215±51 U/I vs 80±15 U/I in pair-fed mice, FIG. 7J), upregulation of P4502E1 (CYP2E1, ↑5 fold increase vs pair-fed mice, FIG. 8K). Hepatic steatosis and the triglycerides content (↑1.5 fold vs pair-fed mice, FIG. 8J) were strongly increased in IG alcohol-fed mice, while expression of beta-oxidation genes (PPARα) was suppressed (↓2 fold, FIG. 8M). Induction of lipid peroxidation enzymes 4-HNE (↑3 fold, FIG. 8J) and TBARS (↑2 fold) was associated with reduced levels of the GSH (↓2 fold) (FIG. 8L), indicative of development of intrahepatic oxidative stress and severe liver injury. In support, we observed significant increase in expression of NOX1, NOX2, and p67 Phox (FIG. 8N). Unlike chronic-multiple binge alcohol fed mice (FIG. 8N), expression of hepatic NOX4 was not changed in IG alcohol-fed mice, indicating that differential expression of alcohol-induced genes depends on the regiment/duration of alcohol administration (similar to that observed in patients with different stages of ALD). In agreement, IG alcohol-fed mice developed severe fibrosis and inflammation, as shown by increased positive area of Sirius Red staining (↑3.5 fold vs pair-fed mice), and staining for $F4/80^+$ Kupffer cells (increase ↑3.5 fold) (FIG. 8J). We observed strong induction of hepatic α-SMA (↑6 fold), Colla1 (↑14 fold), and TIMP1 (↑50 fold) in livers of IG alcohol-fed mice (FIG. 7C), which correlated with increased number of activated $Desmin^+$ HSCs (↑2 fold vs pair-fed mice, Suppl. FIG. 3B). Development of liver fibrosis in these mice was associated with release of profibrogenic factor TGF-β1 (↑7 fold, FIG. 2C) and the variety of pro-inflammatory cytokines IL-6 (↑15 fold), IL-1β (↑15 fold), TNFα (15 fold) (FIG. 7D), including chemoattractant MIP-1 (↑13 fold) and MIP-2 (↑16 fold) (FIG. 8O). Furthermore, expression of IL-8 and Ly6G was not changed between IG alcohol- and pair-fed mice (FIG. 8O), suggesting that Kupffer cells (but no longer neutrophils) critically mediate progression from steatohepatitis to fibrosis at this stage of ALD.

FIG. 12A-D

Activated Astrocytes Serve as a Significant Source of Cytokines and Chemokines (Supports FIG. 14)

Figure 14B:
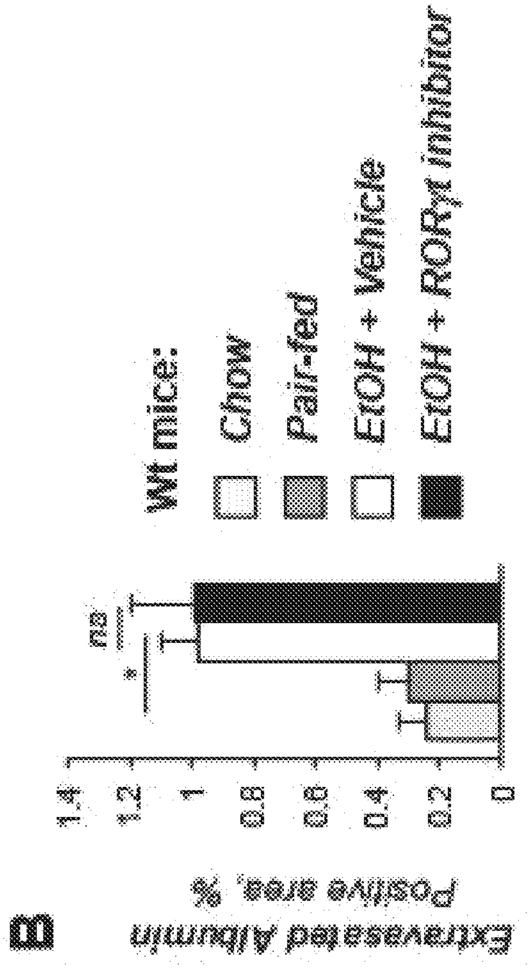
FIG. 14A-C illustrate data showing that IL17A signaling facilitates proliferation/activation of astrocytes and promotes neuroinflammation in IG alcohol-fed mice.

In response to IL17A stimulation, microglial cells produce TGF-β1 and IL-β1. To determine the effect of microglia-derived cytokines on astrogliosis 21,22, cultured $GFAP^+$F4/80-astrocytes were in vitro stimulated with TGF-β1 or IL-β. We confirmed that astrocytes do not express IL17A family of cytokines (IL17AA, IL17AB, IL17AC, IL17AF, except IL17AD)[23], but express all three IL17A receptors (IL17ARA, IL17ARC and IL17ARD. Cultured astrocytes highly expressed IL-11, IL-18, IL-27, IL-33 (and IL-33RA), TGF-α and β, tenascin C (Tnc), and IK cytokine mRNA, but did not express IL-1α or β, or TNF-α mRNA. Upon stimulation with IL-β1, astrocytes strongly induced the hallmark inflammatory response, hallmark complement; response to cytokines, response to toxic substances, regulation of cell-cell adhesion (see the GO enrichment profile, FIG. 14B), and serve as a significant source of pro-inflammatory cytokines and chemokines, such as CCL7 (↑400 fold vs vehicle), CCL2 (↑200 fold), IL-6 (↑20 fold), Cxcl1 (↑14 fold), and CCL5 (↑13 fold) (FIG. 12D). IL-1β-stimulated astrocytes also upregulated expression of IL-1R1, IL-10Rb, IL-13Ra, IL-15Ra, IL-4Ra mRNA, suggesting that IL-1β signaling exerts inflammatory responses in activated astrocytes (FIG. 14B). Different set of genes was induced in TGF-β1-stimulated astrocytes, and was associated with cellular response to growth factor stimulus, hallmark of TGF-β and TNF-α signaling, tissue morphogenesis, negative regulation of cell death (see the GO enrichment profile, FIG.

14C), strongly upregulated expression of TGF-β1 and TGFβRI, NOX4, PA-1, TIMPs, fibronectin, IL-6, PDGFα and β, CTGF, IL-11, FGF2 and 18, several kinases (Irak2 and Jag1, Jun B), integrins (Itga 11, Itga 5 fibronectin receptor a, Itgb5), several members of actin and kinesin families (FIG. 14D). In addition, cultured astrocytes expressed glutamate receptors (mGluRs) that mediate neuron-astrocyte signaling (FIG. 14D). Under pathological conditions, neurodegeneration triggers expansion of reactive astrocytes, upregulation of TGF-β 1, and mGuRs, which together generate neuroprotective effects[24]. Here we demonstrate TGF-β1 induced expression of glutamate transporters (Slc1a4, Slc20a1, Slc22a23) in astrocytes, in contrasts to IL-1β which suppressed expression of glutamate receptors Gria 1 and 4 in astrocytes, suggesting that IL-1β and TGF-β1 have opposing effects on glial-neuronal communication.

FIG. 15

Experimental Model of Alcohol Dependence in CIE-2BC Mice (Supports FIG. 16)

Figure 16A:
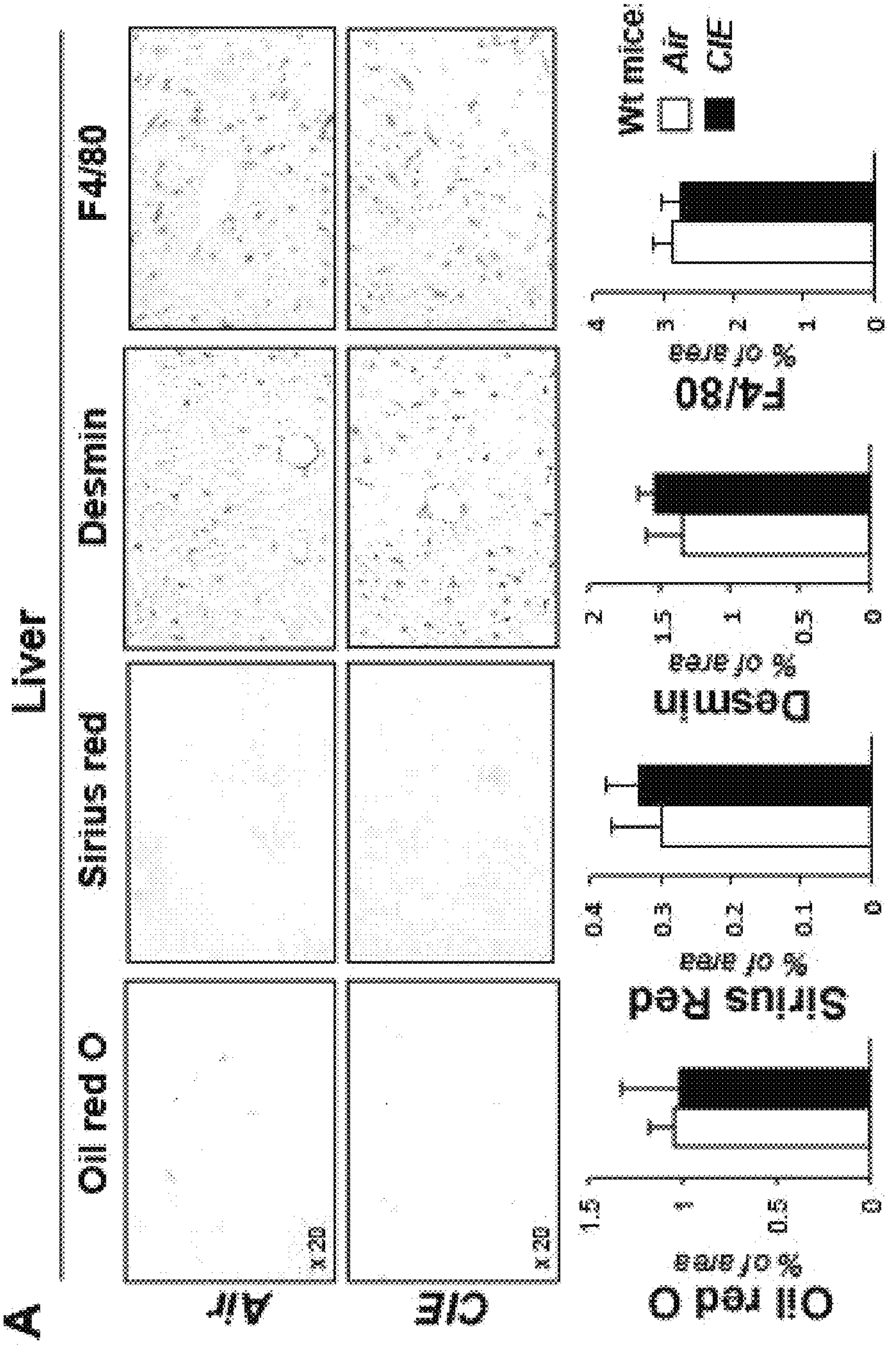
FIG. 16A-G illustrate data showing that blockage of IL17A suppresses volunteer alcohol drinking in alcohol-dependent mice: naïve co-housed mice developed alcohol dependence (CIE) vs non-dependent controls (Air) and subjected to sessions of volunteer alcohol drinking (2BC)
Figure 16B:
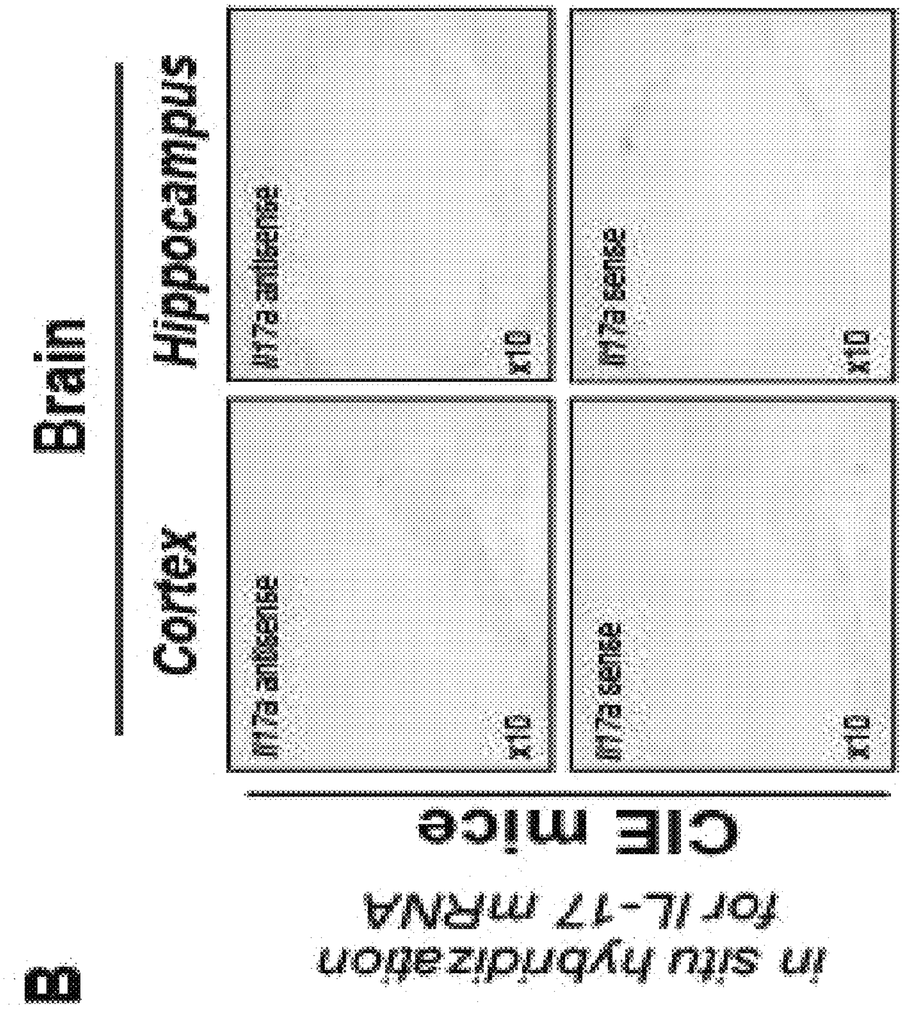
Figure 16C:
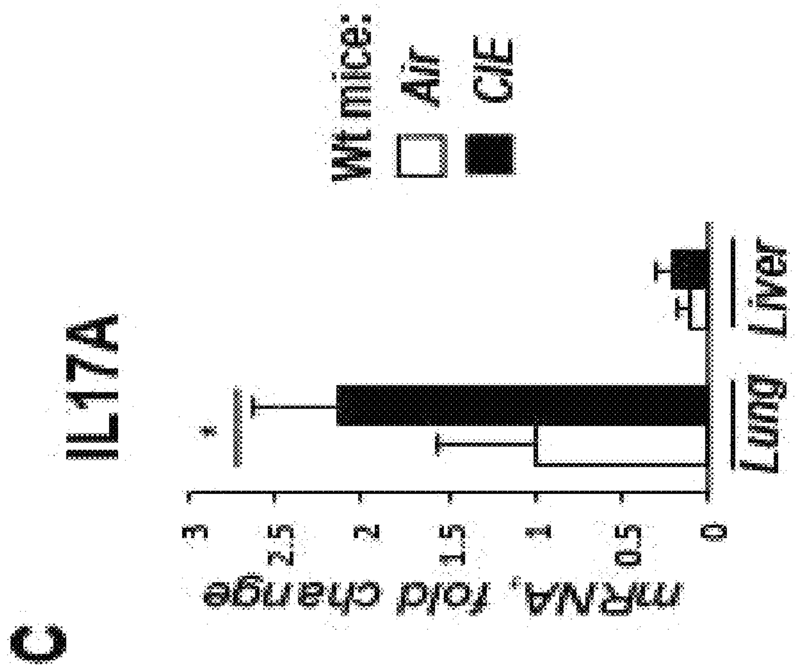
Figure 16D:
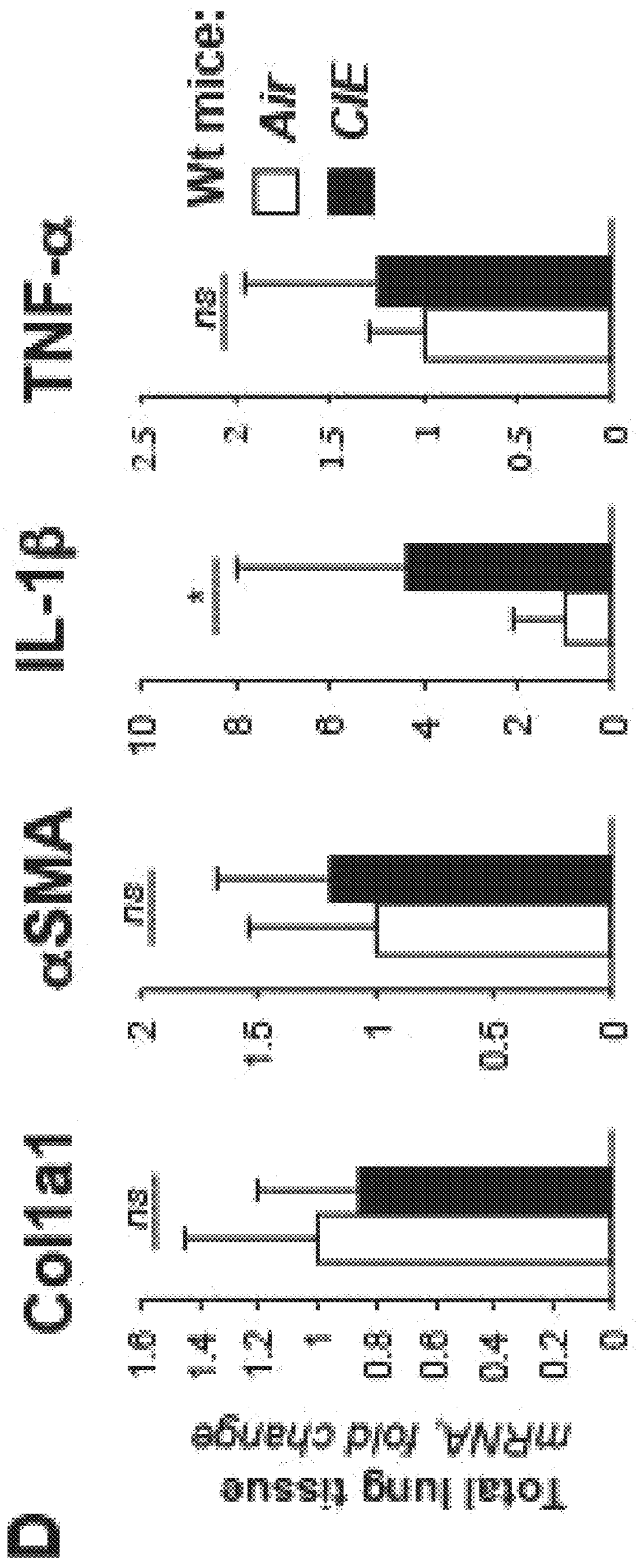
Figure 16E:
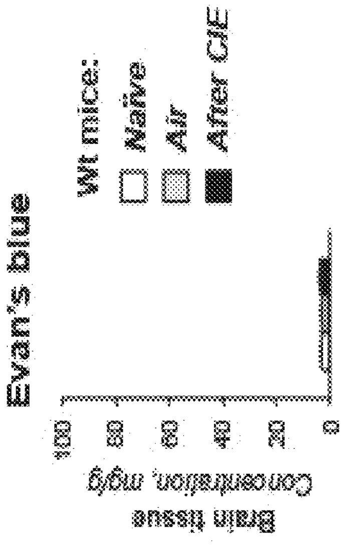
Figure 16F:
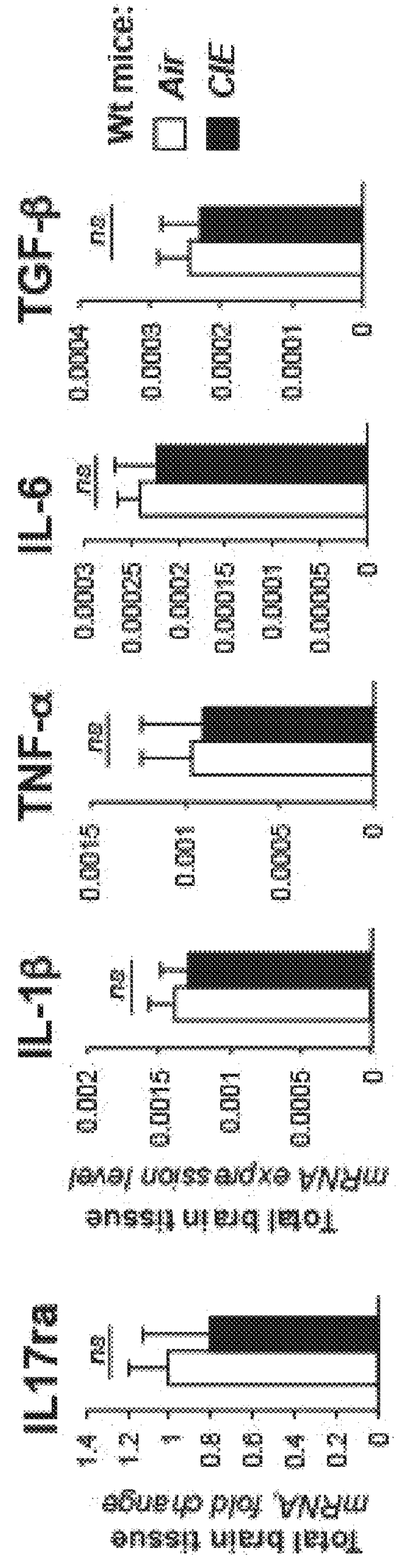
Figure 16G:
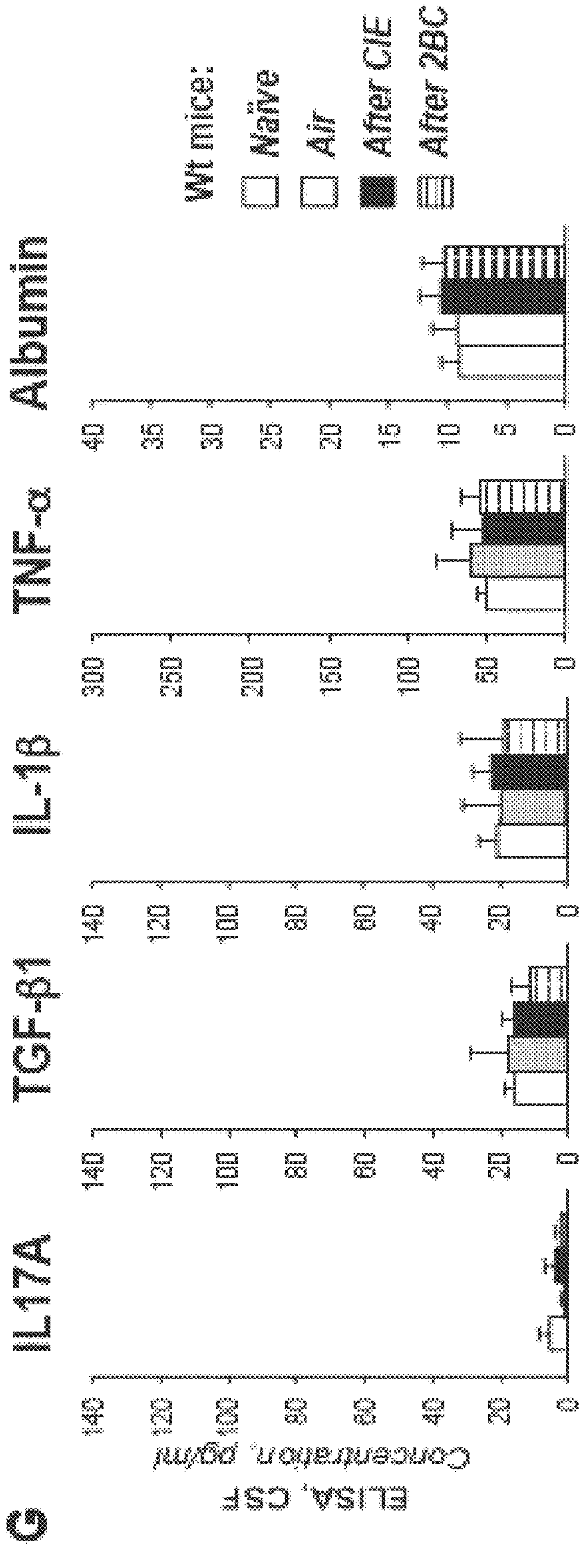

Diffusion of serum IL17A through the damaged BBB and neuroinflammation and were identified as key mechanisms underlying IG alcohol-induced brain injury in mice (FIG. 9E). Here we tested if similar mechanisms are activated in alcohol-dependent 2BC-CIE mice. To establish the relationship between increased serum IL17A and astrocyte activation in CIE mice, cerebrospinal fluid (CSF), and total brain tissues were collected from 2BC-Air and 2BC-CIE mice±anti-IL17A Ab, and analyzed by RT-PCR and ELISA (FIG. 16F-G). Hence, we were not able to detect IL17A protein (or other inflammatory cytokines TNF-α, IL-1β, TGF-β1, or IL-6) in the CSF of 2BC-CIE mice (FIG. 16G). In support, albumin was not present in CSF (FIG. 15G), or brain tissues (as shown by measurement of extravasation of Evans Blue dye) of 2BC-CIE mice (FIG. 16E), suggesting that the integrity of BBB was not compromised in these mice. Consistent with our findings in CSF, expression of IL17ARA, TNF-α, IL-1β, TGF-β1, or IL-6 mRNA was low or not induced in the brains of 2BC-CIE mice (vs 2BC-Air mice, FIG. 16F), suggesting that development of alcohol dependence in CIE mice does not require neuroinflammation or loss of BBB barrier.

FIG. 16A-D

Alcohol-Injured Lungs are the Source of Circulating IL17A in Alcohol-Dependent Mice To identify the source of IL17A, livers, brains, and lungs of CIE and Air mice were examined. Since alcohol metabolism was deliberately blocked in the livers of CIE mice (by pyrazol administration) to maximize the effect of alcohol on development of alcohol-dependence in mice, CIE mice were protected from alcohol-induced liver injury (FIG. 16A). Therefore, lungs served as a major source of IL17A in CIE mice (FIG. 16C). Similarly to IG alcohol-fed mice (FIG. 13D), IL17A was not expressed in the brains of CIE mice (FIG. 16B). In turn, IL17A mRNA was strongly induced (↑2 fold vs Air mice) in the lungs of CIE mice (FIG. 16C-D), suggesting the alcohol-injured lungs are the major source of IL17A in alcohol-dependent CIE mice. Upregulation of IL17A in the lungs of CIE mice (vs livers of IG alcohol-fed mice) was largely determined by the route of alcohol administration (vapor inhalation vs ingestion), demonstrating that development of alcohol-dependence in mice can be achieved in the absence of alcohol-induced liver injury.

We and others[25] showed that IL17A is not produced in the brain, but enters the cerebrospinal fluid (CSF) from circulation either via alcohol-damaged BBB[26], or via interaction with the BBB-forming endothelial cells[27]. Indeed, ingress of serum IL17A into the brains of IG alcohol-fed mice occurs by passive diffusion across the permeabilized BBB. In turn, in alcohol-dependent mice, IL17A is, most likely, transported into the brains through cytokine specific receptor-activated transport system(s), recently described in the brain endothelial cells[28] (FIG. 16G). Because of close interconnection between astrocytes and endothelial cells, small concentrations of IL17A might be sufficient to increase reactivity of astrocytes in hippocampus and amygdala. In addiction, BBB-forming endothelial cells themselves might respond to IL17A signaling[27], and as a result, further stimulate astrocyte reactivity.

FIG. 6E-H

Progression of ALD in Patients is Associated with Upregulation of IL17A

Figure 6E:
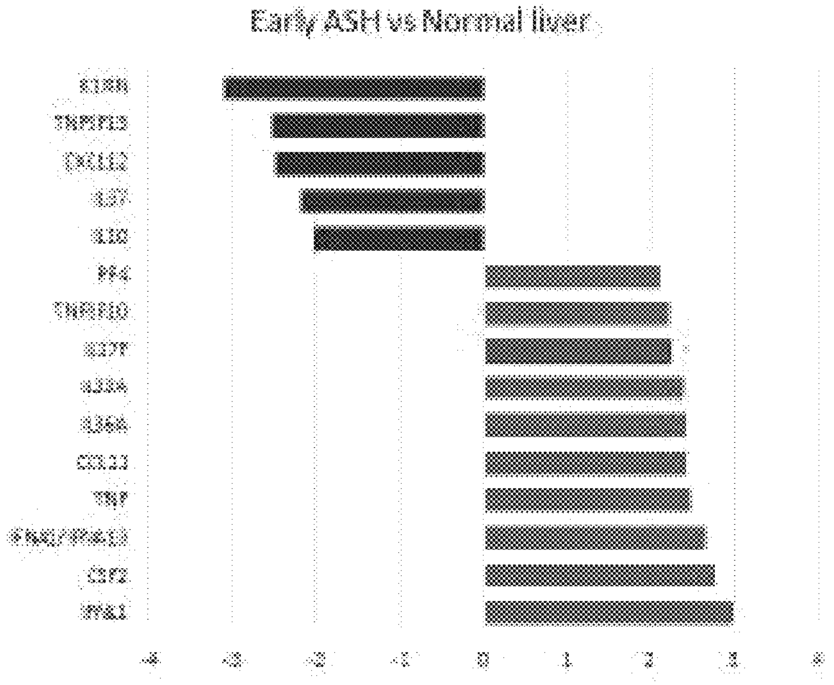
Figure 6F:
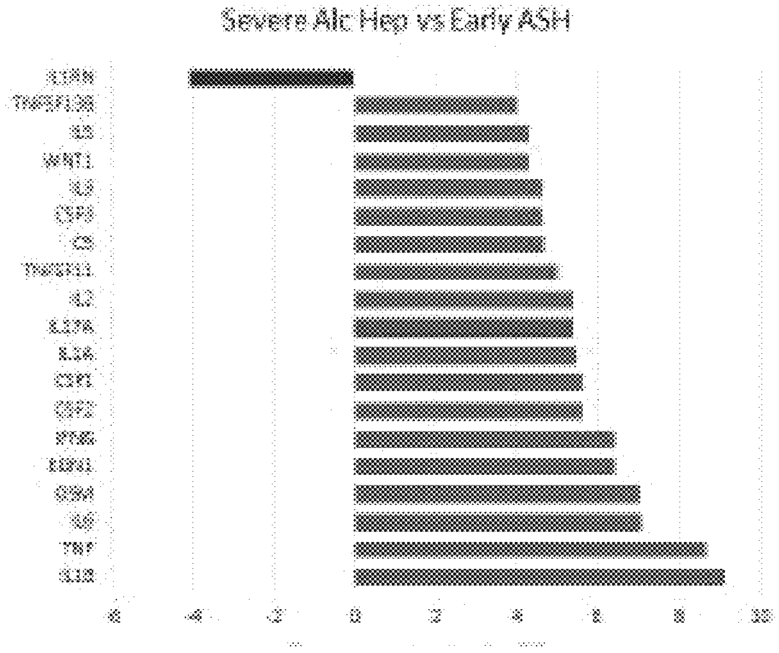
Figure 6G:
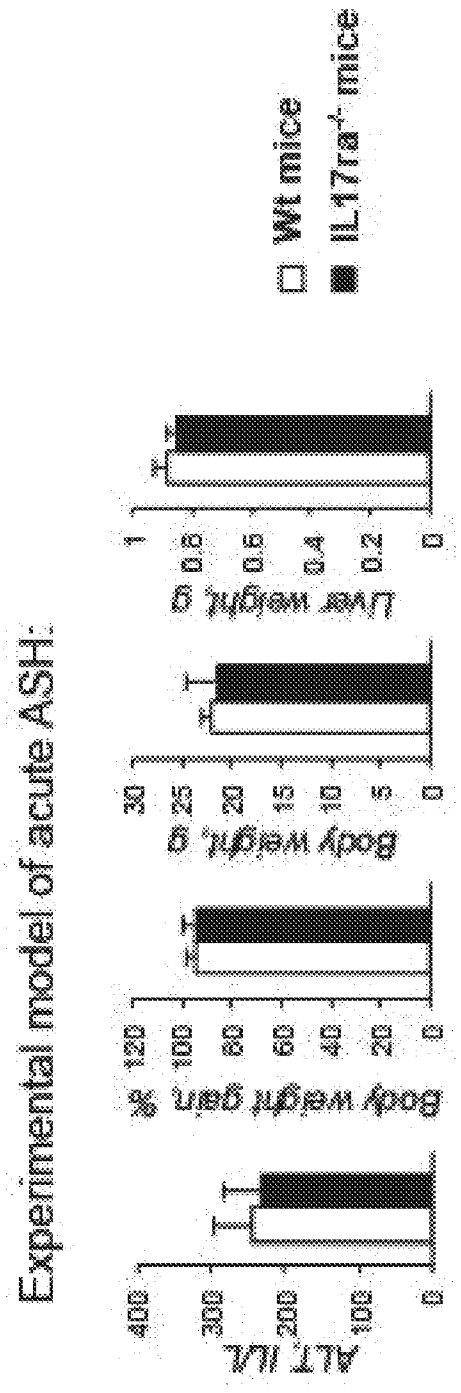
FIG. 6G-H graphically illustrate that development of acute alcoholic steatohepatitis is not attenuated in IL17ra$^{-/-}$ mice; as described in detail in Example 2, below.
Figure 6H:
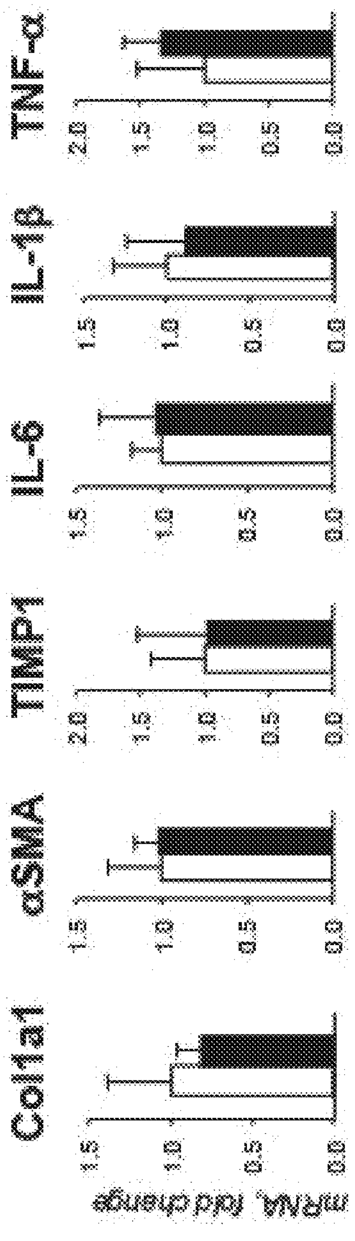

Archived liver biopsies were collected as a part of a standard care and subjected to the RNA-Seq. FIG. 6E: Patients with early steatohepatitis (ASH, vs healthy controls) activated IL-23 and IL17F (but not IL17A) cytokine signaling pathways, as well as downregulation of IL10 cytokine (as predicted by GO term). FIG. 6F: Patients with severe ASH vs healthy controls activated IL17A is arthritis pathway (but not IL-23 cytokine signaling pathway). FIG. 6G: IL17A signaling was induced in mice with alcoholic steatohepatitis. C57BL/6 mice (female, 8 w old, n=7/group) were subjected to acute steatohepatitis. Control age-matched littermates were pair-fed[29]. Mice were sacrificed 9 h after the alcohol-binge treatment. Livers were analyzed by qRT-PCR. Expression of fibrogenic genes (Colla1, αSMA, TGFRβI) was not induced, while expression of inflammatory genes (IL17A, IL17ARA, IL-23) was upregulated (2 fold vs pair-fed mice), indicating that IL17A signaling may play a role in early development of alcoholic steatohepatitis. FIG. 6H: Development of acute steatohepatitis was compared in wt and IL17ARA$^{-/-}$ mice (C57BL/6 female mice, 8 w old, n=6). Serum level of ALT (U/I), body and liver weight, expression of fibrogenic genes (Colla1, αSMA, TIMP1) and inflammatory genes (IL-6, IL-1β, TNF-α) was not changed between wt and IL17ARA$^{-/-}$ mice. The data are the means SEM, ns—non-specific. Student's test, *p<0.05 and **p<0.01.

FIG. 7E-M:

Chronic Alcoholic Steatohepatitis is Reduced in IL17ARA$^{-/-}$ Mice (Supporting FIG. 6A-B)

Figure 7E:
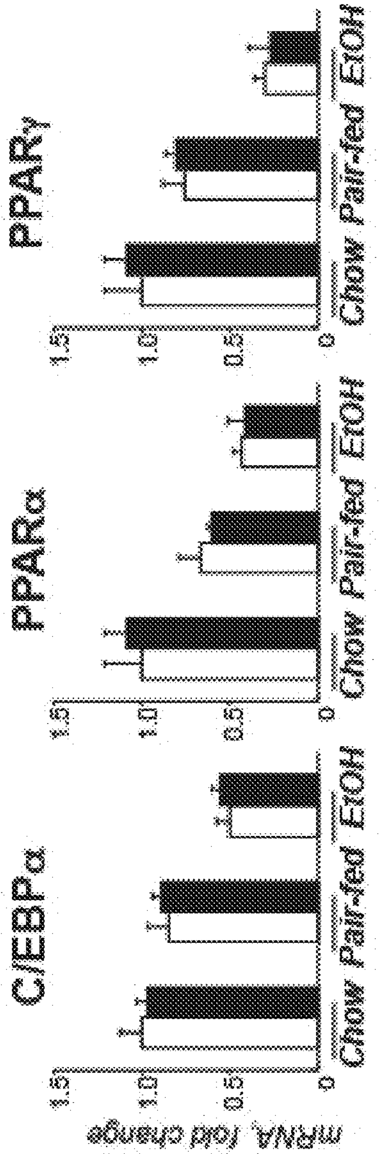
FIG. 7E-M illustrates data using an experimental model of chronic alcoholic steatohepatitis in wt mice.
Figure 7F:
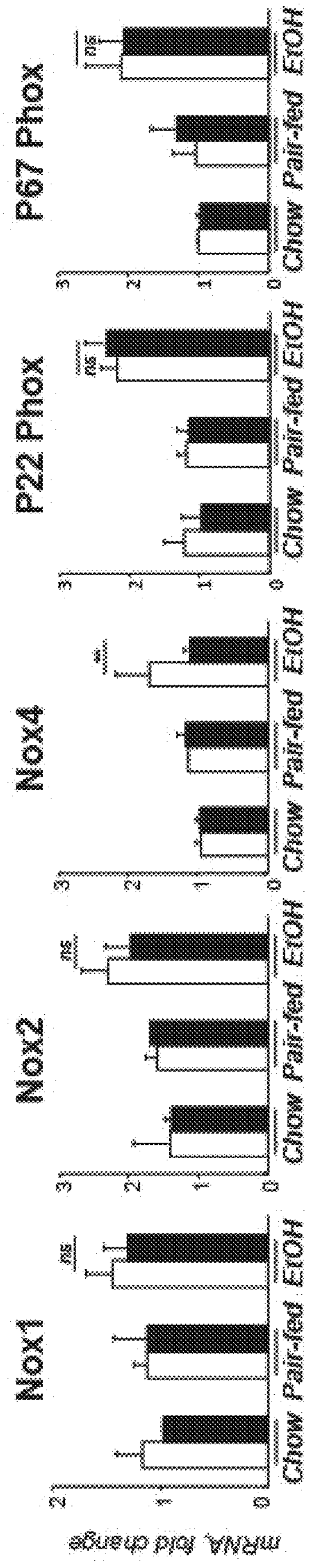
Figure 7G:
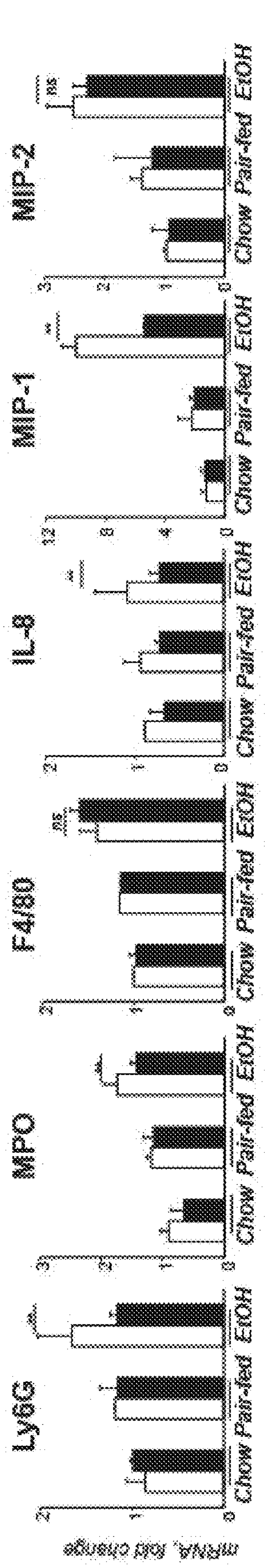
Figure 7H:
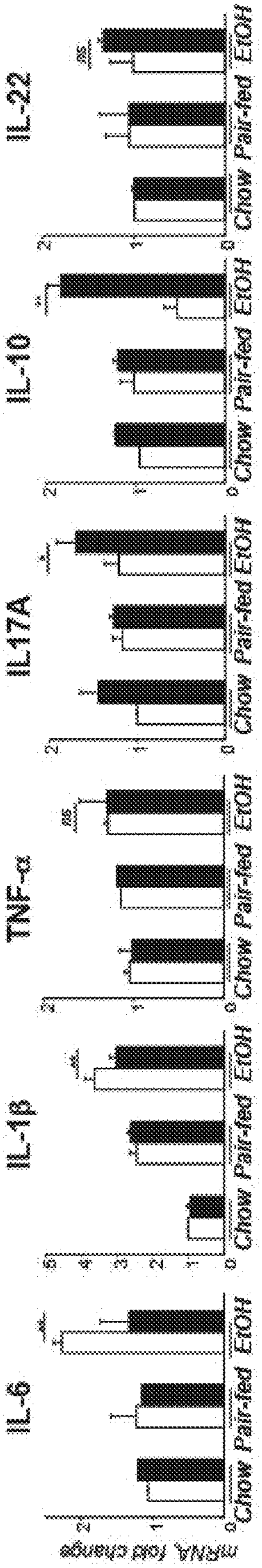
Figure 7I:
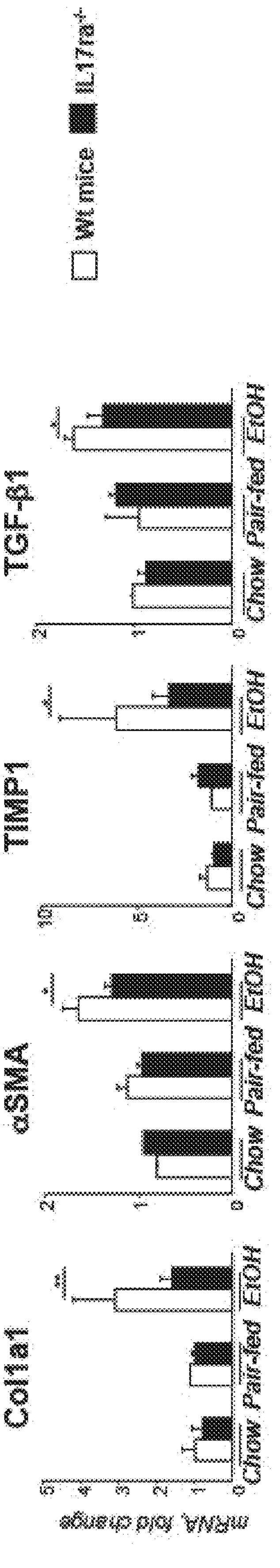
Figure 7L:
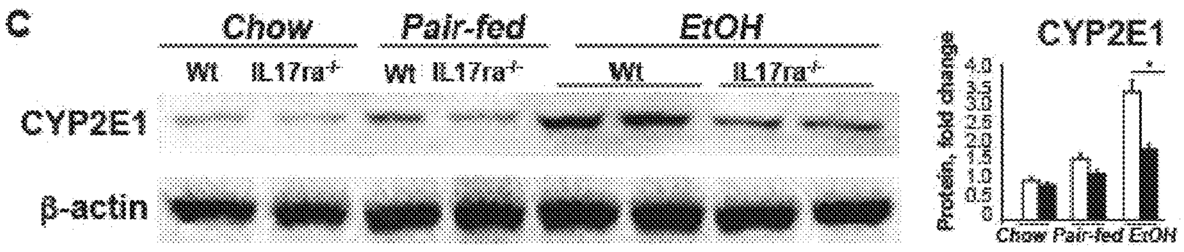
Figure 7M:
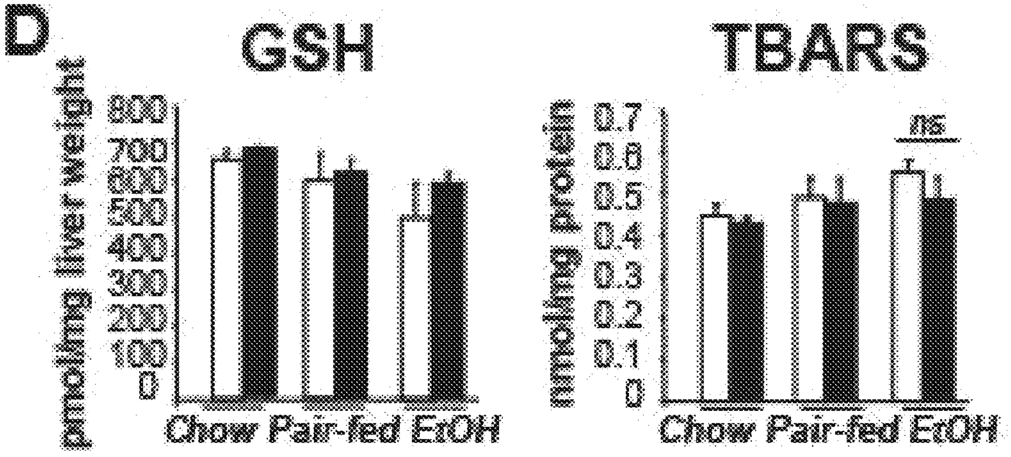

Development of chronic steatohepatitis was compared in wt mice and IL17ARA$^{-/-}$ mice C57BL/6 mice (males, 8 w old, n=12/group, 2 independent experiments) and to pair-fed or chow-fed littermates (males, 8 w old, n=6-8, see Suppl. text). FIG. 7J: Serum levels of ALT and AST, blood alcohol; liver and liver/body weight were measured for each group of mice; the gross liver images are shown for wt and IL17ARA$^{-/-}$ mice with chronic alcoholic steatohepatitis FIG. 7K: Steatosis (H&E, triglycerides), liver fibrosis (Sirius Red), the number of activated α-SMA$^+$ and Desmin$^+$ HSCs, Ly6G$^+$ neutrophils and F4/80$^+$ Kupffer cells, lipid peroxidation (4-HNE) were analyzed by immunostaining and quantified using Image J. The data are percent of positive area. Representative images are taken using ×10, and ×20 objectives. FIG. 7L: Expression of CYP2E1 protein was analyzed in each group of mice using Western blotting, and quantified (normalized to expression level of β-actin). FIG. 7M: Thiobarbituric Acid Reactive Substances and glutathione S-transferase (GST) were measured to access lipid peroxidation. FIG. 7E: mRNA expression of lipogenic genes, FIG. 7F: ROS production, FIG. 7G: neutrophil and macrophage-specific markers and chemokines, FIG. 7H: inflammatory cytokines, and FIG. 7I: fibrogenic genes were measured using qRT-PCR in wt and alcohol-fed $IL17ARA^{-/-}$. One way ANOVA, *p<0.05 and **p<0.01.

FIG. 8I-P

Alcoholic Liver Fibrosis is Reduced in $IL17ARA^{-/-}$ Mice (Supporting FIG. 7)

Development of alcoholic liver fibrosis was compared in wt mice and $IL17ARA^{-/-}$ mice (males, 8 w old, n=8, 2 independent experiments) and to pair-fed or chow-fed littermates (males, 8 w old, n=8-11) and to pair-fed or chow-fed littermates. FIG. 8I: Serum levels of AST; liver and liver/body weight were measured for each group of mice; the gross liver images are shown for wt and $IL17ARA^{-/-}$ mice with alcoholic liver fibrosis (see Suppl. text). FIG. 8J: Steatosis (H&E, triglycerides), liver fibrosis (Sirius Red), the number of activated $\alpha$-$SMA^+$ and $Desmin^+$ HSCs, $Ly6G^+$ neutrophils and $F4/80^+$ Kupffer cells, lipid peroxidation (4-HNE) were analyzed by immunostaining and quantified. The data are percent of positive area. Representative images (×10, ×20 objectives). FIG. 8K: Expression of CYP2E1 protein was analyzed in each group of mice using Western blotting, and quantified (normalized to expression level of $\beta$-actin), FIG. 8L: Thiobarbituric Acid Reactive Substances and glutathione S-transferase (GST) were measured. FIG. 8M: mRNA expression of lipogenic genes, FIG. 8N: ROS production, FIG. 8O: macrophage and neutrophil-specific markers and chemokines, FIG. 8P: inflammatory cytokines, and were measured using qRT-PCR in wt and alcohol-fed $IL17ARA^{-/-}$. One way ANOVA, *p<0.05 and **p<0.01.

FIG. 9F-M

Therapeutic Blocking of IL17A Reduces Alcoholic Liver Fibrosis (Supporting FIG. 8)

Figure 9L:
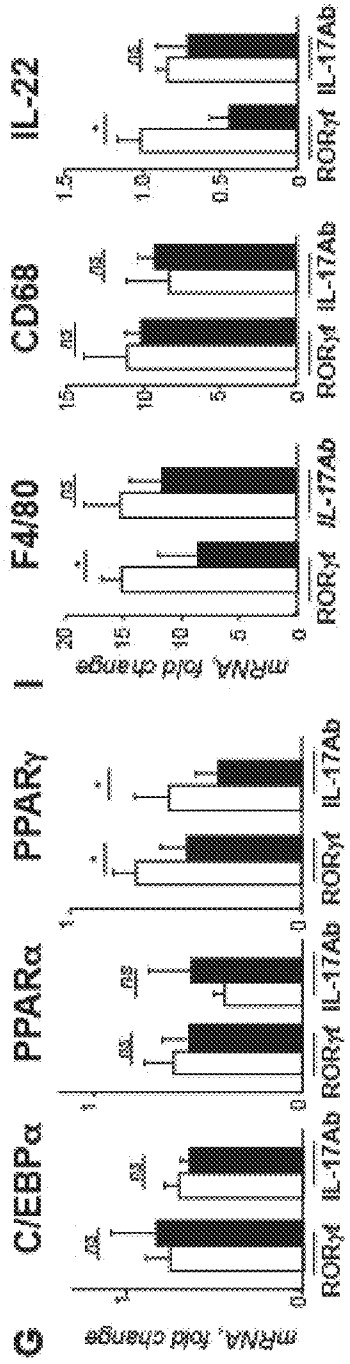
Figure 9M:
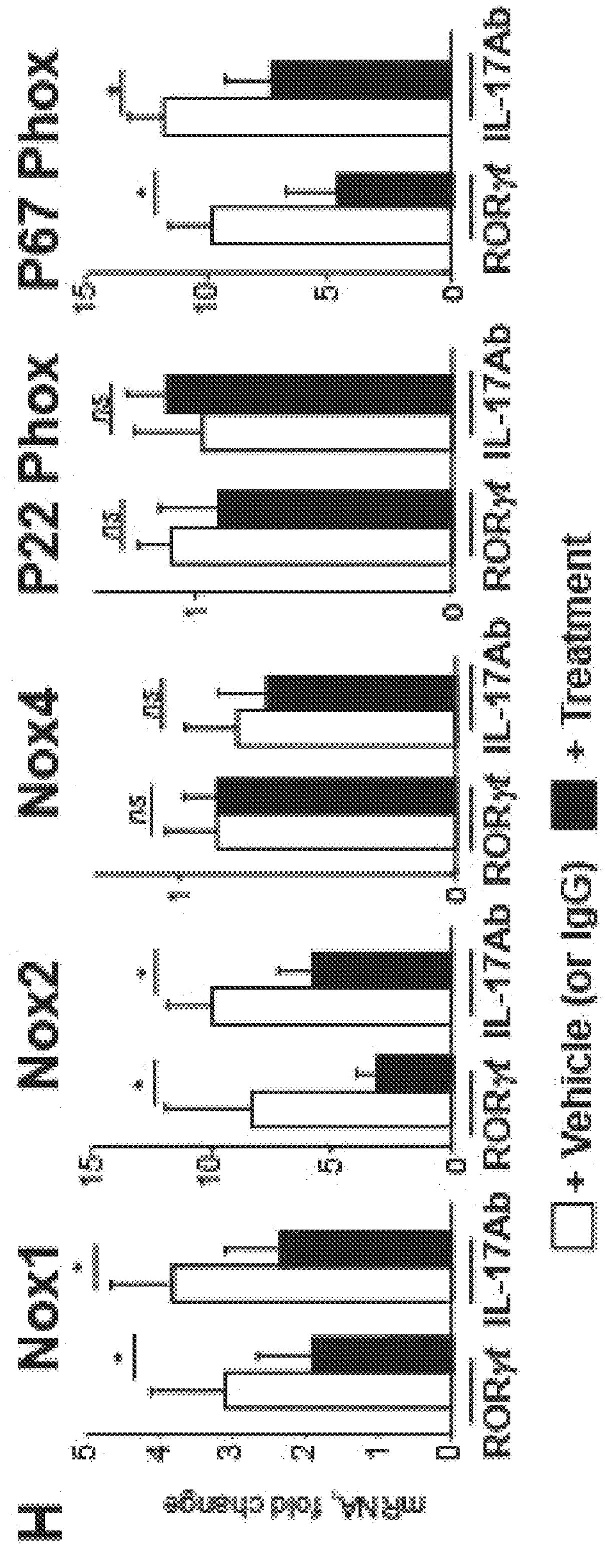

FIG. 9F: Outline of the experiment: IG alcohol-fed wt mice (♂ C57BL/6, 8 w old, n=12/group/treatment, 3 independent experiments) were therapeutically treated (10 days delay) with RORγt inhibitor (50 mg/kg/weight vs vehicle, oral gavage 4× week, or vehicle), or anti-IL17A neutralizing Ab (25 mg/kg/weight vs IgG, i.p. once×week). Serum AST; liver weight was measured for each group of mice. FIG. 9G: Serum levels of IL-6, IL-1$\beta$, TNF-$\alpha$, and IL-10 were measured using ELISA (pg/ml). FIG. 9H: Hepatic expression IL17A was analyzed by Western blotting, and FIG. 9I: qRT-PCR of whole livers from IG alcohol-fed wt mice treatment. FIG. 9J: Livers from IG alcohol-fed wt mice RORγt and FIG. 9K: IG alcohol-fed wt mice anti-IL17A Ab were immunostained for $\alpha$-SMA, Desmin, Ly6G, F4/80, positive areas were quantified. Representative images (×10, and ×20 objectives). FIG. 9L: mRNA expression of lipogenic genes, FIG. 9M: ROS production, Student test, *p<0.05, **p<0.01.

FIG. 10F-J

Therapeutic Blocking of IL17A Suppresses Hepatic Steatosis and Activation of Kuppfer Cells in IG Alcohol-Fed Mice (Supporting FIG. 8)

Figure 10F:
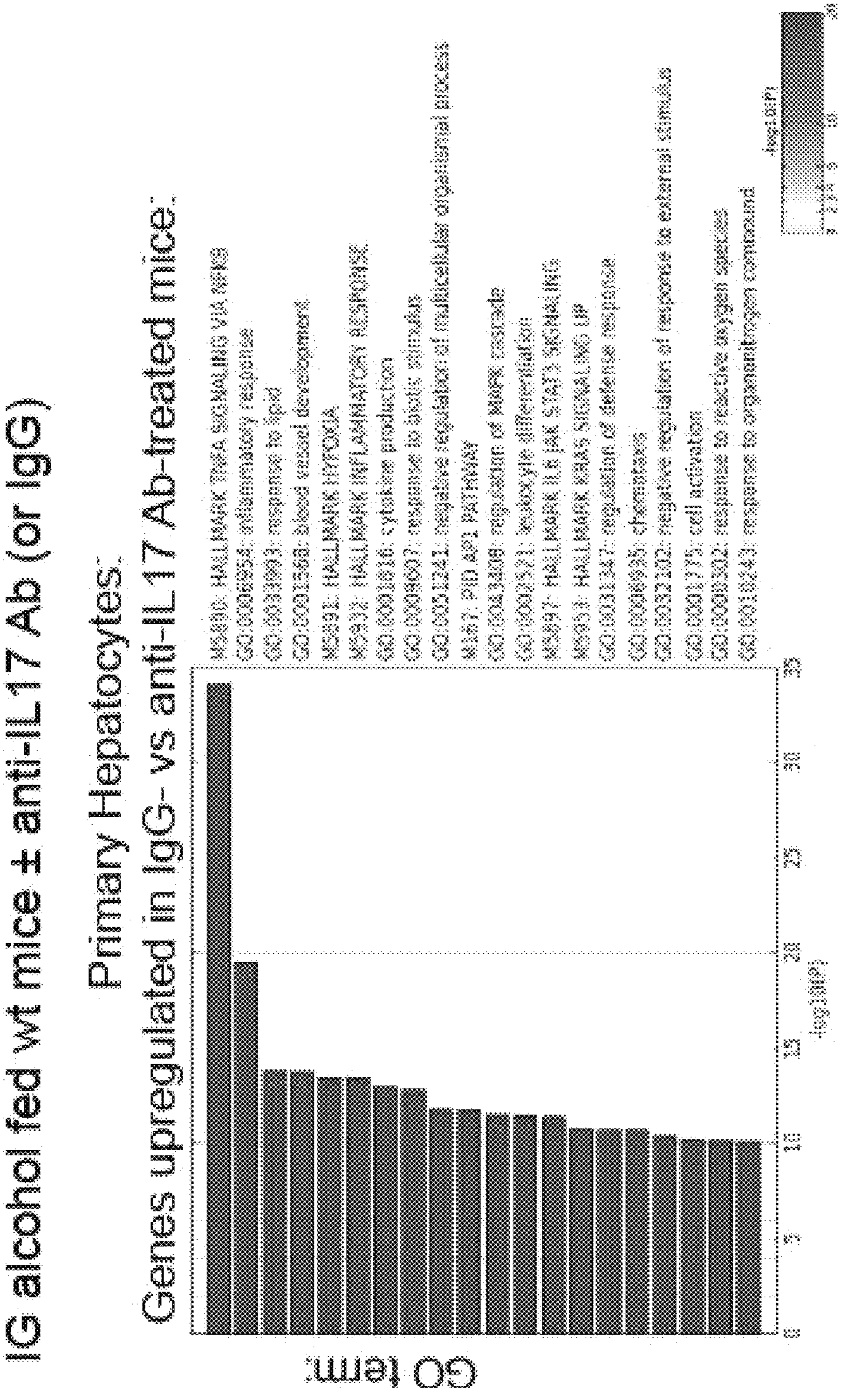
FIG. 10F-J illustrate data showing that therapeutic blocking of IL17A suppresses hepatic steatosis and activation of Kuppfer cells in IG alcohol-fed mice: primary hepatocytes and Kupffer cells were isolated from IG alcohol-fed mice±anti-IL17A Ab using gradient centrifugation method and subjected to the RNA-seq analysis.
Figure 10G:
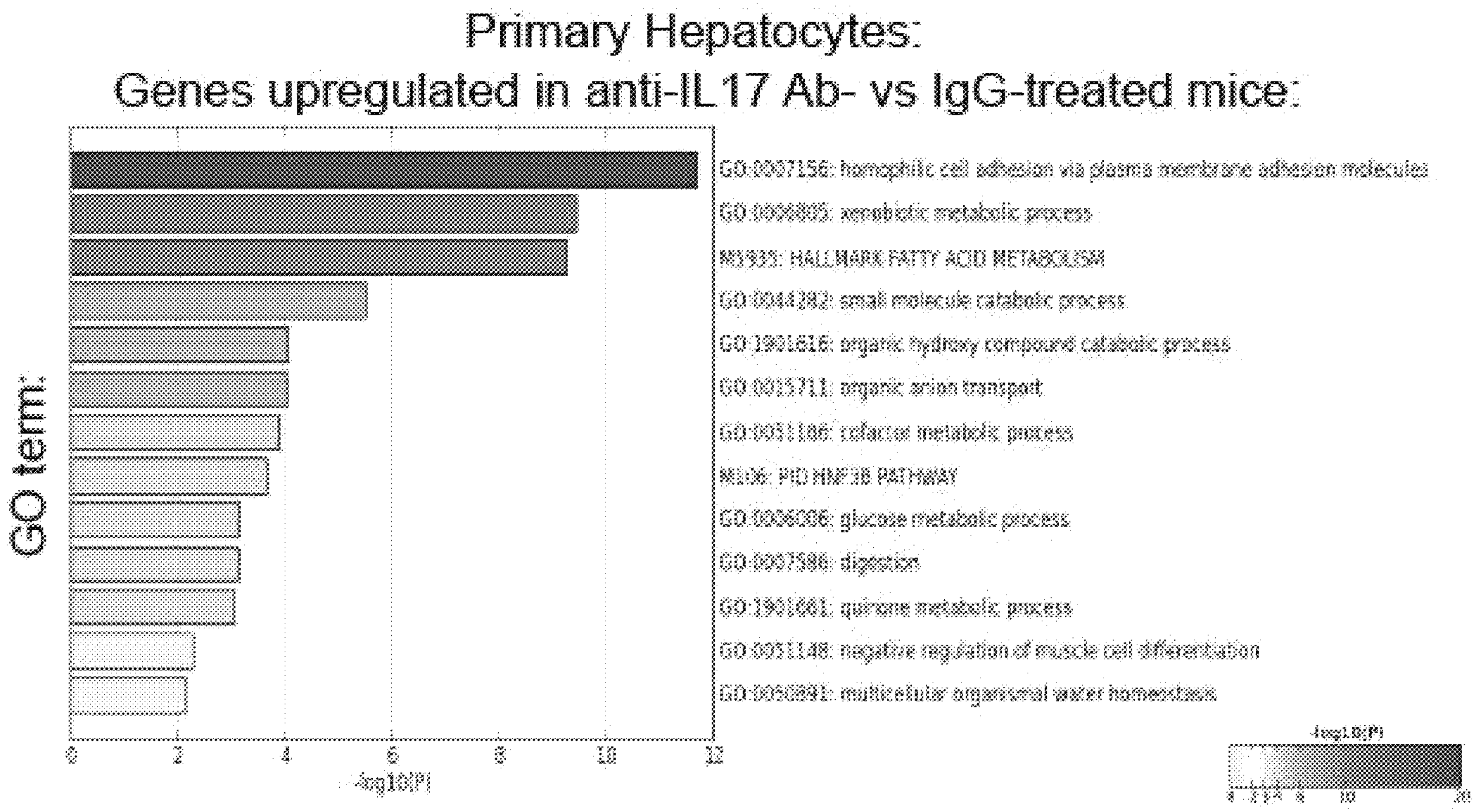
Figure 10H:
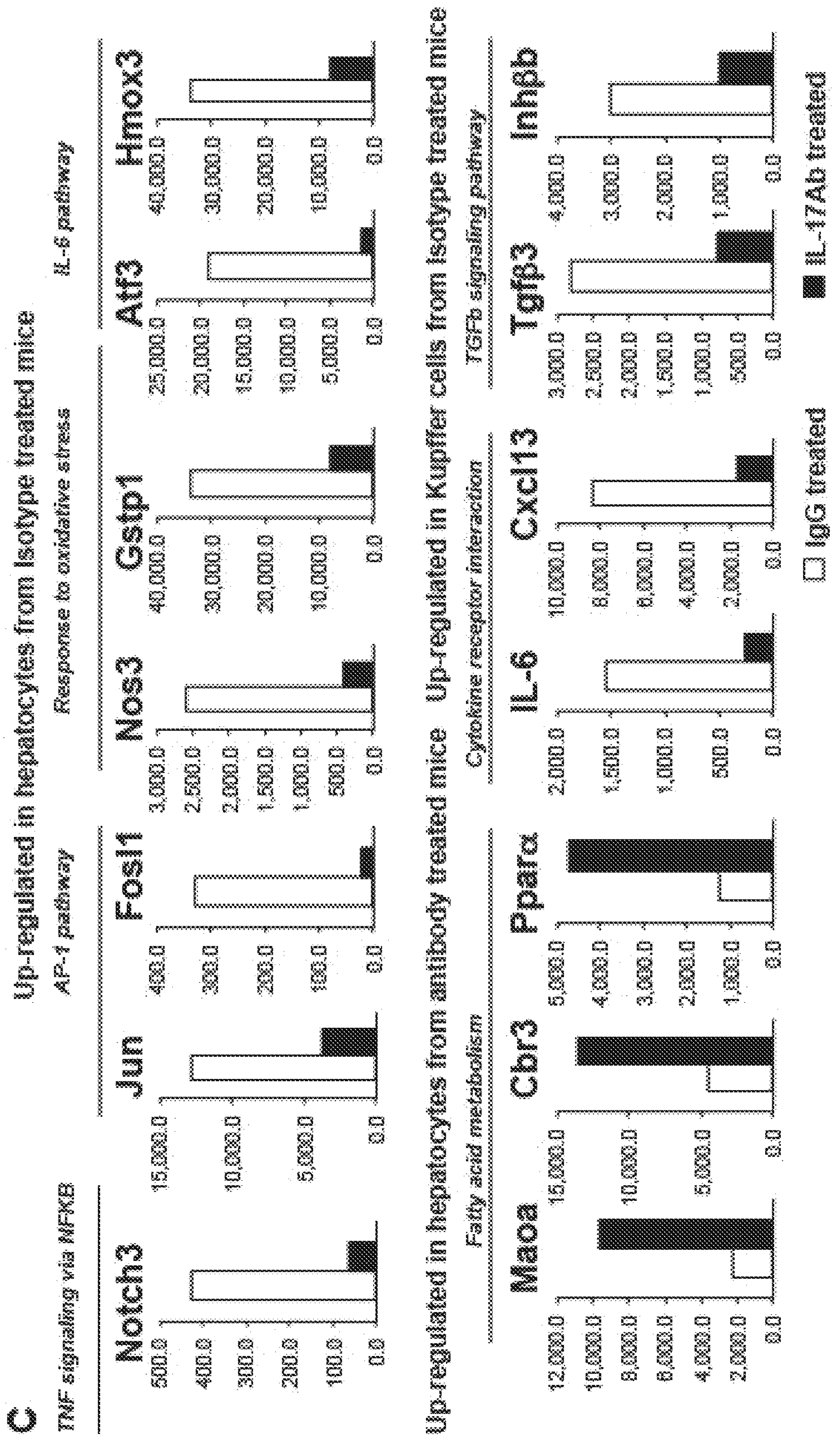
Figure 10I:
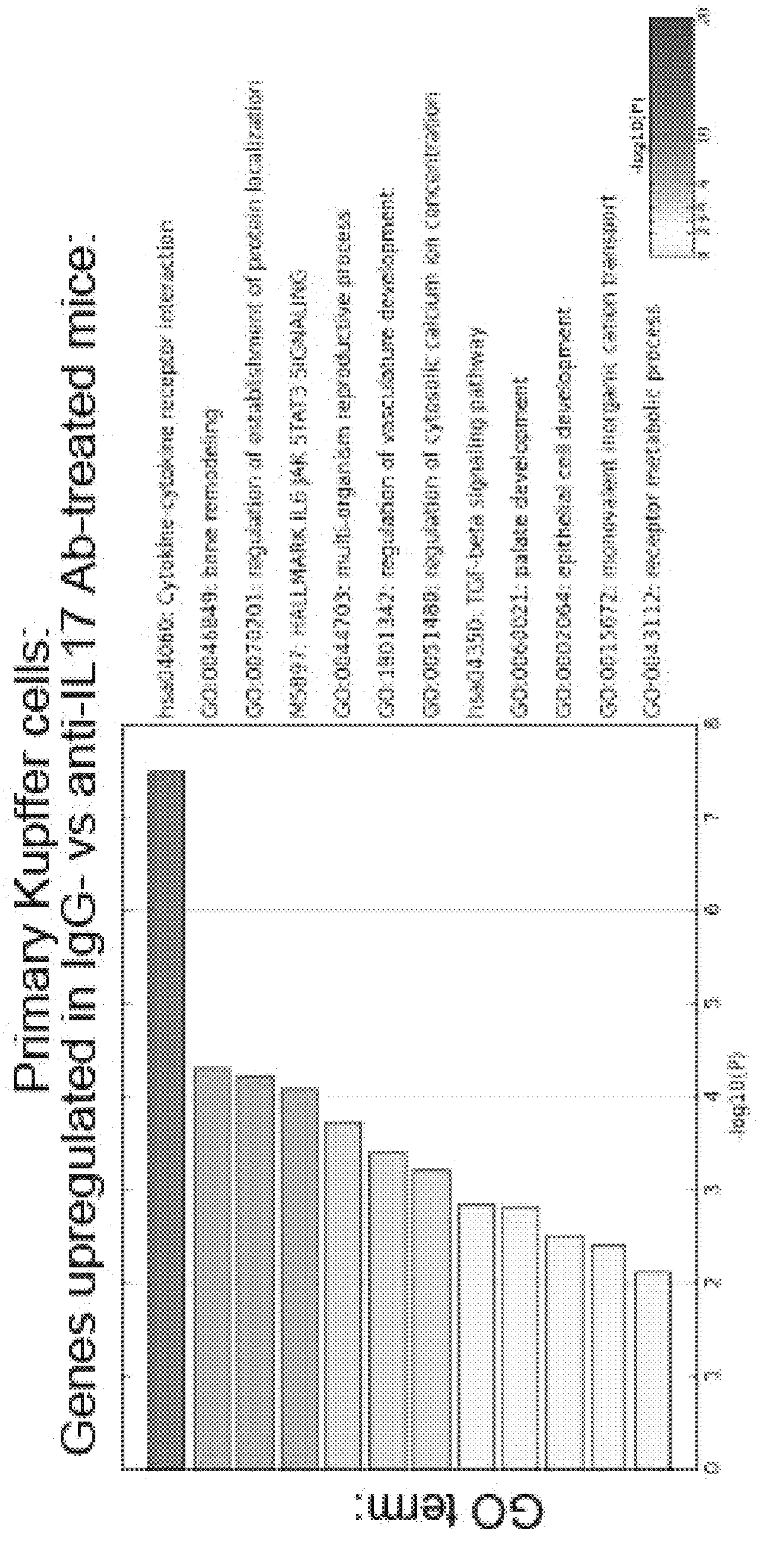
Figure 10J:
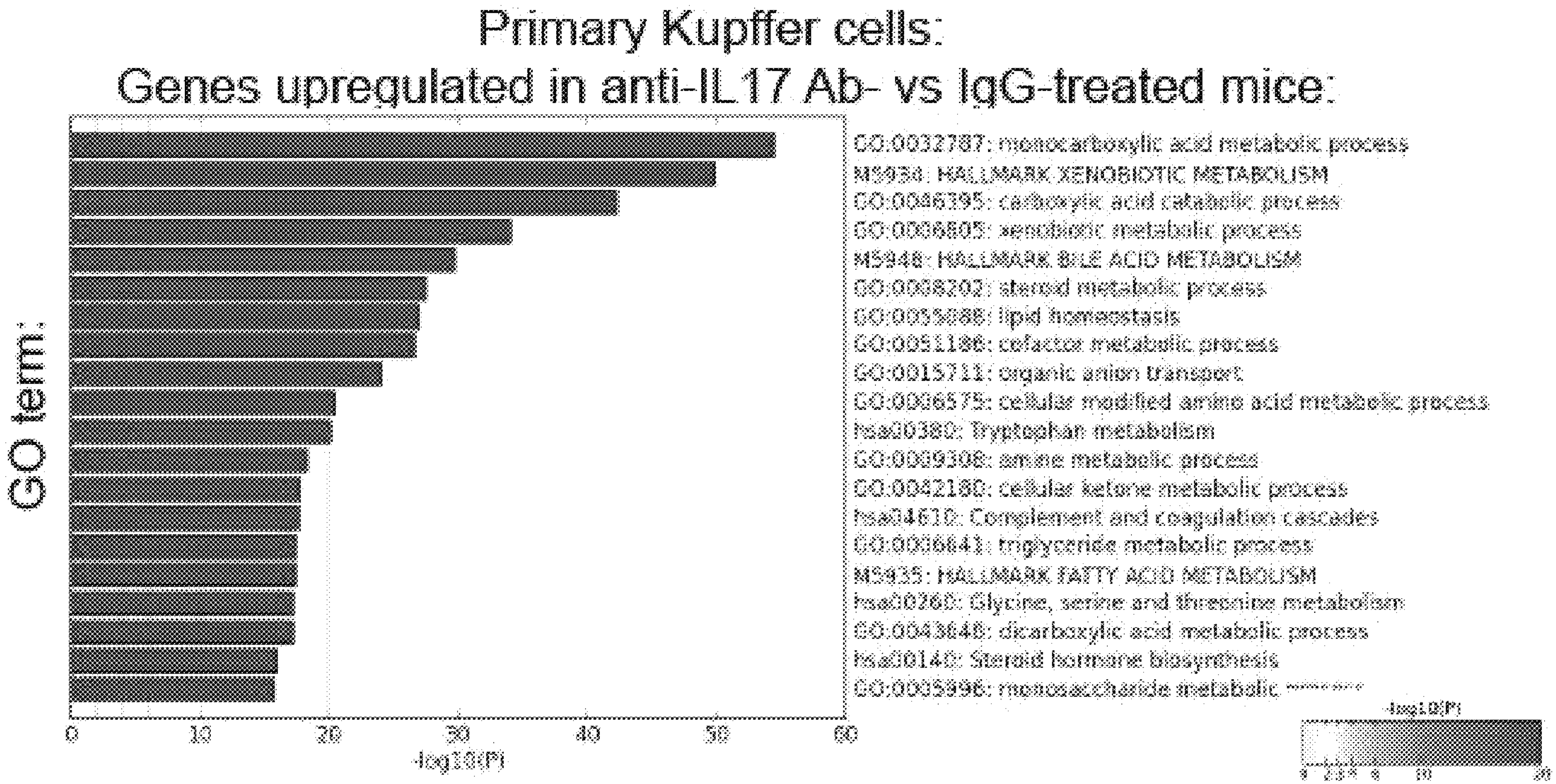

Primary hepatocytes and Kupffer cells were isolated from IG alcohol-fed mice±anti-IL17A Ab using gradient centrifugation method, and subjected to the RNA-seq analysis. The effect of IL17A blocking on the cross-talk between hepatocytes and Kupffer cells was evaluated using GO enrichment profiling based on mRNA expression. FIG. 10F: GO terms of the genes upregulated in hepatocytes from IgG- (vs anti-IL17A Ab-) treated mice. FIG. 10G: GO terms of the genes upregulated in hepatocytes from anti-IL17A Ab-(vs IgG-) treated mice. FIG. 10H: Representative genes from selected from GO terms enriched in hepatocytes isolated from IgG or anti-IL17A Ab treated mice; FIG. 10I: GO terms of the genes upregulated in Kupffer cells from IgG (vs anti-IL17A Ab-) treated mice. FIG. 10J: GO terms of the genes upregulated in Kupffer cells from anti-IL17A Ab (vs IgG-) treated mice. Significance of the GO terms were indicated as −log 10 (P).

FIG. 11G-L

Therapeutic Blocking of IL17A Reduces Alcohol-Induced Brain Injury and Neuroinflammation (Supporting FIG. 9)

Figure 11L:
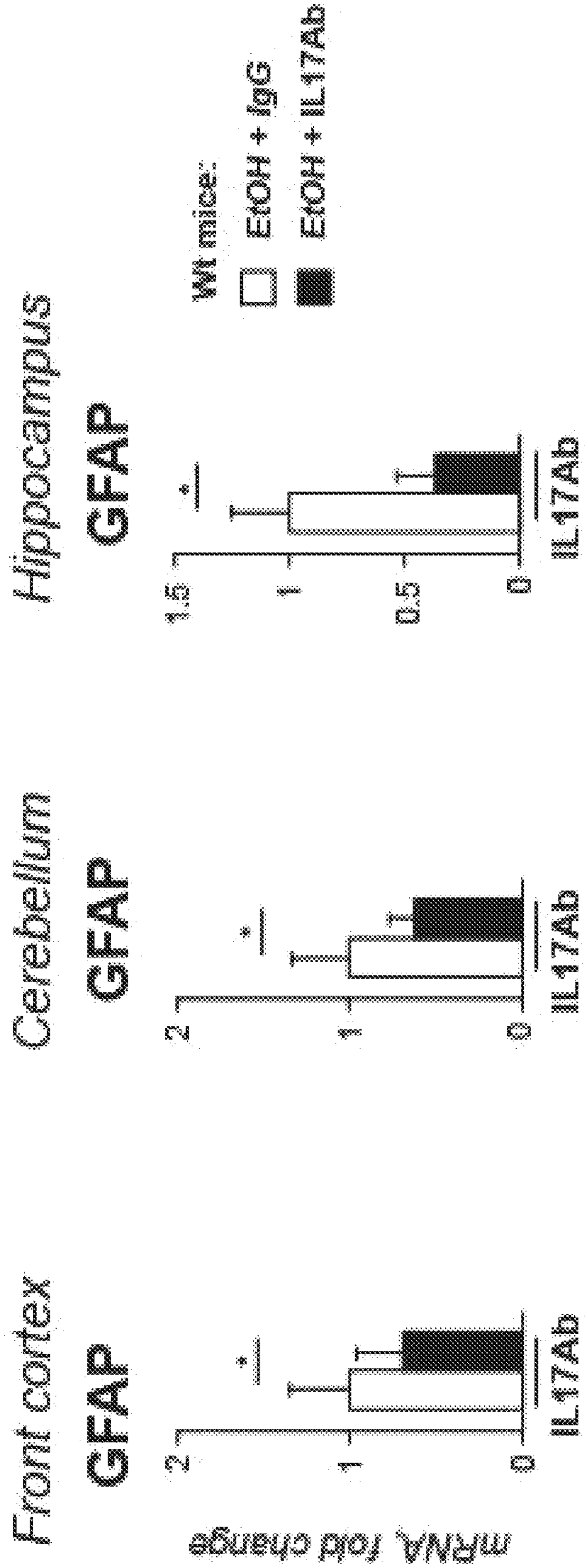

Brains were collected from IG alcohol-fed mice RORγt inhibitor (or anti-IL17A Ab) and analyzed. FIG. 11G: Coronal brain sections were immunostained for Iba1 and DAPI to visualize microglial cells. Representative images are taken using ×20 and ×100 objectives). FIG. 11H: The percent of $Iba1^+$ staining area and FIG. 11I: The number of $Iba1^+$ $DAPI^+$ cells in hippocampus was calculated as percent (%) of all $DAPI^+$ cells. FIG. 11J: mRNA expression of IL17ARA, and IL-1$\beta$ were measured from total brain tissue from chow, Pair-fed and IG alcohol-fed±anti-IL17A Ab mice by qRT-PCR. FIG. 11K: Coronal brain sections were immunostained for active Caspase 3 to visualize apoptotic neurons. Caspase $3^+$ staining was detected in the cerebellum of IG alcohol-fed mice anti-IL17A Ab along the axons of dead neurons, but was markedly reduced by anti-IL17A Ab treatment. Representative images (×20 and ×100 objectives). FIG. 11L: Frontal cortex, cerebellum, and hippocampus were microdissected from brains of IG alcohol-fed mice±anti-IL17A Ab, expression of GFAP mRNA was measured using qRT-PCR. One way ANOVA, *p<0.05 and **p<0.01.

FIG. 12A-D

IG Alcohol-Induced Brain Injury is Associated with Development of Neuroinflammation (Supporting FIG. 9)

FIG. 12A: Expression of IL17A and IL17ARA mRNA was compared in the brains and livers isolated from the same IG alcohol-fed wt mice (vs chow-, and pair-fed wt mice, n=4-6 per group). IL17A mRNA was induced in the livers but not in the brains of IG alcohol-fed wt mice (the data are relative mRNA expression level). IL17ARA mRNA was induced in both livers and brains of alcohol-fed mice, but at much lower level in the brains (↑1.5 fold) than livers (↑10 fold, vs chow-fed mice). FIG. 12B: Cortex, hippocampus, and cerebellum were microdissected from the brains of IG alcohol-fed wt mice (vs chow-, and pair-fed wt mice, n=3-4 per group) and analyzed by qRT-PCR for expression of IL17ARA, GFAP, TGF-$\beta$1, and TNF-$\alpha$, IL-1$\beta$, CCL7, and IL-6). Upregulation of IL17ARA mRNA was observed in brains of IG alcohol-fed mice, especially in the hippocampus (↑1.7 fold vs chow-fed mice). FIG. 12C: Coronal brain sections were analyzed by RNA in situ hybridization for expression of IL17A mRNA in IG alcohol-fed mice. IL17A mRNA signal was observed in the livers but not in the brains (isolated from the same IG alcohol-fed wt mice). FIG. 12D: Cerebrospinal fluid (CSF) was isolated from IG-alcohol-fed wt mice (vs chow-, and pair-fed wt mice, n=7-10 per group) and analyzed for the presence of IL17A and other inflammatory cytokines using ELISA. IL17A cytokine was detected in CSF of IG-alcohol-fed mice (↑6 fold vs pair-fed). The CSF levels of other pro-inflammatory cytokines (↑2 fold IL-1$\beta$, ↑2 fold TGF-$\beta$1, and ↑1.3 fold TNF-$\alpha$), that are indicative of alcohol-induced neuroinflammation, were also increased in these mice. student's test, *p<0.05, **p<0.01.

FIG. 13A-E

Development of Neuroinflammation in IG Alcohol-Fed Mice is Associated with Increased BBB Permeability (Supporting FIG. 9)

Figure 13A:
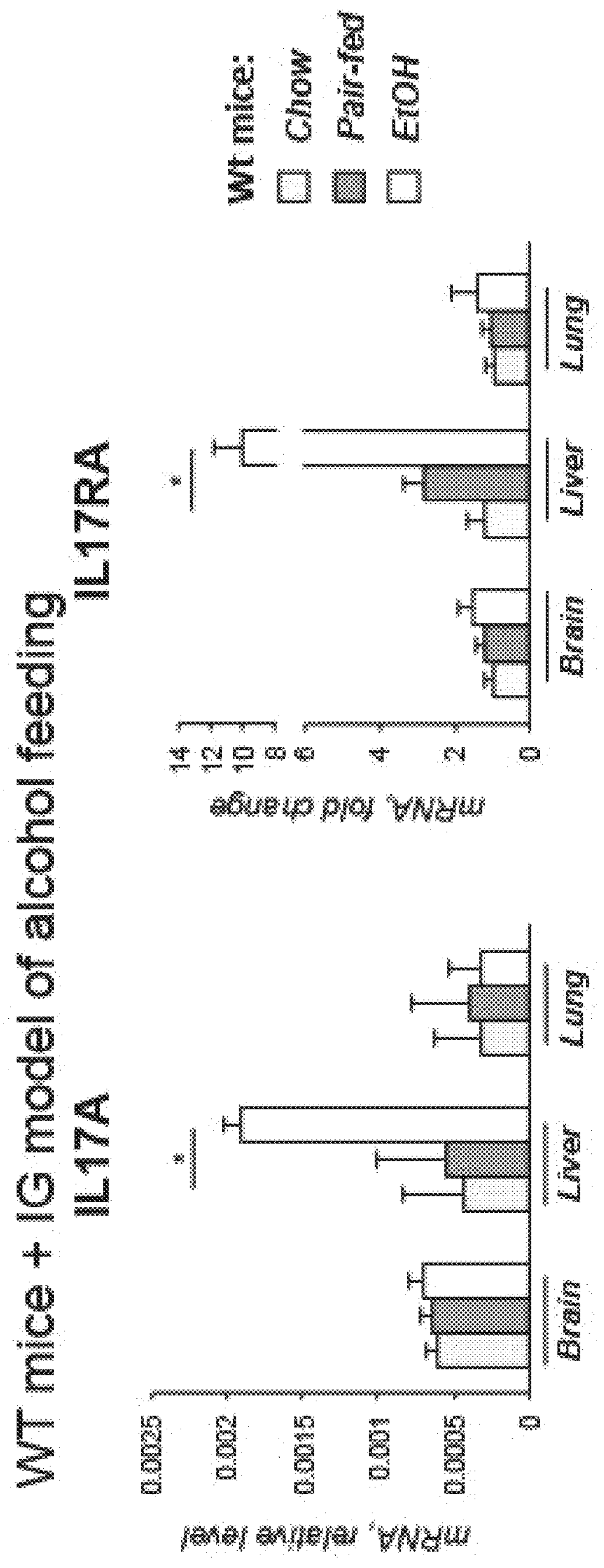
FIG. 13A-E illustrate data showing that development of neuroinflammation in IG alcohol-fed mice is associated with increased BBB permeability.
Figure 13B:
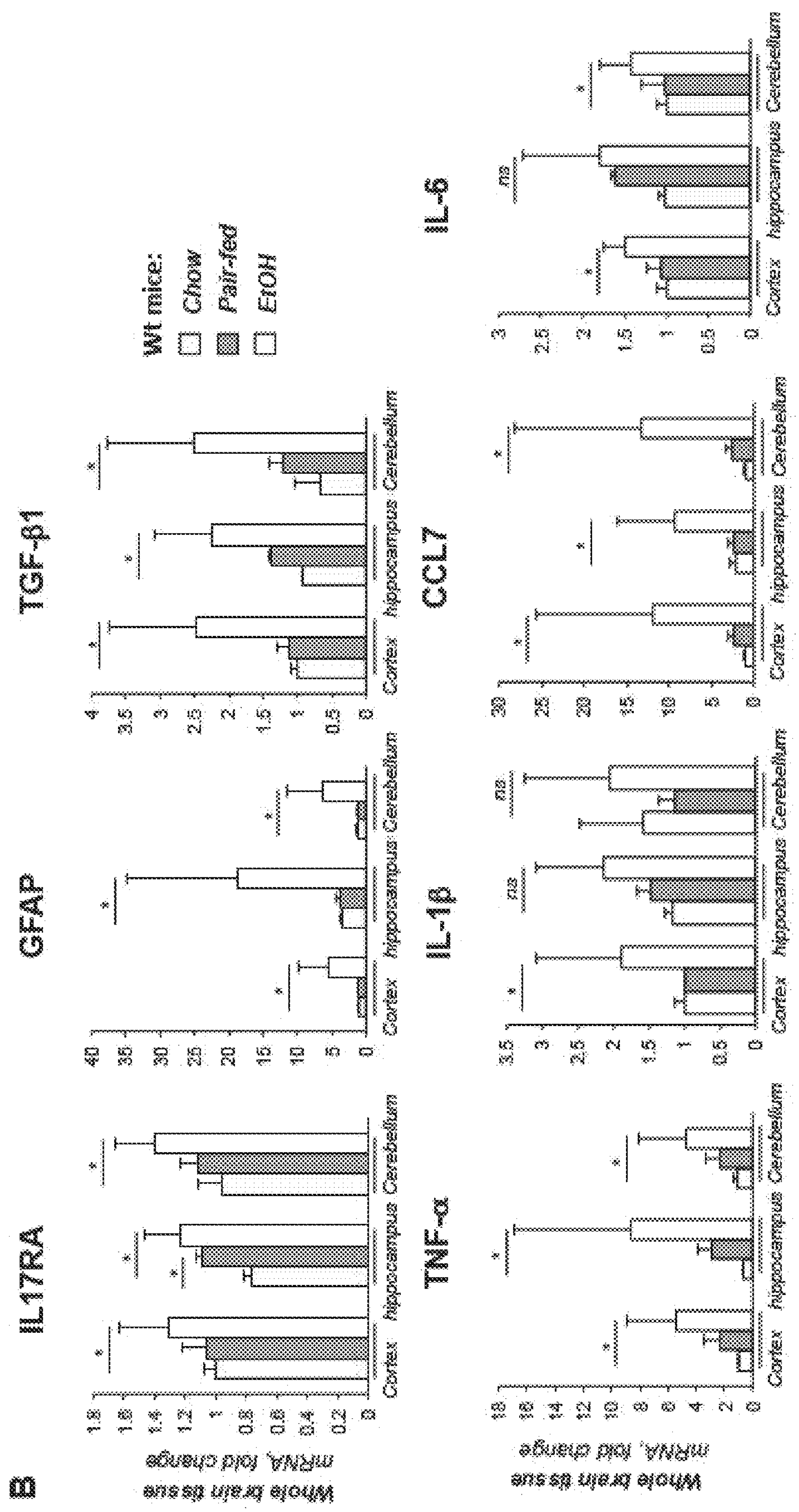
Figure 13C:
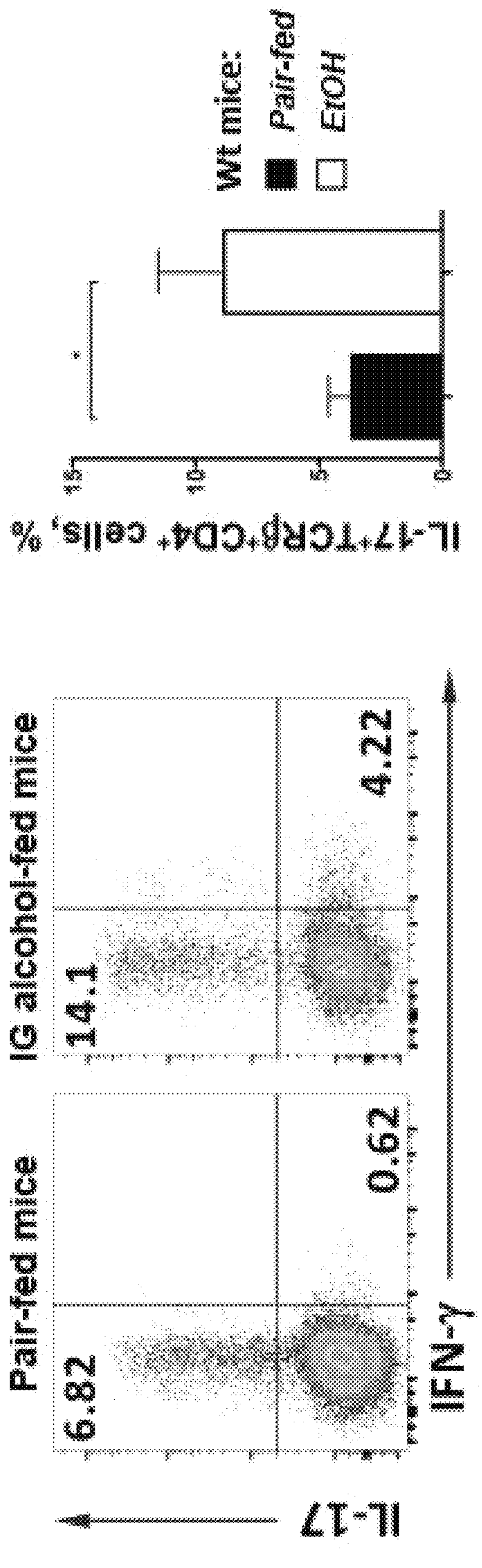
Figure 13D:
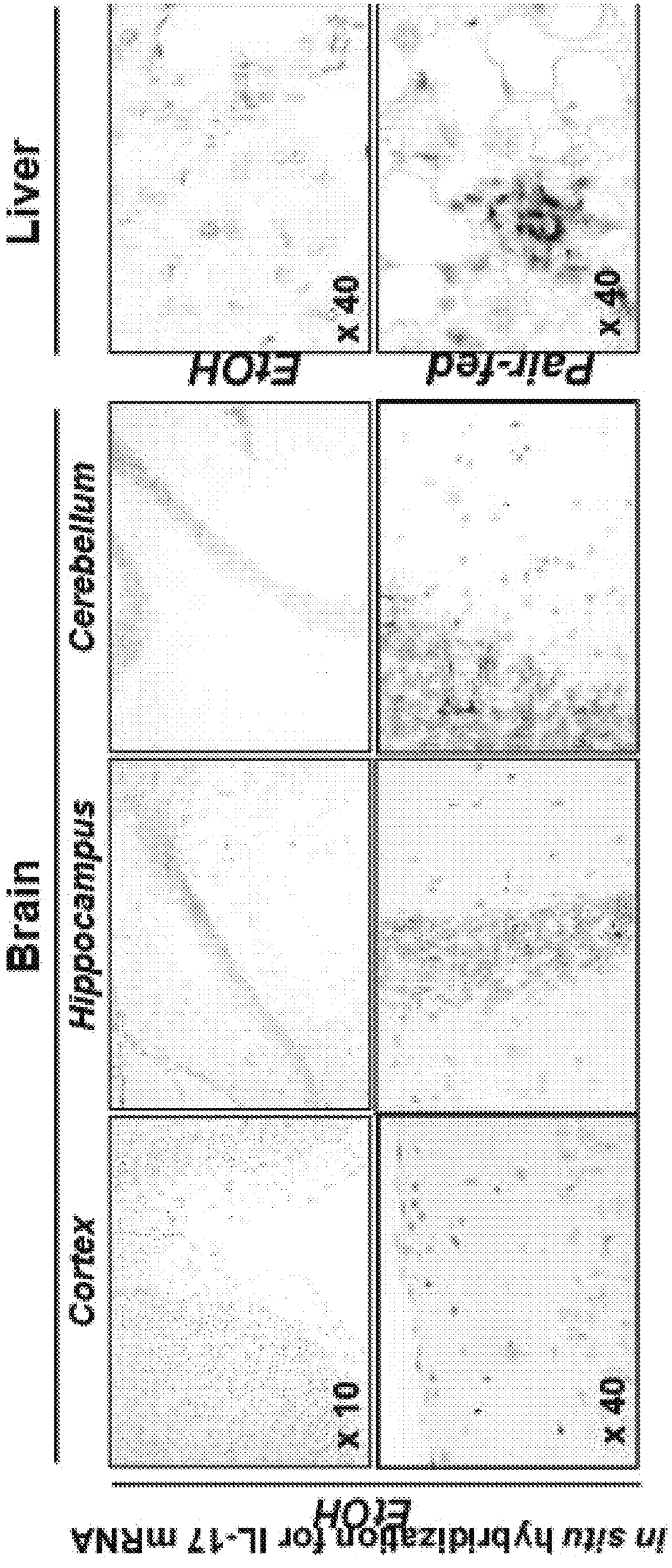
Figure 13E:
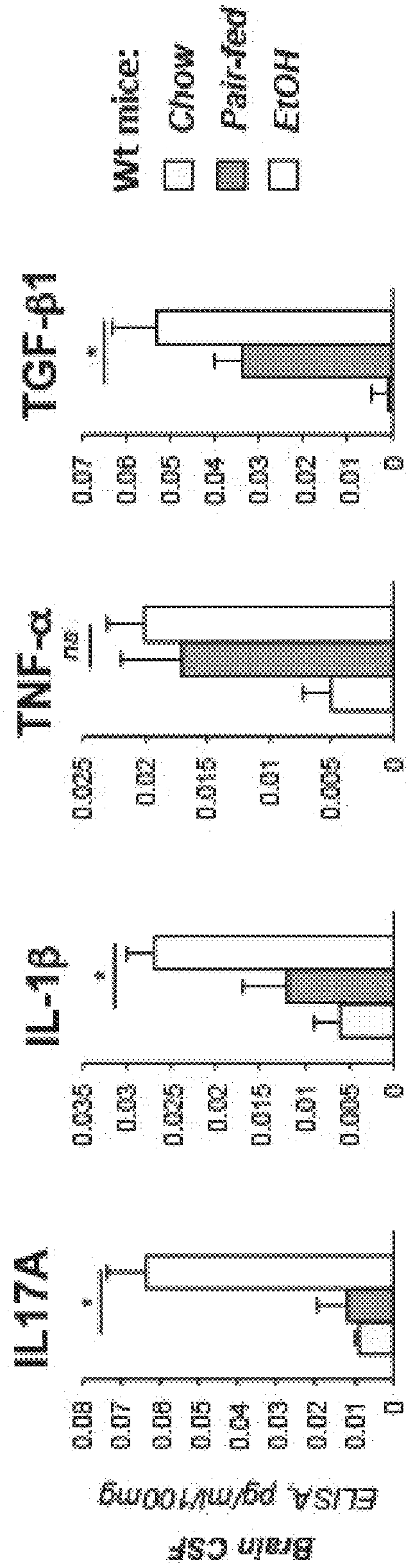

FIG. 13A: The presence of albumin CSF was tested in the CSF using ELISA, the data are pg/ml. The presence of albumin in the brain parenchyma and CSF is indicative of increased BBB permeability in IG alcohol-fed mice (vs pair-fed mice). Blocking of IL17A signaling did not reduce albumin content in IG alcohol-fed mice±RORγt inhibitor, indicating that BBB permeability in these mice is caused by alcohol (rather than Th-17 cells). FIG. 13B: Positive area of extravasated albumin (red) was quantified (%). FIG. 13C: Brains from IG alcohol-fed and pair-fed mice RORγt inhibitor were co-stained for Zo-1 (tight junction protein expressed by endothelial cells) and albumin (serum marker which does not cross BBB under physiological conditions). Immunoreactivity for albumin in the pair-fed mice was constrained to the blood vessels (yellow arrows). Extravasation of albumin into the brain parenchyma (white arrows) was observed IG alcohol-fed mice RORγt inhibitor. Representative images (×4, ×40 objectives). Student's test, *p<0.05, **p<0.01, ns—non-specific.

FIG. 14A-C

TL17A Signaling Facilitates Proliferation/Activation of Astrocytes and Promotes Neuroinflammation in IG Alcohol-Fed Mice (Supporting FIG. 9)

Figure 14A:
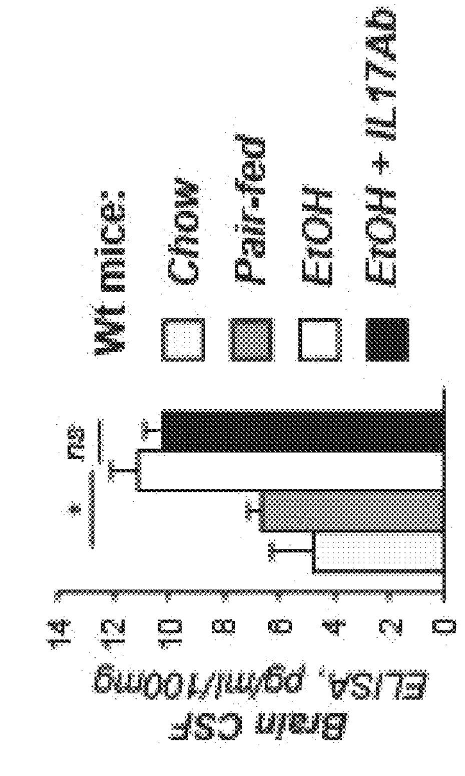
Figure 14C:
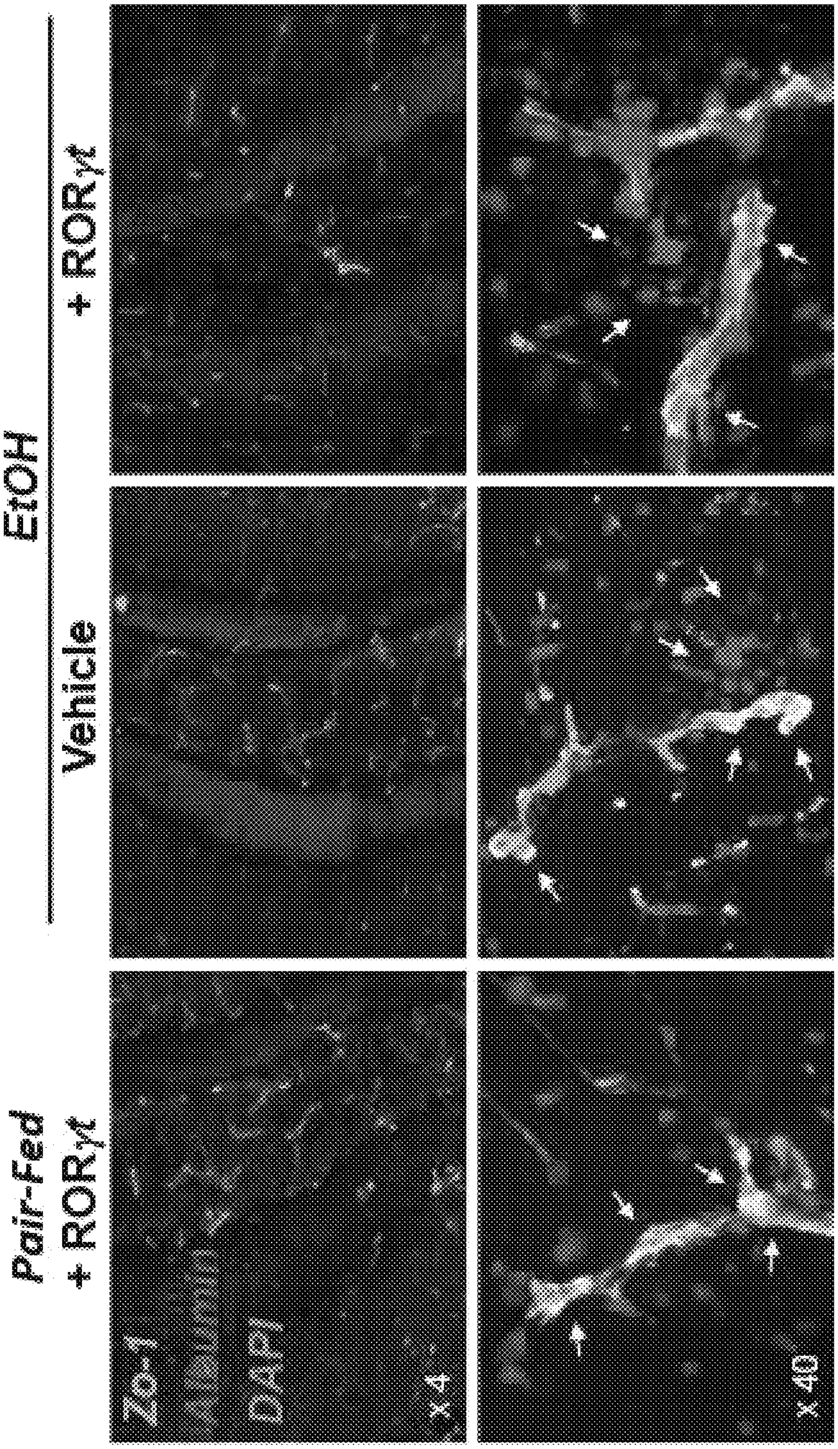

FIG. 14A: Primary $GFAP^+F4/80^-$ astrocytes and $GFAP^-$ $F4/80^+$ microglial cells were isolated from Wt mice, and phenotyped by immunocytochemistry. Cell purity was calculated as percent of total cells (representative images ×20 objective). Cultured astrocytes ($5\times10^5$ cells per ml, Astro) and microglial cells ($1\times10^6$ cells per ml, Micro) were serum starved (for 18 h), stimulated with IL17A (5 ng/ml, for 6 hr), and analyzed by qRT-PCR. The data are average of (triplicates). FIG. 14B-C: Cultured astrocytes ($5\times10^5$ cells per ml) were stimulated with TGF-β1 (5 ng/ml), or IL-1β (5 ng/ml), or PBS, and subjected to the customized gene expression microarray (Agilent. FIG. 14B: GO enrichment profile for IL-1β- and FIG. 14C: TGF-β- (vs PBS-) stimulated astrocytes is shown.

FIG. 15A-E

IL17A Signaling Facilitates Astrocyte Activation in Alcohol-Dependent Mice (Supporting FIG. 10)

Figure 15C:
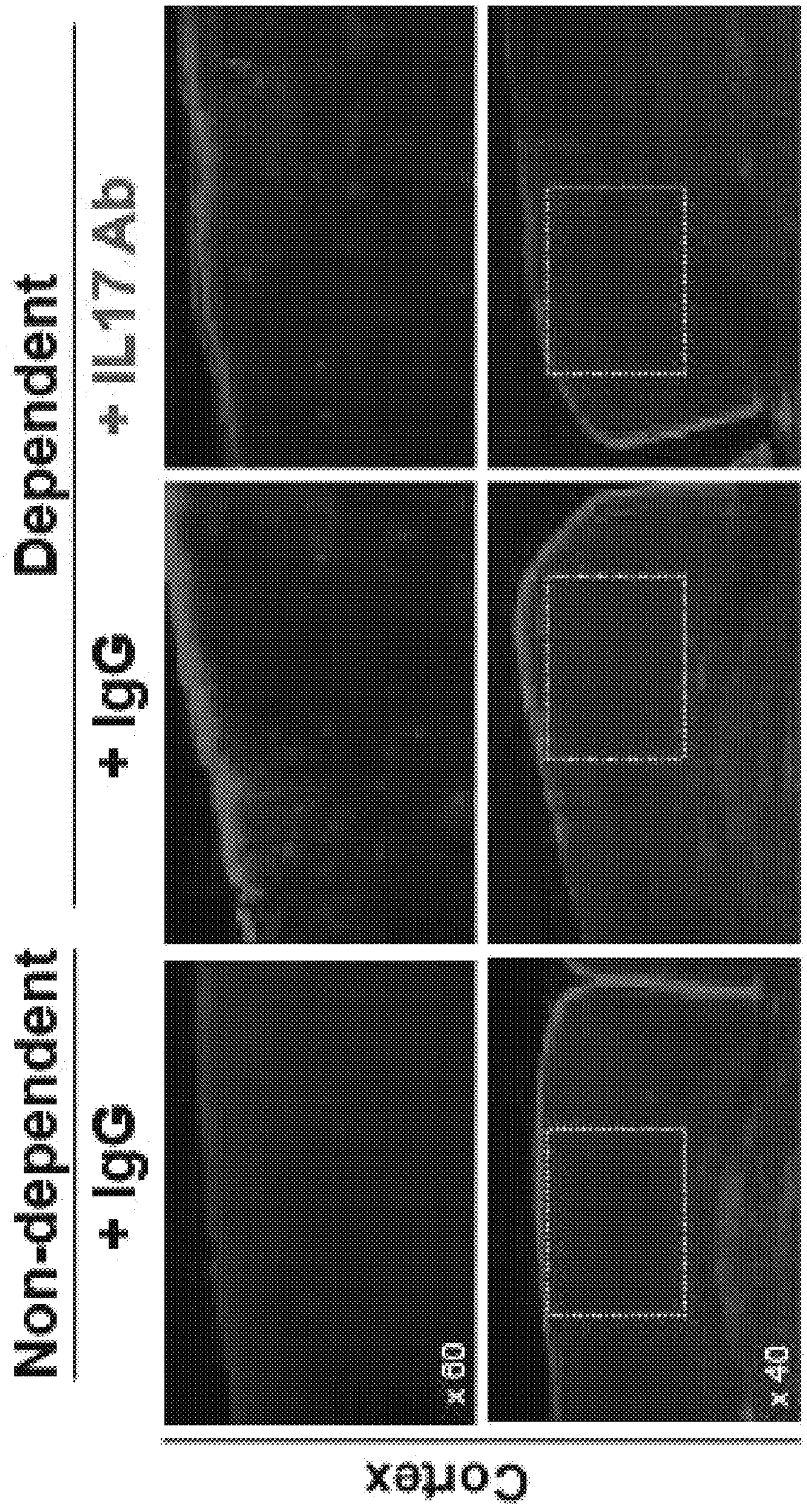
Figure 15D:
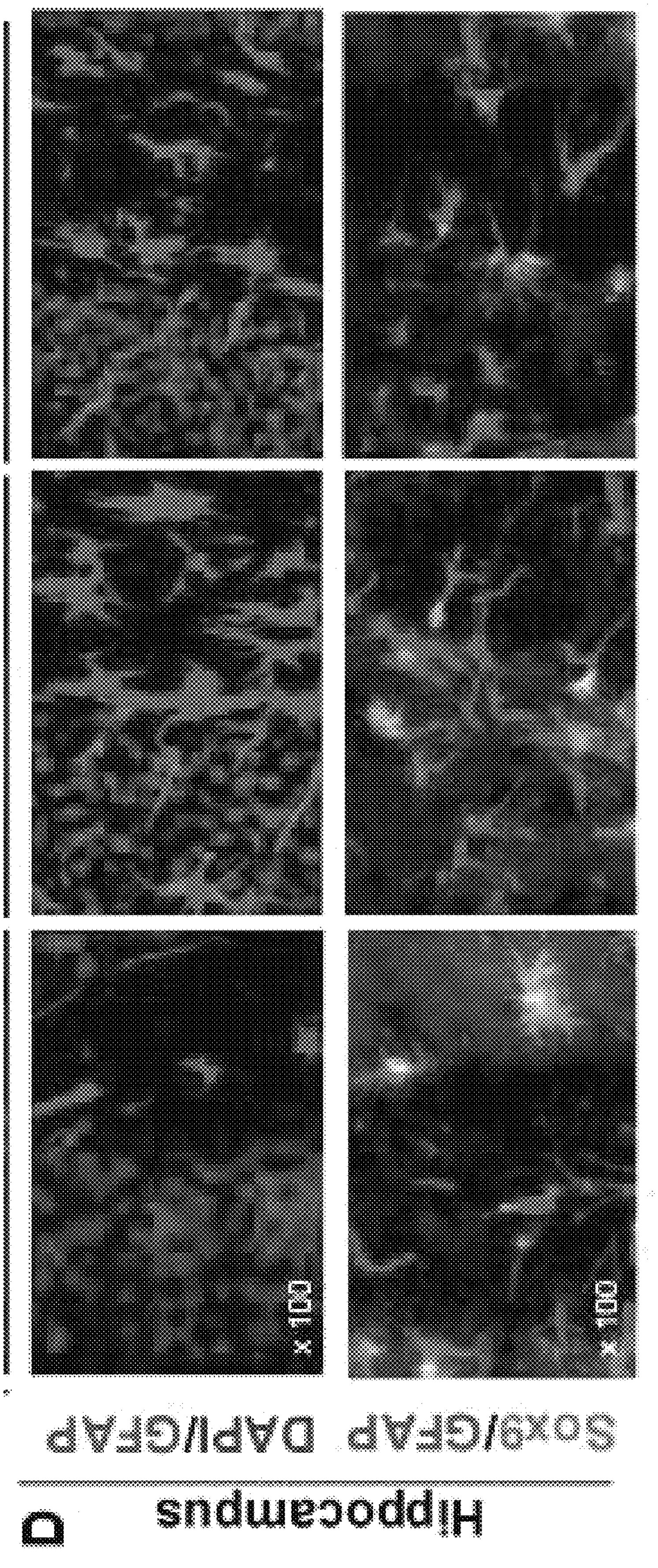
Figure 15E:

FIG. 15A: Serum cytokines (IL17AA, TNF-α and IL-1β,) were measured using ELISA in naïve mice prior to exposure to EtOH vapor (or Air), in alcohol-dependent (after CIE) in non-dependent mice (after Air) mice, and after 2BC sessions. The data are pg/ml, triplicates, 2 independent experiments. FIG. 15B: Mice (♂ C57BL/6, n=10/group) developed alcohol dependence (CIE) vs non-dependent controls (Air), and therapeutically treated with ±anti-IL17A Ab (vs IgG). The regiment of anti-IL17A Ab administration is shown (red arrows). Voluntary alcohol intake (g/kg weight/2 h) was measured in each group of mice during 2BC sessions. FIG. 15C: Coronal brain sections from Air and CIE mice±anti-IL17A Ab were co-stained for GFAP. Representative images of the frontal cortex are shown (×40, ×60 objectives), FIG. 15D: Representative images of the hippocampus (nuclei are visualized by DAPI) are shown (×100 objective). FIG. 15E: GFAP positive area in the cortex or hippocampus area was calculated as percent. Student's test, *p<0.05, **p<0.01.

FIG. 16A-G:

Blockage of IL17A Suppresses Volunteer Alcohol Drinking in Alcohol-Dependent Mice (Supporting FIG. 11)

Naïve co-housed mice (♂ C57BL/6, n=6/group, 4 independent experiments) developed alcohol dependence (CIE) vs non-dependent controls (Air) and subjected to sessions of volunteer alcohol drinking (2BC). FIG. 16A: Livers were isolated from Air and CIE mice and analyzed for steatosis (Oil Red O), development of liver fibrosis (Sirius Red). Livers were stained for Desmin and F4/80 to visualize Hepatic Stellate Cells and Kupffer cells, respectively. Representative images (×20 objective). The positive area was calculated as percent in individual staining. FIG. 16B: Coronal brain sections were analyzed by RNA in situ hybridization for expression of IL17A mRNA in CIE mice. No IL17A mRNA signal was observed in the cortex or hippocampus of these mice. Representative images (×10, and ×40 objectives). FIG. 16C: Total lung and liver tissues were analyzed using qRT-PCR. Strong induction of IL17A mRNA expression was detected in the lungs of CIE (vs Air) mice. FIG. 16D: Expression of fibrogenic and inflammatory genes were analyzed in total lung tissues from CIE vs Air mice. Exposure to the EtOH vapor did not induce lung fibrosis in CIE mice. FIG. 16E: Evans blue dye was injected i.v. into the mice 30 min prior to sacrifice. Brains were perfused, Evans blue dye was extracted from the brain tissues, and analyzed using spectrophotometry, absorption was measured. The data are mg/g brain tissue. FIG. 16F: Expression of IL17ARA and pro-inflammatory cytokines was measured in the total brain tissues using qRT-PCR. FIG. 16G: Cerebrospinal fluid (CSF) was isolated from naïve mice, in alcohol-dependent (after CIE) in non-dependent mice (after Air) mice, and after 2BC sessions. The data are pg/ml, triplicates, 2 independent experiments. IL17A cytokine or serum albumin were not detected in CSF of CIE or AIR mice. Student's test *p<0.05, **p<0.01.

REFERENCES—EXAMPLE 1

1. Kolls, J. K. & Linden, A. Interleukin-17 family members and inflammation. *Immunity* 21, 467-476 (2004).
2. Ivanov, I I, et al. The orphan nuclear receptor RORgammat directs the differentiation program of proinflammatory IL-17+ T helper cells. *Cell* 126, 1121-1133 (2006).
3. Yang, X. O., et al. T helper 17 lineage differentiation is programmed by orphan nuclear receptors ROR alpha and ROR gamma. *Immunity* 28, 29-39 (2008).
4. Iwakura, Y., et al. Functional specialization of interleukin-17 family members. *Immunity* 34, 149-162 (2011).
5. Yao, Z., et al. Herpesvirus Saimiri encodes a new cytokine, IL-17, which binds to a novel cytokine receptor. *Immunity* 3, 811-821 (1995).
6. Andoh, A., et al. IL-17 selectively down-regulates TNF-alpha-induced RANTES gene expression in human colonic subepithelial myofibroblasts. *J Immunol* 169, 1683-1687 (2002).
7. Subramaniam, S. V., et al. Evidence for the involvement of JAK/STAT pathway in the signaling mechanism of interleukin-17. *Biochem Biophys Res Commun* 262, 14-19 (1999).
8. Zhang, J. Y., et al. Interleukin-17-producing CD4(+) T cells increase with severity of liver damage in patients with chronic hepatitis B. *Hepatology* 51, 81-91 (2010).
9. Gao, B. Hepatoprotective and anti-inflammatory cytokines in alcoholic liver disease. *Journal of gastroenterology and hepatology* 27 Suppl 2, 89-93 (2012).
10. Bettelli, E., et al. Reciprocal developmental pathways for the generation of pathogenic effector TH17 and regulatory T cells. *Nature* 441, 235-238 (2006).
11. Mangan, P. R., et al. Transforming growth factor-beta induces development of the T(H)17 lineage. *Nature* 441, 231-234 (2006).
12. Weaver, C. T., et al. Th17: an effector CD4 T cell lineage with regulatory T cell ties. *Immunity* 24, 677-688 (2006).
13. Langrish, C. L., et al. IL-23 drives a pathogenic T cell population that induces autoimmune inflammation. *J Exp Med* 201, 233-240 (2005).

14. Murphy, C. A., et al. Divergent pro- and antiinflammatory roles for IL-23 and IL-12 in joint autoimmune inflammation. *J Exp Med* 198, 1951-1957 (2003).

15. Oppmann, B., et al. Novel p19 protein engages IL-12p40 to form a cytokine, IL-23, with biological activities similar as well as distinct from IL-12. *Immunity* 13, 715-725 (2000).

16. Cua, D. J., et al. Interleukin-23 rather than interleukin-12 is the critical cytokine for autoimmune inflammation of the brain. *Nature* 421, 744-748 (2003).

17. Ye, P., et al. Requirement of interleukin 17 receptor signaling for lung CXC chemokine and granulocyte colony-stimulating factor expression, neutrophil recruitment, and host defense. *J Exp Med* 194, 519-527 (2001).

18. Shen, F. & Gaffen, S. L. Structure-function relationships in the IL-17 receptor: implications for signal transduction and therapy. *Cytokine* 41, 92-104 (2008).

19. Gaffen, S. L. Structure and signalling in the IL-17 receptor family. *Nat Rev Immunol* 9, 556-567 (2009).

20. Faust, S. M., et al. Role of T cell TGFbeta signaling and IL-17 in allograft acceptance and fibrosis associated with chronic rejection. *J Immunol* 183, 7297-7306 (2009).

21. Wilson, M. S., et al. Bleomycin and IL-1beta-mediated pulmonary fibrosis is IL-17A dependent. *J Exp Med* 207, 535-552 (2010).

22. Longhi, M. S., et al. Impairment of CD4(+)CD25(+) regulatory T-cells in autoimmune liver disease. *J Hepatol* 41, 31-37 (2004).

23. Ge, J., et al. Implication of Th17 and Th1 cells in patients with chronic active hepatitis B. *J Clin Immunol* 30, 60-67 (2010).

24. Lemmers, A., et al. The interleukin-17 pathway is involved in human alcoholic liver disease. *Hepatology* 49, 646-657 (2009).

25. Meng, F., et al. Interleukin-17 signaling in inflammatory, Kupffer cells, and hepatic stellate cells exacerbates liver fibrosis in mice. *Gastroenterology* 143, 765-776 e761-763 (2012).

26. Affo, S., et al. Transcriptome analysis identifies TNF superfamily receptors as potential therapeutic targets in alcoholic hepatitis. *Gut* (2012).

27. Kawanokuchi, J., et al. Production and functions of IL-17 in microglia. *J Neuroimmunol* 194, 54-61 (2008).

28. Kebir, H., et al. Human TH17 lymphocytes promote blood-brain barrier disruption and central nervous system inflammation. *Nat Med* 13, 1173-1175 (2007).

29. Matsui, T., Yoshida, Y., Yanagihara, M. & Suenaga, H. Hypothermia at 35 degrees C. reduces the time-dependent microglial production of pro-inflammatory and anti-inflammatory factors that mediate neuronal cell death. *Neurocritical care* 20, 301-310 (2014).

30. Liu, Q., et al. Interleukin-17 inhibits Adult Hippocampal Neurogenesis. *Scientific reports* 4, 7554 (2014).

31. Diehl, A. M. Alcoholic liver disease: natural history. *Liver transplantation and surgery: official publication of the American Association for the Study of Liver Diseases and the International Liver Transplantation Society* 3, 206-211 (1997).

32. Gao, B. & Bataller, R. Alcoholic liver disease: pathogenesis and new therapeutic targets. *Gastroenterology* 141, 1572-1585 (2011).

33. Mello, T., Ceni, E., Surrenti, C. & Galli, A. Alcohol induced hepatic fibrosis: role of acetaldehyde. *Molecular aspects of medicine* 29, 17-21 (2008).

34. Becker, H. C. & Lopez, M. F. An Animal Model of Alcohol Dependence to Screen Medications for Treating Alcoholism. *Int Rev Neurobiol* 126, 157-177 (2016).

35. Vendruscolo, L. F. & Roberts, A. J. Operant alcohol self-administration in dependent rats: focus on the vapor model. *Alcohol* 48, 277-286 (2014).

36. Schnabl, B. & Brenner, D. A. Fibroblast growth factor inducible 14 as potential target in patients with alcoholic hepatitis. *Gut* (2012).

37. Seki, E., Brenner, D. A. & Karin, M. A Liver Full of JNK: Signaling in Regulation of Cell Function and Disease Pathogenesis, and Clinical Approaches. *Gastroenterology* 143, 307-320 (2012).

38. Kisseleva, T., et al. Myofibroblasts revert to an inactive phenotype during regression of liver fibrosis. *Proc Natl Acad Sci USA* 109, 9448-9453 (2012).

39. Iwaisako, K., et al. What's new in liver fibrosis? The origin of myofibroblasts in liver fibrosis. *Journal of gastroenterology and hepatology* 27 Suppl2, 65-68 (2012).

40. Kisseleva, T. & Brenner, D. A. The phenotypic fate and functional role for bone marrow-derived stem cells in liver fibrosis. *J Hepatol* 56, 965-972 (2012).

41. Paik, Y. H. & Brenner, D. A. NADPH oxidase mediated oxidative stress in hepatic fibrogenesis. *Korean J Hepatol* 17, 251-257 (2011).

42. Dong, M. H., et al. Serum levels of alanine aminotransferase decrease with age in longitudinal analysis. *Clinical gastroenterology and hepatology: the official clinical practice journal of the American Gastroenterological Association* 10, 285-290e281(2012).

43. DeLeve, L. D., et al. 15th International Symposium on Cells of the Hepatic Sinusoid, 2010. *Liver Int* 31, 762-772 (2011).

44. Kisseleva, T. & Brenner, D. A. Anti-fibrogenic strategies and the regression of fibrosis. *Best Pract Res Clin Gastroenterol* 25, 305-317 (2011).

45. Gao, B., et al. Innate immunity in alcoholic liver disease. *Am J Physiol Gastrointest Liver Physiol* 300, G516-525 (2011).

46. Loomba, R., et al. Genetic covariance between gamma-glutamyl transpeptidase and fatty liver risk factors: role of beta2-adrenergic receptor genetic variation in twins. *Gastroenterology* 139, 836-845, 845 e831 (2010).

47. Yan, A. W., et al. Enteric dysbiosis associated with a mouse model of alcoholic liver disease. *Hepatology* 53, 96-105 (2011).

48. Inokuchi, S., et al. Toll-like receptor 4 mediates alcohol-induced steatohepatitis through bone marrow-derived and endogenous liver cells in mice. *Alcohol Clin Exp Res* 35, 1509-1518 (2011).

49. Friedman, S. L., Roll, F. J., Boyles, J. & Bissell, D. M. Hepatic lipocytes: the principal collagen-producing cells of normal rat liver. *Proc Natl Acad Sci USA* 82, 8681-8685 (1985).

50. Ma, H. Y., et al. The role of IL-17 signaling in regulation of the liver-brain axis and intestinal permeability in Alcoholic Liver Disease. *Curr Pathobiol Rep* 4, 27-35(2016).

51. Xu, J., et al. New Approaches for Studying Alcoholic Liver Disease. *Curr Pathobiol Rep* 2, 171-183 (2014).

52. Marshall, S. A., et al. Microglial activation is not equivalent to neuroinflammation in alcohol-induced neurodegeneration: The importance of microglia phenotype. *Neurobiol Dis* 54, 239-251 (2013).

53. Kelley, K. W. & Dantzer, R. Alcoholism and inflammation: neuroimmunology of behavioral and mood disorders. *Brain Behav Immun* 25 Suppl 1, S13-20 (2011).

54. Qin, L. & Crews, F. T. Chronic ethanol increases systemic TLR3 agonist-induced neuroinflammation and neurodegeneration. *J Neuroinflammation* 9, 130 (2012).

55. Crews, F. T., et al. High mobility group box 1/Toll-like receptor danger signaling increases brain neuroimmune activation in alcohol dependence. *Biol Psychiatry* 73, 602-612 (2013).

56. Bajo, M., et al. Evaluation of TLR4 Inhibitor, T5342126, in Modulation of Ethanol-Drinking Behavior in Alcohol-Dependent Mice. *Alcohol Alcohol* 51, 541-548(2016).

57. Alfonso-Loeches, S., et al. Ethanol-Induced TLR4/NLRP3 Neuroinflammatory Response in Microglial Cells Promotes Leukocyte Infiltration Across the BBB. *Neurochem Res* 41, 193-209 (2016).

58. Alfonso-Loeches, S., et al. Pivotal role of TLR4 receptors in alcohol-induced neuroinflammation and brain damage. *J Neurosci* 30, 8285-8295 (2010).

59. Pascual, M., et al. Impact of TLR4 on behavioral and cognitive dysfunctions associated with alcohol-induced neuroinflammatory damage. *Brain Behav Immun* 25 Suppl 1, S80-91(2011).

60. Udomuksorn, W., et al, U. Effects of alcohol administration during adulthood on parvalbumin and glial fibrillary acidic protein immunoreactivity in the rat cerebral cortex. *Acta Histochem* 113, 283-289 (2011).

61. Geoffroy, C. G., et al. Evidence for an Age-Dependent Decline in Axon Regeneration in the Adult Mammalian Central Nervous System. *Cell Rep* 15, 238-246 (2016).

62. Haorah, J., et al. Mechanism of alcohol-induced oxidative stress and neuronal injury. *Free radical biology & medicine* 45, 1542-1550 (2008).

63. Fan, Y., et al. Tight junction disruption of blood-brain barrier in white matter lesions in chronic hypertensive rats. *Neuroreport* 26, 1039-1043 (2015).

64. Blanco, A. M., Valles, S. L., Pascual, M. & Guerri, C. Involvement of TLR4/type I IL-1 receptor signaling in the induction of inflammatory mediators and cell death induced by ethanol in cultured astrocytes. *J Immunol* 175, 6893-6899 (2005).

65. de la Monte, S. M., Longato, L., Tong, M., DeNucci, S. & Wands, J. R. The liver-brain axis of alcohol-mediated neurodegeneration: role of toxic lipids. *International journal of environmental research and public health* 6, 2055-2075 (2009).

66. Crews, F. T. & Vetreno, R. P. Neuroimmune basis of alcoholic brain damage. *Int Rev Neurobiol* 118, 315-357 (2014).

67. Sutherland, G. T., Sheedy, D. & Kril, J. J. Neuropathology of alcoholism. *Handbook of clinical neurology* 125, 603-615 (2014).

68. Erdozain, A. M., et al. Alcohol-related brain damage in humans. *PLoS One* 9, e93586 (2014).

69. Szabo, G. & Lippai, D. Converging actions of alcohol on liver and brain immune signaling. *International review of neurobiology* 118, 359-380 (2014).

70. Koob, G. F. & Volkow, N. D. Neurocircuitry of addiction. *Neuropsychopharmacology* 35, 217-238 (2010).

71. Vetreno, R. P. & Crews, F. T. Current hypotheses on the mechanisms of alcoholism. *Handb Clin Neurol* 125, 477-497 (2014).

72. Perdiguero, E. G., et al. The Origin of Tissue-Resident Macrophages: When an Erythro-myeloid Progenitor Is an Erythro-myeloid Progenitor. *Immunity* 43, 1023-1024 (2015).

73. Gomez Perdiguero, E., et al. Tissue-resident macrophages originate from yolk-sac-derived erythro-myeloid progenitors. *Nature* 518, 547-551 (2015).

74. Gilbertson, L. Cre-lox recombination: Cre-ative tools for plant biotechnology. *Trends Biotechnol* 21, 550-555 (2003).

75. Miossec, P. & Kolls, J. K. Targeting IL-17 and TH17 cells in chronic inflammation. *Nature reviews. Drug discovery* 11, 763-776 (2012).

76. Keller, T. L., et al. Halofuginone and other febrifugine derivatives inhibit prolyl-tRNA synthetase. *Nature chemical biology* 8, 311-317 (2012).

77. Sundrud, M. S., et al. Halofuginone inhibits TH17 cell differentiation by activating the amino acid starvation response. *Science* 324, 1334-1338 (2009).

78. Xu, T., et al. Ursolic acid suppresses interleukin-17 (IL-17) production by selectively antagonizing the function of RORgamma t protein. *J Biol Chem* 286, 22707-22710 (2011).

79. Solt, L. A., et al. Suppression of TH17 differentiation and autoimmunity by a synthetic ROR ligand. *Nature* 472, 491-494 (2011).

80. Tsukamoto, H., Mkrtchyan, H. & Dynnyk, A. Intragastric ethanol infusion model in rodents. *Methods Mol Biol* 447, 33-48 (2008).

81. Xiong, S., et al. Hepatic macrophage iron aggravates experimental alcoholic steatohepatitis. *Am J Physiol Gastrointest Liver Physiol* 295, G512-521 (2008).

82. Yan, A. W. & Schnabl, B. Bacterial translocation and changes in the intestinal microbiome associated with alcoholic liver disease. *World journal of hepatology* 4, 110-118 (2012).

83. Zhang, J. P., et al. Increased intratumoral IL-17-producing cells correlate with poor survival in hepatocellular carcinoma patients. *J Hepatol* 50, 980-989 (2009).

84. Kryczek, I, et al. Cutting edge: Th17 and regulatory T cell dynamics and the regulation by IL-2 in the tumor microenvironment. *J Immunol* 178, 6730-6733 (2007).

85. Ueno, A., et al. Mouse intragastric infusion (iG) model. *Nat Protoc* 7, 771-781 (2012).

86. Bull, C., Syed, W. A., Minter, S. C. & Bowers, M. S. Differential response of glial fibrillary acidic protein-positive astrocytes in the rat prefrontal cortex following ethanol self-administration. *Alcohol Clin Exp Res* 39, 650-658 (2015).

87. Cozzolino, R., et al. Use of solid-phase microextraction coupled to gas chromatography-mass spectrometry for determination of urinary volatile organic compounds in autistic children compared with healthy controls. *Analytical and bioanalytical chemistry* 406, 4649-4662 (2014).

88. Li, H., et al. A proton nuclear magnetic resonance metabonomics approach for biomarker discovery in non-alcoholic fatty liver disease. *Journal of proteome research* 10, 2797-2806 (2011).

89. Seki, E., et al. CCR1 and CCR5 promote hepatic fibrosis in mice. *J Clin Invest* 119, 1858-1870 (2009).

90. Iwaisako, K., et al. Origin of myofibroblasts in the fibrotic liver in mice. *Proc Natl Acad Sci USA* 111, E3297-3305 (2014).

91. Paik, Y. H., et al. The nicotinamide adenine dinucleotide phosphate oxidase (NOX) homologues NOX1 and NOX2/gp91(phox) mediate hepatic fibrosis in mice. *Hepatology* 53, 1730-1741 (2011).

92. Menzies, S. A., Hoff, J. T. & Betz, A. L. Extravasation of albumin in ischaemic brain oedema. *Acta Neurochir Suppl* (*Wien*) 51, 220-222 (1990).

93. Hu, M. H., et al. Neuroprotection effect of interleukin (IL)-17 secreted by reactive astrocytes is emerged from a high-level IL-17-containing environment during acute neuroinflammation. *Clin Exp Immunol* 175, 268-284 (2014).

94. Jadidi-Niaragh, F. & Mirshafiey, A. Th17 cell, the new player of neuroinflammatory process in multiple sclerosis. *Scand J Immunol* 74, 1-13 (2011).
95. Altamirano, J. & Bataller, R. Alcoholic liver disease: pathogenesis and new targets for therapy. *Nat Rev Gastroenterol Hepatol* 8, 491-501 (2011).
96. Liu, Y. Y., Li, Y. Y., Wang, S. S. & Shen, Y. [Effect of IL-17 on the expression of monocyte chemoattractant protein-1 in the cardiac myocytes]. *Xi Bao Yu Fen Zi Mian Yi Xue Za Zhi* 28, 163-166 (2012).
97. Duhen, R., et al. Cutting edge: the pathogenicity of IFN-gamma-producing Th17 cells is independent of T-bet. *J Immunol* 190, 4478-4482 (2013).
98. Wang, K., et al. Interleukin-17 receptor a signaling in transformed enterocytes promotes early colorectal tumorigenesis. *Immunity* 41, 1052-1063 (2014).
99. Cho, I. H., et al. Role of microglial IKKbeta in kainic acid-induced hippocampal neuronal cell death. *Brain* 131, 3019-3033 (2008).
100. Seki, E., et al. TLR4 enhances TGF-beta signaling and hepatic fibrosis. *Nat Med* 13, 1324-1332 (2007).
101. Grivennikov, S. I., et al. Adenoma-linked barrier defects and microbial products drive IL-23/IL-17-mediated tumour growth. *Nature* 491, 254-258 (2012).
102. Castano, A. P., et al. Serum amyloid P inhibits fibrosis through Fc gamma R-dependent monocyte-macrophage regulation in vivo. *Sci Transl Med* 1, 5ra13 (2009).
103. Cohen, P., et al. Selective deletion of leptin receptor in neurons leads to obesity. *J Clin Invest* 108, 1113-1121 (2001).
104. Storch, J., Zhou, Y. X. & Lagakos, W. S. Metabolism of apical versus basolateral sn-2-monoacylglycerol and fatty acids in rodent small intestine. *J Lipid Res* 49, 1762-1769 (2008).
105. Liu, Y., et al. Knockdown of acyl-CoA:diacylglycerol acyltransferase 2 with antisense oligonucleotide reduces VLDL TG and ApoB secretion in mice. *Biochim Biophys Acta* 1781, 97-104 (2008).
106. Lu, Y., Wu, D., Wang, X., Ward, S. C. & Cederbaum, A. I. Chronic alcohol-induced liver injury and oxidant stress are decreased in cytochrome P4502E1 knockout mice and restored in humanized cytochrome P4502E1 knock-in mice. *Free radical biology & medicine* 49, 1406-1416 (2010).
107. Cheung, C., et al. The cyp2e1-humanized transgenic mouse: role of cyp2e1 in acetaminophen hepatotoxicity. *Drug metabolism and disposition: the biological fate of chemicals* 33, 449-457 (2005).
108. Mederacke, I, et al. Fate tracing reveals hepatic stellate cells as dominant contributors to liver fibrosis independent of its aetiology. *Nat Commun* 4, 2823 (2013).
109. Blaner, W. S., et al. Hepatic stellate cell lipid droplets: a specialized lipid droplet for retinoid storage. *Biochim Biophys Acta* 1791, 467-473 (2009).
110. D'Ambrosio, D. N., et al. Distinct populations of hepatic stellate cells in the mouse liver have different capacities for retinoid and lipid storage. *PLoS One* 6, e24993 (2011).
111. Kluwe, J., et al. Absence of hepatic stellate cell retinoid lipid droplets does not enhance hepatic fibrosis but decreases hepatic carcinogenesis. *Gut* 60, 1260-1268 (2011).
112. Blank, T. & Prinz, M. CatacLysMic specificity when targeting myeloid cells?*European journal of immunology* 46, 1340-1342 (2016).
113. Goldmann, T., et al. A new type of microglia gene targeting shows TAK1 to be pivotal in CNS autoimmune inflammation. *Nat Neurosci* 16, 1618-1626 (2013).
114. Yona, S., et al. Fate mapping reveals origins and dynamics of monocytes and tissue macrophages under homeostasis. *Immunity* 38, 79-91 (2013).
115. Ma, D. K., Bonaguidi, M. A., Ming, G. L. & Song, H. Adult neural stem cells in the mammalian central nervous system. *Cell Res* 19, 672-682 (2009).
116. Samantaray, S., et al. Chronic intermittent ethanol induced axon and myelin degeneration is attenuated by calpain inhibition. *Brain Res* 1622, 7-21 (2015).
117. Nixon, K., Kim, D. H., Potts, E. N., He, J. & Crews, F. T. Distinct cell proliferation events during abstinence after alcohol dependence: microglia proliferation precedes neurogenesis. *Neurobiol Dis* 31, 218-229 (2008).
118. Zhuo, L., et al. hGFAP-cre transgenic mice for manipulation of glial and neuronal function in vivo. *Genesis* 31, 85-94 (2001).
119. Uylings, H. B., Groenewegen, H. J. & Kolb, B. Do rats have a prefrontal cortex?*Behav Brain Res* 146, 3-17 (2003).
120. Seamans, J. K., Lapish, CC. & Durstewitz, D. Comparing the prefrontal cortex of rats and primates: insights from electrophysiology. *Neurotox Res* 14, 249-262 (2008).
121. Ricci, G., Volpi, L., Pasquali, L., Petrozzi, L. & Siciliano, G. Astrocyte-neuron interactions in neurological disorders. *J Biol Phys* 35, 317-336 (2009).
122. Araque, A., et al. Gliotransmitters travel in time and space. *Neuron* 81, 728-739 (2014).
123. Huppert, J., et al. Cellular mechanisms of IL-17-induced blood-brain barrier disruption. *FASEB J* 24, 1023-1034 (2010).
124. Funae, Y. & Imaoka, S. Simultaneous purification of multiple forms of rat liver microsomal cytochrome P-450 by high-performance liquid chromatography. *Biochim Biophys Acta* 842, 119-132 (1985).
125. Lu, Y., Wang, X. & Cederbaum, A. I. Lipopolysaccharide-induced liver injury in rats treated with the CYP2E1 inducer pyrazole. *Am J Physiol Gastrointest Liver Physiol* 289, G308-319 (2005).
126. Reinke, L. A. & Moyer, M. J. p-Nitrophenol hydroxylation. A microsomal oxidation which is highly inducible by ethanol. *Drug metabolism and disposition: the biological fate of chemicals* 13, 548-552 (1985).
127. Contet, C., et al. Identification of genes regulated in the mouse extended amygdala by excessive ethanol drinking associated with dependence. *Addict Biol* 16, 615-619 (2011).
128. Becker, H. C. & Lopez, M. F. Increased ethanol drinking after repeated chronic ethanol exposure and withdrawal experience in C57BL/6 mice. *Alcohol Clin Exp Res* 28, 1829-1838 (2004).
129. Gorini, G., Roberts, A. J. & Mayfield, R. D. Neurobiological signatures of alcohol dependence revealed by protein profiling. *PLoS One* 8, e82656 (2013).
130. Okuno, H., et al. Inverse synaptic tagging of inactive synapses via dynamic interaction of Arc/Arg3.1 with CaMKIIbeta. Cell 149, 886-898 (2012).
131. Probst, B., Rock, R., Gessler, M., Vortkamp, A. & Puschel, A. W. The rodent Four-jointed ortholog Fjx1 regulates dendrite extension. *Dev Biol* 312, 461-470 (2007).
132. Koob, G. F. Alcoholism: allostasis and beyond. *Alcohol Clin Exp Res* 27, 232-243 (2003).

133. Koob, G. F. Neurocircuitry of alcohol addiction: synthesis from animal models. *Handb Clin Neurol* 125, 33-54 (2014).

134. Sun, J., et al. IL-17A is implicated in lipopolysaccharide-induced neuroinflammation and cognitive impairment in aged rats via microglial activation. *J Neuroinflammation* 12, 165 (2015).

135. Eisenhardt, M., Hansson, A. C., Spanagel, R. & Bilbao, A. Chronic intermittent ethanol exposure in mice leads to an up-regulation of CRH/CRHR1 signaling. *Alcohol Clin Exp Res* 39, 752-762 (2015).

136. Bossert, J. M., Marchant, N. J., Calu, D. J. & Shaham, Y. The reinstatement model of drug relapse: recent neurobiological findings, emerging research topics, and translational research. *Psychopharmacology* (*Berl*) 229, 453-476 (2013).

137. George, O., Le Moal, M. & Koob, G. F. Allostasis and addiction: role of the dopamine and corticotropin-releasing factor systems. *Physiol Behav* 106, 58-64 (2012).

138. Koob, G. F. & Volkow, N. D. Neurobiology of addiction: a neurocircuitry analysis. *Lancet Psychiatry* 3, 760-773 (2016).

139. Geoffroy, C. G., et al. Effects of PTEN and Nogo Codeletion on Corticospinal Axon Sprouting and Regeneration in Mice. *J Neurosci* 35, 6413-6428 (2015).

140. Koob, G. F. & Heinrichs, S. C. A role for corticotropin releasing factor and urocortin in behavioral responses to stressors. *Brain Res* 848, 141-152 (1999).

141. Devito, L. M., Kanter, B. R. & Eichenbaum, H. The hippocampus contributes to memory expression during transitive inference in mice. *Hippocampus* 20, 208-217 (2010).

REFERENCES—EXAMPLE 2

1. Koob, G. F. & Volkow, N. D. Neurocircuitry of addiction. *Neuropsychopharmacology* 35, 217-23 8 (2010).

2. Le Berre, A. P., Fama, R. & Sullivan, E. V. Executive Functions, Memory, and Social Cognitive Deficits and Recovery in Chronic Alcoholism: A Critical Review to Inform Future Research. *Alcohol Clin Exp Res* 41, 1432-1443 (2017).

3. Gao, B. & Bataller, R. Alcoholic liver disease: pathogenesis and new therapeutic targets. *Gastroenterology* 141, 1572-1585 (2011).

4. Crews, F. T., Lawrimore, C. J., Walter, T. J. & Coleman, L. G., Jr. The role of neuroimmune signaling in alcoholism. *Neuropharmacology* 122, 56-73 (2017).

5. Ma, H. Y., et al. The role of IL-17 signaling in regulation of the liver-brain axis and intestinal permeability in Alcoholic Liver Disease. *Curr Pathobiol Rep* 4, 27-35 (2016).

6. Kolls, J. K. & Linden, A. Interleukin-17 family members and inflammation. *Immunity* 21, 467-476 (2004).

7. Meng, F., et al. Interleukin-17 signaling in inflammatory, *Kupffer cells, and* hepatic stellate cells exacerbates liver fibrosis in mice. *Gastroenterology* 143, 765-776 e761-763 (2012).

8. Waisman, A., Hauptmann, J. & Regen, T. The role of IL-17 in CNS diseases. *Acta Neuropathol* 129, 625-637 (2015).

9. Mangan, P. R., et al. Transforming growth factor-beta induces development of the T(H)17 lineage. *Nature* 441, 231-234 (2006).

10. Bataller, R. & Brenner, D. A. Liver fibrosis. *J Clin Invest* 115, 209-218 (2005).

11. Manel, N., Unutmaz, D. & Littman, D. R. The differentiation of human T(H)-17 cells requires transforming growth factor-beta and induction of the nuclear receptor RORgammat. *Nat Immunol* 9, 641-649 (2008).

12. Wilson, M. S., et al. Bleomycin and IL-1beta-mediated pulmonary fibrosis is IL-17A dependent. *J Exp Med* 207, 535-552 (2010).

13. Yoshizaki, A., et al. Cell adhesion molecules regulate fibrotic process via Th1/Th2/Th17 cell balance in a bleomycin-induced scleroderma model. *J Immunol* 185, 2502-2515 (2010).

14. Choi, G. B., et al. The maternal interleukin-17a pathway in mice promotes autism-like phenotypes in offspring. *Science* 351, 933-939 (2016).

15. Heidarianpour, A., et al. Effect of Moderate Exercise on Serum Interferon-Gamma and Interleukin-17 Levels in the Morphine Withdrawal Period. *Int J High Risk Behav Addict* 5, e26907 (2016).

16. Pascual, M., et al. Cytokines and chemokines as biomarkers of ethanol-induced neuroinflammation and anxiety-related behavior: role of TLR4 and TLR2. *Neuropharmacology* 89, 352-359 (2015).

17. Lemmers, A., et al. The interleukin-17 pathway is involved in human alcoholic liver disease. *Hepatology* 49, 646-657 (2009).

18. Lin, F., et al. Alcohol dehydrogenase-specific T-cell responses are associated with alcohol consumption in patients with alcohol-related cirrhosis. *Hepatology* 58, 314-324 (2013).

19. Bertola, A., et al. Mouse model of chronic and binge ethanol feeding (the NIAAA model). *Nat Protoc* 8, 627-637 (2013).

20. Page, A., et al. Alcohol directly stimulates epigenetic modifications in hepatic stellate cells. *J Hepatol* 62, 388-397 (2015).

21. Lazaro, R., et al. Osteopontin deficiency does not prevent but promotes alcoholic neutrophilic hepatitis in mice. *Hepatology* 61, 129-140 (2015).

22. Nakajima, K., et al. Distinct roles of IL-23 and IL-17 in the development of psoriasis-like lesions in a mouse model. *J Immunol* 186, 4481-4489 (2011).

23. Fitzpatrick L R, O. C. R., et al. A Novel ROR-Gamma T Inhibitor (VPR-254)

Attenuates Key Parameters of Innate Immune Colitis in Mice. *Gastroenterology* 152: S30-S31(2017).

24. Fidler, T. L., et al. Intragastric self-infusion of ethanol in high- and low-drinking mouse genotypes after passive ethanol exposure. *Genes Brain Behav* 10, 264-275 (2011).

25. Asatryan, L., et al. Chronic ethanol exposure combined with high fat diet up-regulates P2X7 receptors that parallels neuroinflammation and neuronal loss in C57BL/6J mice. *Journal of neuroimmunology* 285, 169-179 (2015).

26. Hayes, D. M., et al. Determining the threshold for alcohol-induced brain damage: new evidence with gliosis markers. *Alcohol Clin Exp Res* 37, 425-434 (2013).

27. You, T., et al. IL-17 induces reactive astrocytes and up-regulation of vascular endothelial growth factor (VEGF) through JAK/STAT signaling. *Sci Rep* 7, 41779 (2017).

28. Pratt, O. E., et al. The genesis of alcoholic brain tissue injury. *Alcohol Alcohol* 25, 217-230 (1990).

29. Huppert, J., et al. Cellular mechanisms of IL-17-induced blood-brain barrier disruption. *FASEB J* 24, 1023-1034 (2010).

30. Becker, H. C. & Lopez, M. F. Increased ethanol drinking after repeated chronic ethanol exposure and withdrawal experience in C57BL/6 mice. *Alcohol Clin Exp Res* 28, 1829-1838 (2004).

31. Heinz, R. & Waltenbaugh, C. Ethanol consumption modifies dendritic cell antigen presentation in mice. *Alcohol Clin Exp Res* 31, 1759-1771 (2007).
32. Giles, D. A., et al. Thermoneutral housing exacerbates nonalcoholic fatty liver disease in mice and allows for sex-independent disease modeling. *Nat Med* 23, 829-838 (2017).
33. Mandrekar, P., Bataller, R., Tsukamoto, H. & Gao, B. Alcoholic hepatitis: Translational approaches to develop targeted therapies. *Hepatology* 64, 1343-1355 (2016).
34. Burda, J. E. & Sofroniew, M. V. Reactive gliosis and the multicellular response to CNS damage and disease. *Neuron* 81, 229-248 (2014).
35. Gaffen, S. L. Structure and signalling in the IL-17 receptor family. *Nat Rev Immunol* 9, 556-567 (2009).
36. Haak, S., et al. IL-17A and IL-17F do not contribute vitally to autoimmune neuro-inflammation in mice. *J Clin Invest* 119, 61-69 (2009).
37. Starnes, T., et al. Cutting edge: IL-17D, a novel member of the IL-17 family, stimulates cytokine production and inhibits hemopoiesis. *J Immunol* 169, 642-646 (2002).
38. Breese, G. R., et al. Repeated lipopolysaccharide (LPS) or cytokine treatments sensitize ethanol withdrawal-induced anxiety-like behavior. *Neuropsychopharmacology* 33, 867-876 (2008).
39. Heilig, M. & Koob, G. F. A key role for corticotropin-releasing factor in alcohol dependence. *Trends Neurosci* 30, 399-406 (2007).
40. Knapp, D. J., et al. Cytokine involvement in stress may depend on corticotrophin releasing factor to sensitize ethanol withdrawal anxiety. *Brain Behav Immun* 25 Suppl 1, S146-154(2011).
41. Ye, P., et al. Requirement of interleukin 17 receptor signaling for lung CXC chemokine and granulocyte colony-stimulating factor expression, neutrophil recruitment, and host defense. *J Exp Med* 194, 519-527 (2001).
42. US Department of Health and Human Services. National Institute of Health/National Institute on Alcohol Abuse and Alcoholism. Helping Patients who drink too much. A clinician's guide Updated 2005 Edition.

SUPPLEMENTAL METHODS REFERENCES

1. Bertola, A., et al. Mouse model of chronic and binge ethanol feeding (the NIAAA model). *Nat Protoc* 8, 627-637 (2013).
2. Page, A., et al. Alcohol directly stimulates epigenetic modifications in hepatic stellate cells. *J Hepatol* 62, 388-397 (2015).
3. US Department of Health and Human Services. National Institute of Health/National Institute on Alcohol Abuse and Alcoholism. Helping Patients who drink too much. A clinician's guide Updated 2005 Edition. http://pubs.niaaa.nih.gov/publications/Practitioner/CliniciansGuide2005/guide.pdf. (2005).
4. Sobell, L. C. & Sobell, M. B. Timeline follow-back: A technique for assessing self-reported alcohol consumption. in *Measuring alcohol consumption: Psychosocial and biochemical methods* (eds. Litten, R. Z. & Allen, J. P.) 41-72 (Humana Press, Inc, 1992).
5. Sobell, L. C. & Sobell, M. B. *Timeline FollowBack: User's guide*, (Addicition Research Foundation, Toronto, 1996).
6. Wang, F., et al. RNAscope: a novel in situ RNA analysis platform for formalin-fixed, paraffin-embedded tissues. *J Mol Diagn* 14, 22-29 (2012).
7. Seki, E., et al. TLR4 enhances TGF-beta signaling and hepatic fibrosis. *Nat Med* 13, 1324-1332 (2007).
8. Kumamaru, H., et al. Liposomal clodronate selectively eliminates microglia from primary astrocyte cultures. *J Neuroinflammation* 9, 116 (2012).
9. Dobin, A., et al. STAR: ultrafast universal RNA-seq aligner. *Bioinformatics* 29, 15-21 (2013).
10. Li, B. & Dewey, C. N. RSEM: accurate transcript quantification from RNA-Seq data with or without a reference genome. *BMC Bioinformatics* 12, 323 (2011).
11. Culhane, A. C., et al. MADE4: an R package for multivariate analysis of gene expression data. *Bioinformatics* 21, 2789-2790 (2005).
12. Heinz, S., et al. Simple combinations of lineage-determining transcription factors prime cis-regulatory elements required for macrophage and B cell identities. *Mol Cell* 38, 576-589 (2010).
13. Robinson, M. D., et al. edgeR: a Bioconductor package for differential expression analysis of digital gene expression data. *Bioinformatics* 26, 139-140 (2010).
14. Lee, J. D., et al. Blood-brain barrier dysfunction occurring in mice infected with Angiostrongylus cantonensis. *Acta Trop* 97, 204-211 (2006).
15. Meng, F., et al. Interleukin-17 signaling in inflammatory, Kupffer cells, and hepatic stellate cells exacerbates liver fibrosis in mice. *Gastroenterology* 143, 765-776 e761-763 (2012).
16. Radu, M. & Chernoff, J. An in vivo assay to test blood vessel permeability. *J Vis Exp*, e50062 (2013).
17. Tsukamoto, H., Mkrtchyan, H. & Dynnyk, A. Intragastric ethanol infusion model in rodents. *Methods Mol Biol* 447, 33-48 (2008).
18. Xiong, S., et al. Hepatic macrophage iron aggravates experimental alcoholic steatohepatitis. *Am J Physiol Gastrointest Liver Physiol* 295, G512-521 (2008).
19. Yan, A. W., et al. Enteric dysbiosis associated with a mouse model of alcoholic liver disease. *Hepatology* 53, 96-105 (2011).
20. Yan, A. W. & Schnabl, B. Bacterial translocation and changes in the intestinal microbiome associated with alcoholic liver disease. *World journal of hepatology* 4, 110-118 (2012).
21. Acarin, L., Gonzalez, B. & Castellano, B. Neuronal, astroglial and microglial cytokine expression after an excitotoxic lesion in the immature rat brain. *Eur J Neurosci* 12, 3505-3520 (2000).
22. Semple, B. D., et al. Interleukin-1 Receptor in Seizure Susceptibility after Traumatic Injury to the Pediatric Brain. *J Neurosci* 37, 7864-7877 (2017).
23. Iwakura, Y., Ishigame, H., Saijo, S. & Nakae, S. Functional specialization of interleukin-17 family members. *Immunity* 34, 149-162 (2011).
24. Nicoletti, F., et al. Metabotropic glutamate receptors: a new target for the therapy of neurodegenerative disorders? *Trends Neurosci* 19, 267-271 (1996).
25. Shichita, T., et al. Pivotal role of cerebral interleukin-17-producing gammadeltaT cells in the delayed phase of ischemic brain injury. *Nat Med* 15, 946-950 (2009).
26. Varatharaj, A. & Galea, I. The blood-brain barrier in systemic inflammation. *Brain Behav Immun* 60, 1-12 (2017).
27. Huppert, J., et al. Cellular mechanisms of IL-17-induced blood-brain barrier disruption. *FASEB J* 24, 1023-1034 (2010).
28. Pelkmans, L. & Zerial, M. Kinase-regulated quantal assemblies and kiss-and-run recycling of caveolae. *Nature* 436, 128-133 (2005).

29. Ki, S.H., et al. Interleukin-22 treatment ameliorates alcoholic liver injury in a murine model of chronic-binge ethanol feeding: role of signal transducer and activator of transcription 3. *Hepatology* 52, 1291-1300 (2010).

A number of embodiments of the invention have been described. Nevertheless, it can be understood that various modifications may be made without departing from the spirit and scope of the invention. Accordingly, other embodiments are within the scope of the following claims.

What is claimed is:

1. A method for reducing addiction to alcohol in an individual in need thereof, comprising administering to the individual a pharmaceutical composition comprising an antibody or antigen binding fragment thereof that specifically binds IL-17A or IL-17A receptor and inhibits the activity of the IL-17A or IL-17A receptor.

2. The method of claim 1, wherein the pharmaceutical composition is formulated for enteral or parenteral administration.

3. The method of claim 2, wherein the pharmaceutical composition is formulated for oral, intravenous (IV) or intrathecal (IT) administration.

4. The method of claim 3, wherein the pharmaceutical composition is contained in or carried in a nanoparticle, a particle, a micelle or a liposome or lipoplex, a polymersome, a polyplex or a dendrimer.

5. The method of claim 1, wherein the pharmaceutical composition is formulated as, or contained in, a nanoparticle, a liposome, a tablet, a pill, a capsule, a gel, a geltab, a liquid, a powder, an emulsion, a lotion, an aerosol, a spray, a lozenge, an injectable solution, or an implant.

6. The method of claim 1, wherein the pharmaceutical composition is administered orally, parenterally, by inhalation spray, nasally, topically, intrathecally, intracerebrally, epidurally, intracranially or rectally.

7. The method of claim 1, wherein the antibody or antigen binding fragment thereof is a human antibody or antigen binding fragment thereof.

8. The method of claim 1, wherein the antibody is a monoclonal antibody.

9. The method of claim 8, wherein the monoclonal antibody is a fully human monoclonal antibody.

10. The method of claim 9, wherein the fully human monoclonal antibody is secukinumab.

11. The method of claim 9, wherein the fully human monoclonal antibody is brodalumab.

12. The method of claim 8, wherein the monoclonal antibody is a humanized monoclonal antibody.

13. The method of claim 12, wherein the humanized monoclonal antibody is ixekizumab.

* * * * *